(12) United States Patent
Muhsin et al.

(10) Patent No.: US 10,932,705 B2
(45) Date of Patent: Mar. 2, 2021

(54) SYSTEM FOR DISPLAYING AND CONTROLLING MEDICAL MONITORING DATA

(71) Applicant: Masimo Corporation, Irvine, CA (US)

(72) Inventors: Bilal Muhsin, San Clemente, CA (US); Nicholas Evan Barker, Laguna Beach, CA (US)

(73) Assignee: Masimo Corporation, Irvine, CA (US)

( * ) Notice: Subject to any disclaimer, the term of this patent is extended or adjusted under 35 U.S.C. 154(b) by 213 days.

(21) Appl. No.: 15/971,888

(22) Filed: May 4, 2018

(65) Prior Publication Data

US 2018/0317826 A1 Nov. 8, 2018

Related U.S. Application Data

(60) Provisional application No. 62/535,757, filed on Jul. 21, 2017, provisional application No. 62/503,109, filed on May 8, 2017.

(51) Int. Cl.
*A61B 5/1455* (2006.01)
*G16H 10/60* (2018.01)
(Continued)

(52) U.S. Cl.
CPC ........ *A61B 5/14552* (2013.01); *G06F 13/385* (2013.01); *G06F 13/4004* (2013.01);
(Continued)

(58) Field of Classification Search
CPC ..... A61B 5/14552; A61B 5/002; A61B 5/145; G16H 40/67; G16H 40/63; G16H 40/40;
(Continued)

(56) References Cited

U.S. PATENT DOCUMENTS 4,960,128 A 10/1990 Gordon et al.
4,964,408 A 10/1990 Hink et al.
(Continued)

FOREIGN PATENT DOCUMENTS

WO WO 2014/051563 4/2014
WO WO 2018/156804 8/2018
(Continued)

OTHER PUBLICATIONS

International Search Report and Written Opinion from corresponding International Patent Application No. PCT/US2018/031198, dated Aug. 29, 2018, in 12 pages.
(Continued)

*Primary Examiner* — Eric F Winakur
*Assistant Examiner* — Abid A Mustansir
(74) *Attorney, Agent, or Firm* — Knobbe, Martens, Olson & Bear, LLP

(57) ABSTRACT

A first medical device can acquire a physiological parameter value from a patient and communicate the physiological parameter value to a medical network interface. The medical network interface can link a patient ID associated with the physiological parameter and a device ID associated with the first medical device with the medical network interface's device ID. The medical network interface can pass the physiological parameter value to a second medical device for further processing or routing to another medical device.

20 Claims, 134 Drawing Sheets

(51) Int. Cl.
*G06F 13/42* (2006.01)
*G06F 13/40* (2006.01)
*G06F 13/38* (2006.01)
*G16H 40/40* (2018.01)
*G16H 40/63* (2018.01)
*G16H 40/67* (2018.01)

(52) U.S. Cl.
CPC ......... *G06F 13/4282* (2013.01); *G16H 10/60* (2018.01); *G16H 40/40* (2018.01); *G16H 40/63* (2018.01); *G16H 40/67* (2018.01)

(58) Field of Classification Search
CPC ... G16H 10/60; G06F 13/385; G06F 13/4004; G06F 13/4282
See application file for complete search history.

(56) References Cited

U.S. PATENT DOCUMENTS

| | | |
|---|---|---|
| 5,041,187 A | 8/1991 | Hink et al. |
| 5,069,213 A | 12/1991 | Polczynski |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,685,299 A | 11/1997 | Diab et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,010,937 A | 1/2000 | Karam et al. |
| 6,011,986 A | 1/2000 | Diab et al. |
| 6,027,452 A | 2/2000 | Flaherty et al. |
| 6,036,642 A | 3/2000 | Diab et al. |
| 6,040,578 A | 3/2000 | Malin et al. |
| 6,045,509 A | 4/2000 | Caro et al. |
| 6,066,204 A | 5/2000 | Haven |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,115,673 A | 9/2000 | Malin et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | MacKlem et al. |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |

(56) References Cited

U.S. PATENT DOCUMENTS

| | | |
|---|---|---|
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,847,336 B1 | 1/2005 | Lemelson et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,858,012 B2 | 2/2005 | Burns et al. |
| 6,861,639 B2 | 3/2005 | Al-Ali |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,306,560 B2 | 12/2007 | Iliff |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,593,230 B2 | 9/2009 | Abut-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |

(56) References Cited

U.S. PATENT DOCUMENTS

| | | |
|---|---|---|
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,004,396 B2 | 8/2011 | Liu et al. |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,177,704 B1 | 5/2012 | Mohl et al. |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |

(56) References Cited

U.S. PATENT DOCUMENTS

| | | |
|---|---|---|
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,743,148 B2 | 6/2014 | Gegner et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,501,613 B1 | 11/2016 | Hanson et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |

(56) References Cited

U.S. PATENT DOCUMENTS

| | | | |
|---|---|---|---|
| 9,591,975 B2 | 3/2017 | Dalvi et al. |
| 9,622,692 B2 | 4/2017 | Lamego et al. |
| 9,622,693 B2 | 4/2017 | Diab |
| 9,629,570 B2 | 4/2017 | Bar-tal |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,700,218 B2 | 7/2017 | Boyer |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,757,020 B1 | 9/2017 | Elazar et al. |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali et al. |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,892,564 B1 | 2/2018 | Cvetko et al. |
| 9,895,107 B2 | 2/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,955,937 B2 | 5/2018 | Telfort |
| 9,958,681 B2 | 5/2018 | Ko et al. |
| 9,959,620 B2 | 5/2018 | Merlet |
| 9,965,946 B2 | 5/2018 | Al-Ali et al. |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |
| 10,010,276 B2 | 7/2018 | Al-Ali et al. |
| 10,010,379 B1 | 7/2018 | Gibby et al. |
| 10,080,530 B2 | 9/2018 | Cheng et al. |
| 10,086,138 B1 | 10/2018 | Novak, Jr. |
| 10,092,213 B2 | 10/2018 | Gossler et al. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,255,690 B2 | 4/2019 | Bhuruth et al. |
| 10,279,247 B2 | 5/2019 | Kiani |
| 10,292,664 B2 | 5/2019 | Al-Ali |
| 10,299,720 B2 | 5/2019 | Brown et al. |
| 10,304,206 B2 | 5/2019 | Nakazato et al. |
| 10,304,251 B2 | 5/2019 | Pahud et al. |
| 10,318,811 B1 | 6/2019 | Gold et al. |
| 10,327,337 B2 | 6/2019 | Schmidt et al. |
| 10,327,713 B2 | 6/2019 | Barker et al. |
| 10,332,292 B1 | 6/2019 | Arnicar et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| 10,403,047 B1 | 9/2019 | Comer et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0102683 A1 | 5/2004 | Khanuja et al. |
| 2004/0106163 A1 | 6/2004 | Workman, Jr. et al. |

(56) References Cited

U.S. PATENT DOCUMENTS

| | | |
|---|---|---|
| 2005/0055276 A1 | 3/2005 | Kiani et al. |
| 2005/0234317 A1 | 10/2005 | Kiani |
| 2005/0254134 A1 | 11/2005 | Yamamoto |
| 2006/0073719 A1 | 4/2006 | Kiani |
| 2006/0161054 A1 | 7/2006 | Reuss et al. |
| 2006/0189871 A1 | 8/2006 | Al-Ali et al. |
| 2006/0241792 A1 | 10/2006 | Pretlove et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2007/0282478 A1 | 12/2007 | Al-Ali et al. |
| 2008/0015015 A1* | 1/2008 | Walker .................. A63F 13/00 463/29 |
| 2008/0064965 A1 | 3/2008 | Jay et al. |
| 2008/0081982 A1 | 4/2008 | Simon et al. |
| 2008/0094228 A1 | 4/2008 | Welch et al. |
| 2008/0183074 A1 | 7/2008 | Carls et al. |
| 2008/0221418 A1 | 9/2008 | Al-Ali et al. |
| 2008/0270188 A1 | 10/2008 | Garg et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275813 A1 | 11/2009 | Davis |
| 2009/0275844 A1 | 11/2009 | Al-Ali |
| 2009/0311655 A1 | 12/2009 | Karkanias et al. |
| 2009/0312660 A1 | 12/2009 | Guarino et al. |
| 2010/0004518 A1 | 1/2010 | Vo et al. |
| 2010/0030040 A1 | 2/2010 | Poeze et al. |
| 2010/0048134 A1* | 2/2010 | McCarthy ............ H04R 1/1041 455/41.3 |
| 2010/0099964 A1 | 4/2010 | O'Reilly et al. |
| 2010/0234718 A1 | 9/2010 | Sampath et al. |
| 2010/0249540 A1 | 9/2010 | Lisogurski |
| 2010/0270257 A1 | 10/2010 | Wachman et al. |
| 2010/0298656 A1 | 11/2010 | McCombie et al. |
| 2011/0021140 A1* | 1/2011 | Binier .................... G06Q 40/08 455/41.1 |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0066007 A1 | 3/2011 | Banet et al. |
| 2011/0082711 A1 | 4/2011 | Poeze et al. |
| 2011/0087081 A1 | 4/2011 | Kiani et al. |
| 2011/0105854 A1 | 5/2011 | Kiani et al. |
| 2011/0118561 A1 | 5/2011 | Tari et al. |
| 2011/0124996 A1 | 5/2011 | Reinke et al. |
| 2011/0125060 A1 | 5/2011 | Telfort et al. |
| 2011/0137297 A1 | 6/2011 | Kiani et al. |
| 2011/0172498 A1 | 7/2011 | Olsen et al. |
| 2011/0202084 A1 | 8/2011 | Hoem et al. |
| 2011/0208015 A1 | 8/2011 | Welch et al. |
| 2011/0230733 A1 | 9/2011 | Al-Ali |
| 2011/0257552 A1 | 10/2011 | Banet et al. |
| 2011/0295301 A1 | 12/2011 | Hoem et al. |
| 2011/0295302 A1 | 12/2011 | Mohl |
| 2012/0003933 A1 | 1/2012 | Baker et al. |
| 2012/0005624 A1 | 1/2012 | Vesely |
| 2012/0054691 A1 | 3/2012 | Nurmi |
| 2012/0109676 A1 | 5/2012 | Landau |
| 2012/0113140 A1 | 5/2012 | Hilliges et al. |
| 2012/0123231 A1 | 5/2012 | O'Reilly |
| 2012/0124506 A1 | 5/2012 | Stuebe et al. |
| 2012/0157806 A1 | 6/2012 | Steiger et al. |
| 2012/0165629 A1 | 6/2012 | Merritt et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0249741 A1 | 10/2012 | Maciocci et al. |
| 2012/0283524 A1 | 11/2012 | Kiani et al. |
| 2012/0319816 A1 | 12/2012 | Al-Ali |
| 2013/0009993 A1 | 1/2013 | Horseman |
| 2013/0017791 A1 | 1/2013 | Wang et al. |
| 2013/0023214 A1 | 1/2013 | Wang et al. |
| 2013/0023215 A1 | 1/2013 | Wang |
| 2013/0023775 A1 | 1/2013 | Lamego et al. |
| 2013/0041591 A1 | 2/2013 | Lamego |
| 2013/0050258 A1 | 2/2013 | Liu et al. |
| 2013/0050432 A1 | 2/2013 | Perez et al. |
| 2013/0060147 A1 | 3/2013 | Welch et al. |
| 2013/0078977 A1 | 3/2013 | Anderson et al. |
| 2013/0096405 A1 | 4/2013 | Garfio |
| 2013/0096936 A1 | 4/2013 | Sampath et al. |
| 2013/0147838 A1 | 6/2013 | Small et al. |
| 2013/0149684 A1 | 6/2013 | Ezzell et al. |
| 2013/0162632 A1 | 6/2013 | Varga et al. |
| 2013/0234934 A1 | 9/2013 | Champion et al. |
| 2013/0243021 A1 | 9/2013 | Siskavich |
| 2013/0253334 A1 | 9/2013 | Al-Ali et al. |
| 2013/0267792 A1 | 10/2013 | Petersen et al. |
| 2013/0293530 A1 | 11/2013 | Perez et al. |
| 2013/0296672 A1 | 11/2013 | O'Neil et al. |
| 2013/0296713 A1 | 11/2013 | Al-Ali et al. |
| 2013/0316652 A1 | 11/2013 | Wang et al. |
| 2013/0324808 A1 | 12/2013 | Al-Ali et al. |
| 2013/0331660 A1 | 12/2013 | Al-Ali et al. |
| 2013/0337842 A1 | 12/2013 | Wang et al. |
| 2013/0345921 A1 | 12/2013 | Al-Ali et al. |
| 2014/0012100 A1 | 1/2014 | Al-Ali et al. |
| 2014/0012509 A1 | 1/2014 | Barber |
| 2014/0035925 A1 | 2/2014 | Muranjan et al. |
| 2014/0051953 A1 | 2/2014 | Lamego et al. |
| 2014/0065972 A1 | 3/2014 | Wang |
| 2014/0081175 A1 | 3/2014 | Telfort |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0129493 A1 | 5/2014 | Leopold |
| 2014/0135588 A1 | 5/2014 | Al-Ali et al. |
| 2014/0163344 A1 | 6/2014 | Al-Ali |
| 2014/0163376 A1 | 6/2014 | Caluser |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0207489 A1 | 7/2014 | Wartena et al. |
| 2014/0213864 A1 | 7/2014 | Abdul-Hafiz et al. |
| 2014/0222462 A1 | 8/2014 | Shakil et al. |
| 2014/0225918 A1 | 8/2014 | Mittal et al. |
| 2014/0232747 A1 | 8/2014 | Sugimoto et al. |
| 2014/0235166 A1* | 8/2014 | Molettiere ............... H04B 7/26 455/41.2 |
| 2014/0249431 A1 | 9/2014 | Banet et al. |
| 2014/0266790 A1 | 9/2014 | Al-Ali et al. |
| 2014/0266983 A1 | 9/2014 | Christensen |
| 2014/0267419 A1 | 9/2014 | Ballard et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0276115 A1 | 9/2014 | Dalvi et al. |
| 2014/0285521 A1 | 9/2014 | Kimura |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323818 A1 | 10/2014 | Axelgaard et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0342766 A1 | 11/2014 | Wang |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0032029 A1 | 1/2015 | Al-Ali et al. |
| 2015/0038859 A1 | 2/2015 | Dalvi et al. |
| 2015/0067516 A1 | 3/2015 | Park et al. |
| 2015/0067580 A1 | 3/2015 | Um et al. |

(56) References Cited

U.S. PATENT DOCUMENTS

| | | |
|---|---|---|
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0088546 A1 | 3/2015 | Balram et al. |
| 2015/0091943 A1 | 4/2015 | Lee et al. |
| 2015/0094546 A1 | 4/2015 | Al-Ali |
| 2015/0097701 A1 | 4/2015 | Al-Ali et al. |
| 2015/0099458 A1* | 4/2015 | Weisner ............. H04W 84/22 455/15 |
| 2015/0099950 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0119733 A1 | 4/2015 | Grubis |
| 2015/0125832 A1 | 5/2015 | Tran |
| 2015/0150518 A1 | 6/2015 | Cremades Peris et al. |
| 2015/0153571 A1 | 6/2015 | Ballard et al. |
| 2015/0157326 A1 | 6/2015 | Schiemanck et al. |
| 2015/0165312 A1 | 6/2015 | Kiani |
| 2015/0186602 A1 | 7/2015 | Pipke et al. |
| 2015/0196249 A1 | 7/2015 | Brown et al. |
| 2015/0205931 A1 | 7/2015 | Wang et al. |
| 2015/0212576 A1 | 7/2015 | Ambrus et al. |
| 2015/0215925 A1 | 7/2015 | Wang et al. |
| 2015/0216459 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0261291 A1 | 9/2015 | Mikhailov et al. |
| 2015/0272514 A1 | 10/2015 | Kiani et al. |
| 2015/0277699 A1 | 10/2015 | Algreatly |
| 2015/0286515 A1 | 10/2015 | Monk |
| 2015/0301597 A1 | 10/2015 | Rogers et al. |
| 2015/0351697 A1 | 12/2015 | Weber et al. |
| 2015/0356263 A1 | 12/2015 | Chatterjee et al. |
| 2015/0359429 A1 | 12/2015 | Al-Ali et al. |
| 2015/0366507 A1 | 12/2015 | Blank |
| 2016/0019352 A1 | 1/2016 | Cohen et al. |
| 2016/0027216 A1 | 1/2016 | da Veiga et al. |
| 2016/0029906 A1 | 2/2016 | Tompkins et al. |
| 2016/0029932 A1 | 2/2016 | Al-Ali |
| 2016/0058347 A1 | 3/2016 | Reichgott et al. |
| 2016/0066824 A1 | 3/2016 | Al-Ali et al. |
| 2016/0066868 A1 | 3/2016 | Mensinger et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0116979 A1 | 4/2016 | Border |
| 2016/0124501 A1 | 5/2016 | Lam et al. |
| 2016/0135516 A1 | 5/2016 | Cobbett et al. |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0180044 A1 | 6/2016 | Delisle et al. |
| 2016/0183836 A1 | 6/2016 | Muuranto et al. |
| 2016/0189082 A1 | 6/2016 | Garrish et al. |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0225192 A1 | 8/2016 | Jones et al. |
| 2016/0228043 A1 | 8/2016 | O'Neil et al. |
| 2016/0228640 A1 | 8/2016 | Pindado et al. |
| 2016/0233632 A1 | 8/2016 | Scruggs et al. |
| 2016/0234944 A1 | 8/2016 | Schmidt et al. |
| 2016/0235323 A1 | 8/2016 | Tadi et al. |
| 2016/0239252 A1 | 8/2016 | Nakagawa et al. |
| 2016/0270735 A1 | 9/2016 | Diab et al. |
| 2016/0274358 A1 | 9/2016 | Yajima et al. |
| 2016/0278644 A1 | 9/2016 | He |
| 2016/0283665 A1 | 9/2016 | Sampath et al. |
| 2016/0287090 A1 | 10/2016 | Al-Ali et al. |
| 2016/0287207 A1 | 10/2016 | Xue |
| 2016/0287470 A1 | 10/2016 | Lewis et al. |
| 2016/0287786 A1 | 10/2016 | Kiani |
| 2016/0296169 A1 | 10/2016 | McHale et al. |
| 2016/0310005 A1 | 10/2016 | Pekander et al. |
| 2016/0310047 A1 | 10/2016 | Pekander et al. |
| 2016/0310052 A1 | 10/2016 | Al-Ali et al. |
| 2016/0314260 A1 | 10/2016 | Kiani |
| 2016/0314624 A1 | 10/2016 | Li et al. |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0330573 A1 | 11/2016 | Masoud et al. |
| 2016/0331332 A1 | 11/2016 | Al-Ali |
| 2016/0335403 A1 | 11/2016 | Mabotuwana et al. |
| 2016/0335800 A1 | 11/2016 | DeStories |
| 2016/0351776 A1 | 12/2016 | Schneider et al. |
| 2016/0357491 A1 | 12/2016 | Oya |
| 2016/0367173 A1 | 12/2016 | Dalvi et al. |
| 2016/0371886 A1 | 12/2016 | Thompson et al. |
| 2017/0000394 A1 | 1/2017 | Al-Ali et al. |
| 2017/0000422 A1 | 1/2017 | Moturu et al. |
| 2017/0004106 A1 | 1/2017 | Joshua et al. |
| 2017/0007134 A1 | 1/2017 | Al-Ali et al. |
| 2017/0007198 A1 | 1/2017 | Al-Ali et al. |
| 2017/0010850 A1 | 1/2017 | Kobayashi et al. |
| 2017/0014083 A1 | 1/2017 | Diab et al. |
| 2017/0014084 A1 | 1/2017 | Al-Ali et al. |
| 2017/0024748 A1 | 1/2017 | Haider |
| 2017/0027456 A1 | 2/2017 | Kinast et al. |
| 2017/0042488 A1 | 2/2017 | Muhsin |
| 2017/0046872 A1 | 2/2017 | Geselowitz et al. |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0065379 A1 | 3/2017 | Cowburn et al. |
| 2017/0079594 A1 | 3/2017 | Telfort et al. |
| 2017/0083104 A1 | 3/2017 | Namba et al. |
| 2017/0086723 A1 | 3/2017 | Al-Ali et al. |
| 2017/0092002 A1 | 3/2017 | Mullins et al. |
| 2017/0111824 A1 | 4/2017 | Wang et al. |
| 2017/0140101 A1 | 5/2017 | Anderson et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0161455 A1 | 6/2017 | Grady et al. |
| 2017/0172415 A1 | 6/2017 | Wik et al. |
| 2017/0172515 A1 | 6/2017 | Banet et al. |
| 2017/0172696 A1 | 6/2017 | Saget et al. |
| 2017/0173632 A1 | 6/2017 | Al-Ali |
| 2017/0177816 A1 | 6/2017 | Ribble et al. |
| 2017/0178356 A1 | 6/2017 | Bhuruth et al. |
| 2017/0181645 A1 | 6/2017 | Mahalingam et al. |
| 2017/0186157 A1 | 6/2017 | Boettger et al. |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0200296 A1 | 7/2017 | Jones et al. |
| 2017/0202490 A1 | 7/2017 | Al-Ali et al. |
| 2017/0206676 A1 | 7/2017 | Nakazato et al. |
| 2017/0215261 A1 | 7/2017 | Potucek et al. |
| 2017/0215388 A1 | 8/2017 | Delecroix |
| 2017/0216524 A1 | 8/2017 | Haider et al. |
| 2017/0224262 A1 | 8/2017 | Al-Ali |
| 2017/0228516 A1 | 8/2017 | Sampath et al. |
| 2017/0242480 A1 | 8/2017 | Dees et al. |
| 2017/0244796 A1 | 8/2017 | Liu et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0255838 A1 | 9/2017 | Norieda et al. |
| 2017/0258403 A1 | 9/2017 | Abdul-Hafiz et al. |
| 2017/0262064 A1 | 9/2017 | Ofir et al. |
| 2017/0300824 A1 | 10/2017 | Peng et al. |
| 2017/0311891 A1 | 11/2017 | Kiani et al. |

(56) References Cited

U.S. PATENT DOCUMENTS

| | | |
|---|---|---|
| 2017/0315774 A1 | 11/2017 | Meerbeek et al. |
| 2017/0316561 A1 | 11/2017 | Helm et al. |
| 2017/0323479 A1 | 11/2017 | Mokuya |
| 2017/0325684 A1 | 11/2017 | Vartiovaara |
| 2017/0325728 A1 | 11/2017 | Al-Ali et al. |
| 2017/0329480 A1 | 11/2017 | Ishikawa et al. |
| 2017/0332976 A1 | 11/2017 | Al-Ali et al. |
| 2017/0340293 A1 | 11/2017 | Al-Ali et al. |
| 2017/0351909 A1 | 12/2017 | Kaehler |
| 2017/0357397 A1 | 12/2017 | Masumoto |
| 2017/0359467 A1 | 12/2017 | Norris et al. |
| 2017/0360310 A1 | 12/2017 | Kiani et al. |
| 2017/0367632 A1 | 12/2017 | Al-Ali et al. |
| 2017/0367771 A1 | 12/2017 | Tako et al. |
| 2018/0000415 A1 | 1/2018 | Gupta et al. |
| 2018/0005424 A1 | 1/2018 | Niinuma et al. |
| 2018/0008146 A1 | 1/2018 | Al-Ali et al. |
| 2018/0014752 A1 | 1/2018 | Al-Ali et al. |
| 2018/0024630 A1 | 1/2018 | Goossens |
| 2018/0025116 A1 | 1/2018 | Carrington et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0059812 A1 | 3/2018 | Inomata et al. |
| 2018/0064381 A1 | 3/2018 | Shakespeare et al. |
| 2018/0069776 A1 | 3/2018 | Lamego et al. |
| 2018/0074332 A1 | 3/2018 | Li et al. |
| 2018/0075658 A1 | 3/2018 | Lanier et al. |
| 2018/0080774 A1 | 3/2018 | Sink et al. |
| 2018/0082480 A1 | 3/2018 | White et al. |
| 2018/0084224 A1 | 3/2018 | McNelley et al. |
| 2018/0088682 A1 | 3/2018 | Tsang |
| 2018/0103874 A1 | 4/2018 | Lee et al. |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0139203 A1 | 5/2018 | Dolan et al. |
| 2018/0140362 A1 | 5/2018 | Cali et al. |
| 2018/0144497 A1 | 5/2018 | Hirota et al. |
| 2018/0147024 A1 | 5/2018 | Kall et al. |
| 2018/0153445 A1 | 6/2018 | Noda et al. |
| 2018/0157344 A1 | 6/2018 | Toff |
| 2018/0160881 A1 | 6/2018 | Okabe et al. |
| 2018/0181810 A1 | 6/2018 | Jhawar et al. |
| 2018/0188807 A1 | 7/2018 | Cimenser et al. |
| 2018/0188831 A1 | 7/2018 | Lyons |
| 2018/0189556 A1 | 7/2018 | Shamir et al. |
| 2018/0199871 A1 | 7/2018 | Pauley et al. |
| 2018/0200018 A1 | 7/2018 | Silva et al. |
| 2018/0213583 A1 | 7/2018 | Al-Ali |
| 2018/0217734 A1 | 8/2018 | Koenig et al. |
| 2018/0225993 A1 | 8/2018 | Buras et al. |
| 2018/0235478 A1 | 8/2018 | Khachaturian et al. |
| 2018/0242920 A1 | 8/2018 | Hresko et al. |
| 2018/0242926 A1 | 8/2018 | Muhsin et al. |
| 2018/0247024 A1 | 8/2018 | Divine et al. |
| 2018/0247353 A1 | 8/2018 | Al-Ali et al. |
| 2018/0247712 A1 | 8/2018 | Muhsin et al. |
| 2018/0250510 A1 | 9/2018 | Ziv |
| 2018/0251230 A1 | 9/2018 | Chavez et al. |
| 2018/0256087 A1 | 9/2018 | Al-Ali et al. |
| 2018/0261329 A1 | 9/2018 | Blander et al. |
| 2018/0264945 A1 | 9/2018 | Torii |
| 2018/0275837 A1 | 9/2018 | Getz et al. |
| 2018/0279947 A1 | 10/2018 | Ummat |
| 2018/0286132 A1 | 10/2018 | Cvetko et al. |
| 2018/0296161 A1 | 10/2018 | Shreim et al. |
| 2018/0300031 A1 | 10/2018 | Parkinson |
| 2018/0300919 A1 | 10/2018 | Muhsin et al. |
| 2018/0303558 A1 | 10/2018 | Thomas |
| 2018/0310822 A1 | 11/2018 | Indorf et al. |
| 2018/0310823 A1 | 11/2018 | Al-Ali et al. |
| 2018/0315490 A1 | 11/2018 | Jaruzel, II |
| 2018/0333643 A1 | 11/2018 | Luisi et al. |
| 2018/0342079 A1 | 11/2018 | Yaguchi et al. |
| 2018/0344308 A1 | 12/2018 | Nawana et al. |
| 2018/0365897 A1 | 12/2018 | Pahud et al. |
| 2019/0005724 A1 | 1/2019 | Pahud et al. |
| 2019/0015023 A1 | 1/2019 | Monfre |
| 2019/0033989 A1 | 1/2019 | Wang et al. |
| 2019/0034076 A1 | 1/2019 | Vinayak et al. |
| 2019/0043259 A1 | 2/2019 | Wang et al. |
| 2019/0053855 A1 | 2/2019 | Siemionow et al. |
| 2019/0064520 A1 | 2/2019 | Christensen |
| 2019/0066538 A1 | 2/2019 | Chao et al. |
| 2019/0079156 A1 | 3/2019 | Krellmann |
| 2019/0080515 A1 | 3/2019 | Geri et al. |
| 2019/0117070 A1 | 4/2019 | Muhsin et al. |
| 2019/0121522 A1 | 4/2019 | Davis et al. |
| 2019/0138183 A1 | 5/2019 | Rosas et al. |
| 2019/0141291 A1 | 5/2019 | McNelley et al. |
| 2019/0146578 A1 | 5/2019 | Ikuta et al. |
| 2019/0155382 A1 | 5/2019 | Ikuta et al. |
| 2019/0183577 A1 | 6/2019 | Fahim et al. |
| 2019/0200941 A1 | 7/2019 | Chandran et al. |
| 2019/0206104 A1 | 7/2019 | Rahman |
| 2019/0231436 A1 | 8/2019 | Panse et al. |
| 2019/0239787 A1 | 8/2019 | Pauley et al. |
| 2019/0240508 A1 | 8/2019 | Friman et al. |
| 2019/0243138 A1 | 8/2019 | Peltola et al. |
| 2019/0250873 A1 | 8/2019 | Blume et al. |
| 2019/0254754 A1 | 8/2019 | Johnson et al. |
| 2019/0320906 A1 | 10/2019 | Olsen |
| 2019/0333276 A1 | 10/2019 | Brown et al. |
| 2019/0340434 A1 | 11/2019 | Chiu et al. |
| 2019/0340827 A1 | 11/2019 | Abercromie et al. |
| 2019/0348169 A1 | 11/2019 | Gibby et al. |
| 2019/0355182 A1 | 11/2019 | Nozaki et al. |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2019/0380792 A1 | 12/2019 | Poltaretskyi et al. |
| 2019/0387102 A1 | 12/2019 | Norris et al. |
| 2020/0004328 A1 | 1/2020 | Blume et al. |
| 2020/0005542 A1 | 1/2020 | Kocharlakota et al. |
| 2020/0021930 A1 | 1/2020 | Iswanto et al. |
| 2020/0046473 A1 | 2/2020 | Kim et al. |
| 2020/0060869 A1 | 2/2020 | Telfort et al. |
| 2020/0074740 A1 | 3/2020 | Singh |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0125322 A1 | 4/2020 | Wilde |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0210679 A1 | 7/2020 | Kusens et al. |

FOREIGN PATENT DOCUMENTS

| | | |
|---|---|---|
| WO | WO 2018/156809 | 8/2018 |
| WO | WO 2018/208616 | 11/2018 |

OTHER PUBLICATIONS

International Search Report and Written Opinion from corresponding International Patent Application No. PCT/US2018/019283, dated Jul. 27, 2018, in 14 pages.

International Search Report and Written Opinion from corresponding International Patent Application No. PCT/US2018/019288, dated May 30, 2018, in 10 pages.

\* cited by examiner

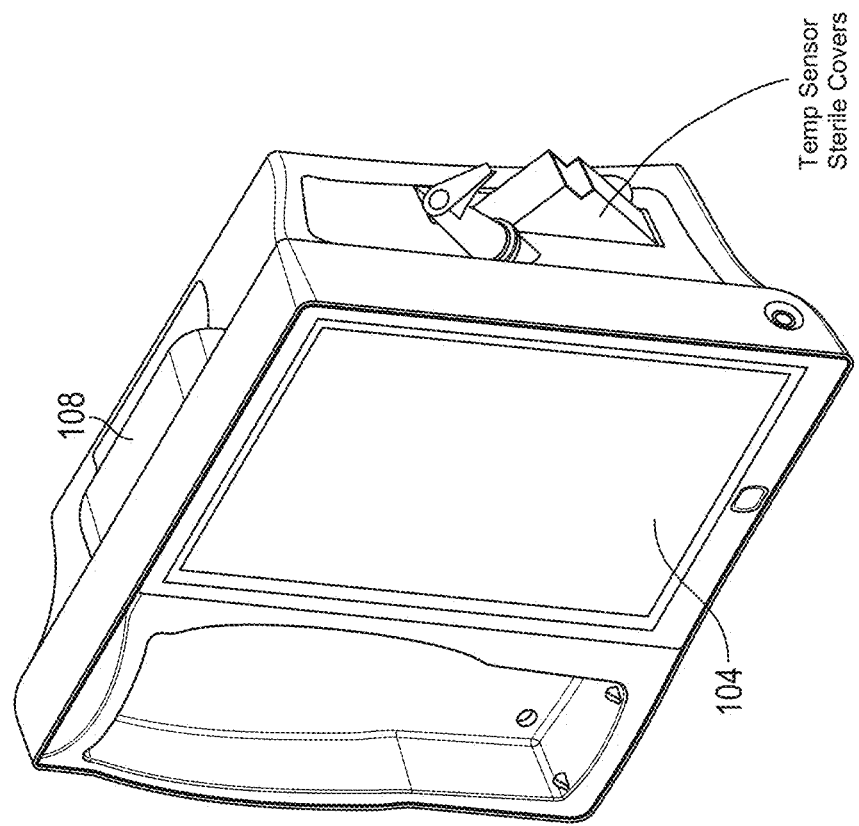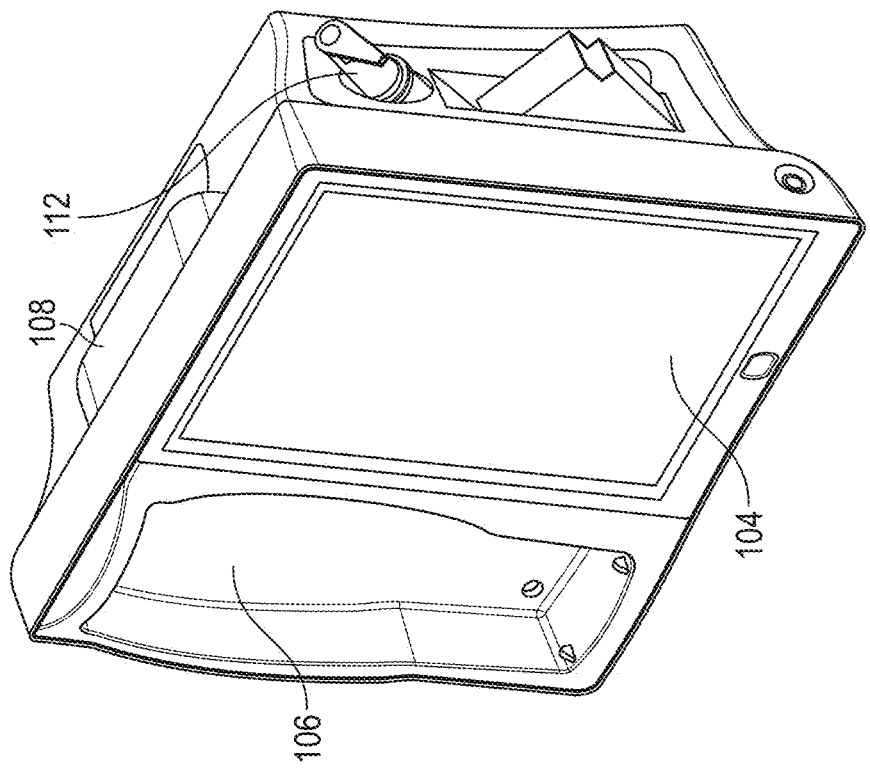
FIG. 1C

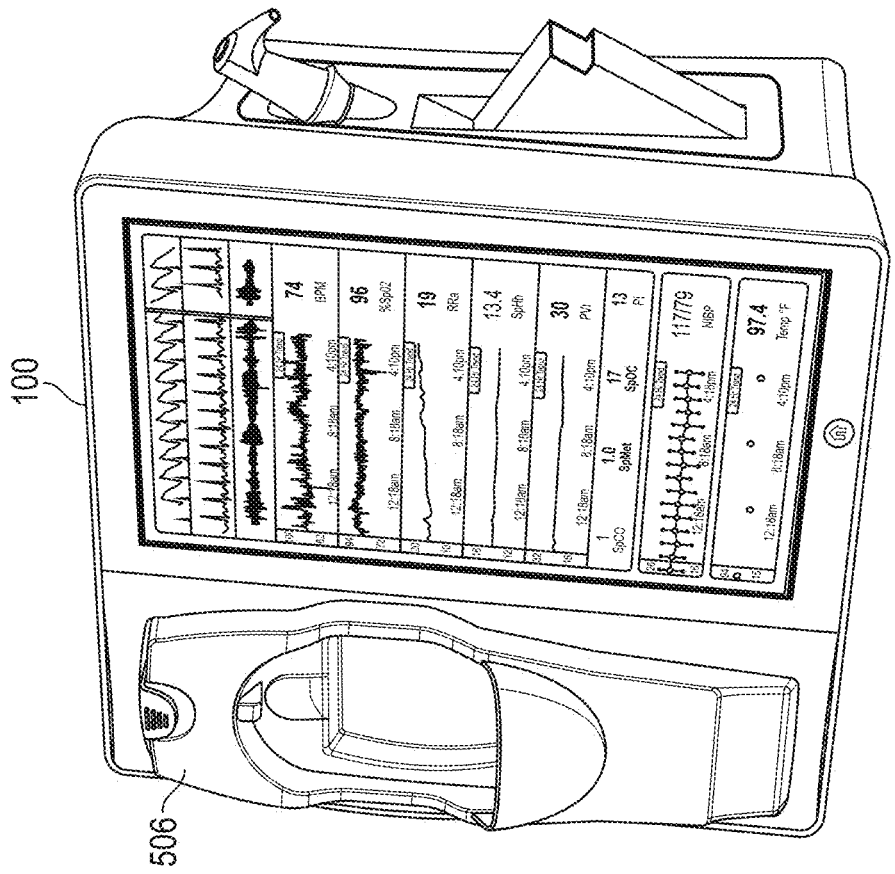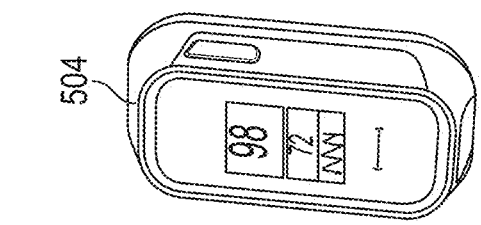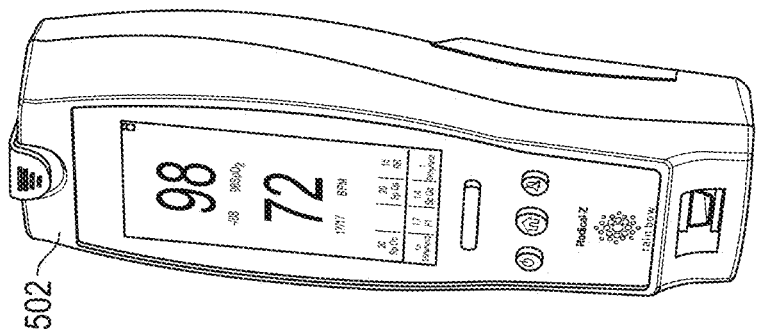
FIG. 5

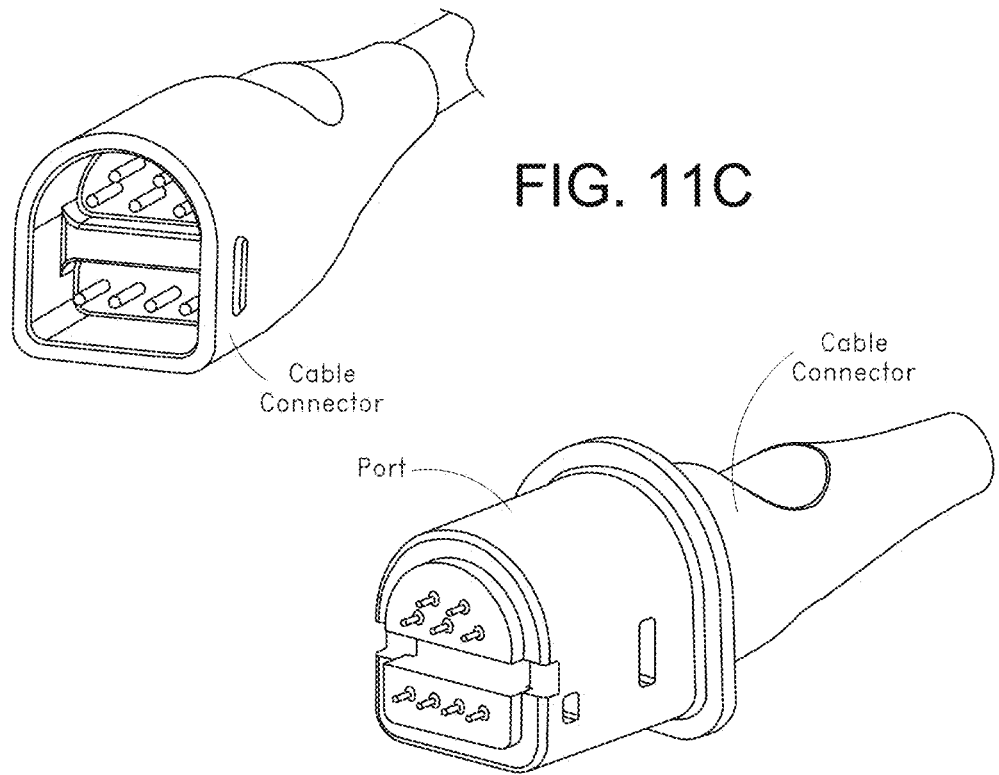
FIG. 11C
FIG. 11D
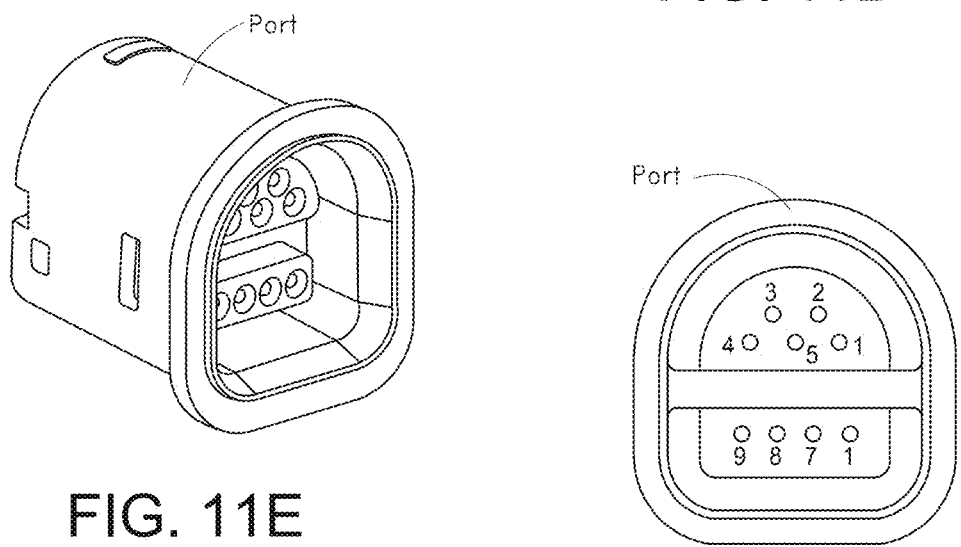
FIG. 11E
FIG. 11F

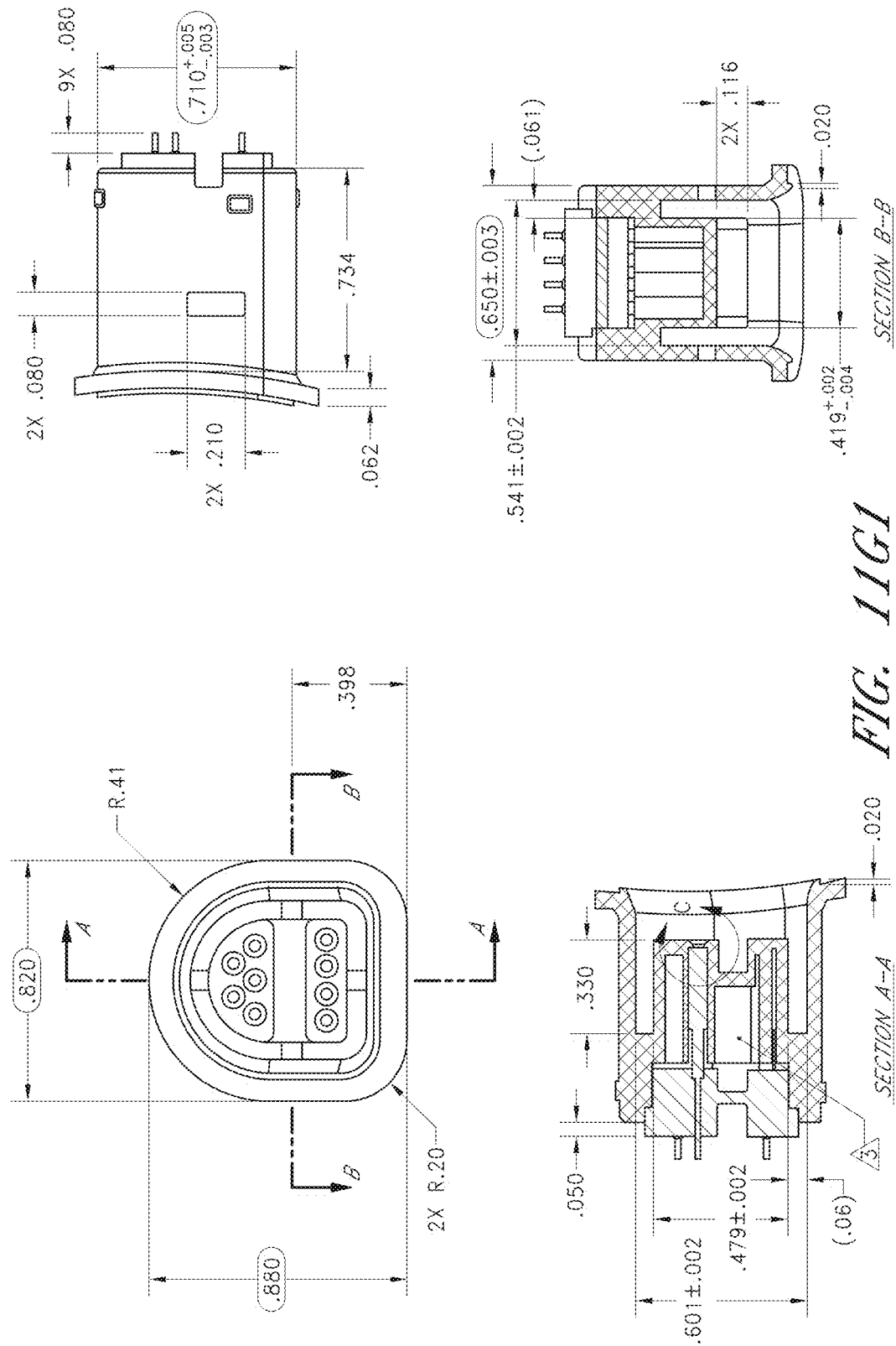
FIG. 11G1

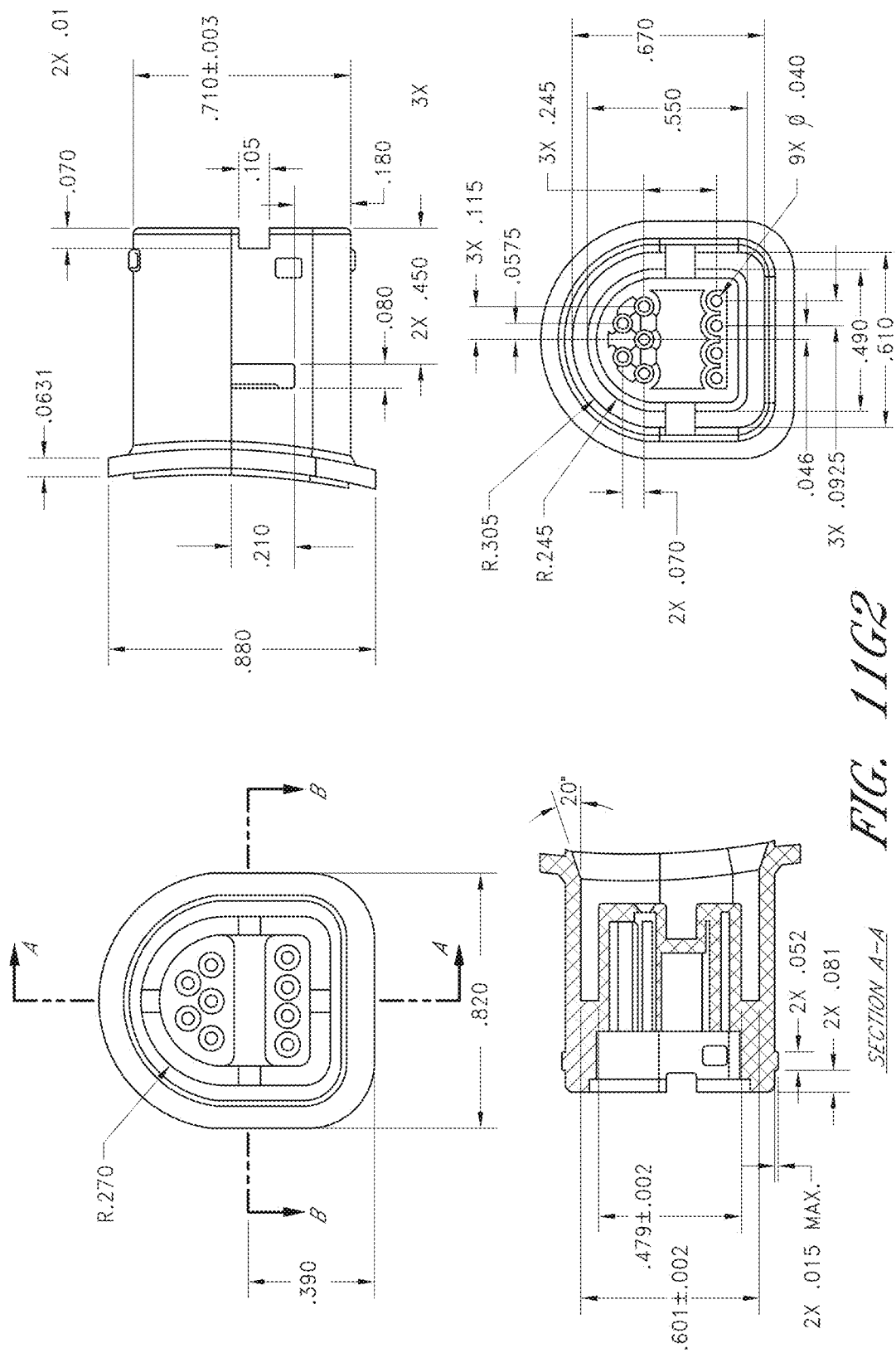
FIG. 11G2

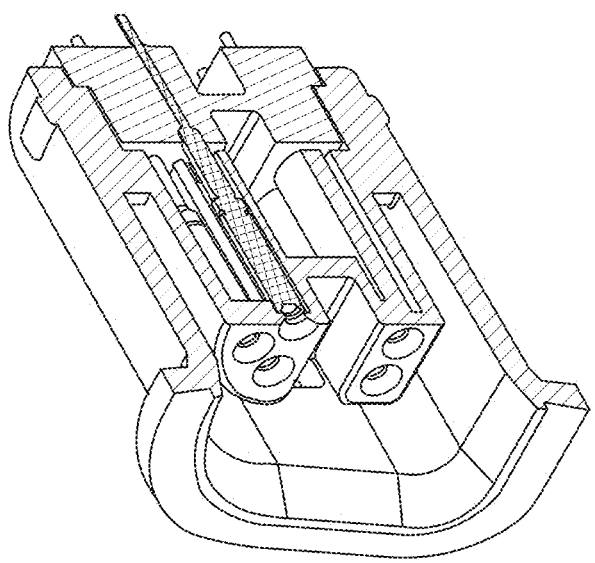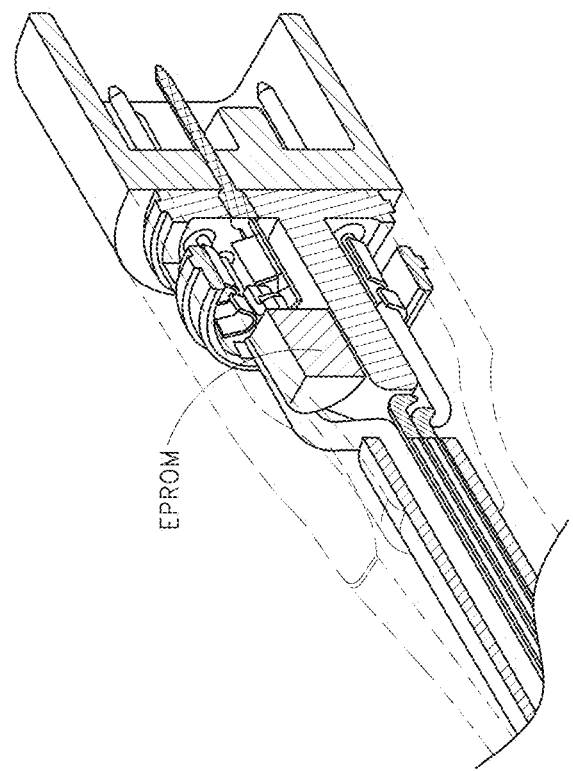
FIG. 11H

```
<SB>
MSH~^\&^VAFC PIMS^50^NPTF-508^200^20091120104609-0600^^ADT~A01^58103^P^^^^^USA<CR>
EVN^A01^20091120104517-0600^^^05<CR>
PID^1^500000003V302090^11~7~M10^^^LONG~BRIAN^^^^1980401^M^^^~0005~''~CDC^^^~"""~P~~~~"
"~~~"""~~VACE~""~""~""~&~''|~"""~"""~""~""~""~""~""~""~""~VACAA~"""~"""~""~""~VACAC~""~""
~^^^^~&~''|~"""~"""~""~""~""~""~""~""~""~VACAO~""~""~""~""~&~''|~"""~"""~""~""~VACAC~""~""
~^^^~0189~""~~CDC^ <CR>
PD1^^^SOFTWARE SERVICE~~050^"""<CR>
ZPD^1~"""~"""~""~""~""~""~""~""~""~""~""~""~""~""~""~""~""~""~""~0^""~""~""<CR>
PV1^1^1^PSYCH-304~1^^^^^^~"""~"""~"""~"""~25~WESSELHOFT~MEGAN^^^94^^^^^NON-VETERAN
(OTHER)^^^25^^^^^^^^^^^^^^^^^^^^^^^^^^^^^^~20091120104517-0600^^^^^^18<CR>
ROL^18-
25*1^C0^""~""~""~""~"""~""~T~"""~VA01^25&50~WESSELHOFT~MEGAN~"""~"""~""~""~"""~"""~"""~VA200|~"""~"""~""~""~"""~"""~"""~SSA<CR>
ROL^18-
25*2^C0^""~""~""~""~"""~""~A~"""~VA01^25&50~WESSELHOFT~MEGAN~"""~"""~""~""~"""~"""~"""~VA200|~"""~"""~""~""~"""~"""~"""~SSA<CR>
DG1^1^^^IBS<CR>
ZSP^1^^0^"""^N^"""~"""~"""~"""~"""~"""~"""~"""<CR>
ZEL^18--~"""~"""~"""~""~""~""~""~""~""~""~""~""~""~""~""~""~""~""~""~0^NON-VETERAN (OTHER)^""~""~""~""~"""~"""~"""~""~""~""~""~""~""~""~""~""~""~""~""<CR>
ZCT^1^1^"""^^^^^^^^^^^^^^^^<CR>
ZEM^1^^^^^^^^^^^^^^;;<CR>
ZIR^<CR>
ZEN^1<CR>
<EB><CR>
```

FIG. 41A

```xml
<?xml version="1.0" encoding="UTF-8" standalone="no" ?>
<ev7>
   <MSH>
      <MSH.1>^</MSH.1>
      <MSH.2>~ |\&</MSH.2>
      <MSH.3>VAFC PIMS</MSH.3>
      <MSH.4>50</MSH.4>
      <MSH.5>NPTF-508</MSH.5>
      <MSH.6>200</MSH.6>
      <MSH.7>20091120104609-0600</MSH.7>
      <MSH.9>
         <component n="1">ADT</component>
         <component n="2">ADT</component>
      <MSH.9>
      <MSH.10>58103</MSH.10>
      <MSH.11>P</MSH.11>
      <MSH.17>USA</MSH.17>
   </MSH>
   <EVN>
      <EVN.1>A01</EVN.1>
      <EVN.2>20091120104517-0600</EVN.2>
      <EVN.4>05</EVN.4>
   </EVN>
   ...
<ev7>
```

FIG. 41B

```xml
<?xml version="1.0" encoding="UTF-8"?>
<ADT_A01>
  <MSH>
    <MSH.1>^</MSH.1>
    <MSH.2>~|\&</MSH.2>
    <MSH.3>
       <HD.1>VAFC PIMS</HD.1>
    </MSH.3>
    <MSH.4>
       <HD.1>50</HD.1>
    </MSH.4>
    <MSH.5>
       <HD.1>NPTF-508</HD.1>
    </MSH.5>
    <MSH.6>
       <HD.1>200</HD.1>
    </MSH.6>
    <MSH.7>
       <TS.1>20091120104609-0600</TS.1>
    </MSH.7>
    <MSH.9>
       <MSG.1>ADT</MSG.1>
       <MSG.2>A01</MSG.2>
    </MSH.9>
    <MSH.10>58103</MSH.10>
    <MSH.11>
       <PT.1>P</PT.1>
    </MSH.11>
    <MSH.17>USA</MSH.17>
  </MSH>
```

FIG. 41C

```
<output-message>
  <ACK>
    <MSH>
      <MSH.1>^</MSH.1>
      <MSH.2>~|\&</MSH.2>
      <MSH.3>
        <HD.1>NPTF-508</HD.1>
      </MSH.3>
      <MSH.4>
        <HD.1>200</HD.1>
      </MSH.4>
      <MSH.5>
        <HD.1>VAFC PIMS</HD.1>
      </MSH.5>
      <MSH.6>
        <HD.1>50</HD.1>
      </MSH.6>
      <MSH.7>
        <TS.1>20091120104609-0600</TS.1>
      </MSH.7>
      <MSH.9>
        <MSG.1>ACK</MSG.1>
        <MSG.3>ACK</MSG.2>
      </MSH.9>
      <MSH.10>856bc9bd-97c8-4aa5-b411-3cd6fe2edd86</MSH.10>
    <MSH>
    <MSA>
      <MSA.1>AA</MSA.1>
      <MSA.2>58103</MSA.2>
    </MSA>
  </ACK>
</output-message>
```

FIG. 41D

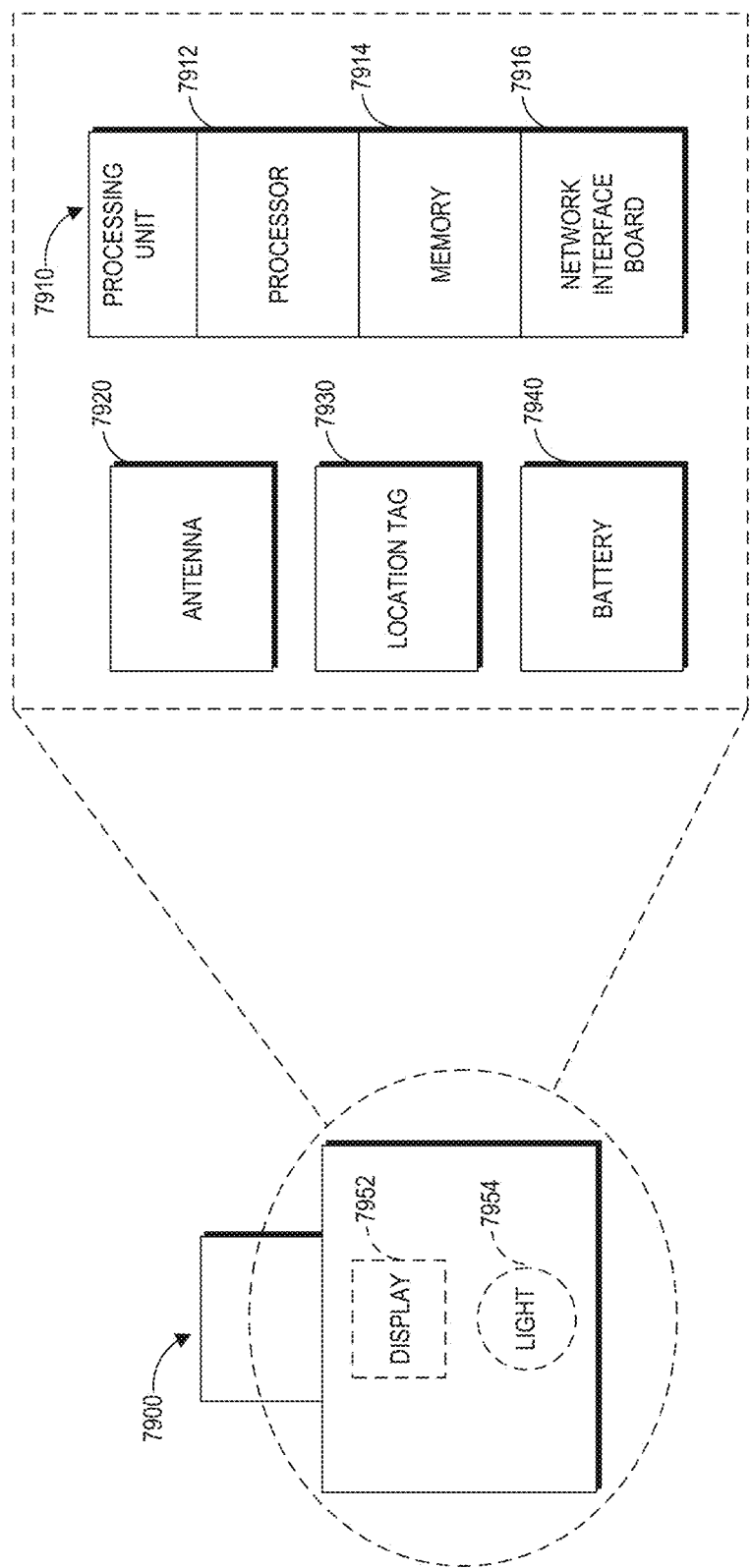

SYSTEM FOR DISPLAYING AND CONTROLLING MEDICAL MONITORING DATA

RELATED APPLICATIONS

This application is related to the following U.S. patent applications, the disclosures of which are incorporated in their entirety by reference herein:

| App. No. | Filing Date | Title |
|---|---|---|
| 62/463,452 | Feb. 24, 2017 | PATIENT MONITOR COMMUNICATION PLATFORM |
| 62/463,297 | Feb. 24, 2017 | MODULAR MULTI-PARAMETER PATIENT MONITORING DEVICE |
| 62/463,517 | Feb. 24, 2017 | SYSTEM FOR DISPLAYING AND CONTROLLING MEDICAL MONITORING DATA |
| 62/503,109 | May 8, 2017 | SYSTEM FOR DISPLAYING AND CONTROLLING MEDICAL MONITORING DATA |
| 62/535,757 | Jul. 21, 2017 | SYSTEM FOR DISPLAYING AND CONTROLLING MEDICAL MONITORING DATA |
| 62/463,614 | Feb. 25, 2017 | PATIENT MONITOR COMMUNICATION PLATFORM |

Many of the embodiments described herein are compatible with embodiments described in the above related applications. Moreover, some or all of the features described herein can be used or otherwise combined with many of the features described in the applications listed above.

FIELD OF THE DISCLOSURE

The present disclosure relates generally to patient monitoring devices and specifically to a patient monitor and medical data communication hub.

BACKGROUND OF THE DISCLOSURE

Today's patient monitoring environments are crowded with sophisticated and often electronic medical devices servicing a wide variety of monitoring and treatment endeavors for a given patient. Generally, many if not all of the devices are from differing manufactures, and many may be portable devices. The devices may not communicate with one another and each may include its own control, display, alarms, configurations and the like. Complicating matters, caregivers often desire to associate all types of measurement and use data from these devices to a specific patient. Thus, patient information entry often occurs at each device. Sometimes, the disparity in devices leads to a need to simply print and store paper from each device in a patient's file for caregiver review.

The result of such device disparity is often a caregiver environment scattered with multiple displays and alarms leading to a potentially chaotic experience. Such chaos can be detrimental to the patient in many situations including surgical environments where caregiver distraction is unwanted, and including recovery or monitoring environments where patient distraction or disturbance may be unwanted.

Various manufacturers produce multi-monitor devices or devices that modularly expand to increase the variety of monitoring or treatment endeavors a particular system can accomplish. However, as medical device technology expands, such multi-monitor devices begin to be obsolete the moment they are installed.

Example Embodiments

This disclosure describes embodiments of a medical monitoring hub as the center of monitoring for a monitored patient. The hub can include configurable medical ports and serial ports for communicating with other medical devices in the patient's proximity. Moreover, the hub can communicate with a portable patient monitor. The monitor, when docked with the hub, may provide display graphics different from when undocked. The display graphics can include anatomical information. The hub can assemble the often vast amount of electronic medical data, associate it with the monitored patient, and in some embodiments, communicate the data to the patient's medical records.

Some aspects of the disclosure describe a first medical device having digital logic circuitry receives a physiological signal associated with a patient from a physiological sensor, obtains a first physiological parameter value based on the physiological signal, and outputs the first physiological parameter value for display. The first medical device can also receive a second physiological parameter value from a second medical device other than the first medical device, where the second physiological parameter value is formatted according to a protocol not used by the first medical device, such that the first medical device is not able to process the second physiological parameter value to produce a displayable output value. The first medical device can pass the physiological parameter data from the first medical device to a separate translation module, receive translated parameter data from the translation module at the first medical device, where the translated parameter data is able to be processed for display by the first medical device, and output a second value from the translated parameter data for display. The first medical device may be, for example, a monitoring hub, a portable physiological monitor, or a multi-patient monitoring system, and the second medical device may be an infusion pump, ventilator, or the like.

For purposes of summarizing the disclosure, certain aspects, advantages and novel features are discussed herein. It is to be understood that not necessarily all such aspects, advantages or features will be embodied in any particular embodiment of the invention and an artisan would recognize from the disclosure herein a myriad of combinations of such aspects, advantages or features.

BRIEF DESCRIPTION OF THE DRAWINGS

The following drawings and the associated descriptions are provided to illustrate embodiments of the present disclosure and do not limit the scope of the claims.

FIGS. 1A-1C illustrate perspective views of an exemplary medical monitoring hub according to an embodiment of the disclosure. For example, FIG. 1A illustrates the hub with an exemplary docked portable patient monitor, FIG. 1B illustrates the hub with a set of medical ports and a noninvasive blood pressure input, and FIG. 1C illustrates the hub with various exemplary temperature sensors attached thereto, all according to various embodiments of the disclosure.

FIG. 5 illustrates a perspective view of exemplary portable patient monitors undocked from the hub of FIG. 1, according to an embodiment of the disclosure. Moreover, FIG. 5 illustrates an exemplary alternative docking station.

FIGS. 9A-9B, 10, 11A-11F, 11G1-11G2, and 11H-11K illustrate simplified block diagrams of exemplary universal medical connectors having a size and shape smaller in cross section than tradition isolation requirements.

FIG. 10 illustrates a perspective view of a side of the hub of FIG. 1, showing exemplary instrument-side channel inputs for exemplary universal medical connectors, according to an embodiment of the disclosure.

FIGS. 11A-11F, 11G1-11G2, and 11H-11K illustrate various views of exemplary male and mating female universal medical connectors, according to embodiments of the disclosure.

FIG. 41A illustrates an example input message received by the translation module.

FIG. 41B illustrates an example message header segment of an input message that has been parsed into fields.

FIG. 41C illustrates an example encoded version of the parsed message header segment of FIG. 41B.

FIG. 41D illustrates an example output message of the translation module based on the input message of FIG. 41A.

FIG. 79 illustrates an example embodiment of a dongle used to pair the medical network interface with another device.

Figure 1A:
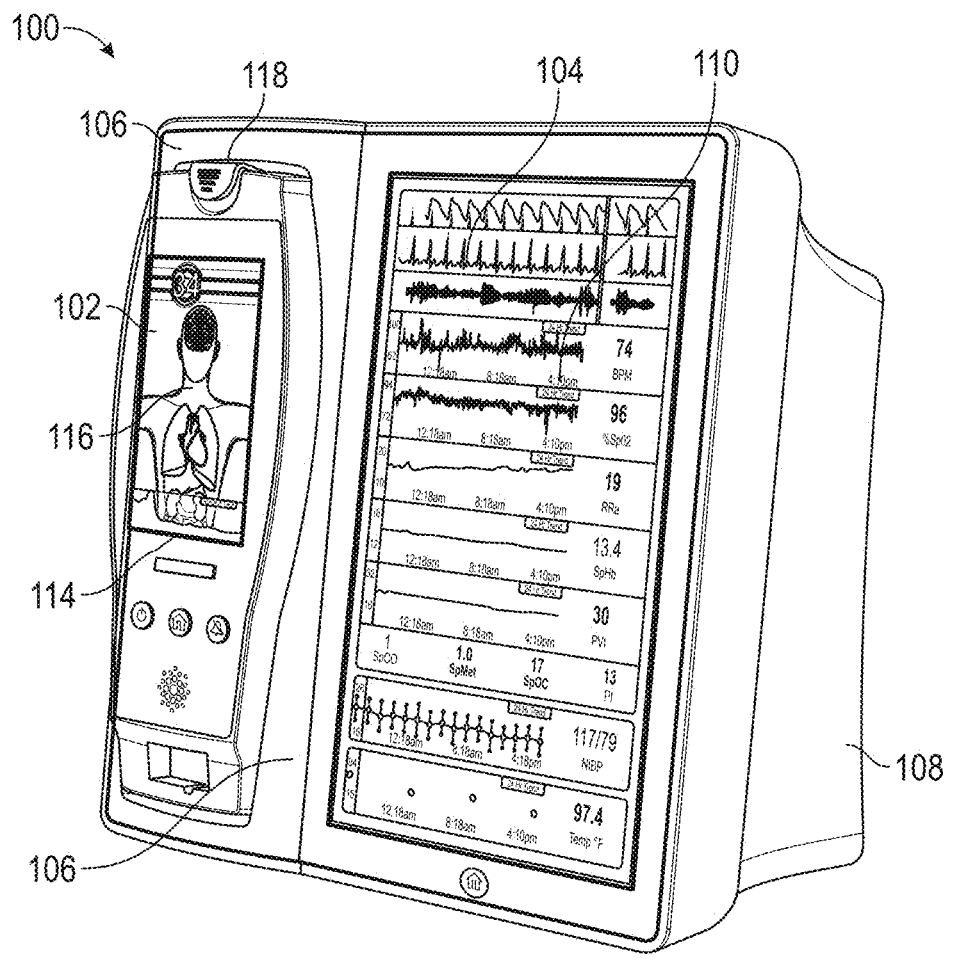

While the foregoing "Brief Description of the Drawings" references generally various embodiments of the disclosure, an artisan will recognize from the disclosure herein that such embodiments are not mutually exclusive. Rather, the artisan would recognize a myriad of combinations of some or all of such embodiments.

DETAILED DESCRIPTION

I. Introduction

Based on at least the foregoing, a solution is needed that coordinates the various medical devices treating or monitoring a patient. Embodiments of such a solution should provide patient identification seamlessly across the device space and embodiments of such a solution should expand for future technologies without necessarily requiring repeated software upgrades. In addition, embodiments of such a solution may include patient electrical isolation where desired.

Therefore, the present disclosure relates to a patient monitoring hub that is the center of patient monitoring and treatment activities for a given patient. Embodiments of the patient monitoring hub interface with legacy devices without necessitating legacy reprogramming, provide flexibility for interfacing with future devices without necessitating software upgrades, and offer optional patient electrical isolation. In an embodiment, the hub includes a large display dynamically providing information to a caregiver about a wide variety of measurement or otherwise determined parameters.

Additionally, in an embodiment, the hub includes a docking station for a portable patient monitor. The portable patient monitor may communicate with the hub through the docking station or through various wireless paradigms known to an artisan from the disclosure herein, including WiFi, Bluetooth, Zigbee, or the like.

In still other embodiments, the portable patient monitor modifies its screen when docked. The undocked display indicia is in part or in whole transferred to a large dynamic display of the hub and the docked display presents one or more anatomical graphics of monitored body parts. For example, the display may present a heart, lungs, a brain, kidneys, intestines, a stomach, other organs, digits, gastrointestinal systems or other body parts when it is docked. In an embodiment, the anatomical graphics may advantageously be animated. In an embodiment, the animation may generally follow the behavior of measured parameters, such as, for example, the lungs may inflate in approximate correlation to the measured respiration rate and/or the determined inspiration portion of a respiration cycle, and likewise deflate according to the expiration portion of the same. The heart may beat according to the pulse rate, may beat generally along understood actual heart contraction patterns, and the like. Moreover, in an embodiment, when the measured parameters indicate a need to alert a caregiver, a changing severity in color may be associated with one or more displayed graphics, such as the heart, lungs, brain, or the like. In still other embodiments, the body portions may include animations on where, when or how to attach measurement devices to measurement sites on the patient. For example, the monitor may provide animated directions for CCHD screening procedures or glucose strip reading protocols, the application of a forehead sensor, a finger or toe sensor, one or more electrodes, an acoustic sensor, and ear sensor, a cannula sensor or the like.

The present disclosure relates to a medical monitoring hub configured to be the center of monitoring activity for a given patient. In an embodiment, the hub comprises a large easily readable display, such as an about ten (10) inch display dominating the majority of real estate on a front face of the hub. The display could be much larger or much smaller depending upon design constraints. However, for portability and current design goals, the preferred display is roughly sized proportional to the vertical footprint of one of the dockable portable patient monitors. Other considerations are recognizable from the disclosure herein by those in the art.

The display provides measurement data for a wide variety of monitored parameters for the patient under observation in numerical or graphic form, and in various embodiments, is automatically configured based on the type of data and information being received at the hub. In an embodiment, the hub is movable, portable, and mountable so that it can be positioned to convenient areas within a caregiver environment. For example, the hub is collected within a singular housing.

In an embodiment, the hub may advantageously receive data from a portable patient monitor while docked or undocked from the hub. Typical portable patient monitors, such as oximeters or co-oximeters can provide measurement data for a large number of physiological parameters derived from signals output from optical and/or acoustic sensors, electrodes, or the like. The physiological parameters include, but not limited to oxygen saturation, carboxy hemoglobin, methemoglobin, total hemoglobin, glucose, pH, bilirubin, fractional saturation, pulse rate, respiration rate, components of a respiration cycle, indications of perfusion including perfusion index, signal quality and/or confidences, plethysmograph data, indications of wellness or wellness indexes or other combinations of measurement data, audio information responsive to respiration, ailment identification or diagnosis, blood pressure, patient and/or measurement site temperature, depth of sedation, organ or brain oxygenation, hydration, measurements responsive to metabolism, combinations of the same or the like, to name a few. In other embodiments, the hub may output data sufficient to accomplish closed-loop drug administration in combination with infusion pumps or the like.

In an embodiment, the hub communicates with other devices in a monitoring environment that are interacting with the patient in a number of ways. For example, the hub advantageously receives serial data from other devices without necessitating their reprogramming or that of the hub. Such other devices include pumps, ventilators, all manner of monitors monitoring any combination of the foregoing parameters, ECG/EEG/EKG devices, electronic patient beds, and the like. Moreover, the hub advantageously receives channel data from other medical devices without necessitating their reprogramming or that of the hub. When a device communicates through channel data, the hub may advantageously alter the large display to include measurement information from that device. Additionally, the hub accesses nurse call systems to ensure that nurse call situations from the device are passed to the appropriate nurse call system.

The hub also communicates with hospital systems to advantageously associate incoming patient measurement and treatment data with the patient being monitored. For example, the hub may communicate wirelessly or otherwise to a multi-patient monitoring system, such as a server or collection of servers, which in turn many communicate with a caregiver's data management systems, such as, for example, an Admit, Discharge, Transfer ("ADT") system and/or an Electronic Medical Records ("EMR") system. The hub advantageously associates the data flowing through it with the patient being monitored thereby providing the electronic measurement and treatment information to be passed to the caregiver's data management systems without the caregiver associating each device in the environment with the patient.

In an embodiment, the hub advantageously includes a reconfigurable and removable docking station. The docking station may dock additional layered docking stations to adapt to different patient monitoring devices. Additionally, the docking station itself is modularized so that it may be removed if the primary dockable portable patient monitor changes its form factor. Thus, the hub is flexible in how its docking station is configured.

In an embodiment, the hub includes a large memory for storing some or all of the data it receives, processes, and/or associates with the patient, and/or communications it has with other devices and systems. Some or all of the memory may advantageously comprise removable SD memory.

The hub communicates with other devices through at least (1) the docking station to acquire data from a portable monitor, (2) innovative universal medical connectors to acquire channel data, (3) serial data connectors, such as RJ ports to acquire output data, (4) Ethernet, USB, and nurse call ports, (5) Wireless devices to acquire data from a portable monitor, (6) other wired or wireless communication mechanisms known to an artisan. The universal medical connectors advantageously provide optional electrically isolated power and communications, are designed to be smaller in cross section than isolation requirements. The connectors and the hub communicate to advantageously translate or configure data from other devices to be usable and displayable for the hub. In an embodiment, a software developers kit ("SDK") is provided to a device manufacturer to establish or define the behavior and meaning of the data output from their device. When the output is defined, the definition is programmed into a memory residing in the cable side of the universal medical connector and supplied as an original equipment manufacture ("OEM") to the device provider. When the cable is connected between the device and the hub, the hub understands the data and can use it for display and processing purposes without necessitating software upgrades to the device or the hub. In an embodiment, the hub can negotiate the schema and even add additional compression and/or encryption. Through the use of the universal medical connectors, the hub organizes the measurement and treatment data into a single display and alarm system effectively and efficiently bringing order to the monitoring environment.

As the hub receives and tracks data from other devices according to a channel paradigm, the hub may advantageously provide processing to create virtual channels of patient measurement or treatment data. In an embodiment, a virtual channel may comprise a non-measured parameter that is, for example, the result of processing data from various measured or other parameters. An example of such a parameter includes a wellness indicator derived from various measured parameters that give an overall indication of the wellbeing of the monitored patient. An example of a wellness parameter is disclosed in U.S. patent application Ser. Nos. 13/269,296, 13/371,767 and 12/904,925, by the assignee of the present disclosure and incorporated by reference herein. By organizing data into channels and virtual channels, the hub may advantageously time-wise synchronize incoming data and virtual channel data.

The hub also receives serial data through serial communication ports, such as RJ connectors. The serial data is associated with the monitored patient and passed on to the multi-patient server systems and/or caregiver backend systems discussed above. Through receiving the serial data, the caregiver advantageously associates devices in the caregiver environment, often from varied manufactures, with a particular patient, avoiding a need to have each individual device associated with the patient and possible communicating with hospital systems. Such association is vital as it reduces caregiver time spent entering biographic and demographic information into each device about the patient. Moreover, in an embodiment, through the SDK the device manufacturer may advantageously provide information associated with any measurement delay of their device, thereby further allowing the hub to advantageously time-wise synchronize serial incoming data and other data associated with the patient.

In an embodiment, when a portable patient monitor is docked, and it includes its own display, the hub effectively increases its display real estate. For example, in an embodiment, the portable patient monitor may simply continue to display its measurement and/or treatment data, which may be now duplicated on the hub display, or the docked display may alter its display to provide additional information. In an embodiment, the docked display, when docked, presents anatomical graphical data of, for example, the heart, lungs, organs, the brain, or other body parts being measured and/or treated. The graphical data may advantageously animate similar to and in concert with the measurement data. For example, lungs may inflate in approximate correlation to the measured respiration rate and/or the determined inspiration/ expiration portions of a respiration cycle, the heart may beat according to the pulse rate, may beat generally along understood actual heart contraction patterns, the brain may change color or activity based on varying depths of sedation, or the like. In an embodiment, when the measured parameters indicate a need to alert a caregiver, a changing severity in color may be associated with one or more displayed graphics, such as the heart, lungs, brain, organs, circulatory system or portions thereof, respiratory system or portions thereof, other body parts or the like. In still other embodiments, the body portions may include animations on where, when or how to attach measurement devices.

The hub may also advantageously overlap parameter displays to provide additional visual information to the caregiver. Such overlapping may be user definable and configurable. The display may also incorporate analog-appearing icons or graphical indicia.

In the interest of clarity, not all features of an actual implementation are described in this specification. An artisan will of course be appreciate that in the development of any such actual implementation (as in any development project), numerous implementation-specific decisions must be made to achieve a developers' specific goals and subgoals, such as compliance with system- and business-related constraints, which will vary from one implementation to another. Moreover, it will be appreciated that such a development effort might be complex and time-consuming, but would nevertheless be a routine undertaking of device engineering for those of ordinary skill having the benefit of this disclosure.

To facilitate a complete understanding of the disclosure, the remainder of the detailed description describes the disclosure with reference to the drawings, wherein like reference numbers are referenced with like numerals throughout.

II. Example Hub Embodiments

FIG. 1A illustrates a monitoring environment including a perspective view of an exemplary medical monitoring hub 100 with an exemplary docked portable patient monitor (PPM) 102 according to an embodiment of the disclosure. The hub 100 includes a display 104, and a docking station 106, which in an embodiment is configured to mechanically and electrically mate with the portable patient monitor 102, each housed in a movable, mountable and portable housing 108. The housing 108 includes a generally upright inclined shape configured to rest on a horizontal flat surface, although the housing 108 can be affixed in a wide variety of positions and mountings and comprise a wide variety of shapes and sizes.

In an embodiment, the display 104 may present a wide variety of measurement and/or treatment data in numerical, graphical, waveform, or other display indicia 110. In an embodiment, the display 104 occupies much of a front face of the housing 108, although an artisan will appreciate the display 104 may comprise a tablet or tabletop horizontal configuration, a laptop-like configuration or the like. Other embodiments may include communicating display information and data to a table computer, smartphone, television, or any display system recognizable to an artisan. The upright inclined configuration of FIG. 1A presents display information to a caregiver in an easily viewable manner.

Figure 1B:
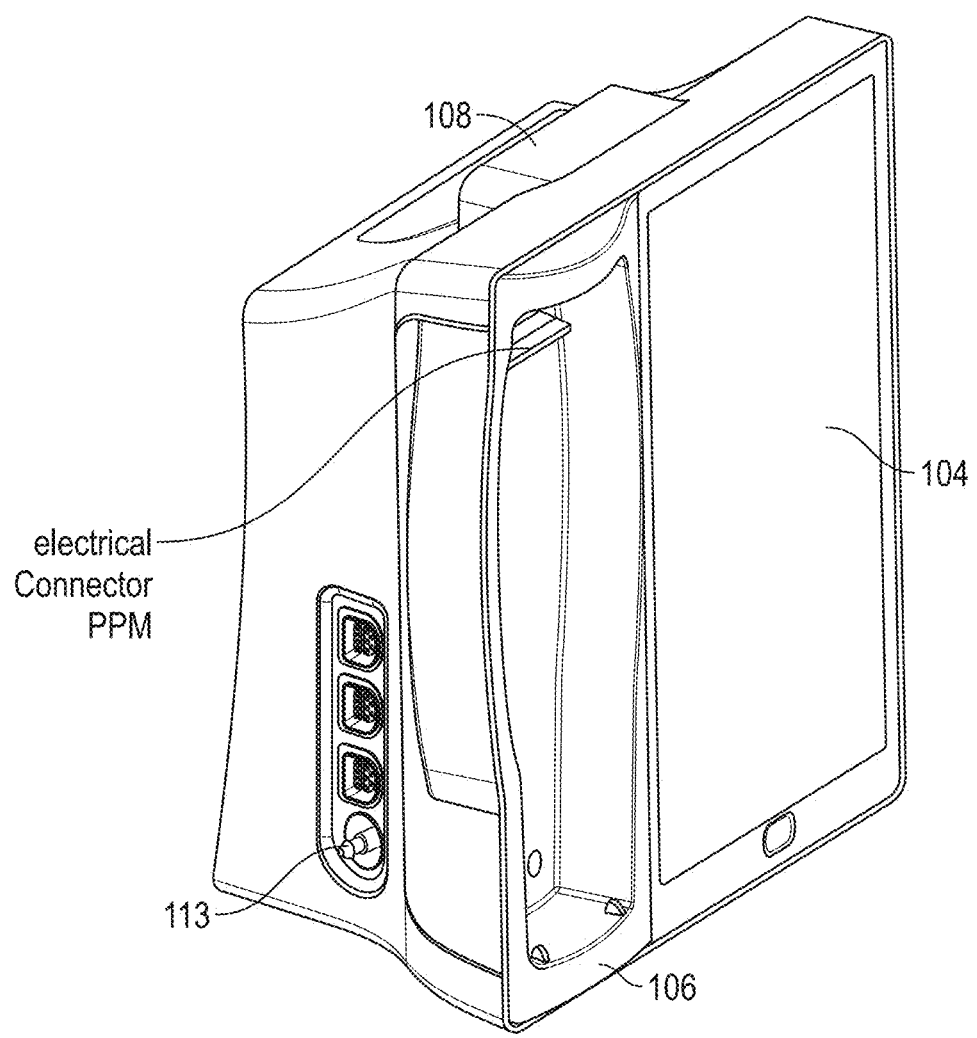

FIG. 1B shows a perspective side view of an embodiment of the hub 100 including the housing 108, the display 104, and the docking station 106 without a portable monitor docked. Also shown is a connector for noninvasive blood pressure.

The portable patient monitor 102 of FIG. 1A may advantageously comprise an oximeter, co-oximeter, respiratory monitor, depth of sedation monitor, noninvasive blood pressure monitor, vital signs monitor or the like, such as those commercially available from Masimo Corporation of Irvine, Calif., and/or disclosed in U.S. Pat. Pub. Nos. 2002/0140675, 2010/0274099, 2011/0213273, 2012/0226117, 2010/0030040; U.S. Pat. App. Ser. Nos. 61/242,792, 61/387457, 61/645,570, Ser. No. 13/554,908 and U.S. Pat. Nos. 6,157,850, 6,334,065, and the like. The monitor 102 may communicate with a variety of noninvasive and/or minimally invasive devices such as optical sensors with light emission and detection circuitry, acoustic sensors, devices that measure blood parameters from a finger prick, cuffs, ventilators, and the like. The monitor 102 may include its own display 114 presenting its own display indicia 116, discussed below with reference to FIGS. 19A-19J. The display indicia may advantageously change based on a docking state of the monitor 102. When undocked, the display indicia may include parameter information and may alter orientation based on, for example, a gravity sensor or accelerometer.

In an embodiment, the docking station 106 of the hub 100 includes a mechanical latch 118, or mechanically releasable catch to ensure that movement of the hub 100 doesn't mechanically detach the monitor 102 in a manner that could damage the same.

Although disclosed with reference to particular portable patient monitors 102, an artisan will recognize from the disclosure herein a large number and wide variety of medical devices that may advantageously dock with the hub 100. Moreover, the docking station 106 may advantageously electrically and not mechanically connect with the monitor 102, and/or wirelessly communicate with the same.

Figure 2:
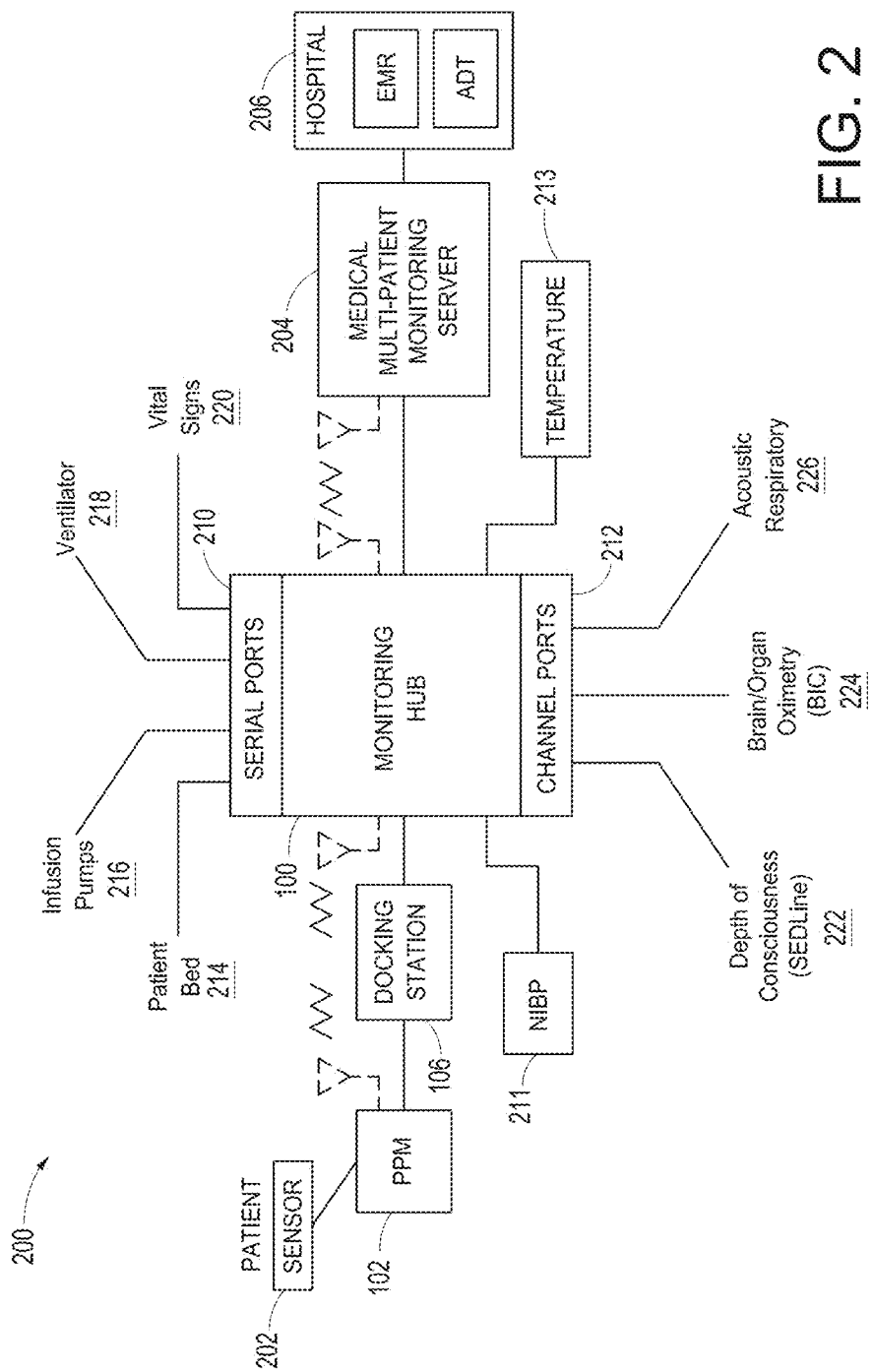
FIG. 2 illustrates a simplified block diagram of an exemplary monitoring environment including the hub of FIG. 1, according to an embodiment of the disclosure.

FIG. 2 illustrates a simplified block diagram of an exemplary monitoring environment 200 including the hub 100 of FIG. 1, according to an embodiment of the disclosure. As shown in FIG. 2, the environment may include the portable patient monitor 102 communicating with one or more patient sensors 202, such as, for example, oximetry optical sensors, acoustic sensors, blood pressure sensors, respiration sensors or the like. In an embodiment, additional sensors, such as, for example, a NIBP sensor or system 211 and a temperature sensor or sensor system 213 may communicate directly with the hub 100. The sensors 202, 211 and 213 when in use are typically in proximity to the patient being monitored if not actually attached to the patient at a measurement site.

As disclosed, the portable patient monitor 102 communicates with the hub 100, in an embodiment, through the docking station 106 when docked and, in an embodiment, wirelessly when undocked, however, such undocked communication is not required. The hub 100 communicates with one or more multi-patient monitoring servers 204 or server systems, such as, for example, those disclosed with in U.S. Pat. Pub. Nos. 2011/0105854, 2011/0169644, and 2007/0180140. In general, the server 204 communicates with caregiver backend systems 206 such as EMR and/or ADT systems. The server 204 may advantageously obtain through push, pull or combination technologies patient information entered at patient admission, such as demographical information, billing information, and the like. The hub 100 accesses this information to seamlessly associate the monitored patient with the caregiver backend systems 206. Communication between the server 204 and the monitoring hub 100 may be any recognizable to an artisan from the disclosure herein, including wireless, wired, over mobile or other computing networks, or the like.

FIG. 2 also shows the hub 100 communicating through its serial data ports 210 and channel data ports 212. As disclosed in the forgoing, the serial data ports 210 may provide data from a wide variety of patient medical devices, including electronic patient bed systems 214, infusion pump systems 216 including closed loop control systems, ventilator systems 218, blood pressure or other vital sign measurement systems 220, or the like. Similarly, the channel data ports 212 may provide data from a wide variety of patient medical devices, including any of the foregoing, and other medical devices. For example, the channel data ports 212 may receive data from depth of consciousness monitors 222, such as those commercially available from SEDLine, brain or other organ oximeter devices 224, noninvasive blood pressure or acoustic devices 226, or the like. In an embodiment, channel device may include board-in-cable ("BIC") solutions where the processing algorithms and the signal processing devices that accomplish those algorithms are mounted to a board housed in a cable or cable connector, which in some embodiments has no additional display technologies. The BIC solution outputs its measured parameter data to the channel port 212 to be displayed on the display 104 of hub 100. In an embodiment, the hub 100 may advantageously be entirely or partially formed as a BIC solution that communicates with other systems, such as, for example, tablets, smartphones, or other computing systems.

Although disclosed with reference to a single docking station 106, the environment 200 may include stacked docking stations where a subsequent docking station mechanically and electrically docks to a first docking station to change the form factor for a different portable patent monitor as discussed with reference to FIG. 5. Such stacking may include more than 2 docking stations, may reduce or increase the form fact for mechanical compliance with mating mechanical structures on a portable device.

Figure 3:
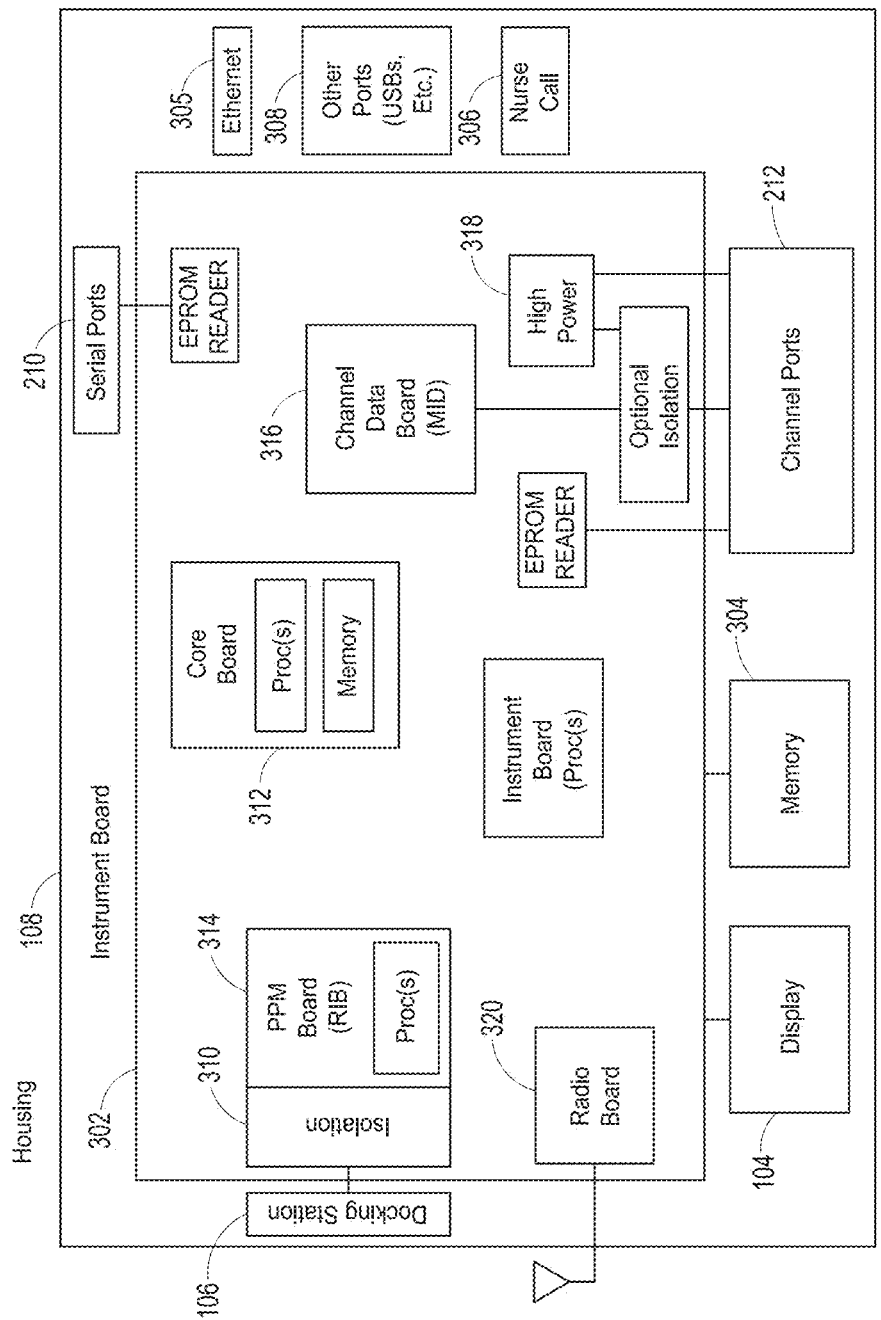
FIG. 3 illustrates a simplified exemplary hardware block diagram of the hub of FIG. 1, according to an embodiment of the disclosure.

FIG. 3 illustrates a simplified exemplary hardware block diagram of the hub 100 of FIG. 1, according to an embodiment of the disclosure. As shown in FIG. 3, the housing 108 of the hub 100 positions and/or encompasses an instrument board 302, the display 104, memory 304, and the various communication connections, including the serial ports 210, the channel ports 212, Ethernet ports 305, nurse call port 306, other communication ports 308 including standard USB or the like, and the docking station interface 310. The instrument board 302 comprises one or more substrates including communication interconnects, wiring, ports and the like to enable the communications and functions described herein, including inter-board communications. A core board 312 includes the main parameter, signal, and other processor(s) and memory, a portable monitor board ("RIB") 314 includes patient electrical isolation for the monitor 102 and one or more processors, a channel board ("MID") 316 controls the communication with the channel ports 212 including optional patient electrical isolation and power supply 318, and a radio board 320 includes components configured for wireless communications. Additionally, the instrument board 302 may advantageously include one or more processors and controllers, busses, all manner of communication connectivity and electronics, memory, memory readers including EPROM readers, and other electronics recognizable to an artisan from the disclosure herein. Each board comprises substrates for positioning and support, interconnect for communications, electronic components including controllers, logic devices, hardware/software combinations and the like to accomplish the tasks designated above and others.

An artisan will recognize from the disclosure herein that the instrument board 302 may comprise a large number of electronic components organized in a large number of ways. Using different boards such as those disclosed above advantageously provides organization and compartmentalization to the complex system.

Figure 4:
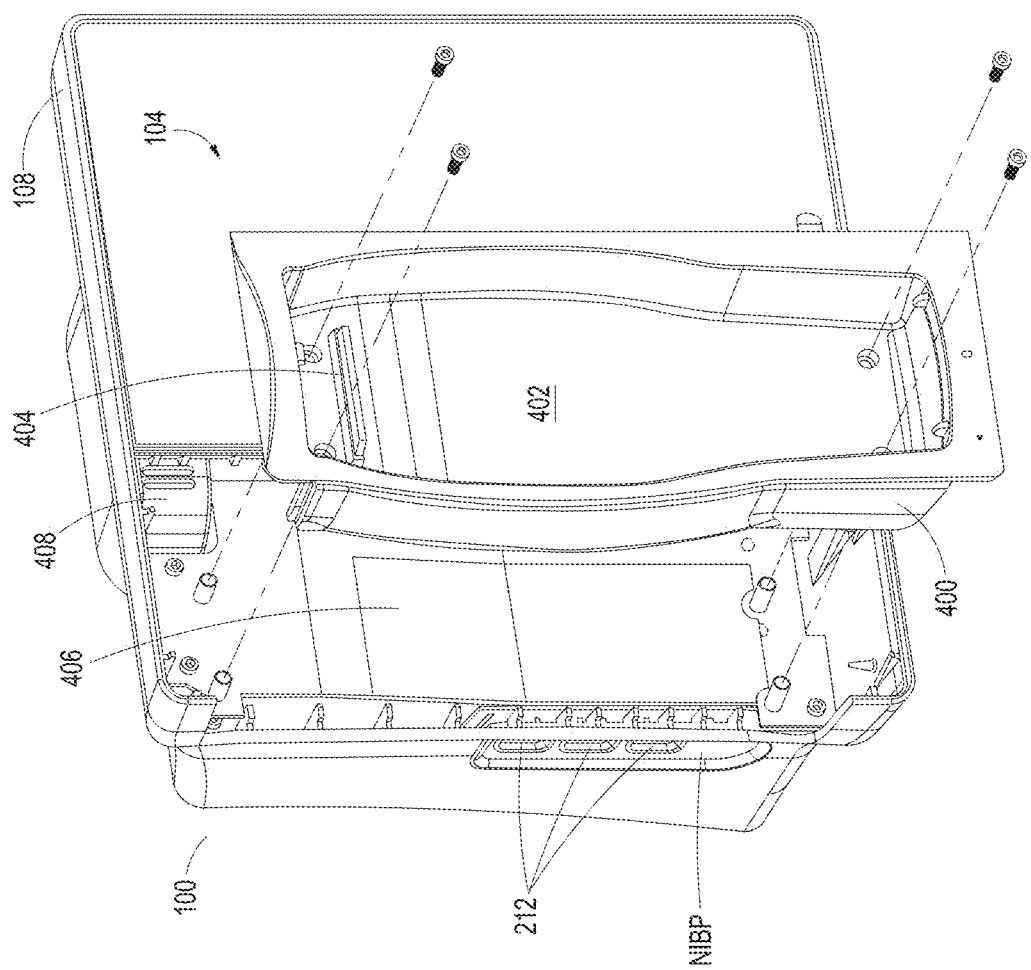
FIG. 4 illustrates a perspective view of an exemplary removable docking station of the hub of FIG. 1, according to an embodiment of the disclosure.

FIG. 4 illustrates a perspective view of an exemplary removable docking station 400 of the hub 100 of FIG. 1, according to an embodiment of the disclosure. As shown in FIG. 4, the docking station 400 provides a mechanical mating to portable patient monitor 102 to provide secure mechanical support when the monitor 102 is docked. The docking station 400 includes a cavity 402 shaped similar to the periphery of a housing of the portable monitor 102. The station 400 also includes one or more electrical connectors 404 providing communication to the hub 100. Although shown as mounted with bolts, the docking station 400 may snap fit, may use movable tabs or catches, may magnetically attach, or may employ a wide variety or combination of attachment mechanisms know to an artisan from the disclosure herein. In an embodiment, the attachment of the docking station 400 should be sufficiently secure that when docked, the monitor 102 and docking station cannot be accidentally detached in a manner that could damage the instruments, such as, for example, if the hub 100 was accidently bumped or the like, the monitor 102 and docking station 400 should remain intact.

The housing 108 of the hub 100 also includes cavity 406 housing the docking station 400. To the extent a change to the form factor for the portable patient monitor 102 occurs, the docking station 400 is advantageously removable and replaceable. Similar to the docking station 400, the hub 100 includes within the cavity 406 of the housing 108 electrical connectors 408 providing electrical communication to the docking station 400. In an embodiment, the docking station 400 includes its own microcontroller and processing capabilities, such as those disclosed in U.S. Pat. Pub. No. 2002/0140675. In other embodiments, the docking station 400 passes communications through to the electrical connector 408.

FIG. 4 also shows the housing 108 including openings for channel ports 212 as universal medical connectors discussed in detail below.

FIG. 5 illustrates a perspective view of exemplary portable patient monitors 502 and 504 undocked from the hub 100 of FIG. 1, according to an embodiment of the disclosure. As shown in FIG. 5, the monitor 502 may be removed and other monitors, like monitor 504 may be provided. The docking station 106 includes an additional docking station 506 that mechanically mates with the original docking station 106 and presents a form factor mechanically matable with monitor 504. In an embodiment, the monitor 504 mechanically and electrically mates with the stacked docking stations 506 and 106 of hub 100. As can be readily appreciated by and artisan from the disclosure herein, the stackable function of the docking stations provides the hub 100 with an extremely flexible mechanism for charging, communicating, and interfacing with a wide variety of patient monitoring devices. As noted above, the docking stations may be stacked, or in other embodiments, removed and replaced.

Figure 6:
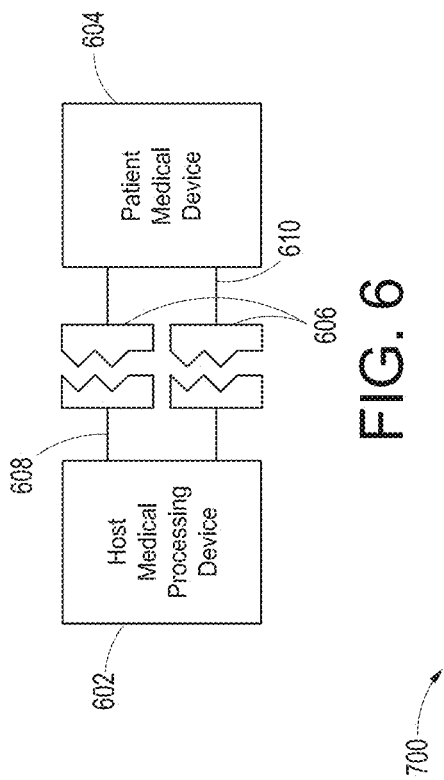
FIG. 6 illustrates a simplified block diagram of traditional patient device electrical isolation principles.

FIG. 6 illustrates a simplified block diagram of traditional patient electrical isolation principles. As shown in FIG. 6, a host device 602 is generally associated with a patient device 604 through communication and power. As the patient device 604 often comprises electronics proximate or connected to a patient, such as sensors or the like, certain safety requirements dictate that electrical surges of energy from, for example, the power grid connected to the host device, should not find an electrical path to the patient. This is generally referred to a "patient isolation" which is a term known in the art and includes herein the removing of direct uninterrupted electrical paths between the host device 602 and the patient device 604. Such isolation is accomplished through, for example, isolation devices 606 on power conductors 608 and communication conductors 610. Isolation devices 606 can include transformers, optical devices that emit and detect optical energy, and the like. Use of isolation devices, especially on power conductors, can be expensive component wise, expensive size wise, and drain power. Traditionally, the isolation devices were incorporated into the patient device 604, however, the patient devices 604 are trending smaller and smaller and not all devices incorporate isolation.

Figure 7B:
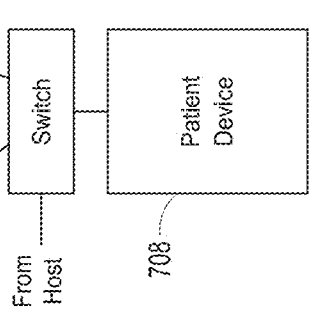
FIG. 7A illustrates a simplified block diagram of an exemplary optional patient device isolation system according to an embodiment of the disclosure, while FIG. 7B adds exemplary optional non-isolation power levels for the system of FIG. 7A, also according to an embodiment of the disclosure.
Figure 7A:
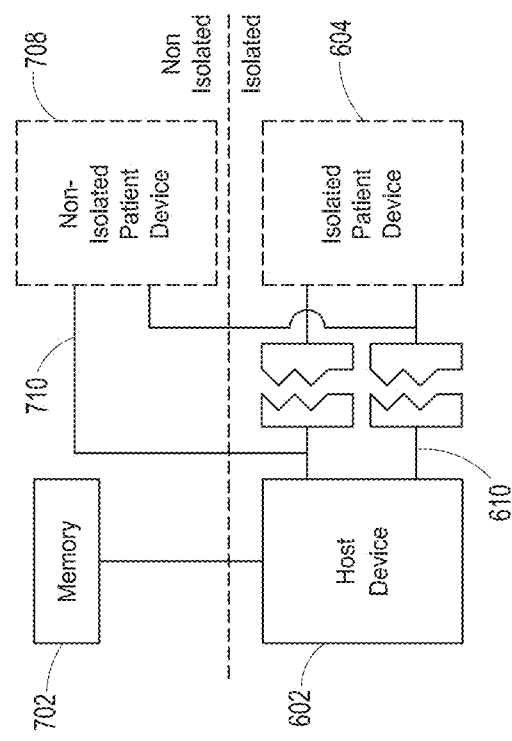

FIG. 7A illustrates a simplified block diagram of an exemplary optional patient isolation system according to an embodiment of the disclosure. As shown in FIG. 7A, the host device 602 communicates with an isolated patient device 604 through isolation devices 606. However, a memory 702 associated with a particular patient device informs the host 602 whether that device needs isolated power. If a patient device 708 does not need isolated power, such as some types of cuffs, infusion pumps, ventilators, or the like, then the host 602 can provide non-isolated power through signal path 710. This power may be much higher that what can cost-effectively be provided through the isolated power conductor 608. In an embodiment, the non-isolated patient devices 708 receive isolated communication as such communication is typically at lower voltages and is not cost prohibitive. An artisan will recognize from the disclosure herein that communication could also be non-isolated. Thus, FIG. 7A shows a patient isolation system 700 that provides optional patient isolation between a host 602 and a wide variety of potential patient devices 604, 708. In an embodiment, the hub 100 includes the channel ports 212 incorporating similar optional patient isolation principles.

FIG. 7B adds an exemplary optional non-isolation power levels for the system of FIG. 7A according to an embodiment of the disclosure. As shown in FIG. 7B, once the host 602 understands that the patient device 604 comprises a self-isolated patient device 708, and thus does not need isolated power, the host 602 provides power through a separate conductor 710. Because the power is not isolated, the memory 702 may also provide power requirements to the host 602, which may select from two or more voltage or power levels. In FIG. 7B, the host 602 provides either high power, such as about 12 volts, but could have a wide range of voltages or very high power such as about 24 volts or more, but could have a wide range of voltages, to the patient device 708. An artisan will recognize that supply voltages can advantageously be altered to meet the specific needs of virtually any device 708 and/or the memory could supply information to the host 602 which provided a wide range of non-isolated power to the patient device 708.

Moreover, using the memory 702, the host 602 may determine to simply not enable any unused power supplies, whether that be the isolated power or one or more of the higher voltage non-isolated power supplies, thereby increasing the efficiency of the host.

Figure 8:
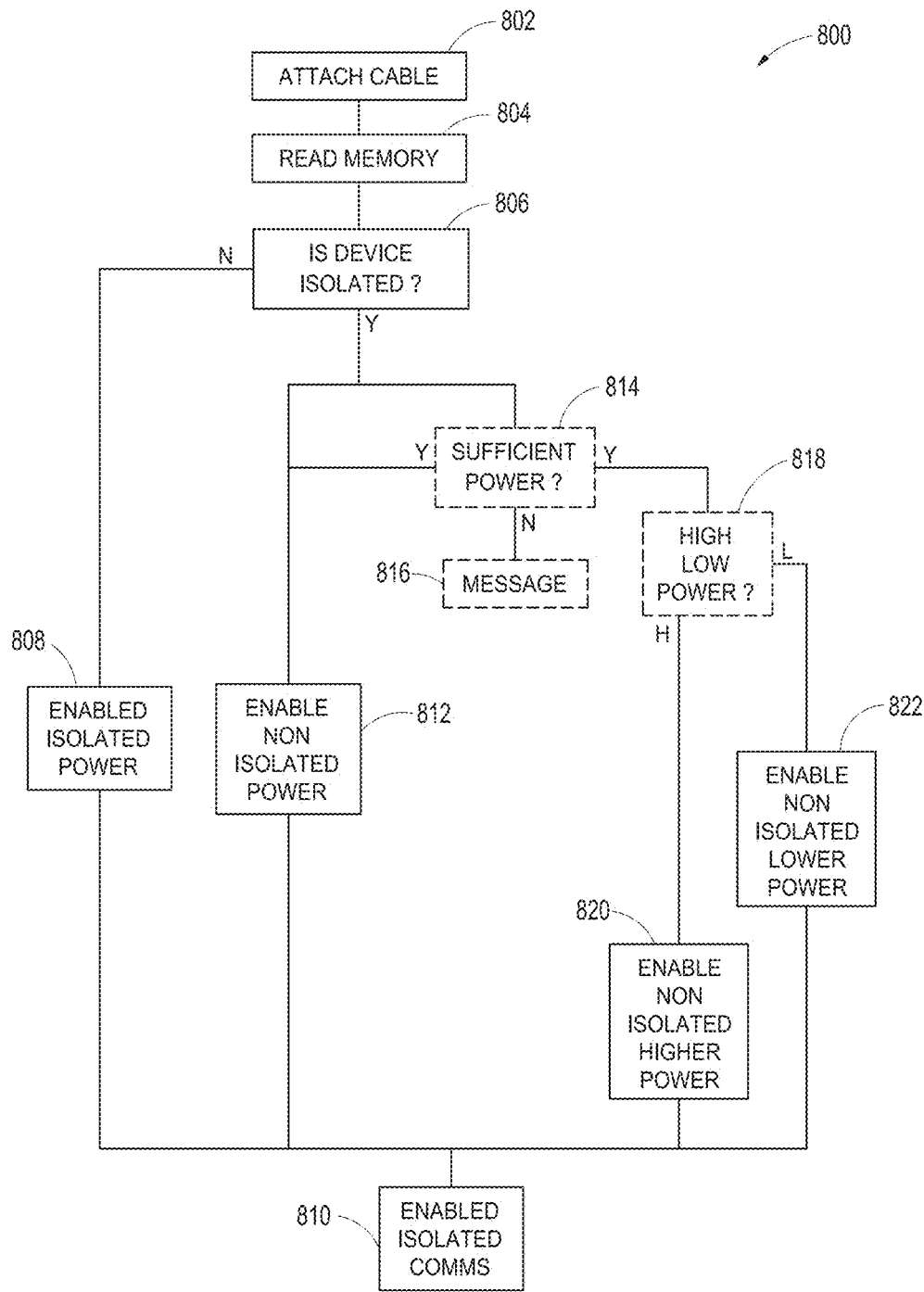
FIG. 8 illustrates a simplified exemplary universal medical connector configuration process, according to an embodiment of the disclosure.

FIG. 8 illustrates a simplified exemplary universal medical connector configuration process 800, according to an embodiment of the disclosure. As shown in FIG. 8, the process includes step 802, where a cable is attached to a universal medical connector incorporating optional patient isolation as disclosed in the foregoing. In step 804, the host device 602 or the hub 100, more specifically, the channel data board 316 or EPROM reader of the instrument board, reads the data stored in the memory 702 and in step 806, determines whether the connecting device requires isolated power. In step 808, when the isolated power is required, the hub 100 may advantageously enable isolated power and in step 810, enable isolated communications. In step 806, when isolated power is not needed, the hub 100 may simply in optional step 812 enable non-isolated power and in embodiments where communications remain isolated, step 810 enable isolated communications. In other optional embodiments, in step 806, when isolated power is not needed, the hub 100 in step 814 may use information from memory 702 to determine the amount of power needed for the patient device 708. When sufficient power is not available, because for example, other connected devices are also using connected power, in step 816 a message may be displayed indicating the same and power is not provided. When sufficient power is available, optional step 812 may enable non-isolated power. Alternatively, optional step 818 may determine whether memory 702 indicates higher or lower power is desired. When higher power is desired, the hub 100 may enable higher power in step 820 and when not, may enable lower power in step 822. The hub 100 in step 810 then enables isolated communication. In an embodiment, the hub 100 in step 818 may simply determine how much power is needed and provide at least sufficient power to the self-isolated device 708.

An artisan will recognize from the disclosure herein that hub 100 may not check to see if sufficient power is available or may provide one, two or many levels of non-isolated voltages based on information from the memory 702.

Figure 9A:
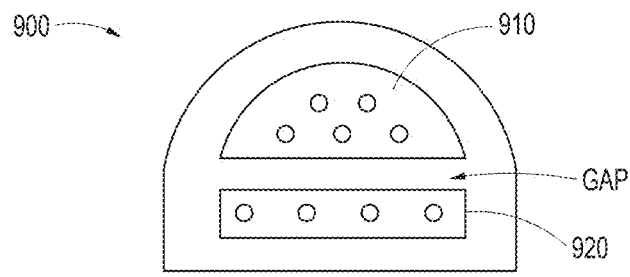
Figure 9B:
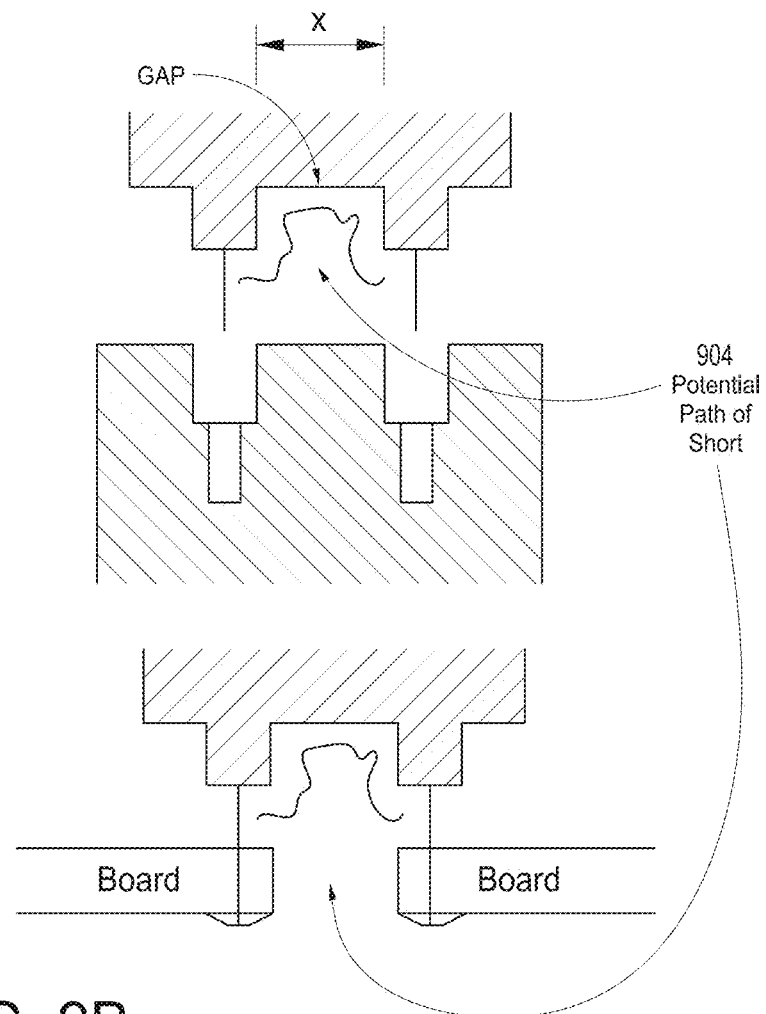

FIGS. 9A and 9B illustrate simplified block diagrams of exemplary universal medical connectors 900 having a size and shape smaller in cross section than tradition isolation requirements. In an embodiment, the connector 900 physically separates non-isolated signals on one side 910 from isolated signals on another side 920, although the sides could be reversed. The gap between such separations may be dictated at least in part by safety regulations governing patient isolation. In an embodiment, the distance between the sides 910 and 920 may appear to be too small.

As shown from a different perspective in FIG. 9B, the distance between connectors "x" appears small. However, the gap causes the distance to includes a non-direct path between conductors. For example, any short would have to travel path 904, and the distance of such path is within or beyond such safety regulations, in that the distance is greater than "x." It is noteworthy that the non-straight line path 904 occurs throughout the connector, such as, for example, on the board connector side where solder connects various pins to a PCB board.

Figure 10:
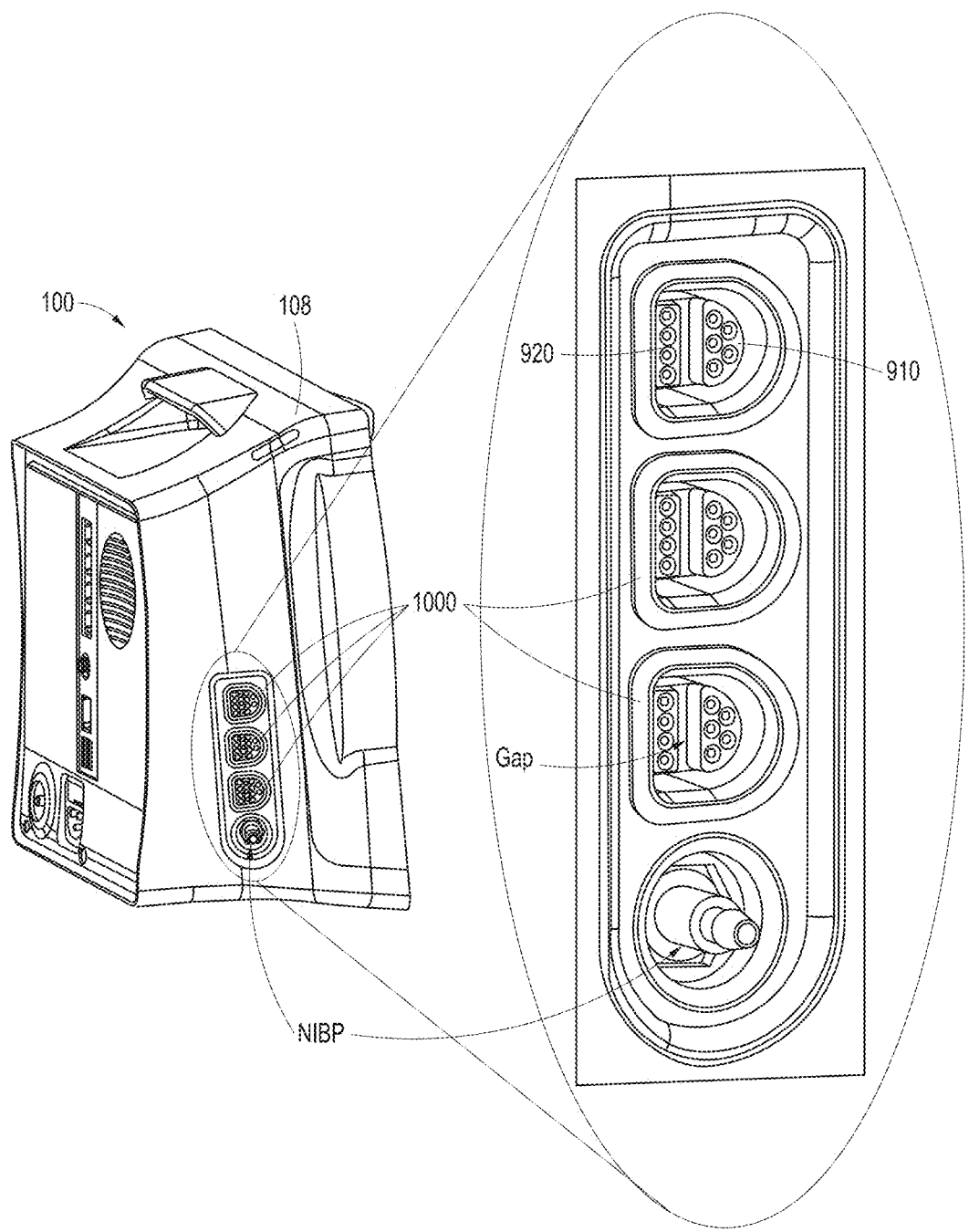

FIG. 10 illustrates a perspective view of a side of the hub 100 of FIG. 1, showing exemplary instrument-side channel inputs 1000 as exemplary universal medical connectors. As shown in FIG. 10, the inputs include the non-isolated side 910, the isolated side 920, and the gap. In an embodiment, the memory 710 communicates through pins on the non-isolated side.

Figure 11A:
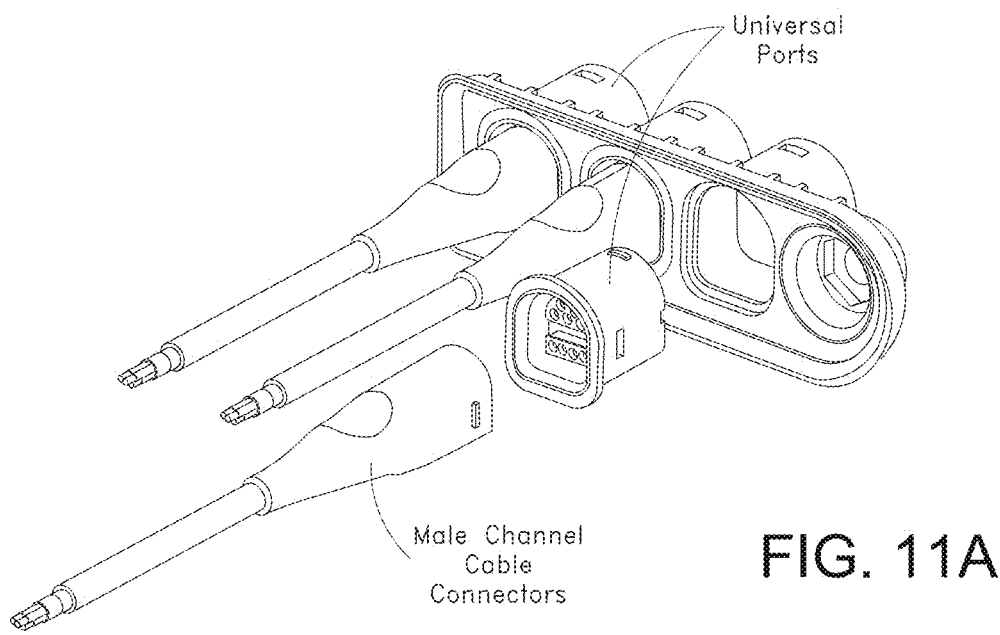
Figure 11B:
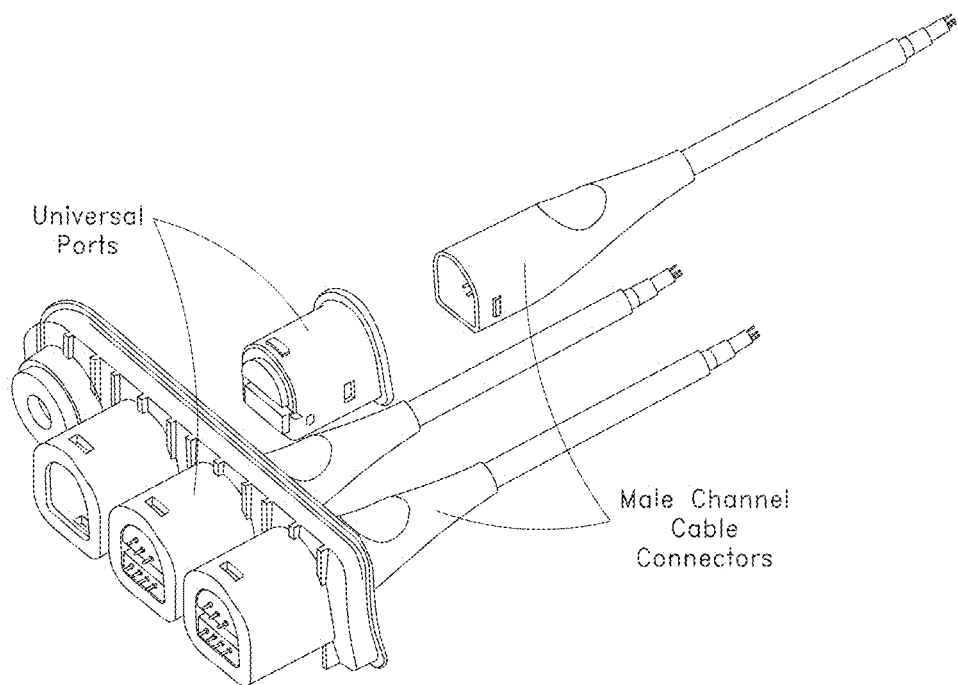
Figure 11J:
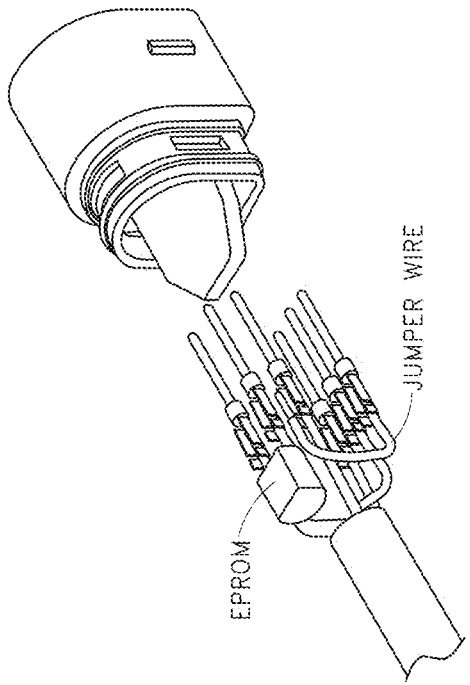
Figure 11I:
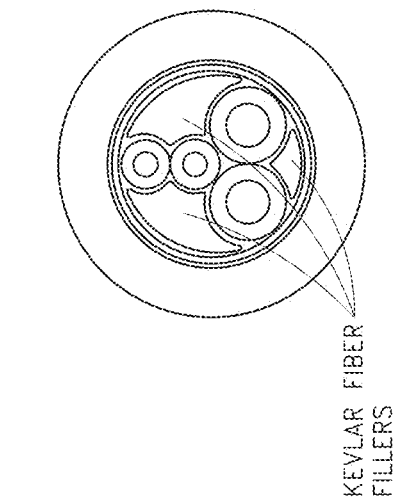
Figure 11K:
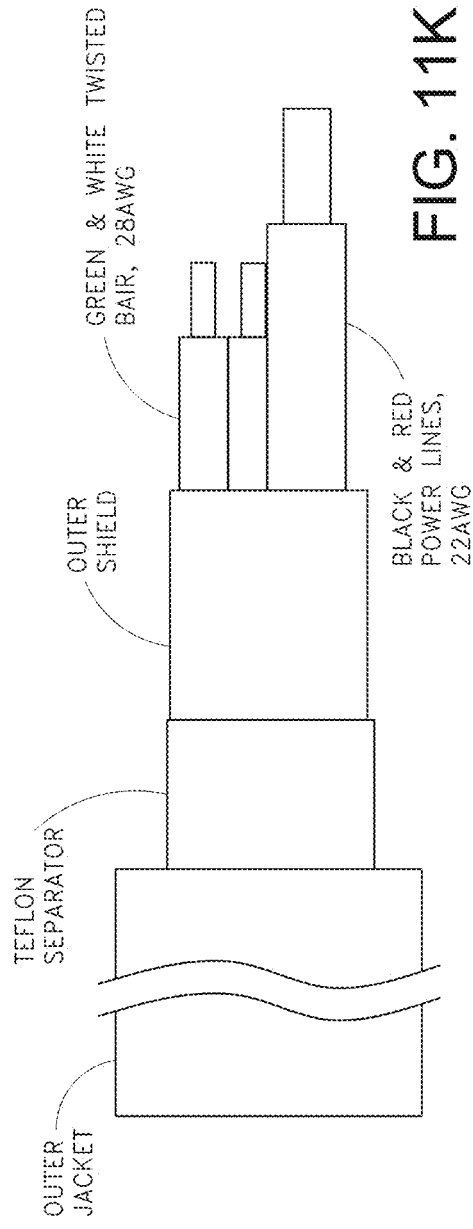

FIGS. 11A-11K illustrate various views of exemplary male and mating female universal medical connectors, according to embodiments of the disclosure. For example, FIGS. 11G1 and 11G2 shows various preferred but not required sizing, and FIG. 11H shows incorporation of electronic components, such as the memory 702 into the connectors. FIGS. 11I-11K illustrate wiring diagrams and cabling specifics of the cable itself as it connects to the universal medical connectors.

Figure 12:
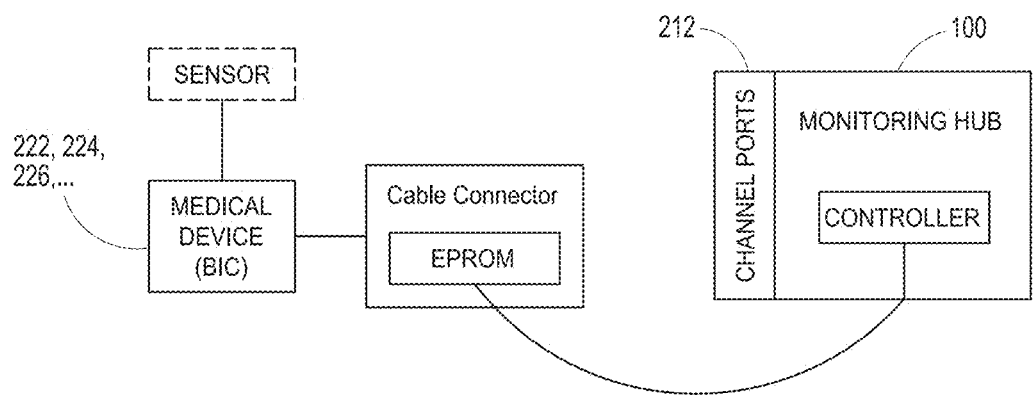
FIG. 12 illustrates a simplified block diagram of a channel system for the hub of FIG. 1, according to an embodiment of the disclosure.

FIG. 12 illustrates a simplified block diagram of a channel system for the hub of FIG. 1, according to an embodiment of the disclosure. As shown in FIG. 12, a male cable connector, such as those shown in FIG. 11 above, includes a memory such as an EPROM. The memory advantageously stores information describing the type of data the hub 100 can expect to receive, and how to receive the same. A controller of the hub 100 communicates with the EPROM to negotiate how to receive the data, and if possible, how to display the data on display 104, alarm when needed, and the like. For example, a medical device supplier may contact the hub provider and receive a software developers' kit ("SDK") that guides the supplier through how to describe the type of data output from their device. After working with the SDK, a map, image, or other translation file may advantageously be loaded into the EPROM, as well as the power requirements and isolation requirements discussed above. When the channel cable is connected to the hub 100 through the channel port 212, the hub 100 reads the EPROM and the controller of the hub 100 negotiates how to handle incoming data.

Figure 13:
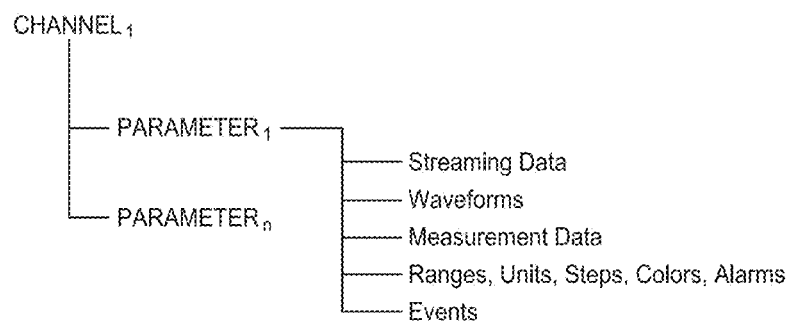
FIG. 13 illustrates an exemplary logical channel configuration, according to an embodiment of the disclosure.

FIG. 13 illustrates an exemplary logical channel configuration that may be stored in the EPROM of FIG. 12. As shown in FIG. 13, each incoming channel describes one or more parameters. Each parameter describes whatever the hub 100 should know about the incoming data. For example, the hub 100 may want to know whether the data is streaming data, waveform data, already determined parameter measurement data, ranges on the data, speed of data delivery, units of the data, steps of the units, colors for display, alarm parameters and thresholds, including complex algorithms for alarm computations, other events that are parameter value driven, combinations of the same or the like. Additionally, the parameter information may include device delay times to assist in data synchronization or approximations of data synchronization across parameters or other data received by the hub 100. In an embodiment, the SDK presents a schema to the device supplier which self-describes the type and order of incoming data. In an embodiment, the information advantageously negotiates with the hub 100 to determine whether to apply compression and/or encryption to the incoming data stream.

Such open architecture advantageously provides device manufacturers the ability to port the output of their device into the hub 100 for display, processing, and data management as disclosed in the foregoing. By implementation through the cable connector, the device manufacturer avoids any reprogramming of their original device; rather, they simply let the hub 100 know through the cable connector how the already existing output is formatted. Moreover, by describing the data in a language already understood by the hub 100, the hub 100 also avoids software upgrades to accommodate data from "new-to-the-hub" medical devices.

Figure 14:
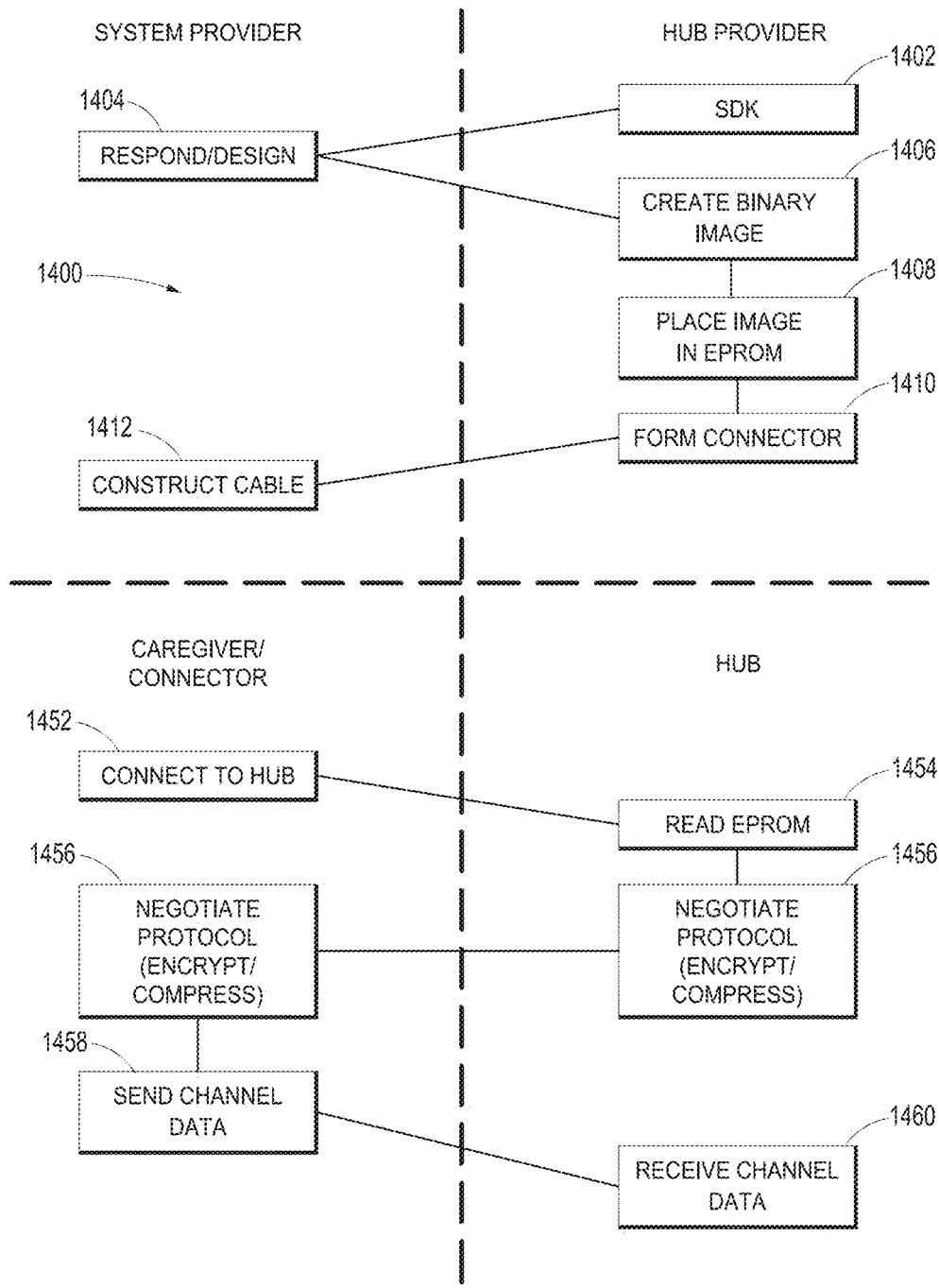
FIG. 14 illustrates a simplified exemplary process for constructing a cable and configuring a channel according to an embodiment of the disclosure.

FIG. 14 illustrates a simplified exemplary process for configuring a channel according to an embodiment of the disclosure. As shown in FIG. 14, the hub provider provides a device manufacturer with an SDK in step 1402, who in turn uses the SDK to self-describe the output data channel from their device in step 1404. In an embodiment, the SDK is a series of questions that guide the development, in other embodiments, the SDK provides a language and schema to describe the behavior of the data.

Once the device provider describes the data, the hub provider creates a binary image or other file to store in a memory within a cable connector in step 1405; however, the SDK may create the image and simply communicated it to the hub provider. The cable connector is provided as an OEM part to the provider in step 1410, who constructs and manufactures the cable to mechanically and electrically mate with output ports on their devices in step 1412.

Once a caregiver has the appropriately manufactured cable, with one end matching the device provider's system and the other OEM'ed to match the hub 100 at its channel ports 212, in step 1452 the caregiver can connect the hub between the devices. In step 1454, the hub 100 reads the memory, provides isolated or non-isolated power, and the cable controller and the hub 100 negotiate a protocol or schema for data delivery. In an embodiment, a controller on the cable may negotiated the protocol, in an alternative embodiment, the controller of the hub 100 negotiates with other processors on the hub the particular protocol. Once the protocol is set, the hub 100 can use, display and otherwise process the incoming data stream in an intelligent manner.

Through the use of the universal medical connectors described herein, connection of a myriad of devices to the hub 100 is accomplished through straightforward programming of a cable connector as opposed to necessitating software upgrades to each device.

Figure 15:
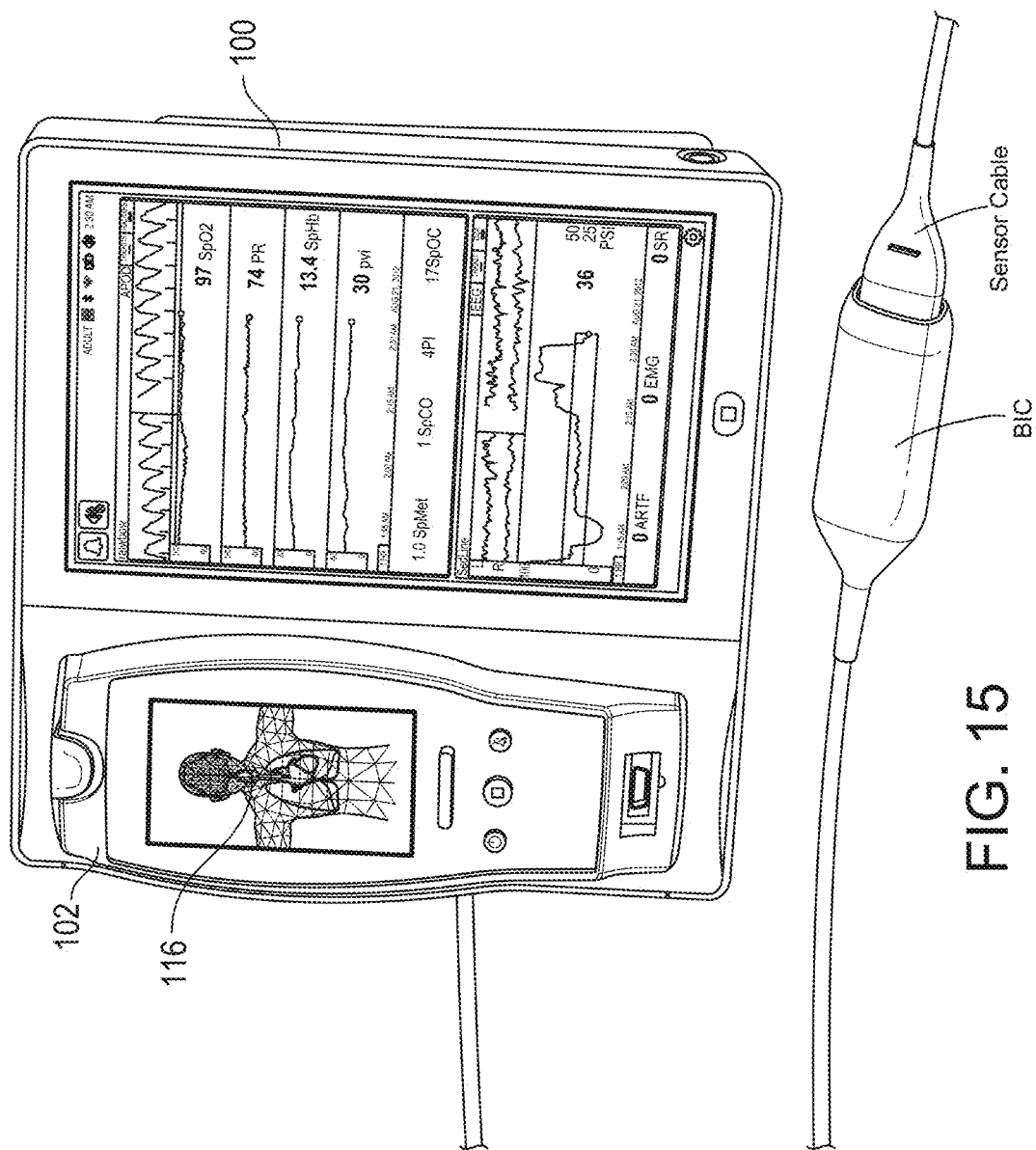
FIG. 15 illustrates a perspective view of the hub of FIG. 1, including an exemplary attached board-in-cable to form an input channel, according to an embodiment of the disclosure.

FIG. 15 illustrates a perspective view of the hub of FIG. 1 including an exemplary attached board-in-cable ("BIC") to form an input channel according to an embodiment of the disclosure. As shown in FIG. 15, a SEDLine depth of consciousness board communicates data from an appropriate patient sensor to the hub 100 for display and caregiver review. As described, the provider of the board need only use the SDK to describe their data channel, and the hub 100 understands how to present the data to the caregiver.

Figure 16:
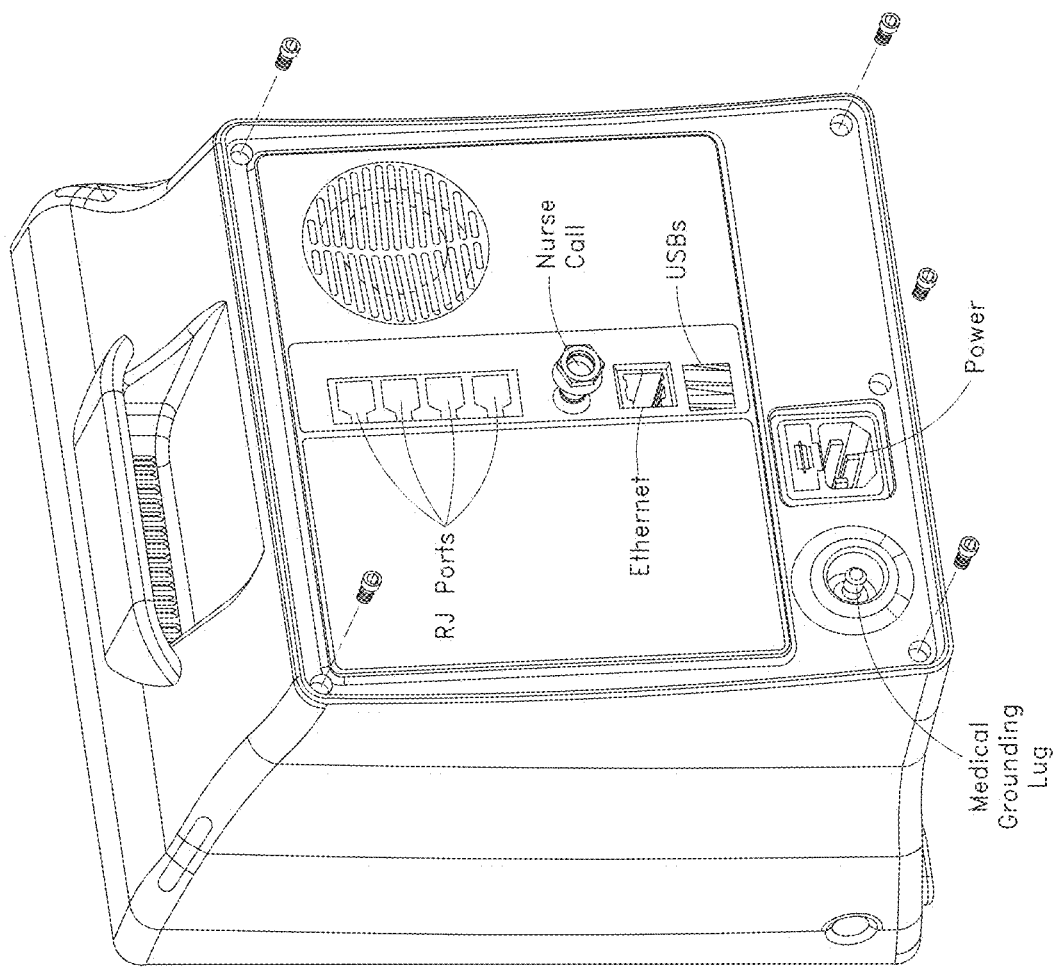
FIG. 16 illustrates a perspective view of a back side of the hub of FIG. 1, showing an exemplary instrument-side serial data inputs, according to an embodiment of the disclosure.

FIG. 16 illustrates a perspective view of a back side of the hub 100 of FIG. 1, showing an exemplary serial data inputs. In an embodiment, the inputs include such as RJ 45 ports. As is understood in the art, these ports include a data ports similar to those found on computers, network routers, switches and hubs. In an embodiment, a plurality of these ports are used to associate data from various devices with the specific patient identified in the hub 100. FIG. 16 also shows a speaker, the nurse call connector, the Ethernet connector, the USBs, a power connector and a medical grounding lug.

Figure 17A:
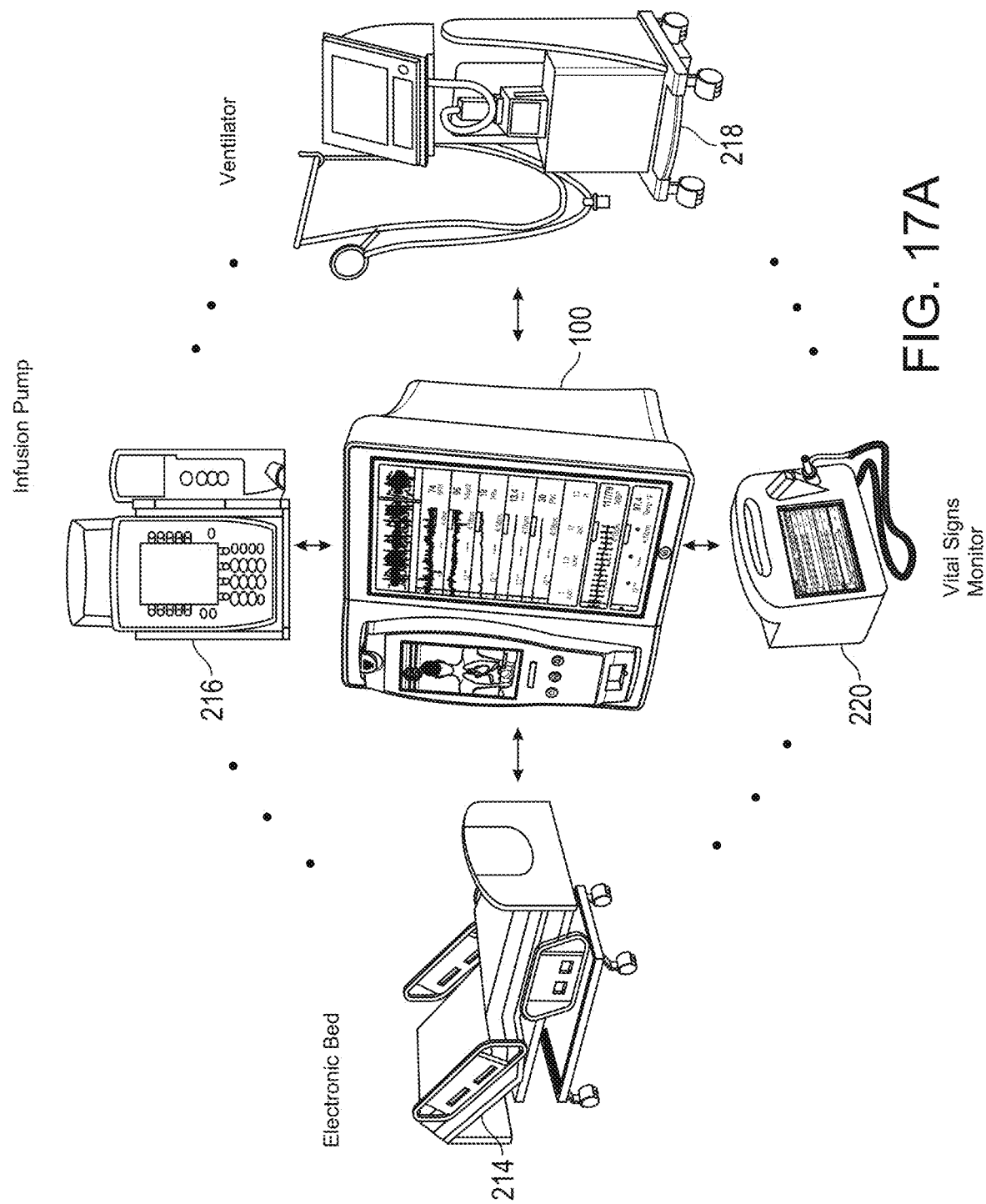
FIG. 17A illustrates an exemplary monitoring environment with communication through the serial data connections of FIG. 16, according to embodiments of the disclosure.

FIG. 17A illustrates an exemplary monitoring environment with communication through the serial data connections of the hub 100 of FIG. 1, according to an embodiment of the disclosure. As shown and as discussed in the foregoing, the hub 100 may use the serial data ports 210 to gather data from various devices within the monitoring environment, including an electronic bed, infusion pumps, ventilators, vital sign monitors, and the like. The difference between the data received from these devices and that received through the channel ports 212 is that the hub 100 may not know the format or structure of this data. The hub 100 may not display information from this data or use this data in calculations or processing. However, porting the data through the hub 100 conveniently associates the data with the specifically monitored patient in the entire chain of caregiver systems, including the foregoing server 214 and backend systems 206. In an embodiment, the hub 100 may determine sufficient information about the incoming data to attempt to synchronize it with data from the hub 100.

Figure 17B:
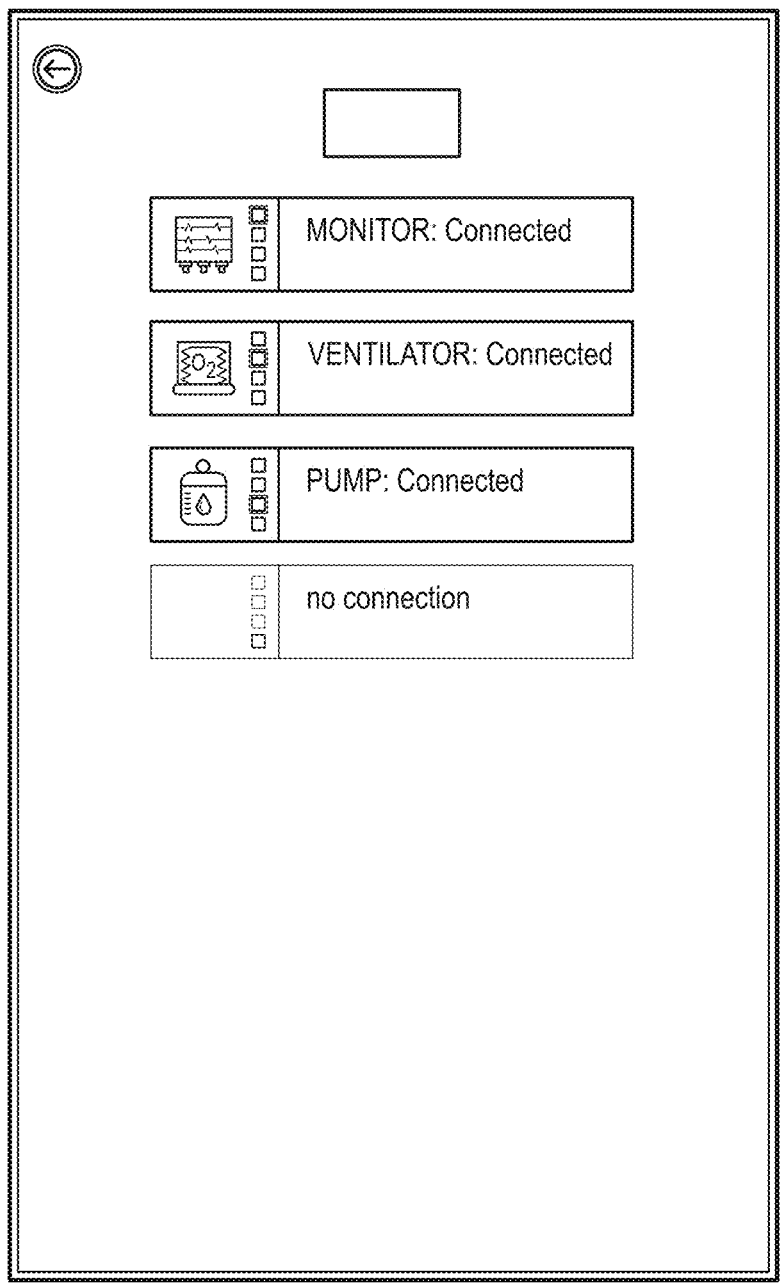
FIG. 17B illustrates an exemplary connectivity display of the hub of FIG. 1, according to embodiments of the disclosure.

In FIG. 17B, a control screen may provide information on the type of data being received. In an embodiment, a green light next to the data indicates connection to a device and on which serial input the connection occurs.

Figure 18:
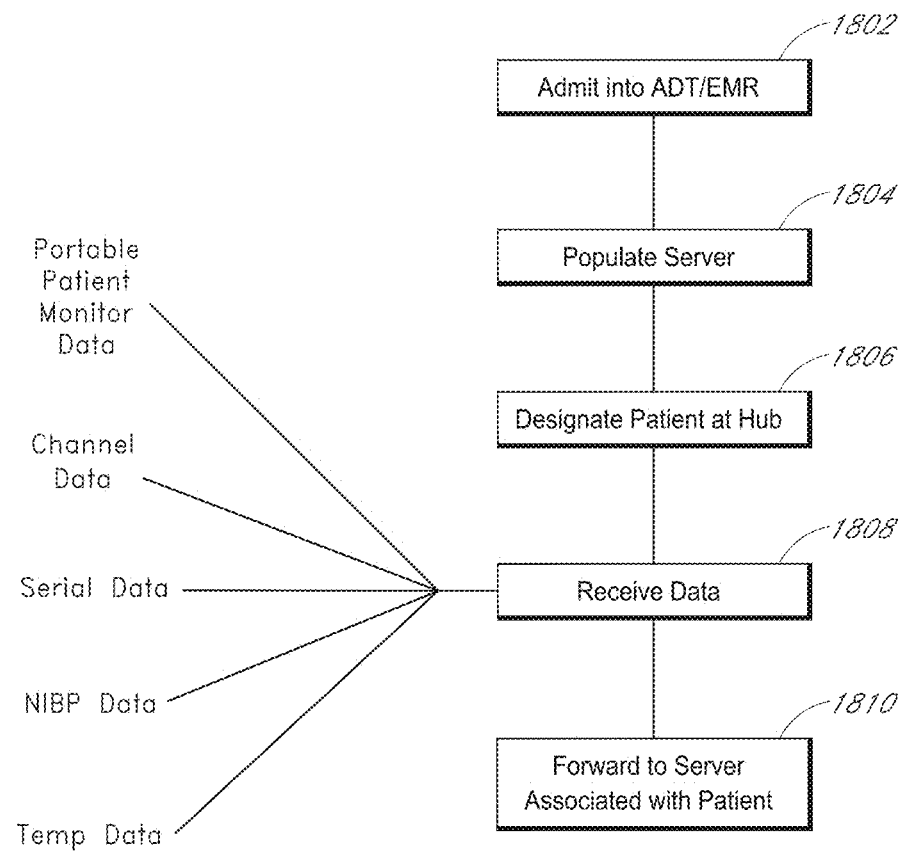
FIG. 18 illustrates a simplified exemplary patient data flow process, according to an embodiment of the disclosure.

FIG. 18 illustrates a simplified exemplary patient data flow process, according to an embodiment of the disclosure. As shown, once a patient is admitted into the caregiver environment at step 1802, data about the patient is populated on the caregiver backend systems 206. The server 214 may advantageously acquire or receive this information in step 1804, and then make it accessible to the hub 100. When the caregiver at step 1806 assigns the hub 100 to the patient, the caregiver simply looks at the presently available patient data and selects the particular patient being currently monitored. The hub 100 at step 1808 then associates the measurement, monitoring and treatment data it receives and determines with that patient. The caregiver need not again associate another device with the patient so long as that device is communicating through the hub 100 by way of (1) the docking station, (2) the universal medical connectors, (3) the serial data connectors, or (4) other communication mechanisms known to an artisan. At step 1810, some or the entirety of the received, processed and/or determined data is passed to the server systems discussed above.

Figure 19A:
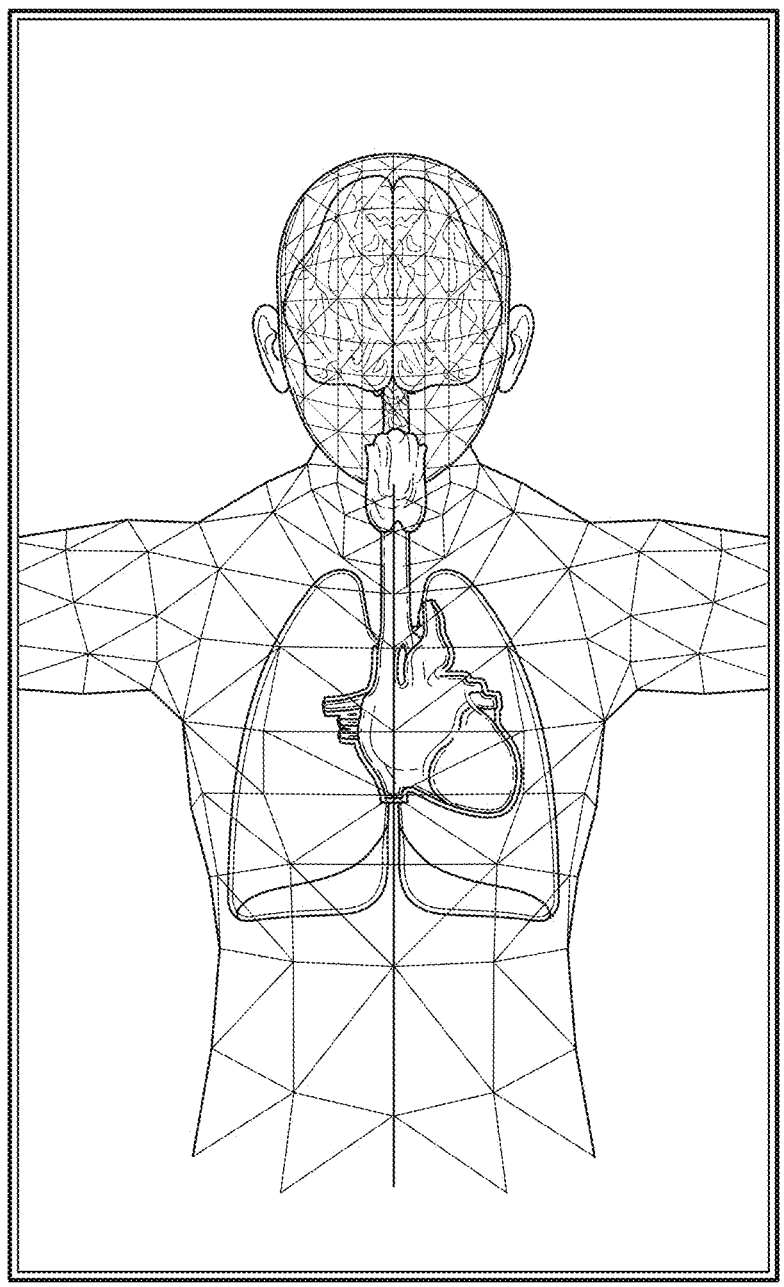
FIGS. 19A-19J illustrate exemplary displays of anatomical graphics for the portable patient monitor of FIG. 1 docked with the hub of FIG. 1, according to embodiments of the disclosure.

FIGS. 19A-19J illustrate exemplary displays of anatomical graphics for the portable patient monitor docked with the hub 100 of FIG. 1, according to embodiments of the disclosure. As shown in FIG. 19A, the heart, lungs and respiratory system are shown while the brain is not highlighted. Thus, a caregiver can readily determine that depth of consciousness monitoring or brain oximetry systems are not currently communicating with the hub 100 through the portable patient monitor connection or the channel data ports. However, it is likely that acoustic or other respiratory data and cardiac data is being communicated to or measured by the hub 100. Moreover, the caregiver can readily determine that the hub 100 is not receiving alarming data with respect to the emphasized body portions. In an embodiment, the emphasized portion may animate to show currently measured behavior or, alternatively, animate in a predetermined fashion.

Figure 19B:
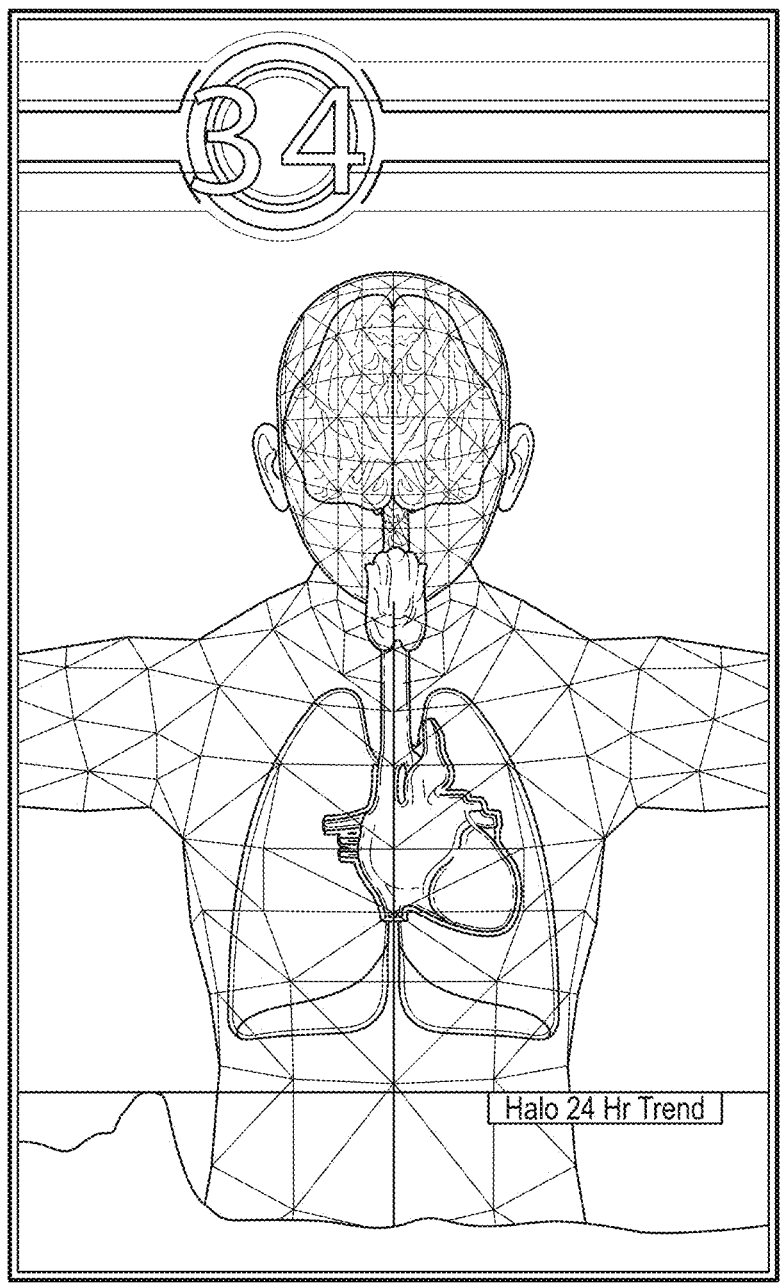
Figure 19C:
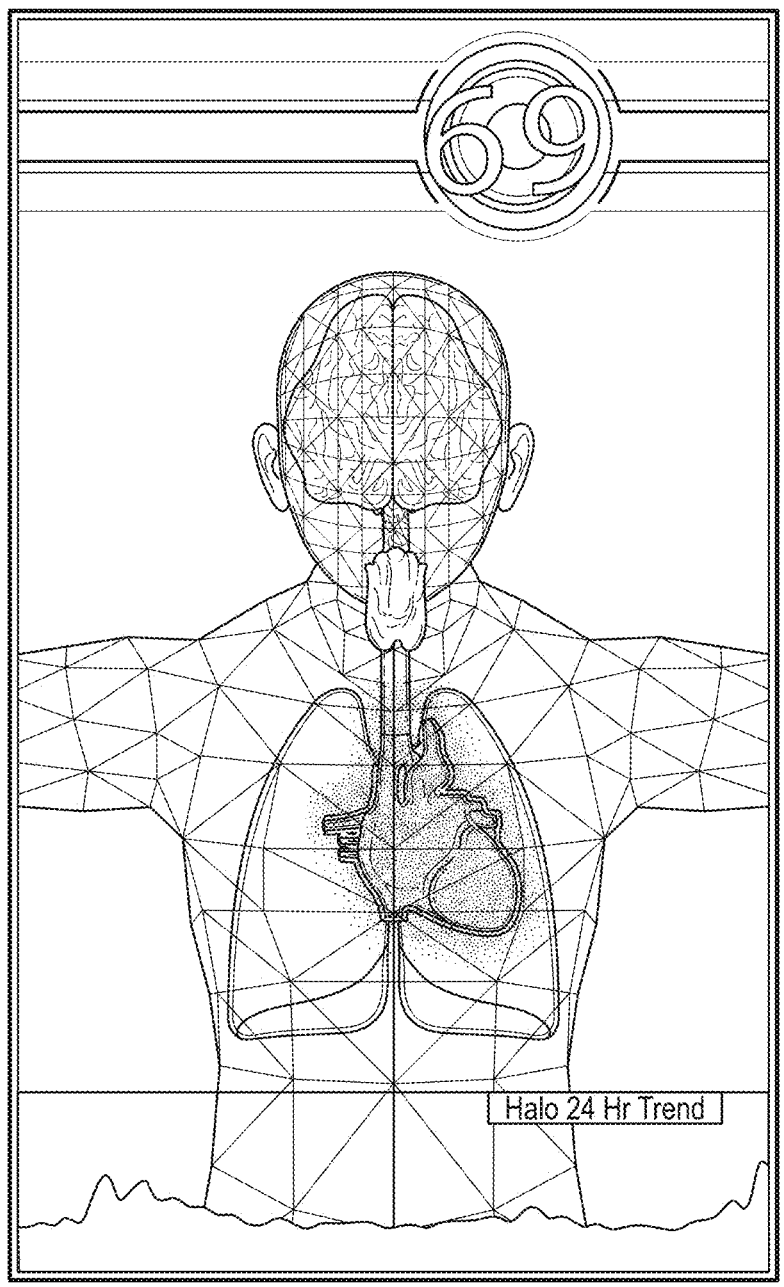

FIG. 19B shows the addition of a virtual channel showing an indication of wellness. As shown in FIG. 19B, the indication is positive as it is a "34" on an increasingly severity scale to "100." The wellness indication may also be shaded to show problems. In contrast to FIG. 19B, FIG. 19C shows a wellness number that is becoming or has become problematic and an alarming heart graphic. Thus, a caregiver responding to a patient alarm on the hub 100 or otherwise on another device or system monitoring or treating the patient can quickly determine that a review of vital signs and other parameters relating to heart function is needed to diagnose and/or treat the patient.

Figure 19D:
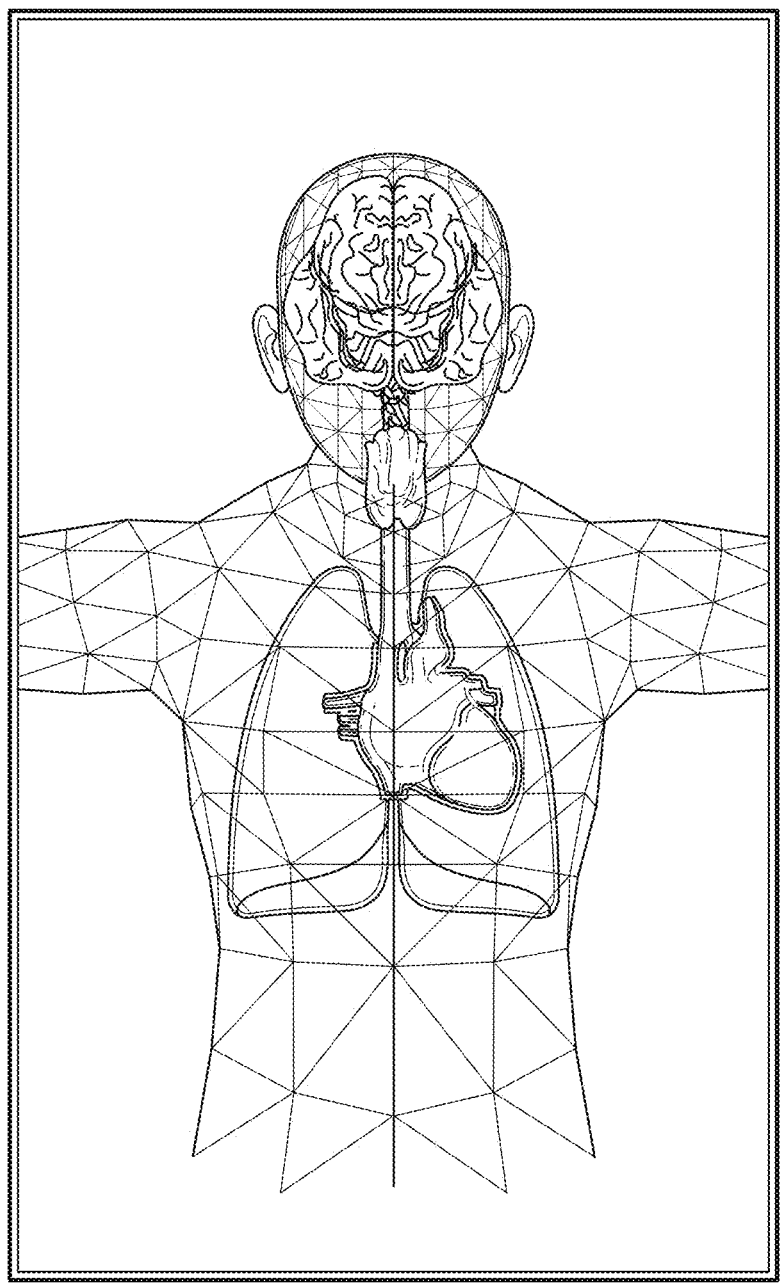
Figure 19E:
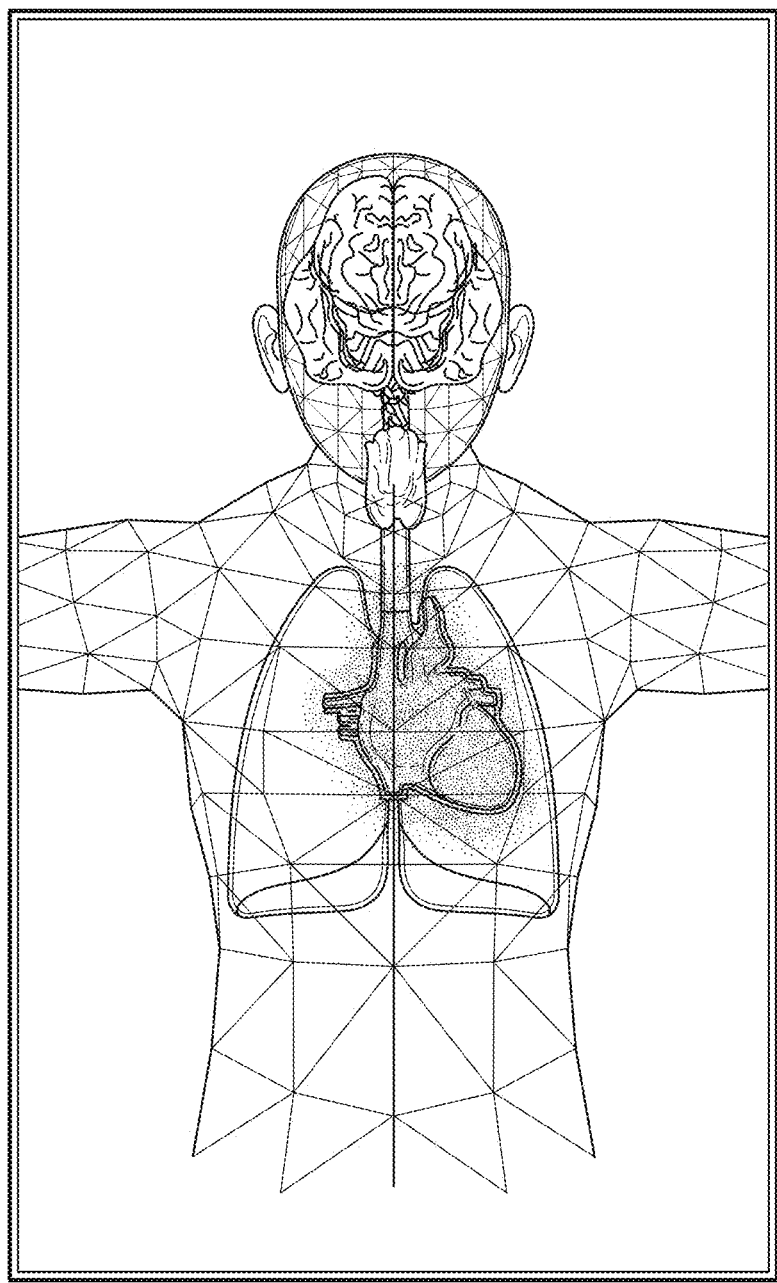

FIGS. 19D and 19E show the brain included in the emphasized body portions meaning that the hub 100 is receiving data relevant to brain functions, such as, for example, depth of sedation data or brain oximetry data. FIG. 19E additionally shows an alarming heart function similar to FIG. 19C.

Figure 19F:
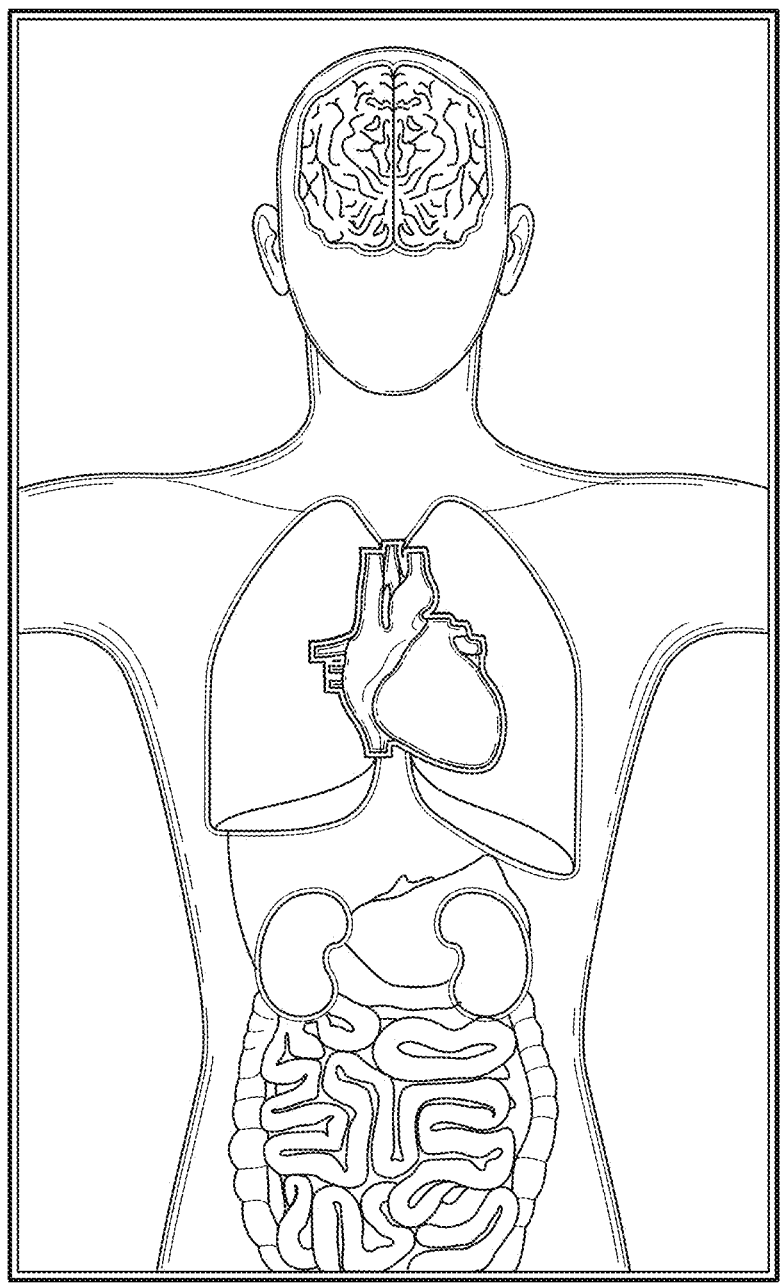
Figure 19G:
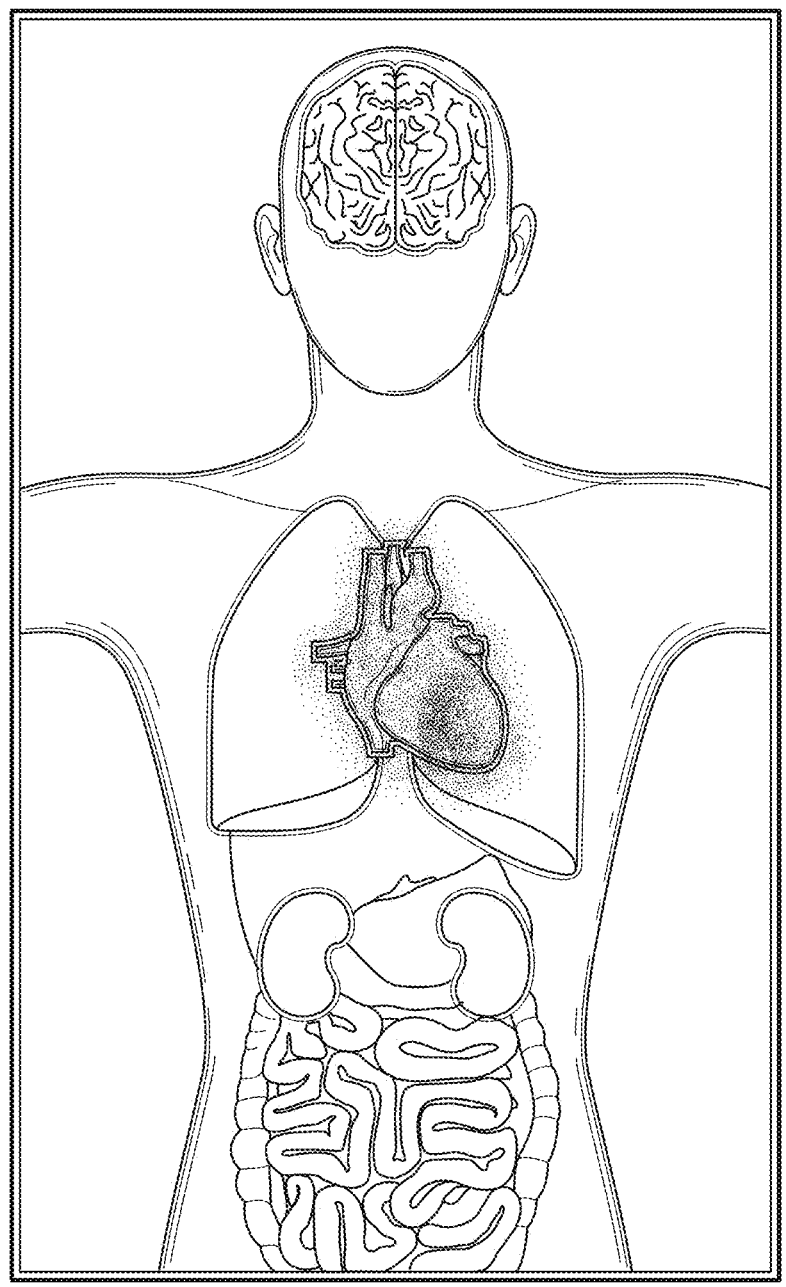
Figure 19H:
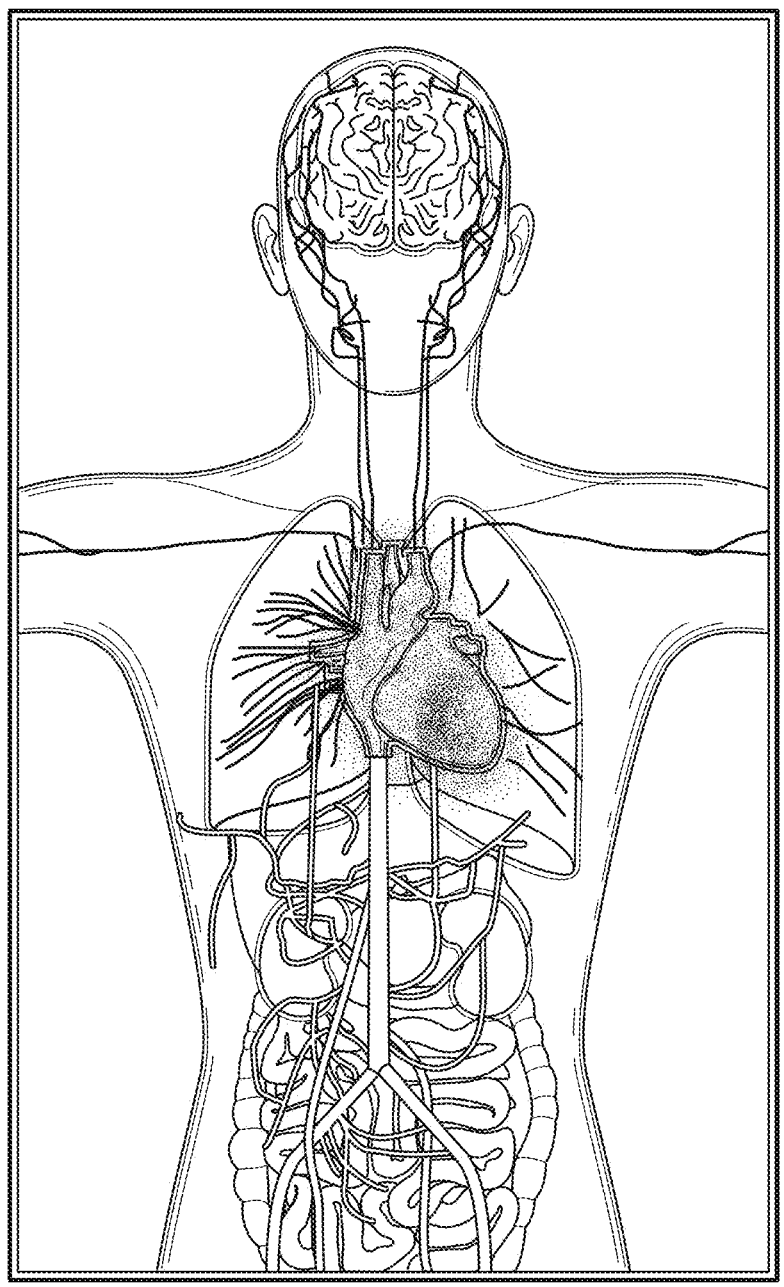
Figure 19I:
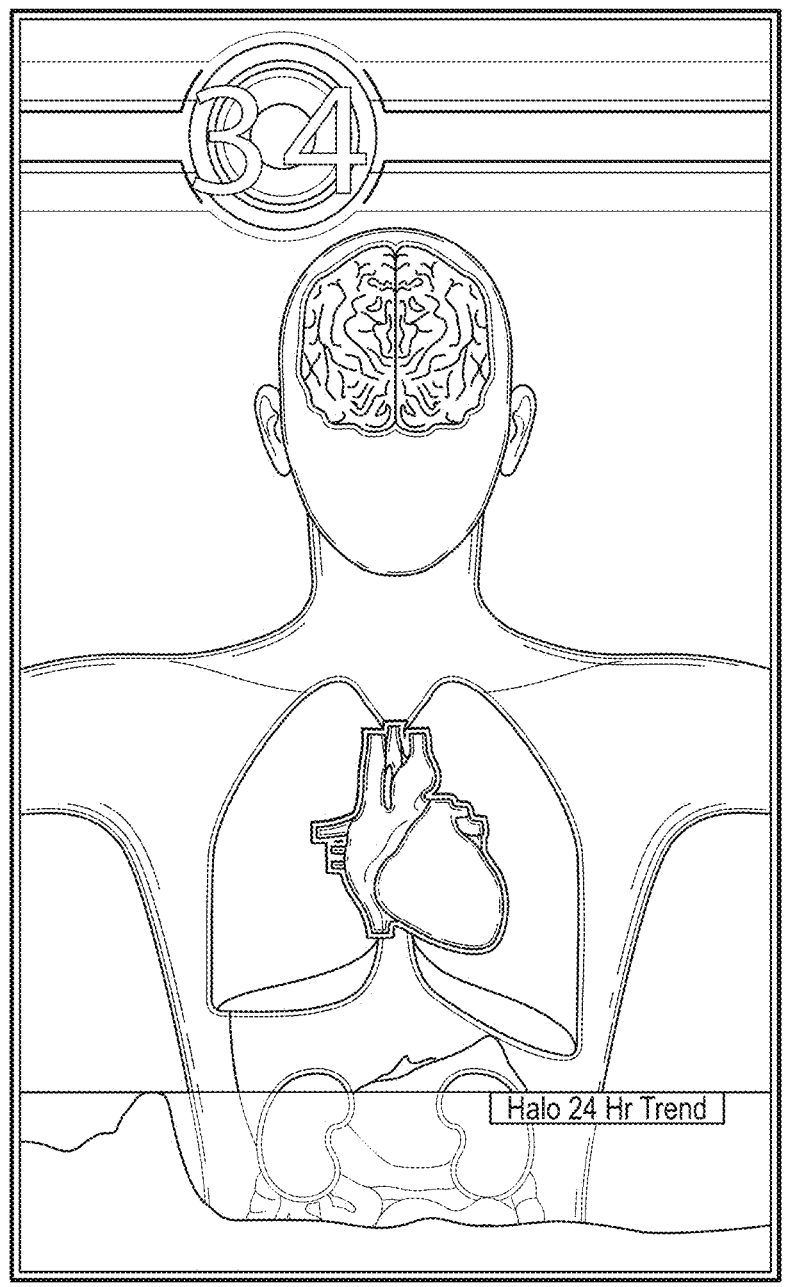
Figure 19J:
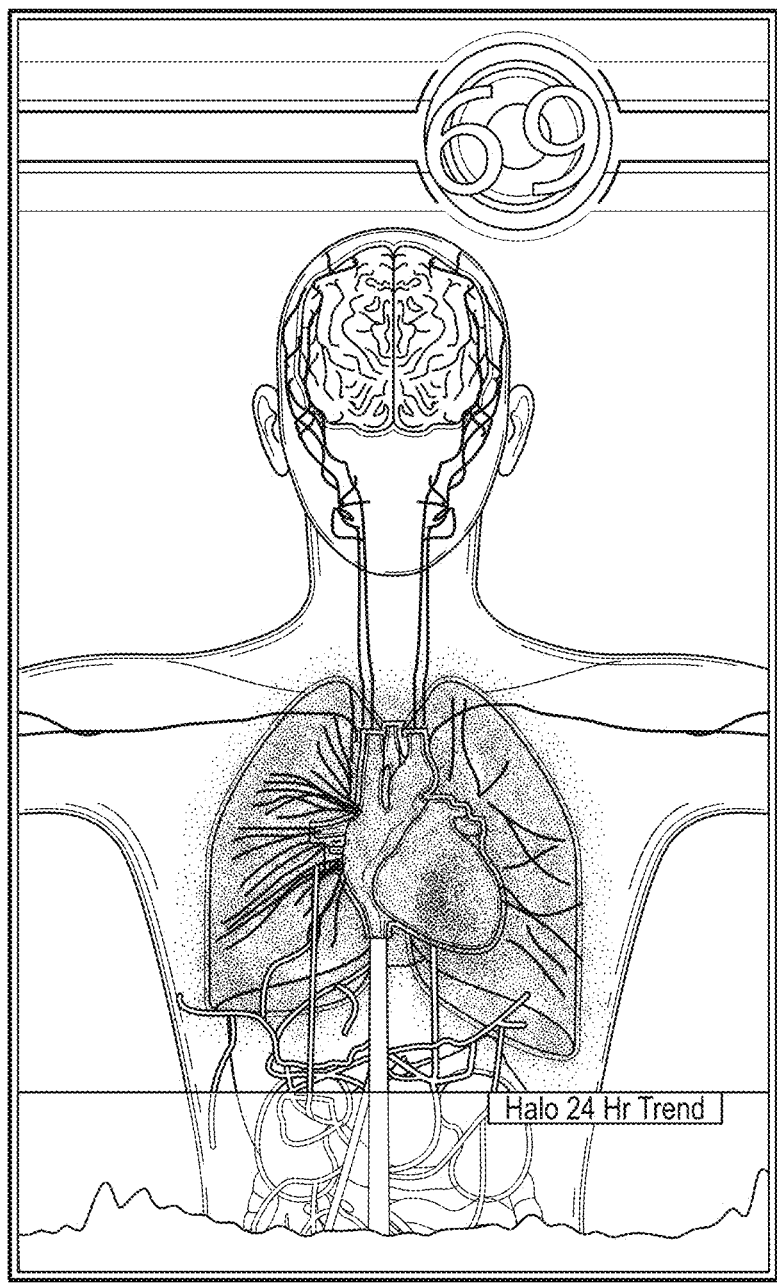

In FIG. 19F, additional organs, such as the kidneys are being monitored, but the respiratory system is not. In FIG. 19G, an alarming hear function is shown, and in FIG. 19H, an alarming circulatory system is being shown. FIG. 19I shows the wellness indication along with lungs, heart, brain and kidneys. FIG. 19J shows alarming lungs, heart, and circulatory system as well as the wellness indication. Moreover, FIG. 19J shows a severity contrast, such as, for example, the heart alarming red for urgent while the circulatory system alarms yellow for caution. An artisan will recognize other color schemes that are appropriate from the disclosure herein.

Figure 20A:
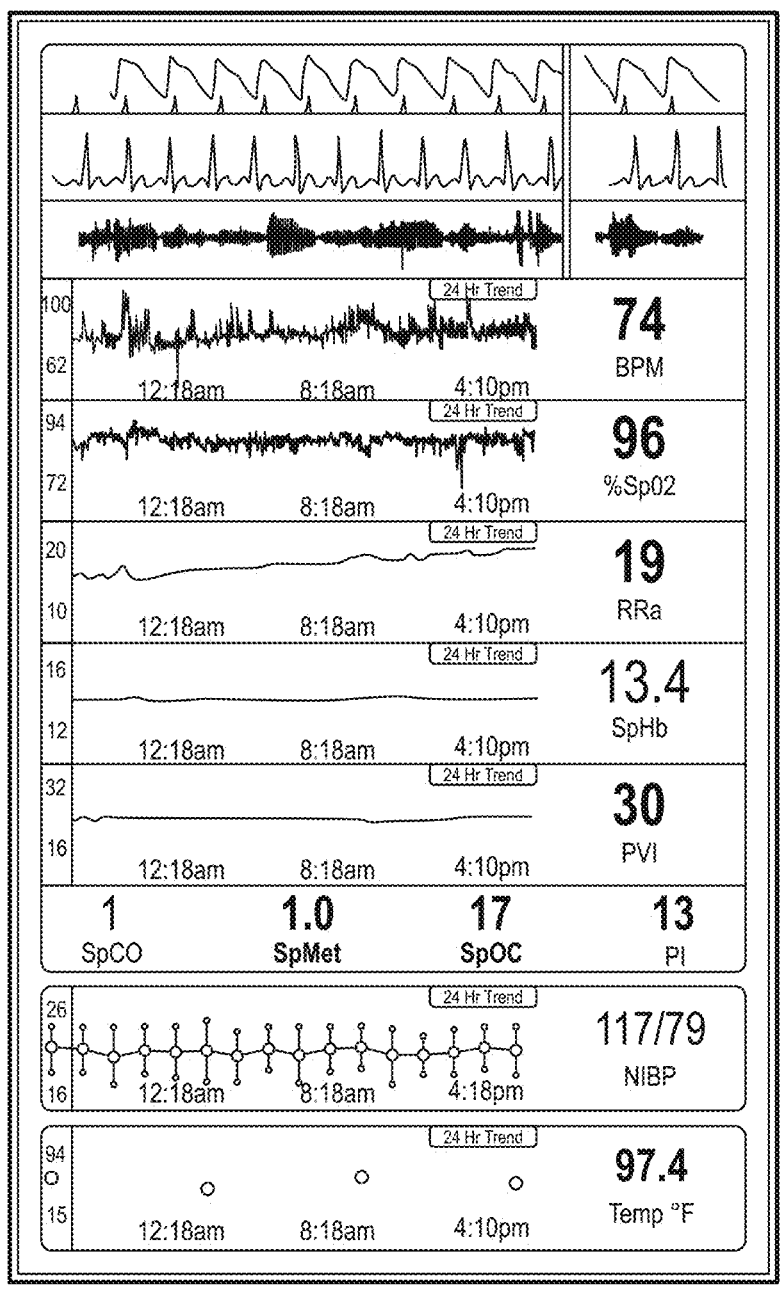
FIGS. 20A-20C illustrate exemplary displays of measurement data showing data separation and data overlap on a display of the hub of FIG. 1, respectively, according embodiments of the disclosure.
Figure 20B:
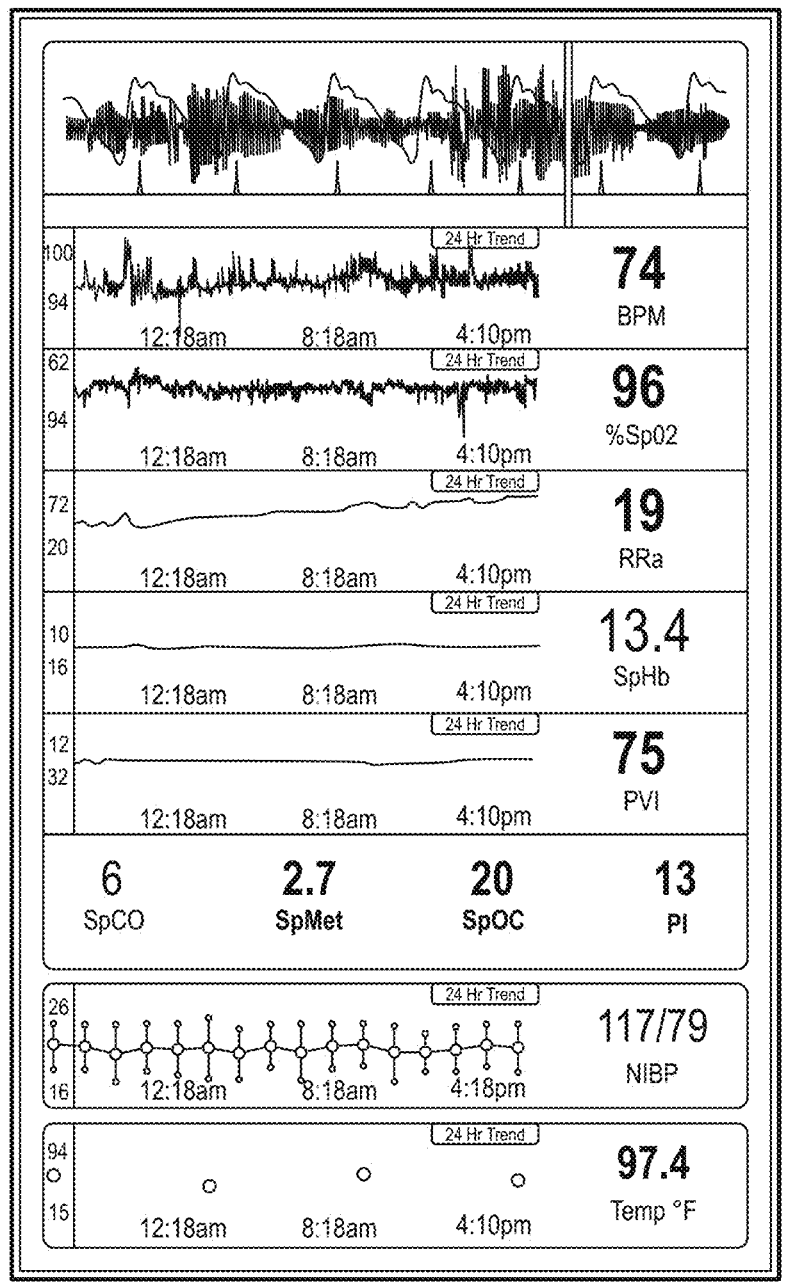
Figure 20C:
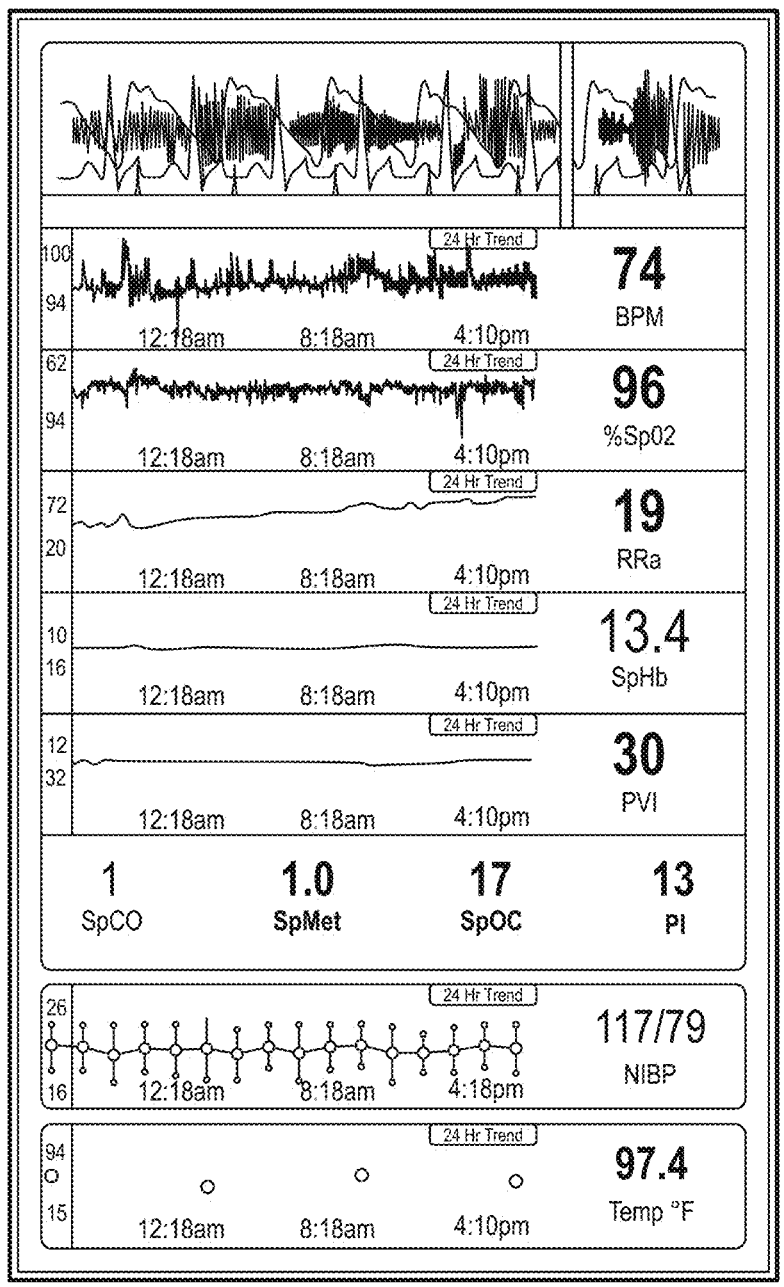
Figure 21A:
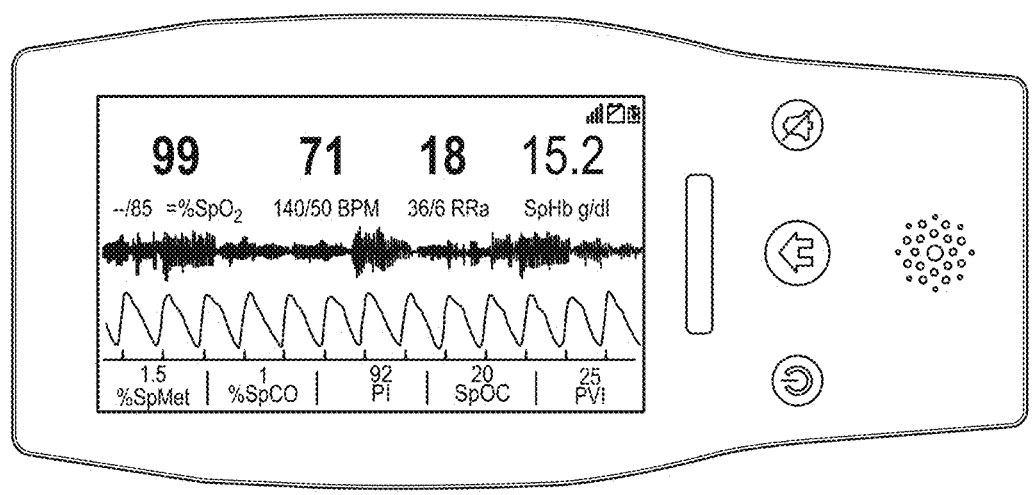
FIGS. 21A and 21B illustrate exemplary displays of measurement data showing data separation and data overlap on a display of the portable patient monitor of FIG. 1, respectively, according to embodiments of the disclosure.
Figure 21B:
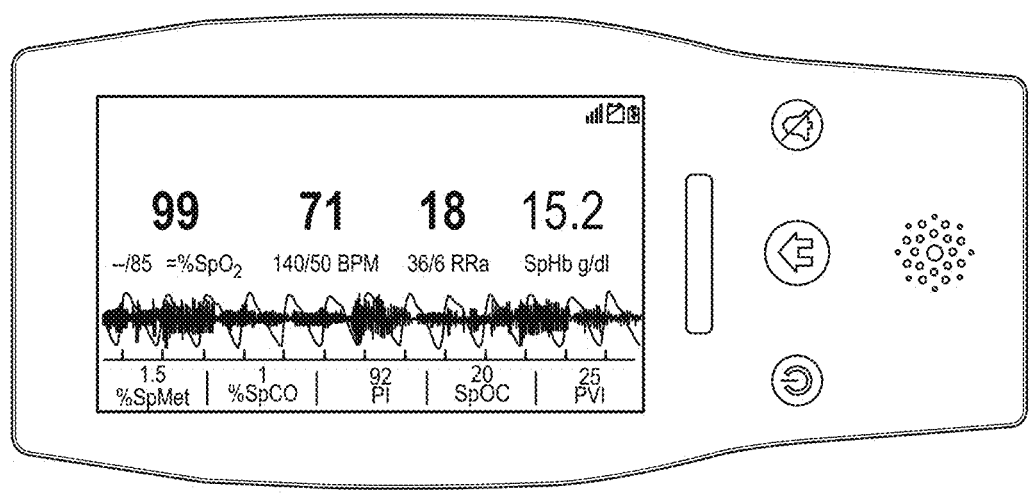

FIGS. 20A-20C illustrate exemplary displays of measurement data showing data separation and data overlap, respectively, according to embodiments of the disclosure. FIGS. 21A and 21B illustrate exemplary displays of measurement data also showing data separation and data overlap, respectively, according to embodiments of the disclosure.

For example, acoustic data from an acoustic sensor may advantageously provide breath sound data, while the plethysmograph and ECG or other signals can also be presented in separate waveforms (FIG. 20A, top of the screen capture). The monitor may determine any of a variety of respiratory parameters of a patient, including respiratory rate, expiratory flow, tidal volume, minute volume, apnea duration, breath sounds, riles, rhonchi, stridor, and changes in breath sounds such as decreased volume or change in airflow. In addition, in some cases a system monitors other physiological sounds, such as heart rate to help with probe off detection, heart sounds (S1, S2, S3, S4, and murmurs), and change in heart sounds such as normal to murmur or split heart sounds indicating fluid overload.

Providing a visual correlation between multiple physiological signals can provide a number of valuable benefits where the signals have some observable physiological correlation. As one example of such a correlation, changes in morphology (for example, envelope and/or baseline) of the plethysmographic signal can be indicative of patient blood or other fluid levels. And, these changes can be monitored to detect hypovolemia or other fluid-level related conditions. A pleth variability index may provide an indication of fluid levels, for example. And, changes in the morphology of the plethysmographic signal are correlated to respiration. For example, changes in the envelope and/or baseline of the plethysmographic signal are correlated to breathing. This is at least in part due to aspects of the human anatomical structure, such as the mechanical relationship and interaction between the heart and the lungs during respiration.

Thus, superimposing a plethysmographic signal and a respiratory signal (FIG. 20B) can give operators an indication of the validity of the plethysmographic signal or signals derived therefrom, such as a pleth variability index. For example, if bursts in the respiration signal indicative of inhalation and exhalation correlate with changes in peaks and valleys of the plethysmographic envelope, this gives monitoring personnel a visual indication that the plethysmographic changes are indeed due to respiration, and not some other extraneous factor. Similarly, if the bursts in the respiration signal line up with the peaks and valleys in the plethysmographic envelope, this provides monitoring personnel an indication that the bursts in the respiration signal are due to patient breathing sounds, and not some other non-targeted sounds (for example, patient non-breathing sounds or non-patient sounds).

The monitor may also be configured to process the signals and determine whether there is a threshold level of correlation between the two signals, or otherwise assess the correlation. However, by additionally providing a visual indication of the correlation, such as by showing the signals superimposed with one another, the display provides operators a continuous, intuitive and readily observable gauge of the particular physiological correlation. For example, by viewing the superimposed signals, users can observe trends in the correlation over time, which may not be otherwise ascertainable.

The monitor can visually correlate a variety of other types of signals instead of, or in addition to plethysmographic and respiratory signals. For example, FIG. 20C depicts a screen shot of another example monitoring display. As shown in the upper right portion of FIG. 20C, the display superimposes a plethysmographic signal, an ECG signal, and a respiration signal. In other configurations, more than three different types of signals may be overlaid onto one another.

In one embodiment, the hub 100 nothing provides an interface through which the user can move the signals together to overlay on one another. For example, the user may be able to drag the respiration signal down onto the plethysmographic signal using a touch screen interface. Conversely, the user may be able to separate the signals, also using the touch screen interface. In another embodiment, the monitor includes a button the user can press, or some other user interface allowing the user to overlay and separate the signals, as desired. FIGS. 21A and 21B show similar separation and joining of the signals.

In certain configurations, in addition to providing the visual correlation between the plethysmographic signal and the respiratory signal, the monitor is additionally configured to process the respiratory signal and the plethysmographic signal to determine a correlation between the two signals. For example, the monitor may process the signals to determine whether the peaks and valleys in the changes in the envelope and/or baseline of the plethysmographic signal correspond to bursts in the respiratory signal. And, in response to the determining that there is or is not a threshold level of correlation, the monitor may provide some indication to the user. For example, the monitor may provide a graphical indication (for example, a change in color of pleth variability index indicator), an audible alarm, or some other indication. The monitor may employ one or more envelope detectors or other appropriate signal processing componentry in making the determination.

In certain embodiments, the system may further provide an audible indication of the patient's breathing sounds instead of, or in addition to the graphical indication. For example, the monitor may include a speaker, or an earpiece (for example, a wireless earpiece) may be provided to the monitoring personnel providing an audible output of the patient sounds. Examples of sensors and monitors having such capability are described in U.S. Pat. Pub. No. 2011/0172561 and are incorporated by reference herein.

In addition to the above described benefits, providing both the acoustic and plethysmographic signals on the same display in the manner described can allow monitoring personnel to more readily detect respiratory pause events where there is an absence of breathing, high ambient noise that can degrade the acoustic signal, improper sensor placement, etc.

Figure 22A:
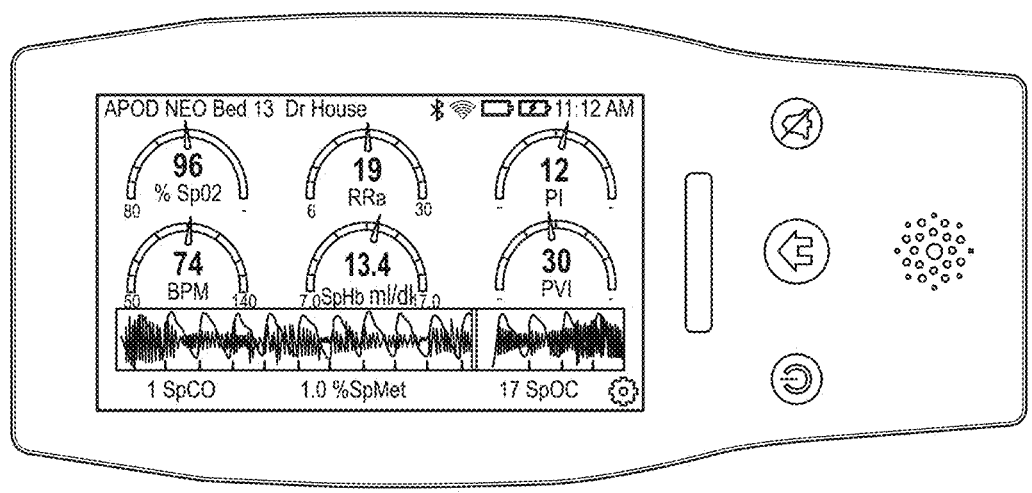
FIGS. 22A and 22B illustrate exemplary analog display indicia according to an embodiment of the disclosure.
Figure 22B:
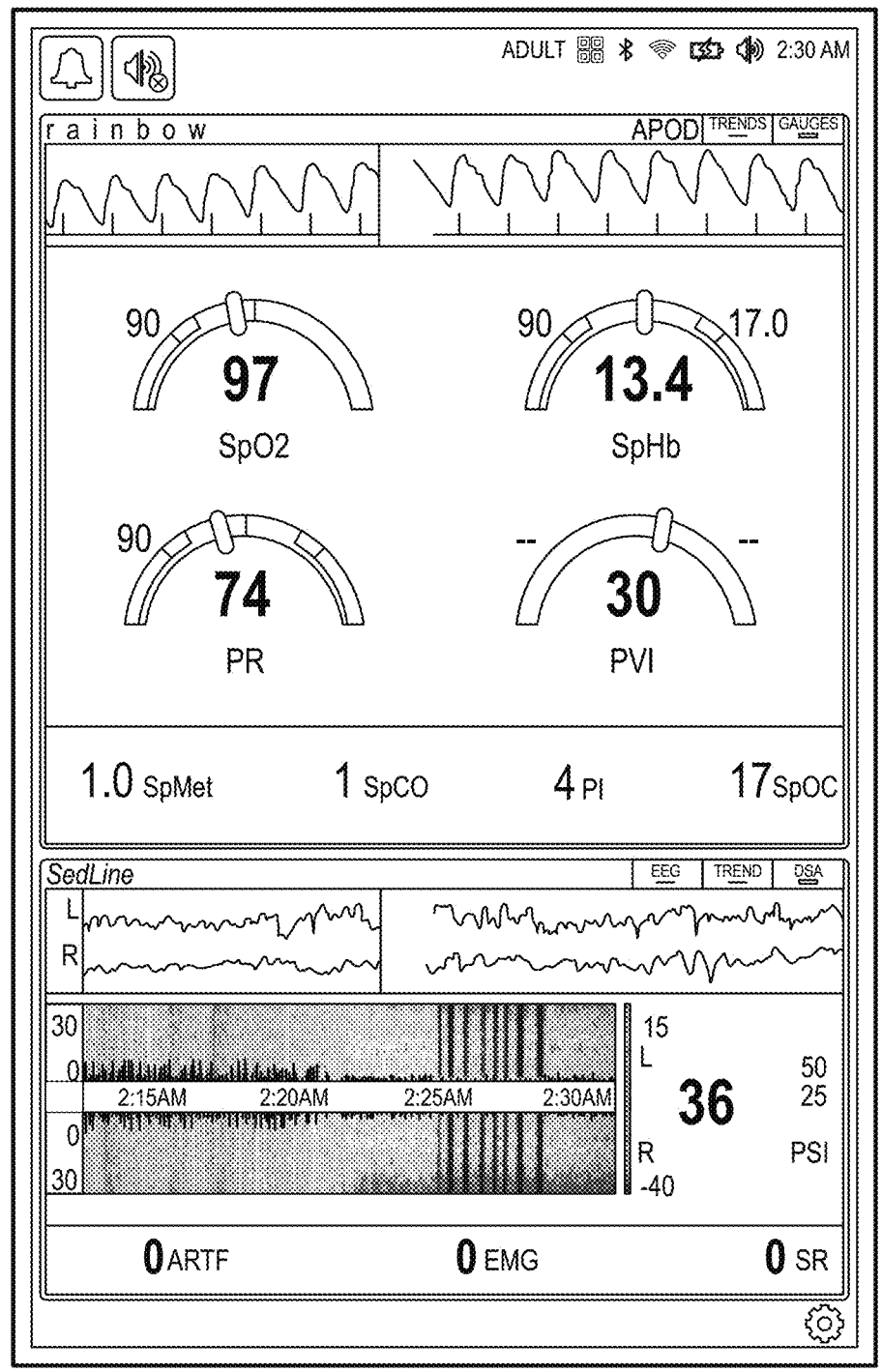

FIGS. 22A-22B illustrate exemplary analog display indicia, according to an embodiment of the disclosure. As shown in FIGS. 22A and 22B, the screen shots displays health indicators of various physiological parameters, in addition to other data. Each health indicator can include an analog indicator and/or a digital indicator. In embodiments where the health indicator includes an analog and a digital indicator, the analog and digital indicators can be positioned in any number of formations, such as side-by-side, above, below, transposed, etc. In the illustrated embodiment, the analog indicators are positioned above and to the sides of the digital indicators. As shown more clearly in FIG. 22B, the analog displays may include colored warning sections, dashes indicating position on the graph, and digital information designating quantitate information form the graph. In FIG. 22B, for example, the pulse rate PR graph shows that from about 50 to about 140 beats per minute, the graph is either neutral or beginning to be cautionary, whereas outside those numbers the graph is colored to indicate a severe condition. Thus, as the dash moves along the arc, a caregiver can readily see where in the range of acceptable, cautionary, and extreme the current measurements fall.

Each analog indicator of the health indicator can include a dial that moves about an arc based on measured levels of monitored physiological parameters. As the measured physiological parameter levels increase the dial can move clockwise, and as the measured physiological parameter levels decrease, the dial can move counter-clockwise, or vice versa. In this way, a user can quickly determine the patient's status by looking at the analog indicator. For example, if the dial is in the center of the arc, the observer can be assured that the current physiological parameter measurements are normal, and if the dial is skewed too far to the left or right, the observer can quickly assess the severity of the physiological parameter levels and take appropriate action. In other embodiments, normal parameter measurements can be indicated when the dial is to the right or left, etc.

In some embodiments, the dial can be implemented as a dot, dash, arrow, or the like, and the arc can be implemented as a circle, spiral, pyramid, or other shape, as desired. Furthermore, the entire arc can be lit up or only portions of the arc can be lit up based on the current physiological parameter measurement level. Furthermore, the arc can turn colors or be highlighted based on the current physiological parameter level. For example, as the dial approaches a threshold level, the arc and/or dial can turn from green, to yellow, to red, shine brighter, flash, be enlarged, move to the center of the display, or the like.

Different physiological parameters can have different thresholds indicating abnormal conditions. For example, some physiological parameters may upper a lower threshold levels, while others only have an upper threshold or a lower threshold. Accordingly, each health indicator can be adjusted based on the physiological parameter being monitored. For example, the SpO2 health indicator can have a lower threshold that when met activates an alarm, while the respiration rate health indicator can have both a lower and upper threshold, and when either is met an alarm is activated. The thresholds for each physiological parameter can be based on typical, expected thresholds and/or user-specified thresholds.

The digital indicator can provide a numerical representation of the current levels of the physiological parameter the digital indicator may indicate an actual level or a normalized level and can also be used to quickly assess the severity of a patient condition. In some embodiments, the display includes multiple health indicators for each monitored physiological parameter. In certain embodiments, the display includes fewer health indicators than the number of monitored physiological parameters. In such embodiments, the health indicators can cycle between different monitored physiological parameters.

Figure 23A:
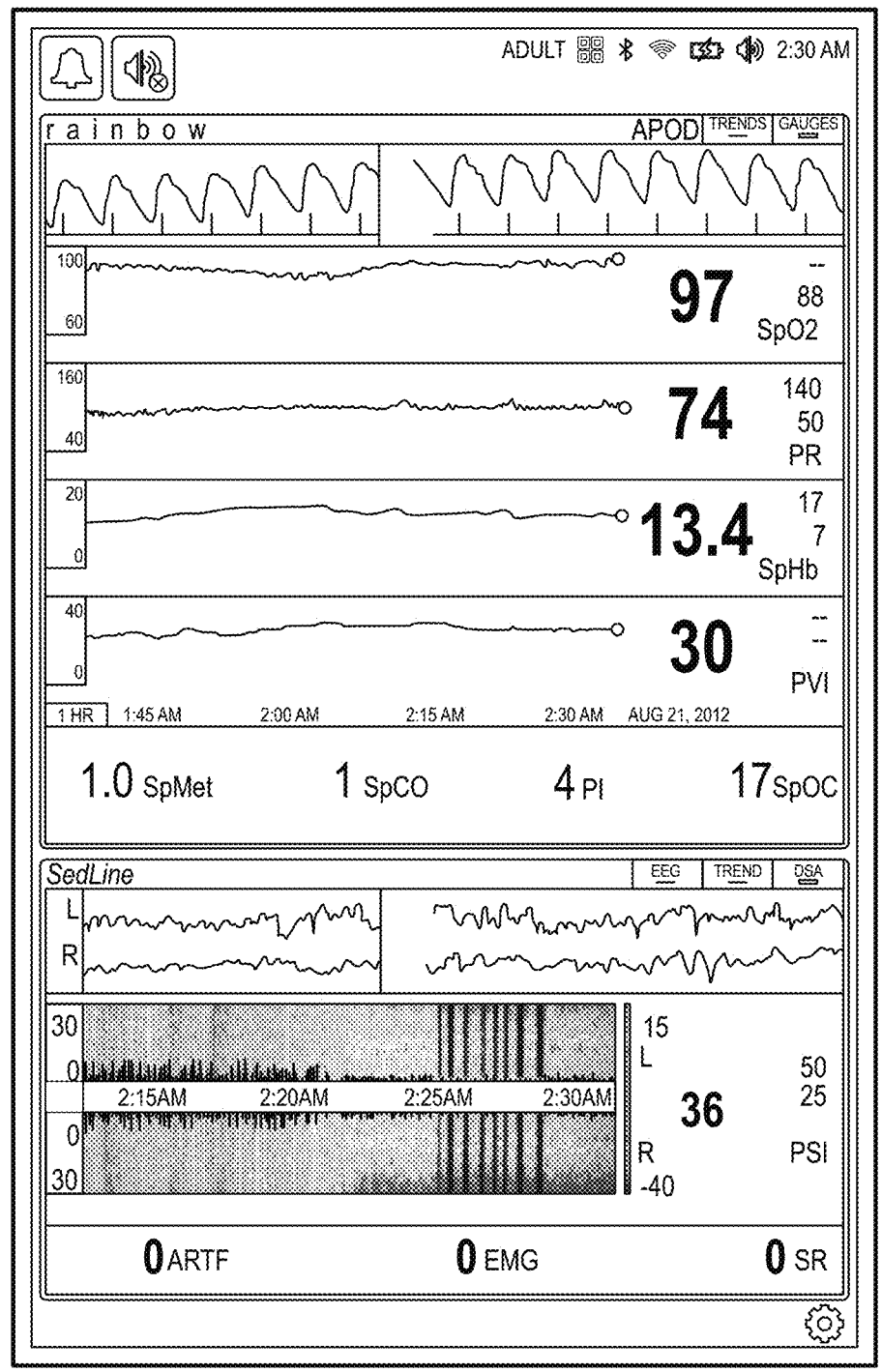
FIGS. 23A-23F illustrate exemplary displays of measurement data showing, for example, data presentation in FIGS. 23A-23D when a depth of consciousness monitor is connected to a channel port of the hub of FIG. 1, data presentation in FIG. 23E when temperature and blood pressure sensors communicate with the hub of FIG. 1 and data presentation in FIG. 23F when an acoustic sensor is also communicating with the hub of FIG. 1, according embodiments of the disclosure.
Figure 23B:
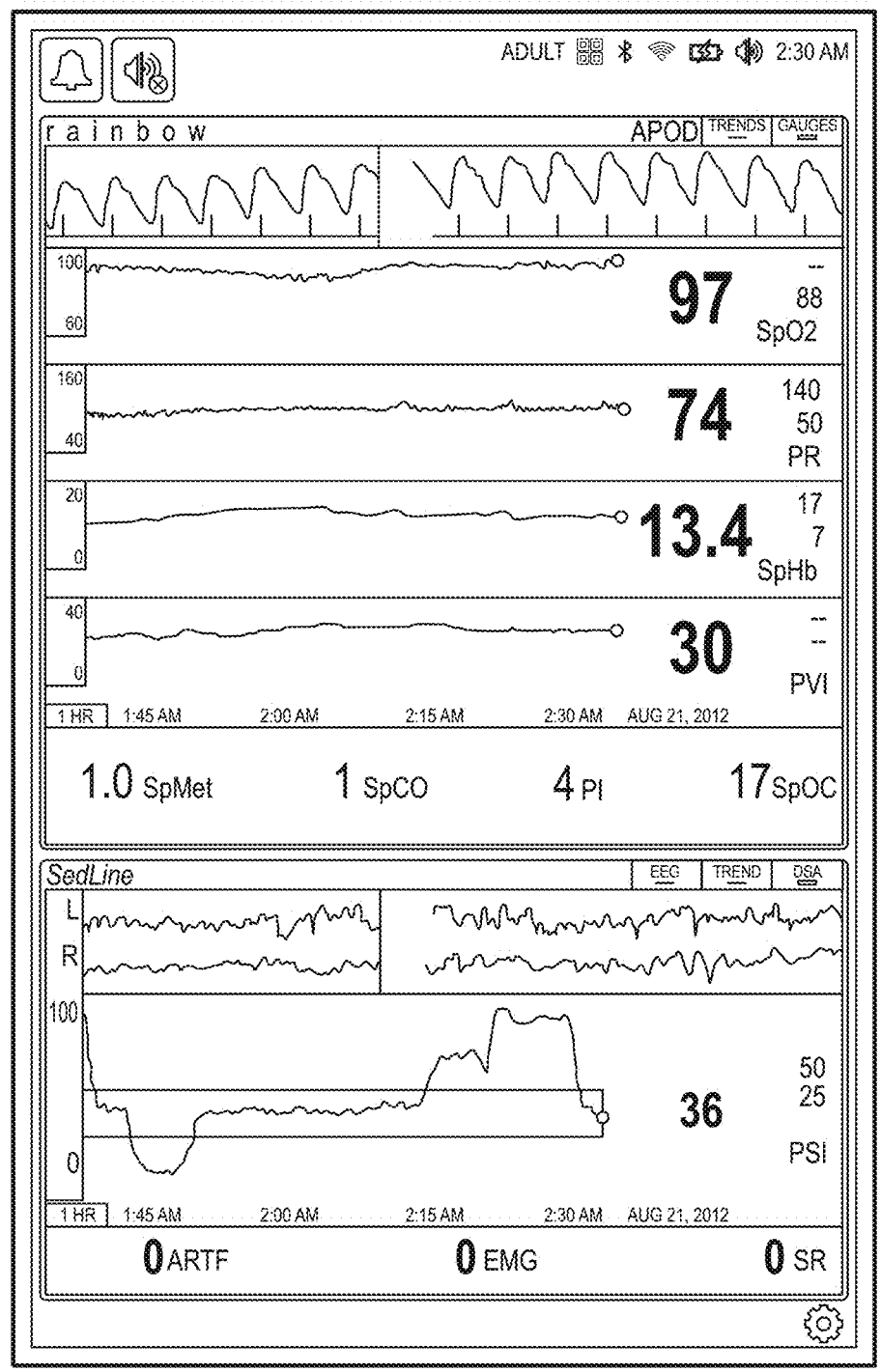
Figure 23C:
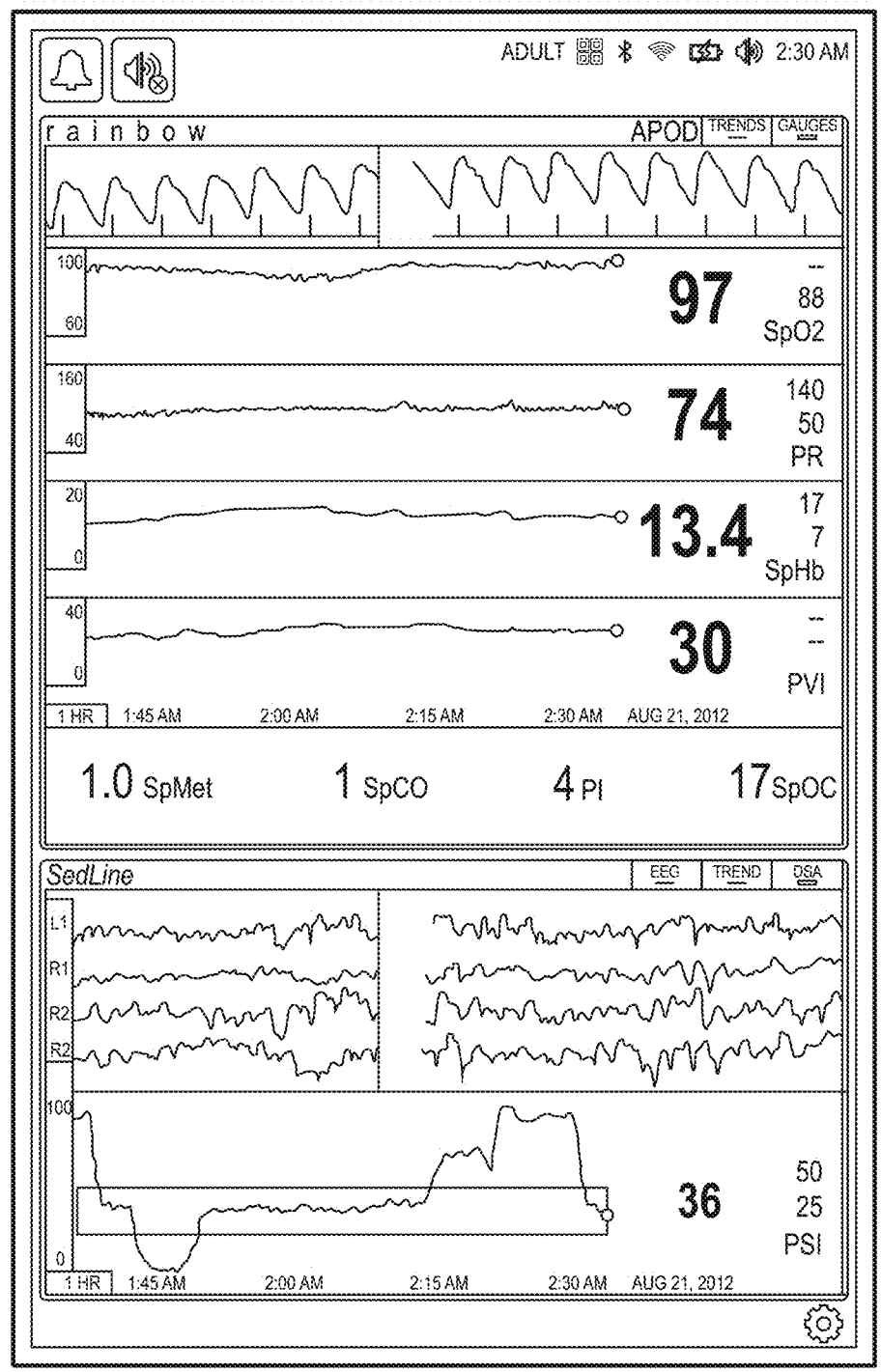
Figure 23D:
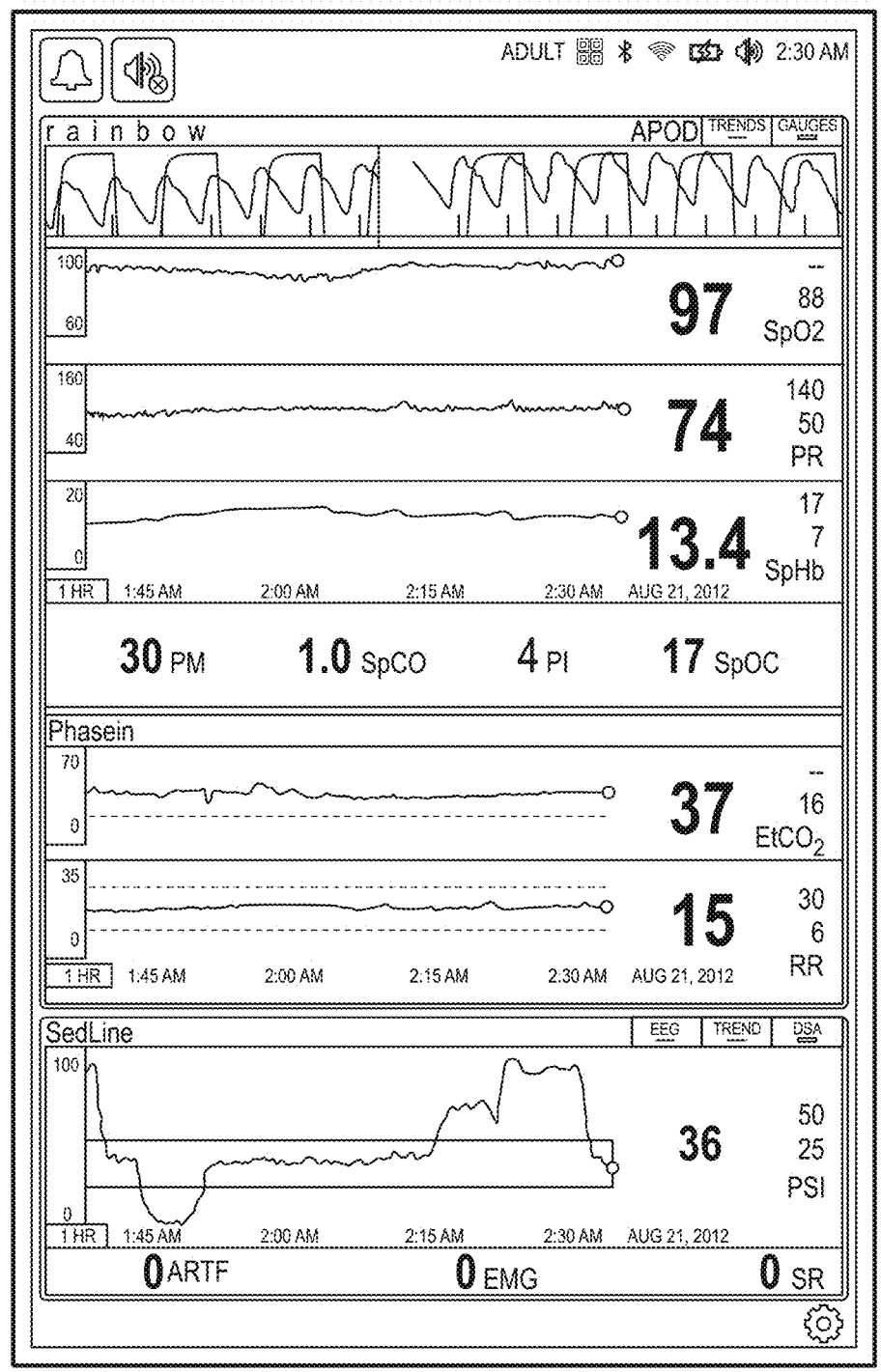
Figure 23E:
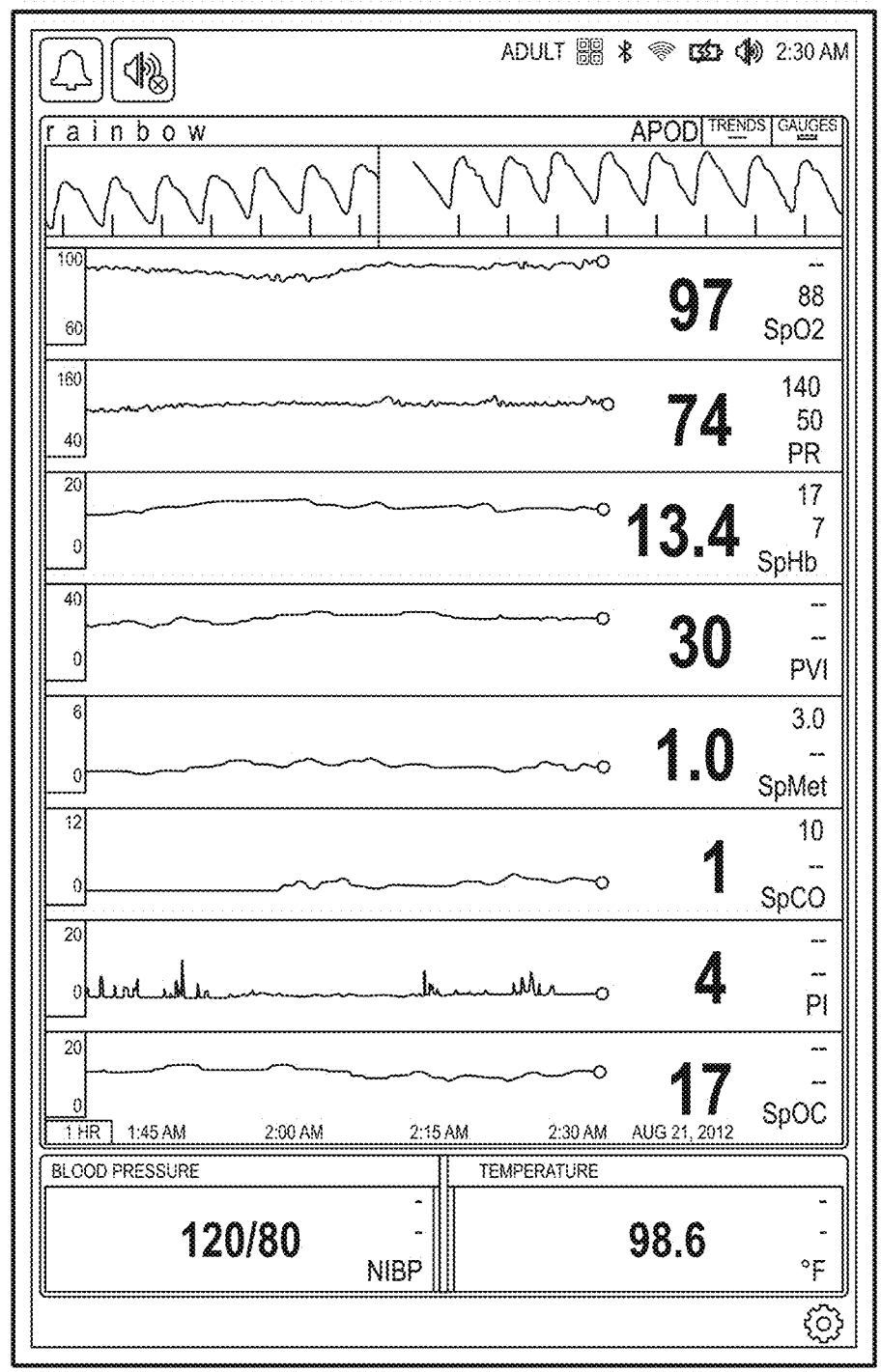
Figure 23F:
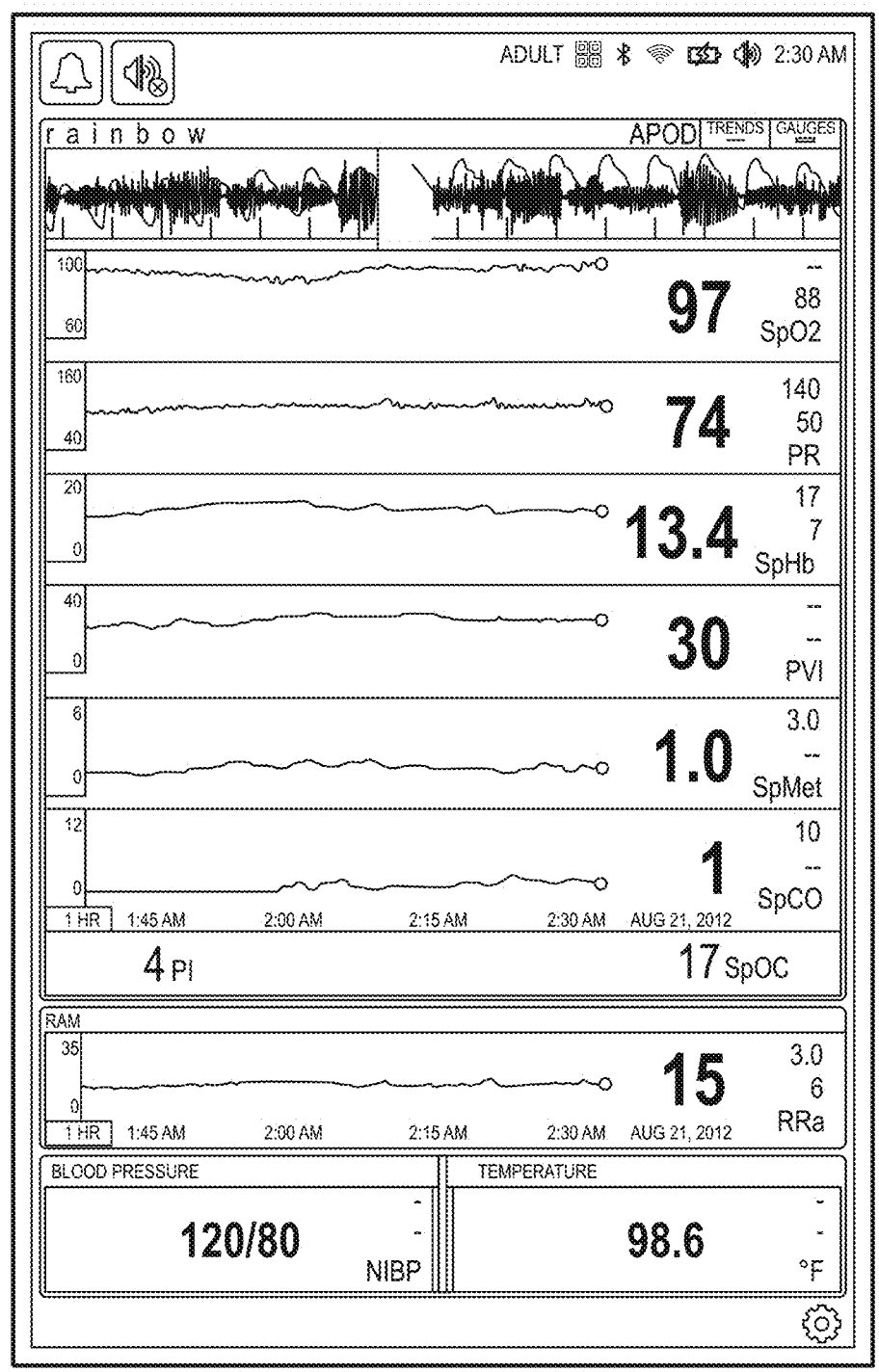

FIGS. 23A-23F illustrate exemplary displays of measurement data showing, for example, data presentation in FIGS. 23A-23D when a depth of consciousness monitor is connected to a channel port of the hub of FIG. 1. As shown in FIGS. 23A-23C, the hub 100 advantageously roughly bifurcates its display 104 to show various information from the, for example, SEDLine device, commercially available from Masimo Corp. of Irvine, Calif. In FIG. 23D, the hub 100 includes an attached PhaseIn device, commercially available by PHASEIN AB of Sweden, providing, for example, information about the patient's respiration. The hub 100 also includes the SEDLine information, so the hub 100 has divided the display 104 appropriately. In FIG. 23E, temperature and blood pressure sensors communicate with the hub of FIG. 1 and the hub 100 creates display real estate appropriate for the same. In FIG. 23F, an acoustic sensor is also communicating with the hub of FIG. 1, as well as the forgoing blood pressure and temperature sensor. Accordingly, the hub 100 adjust the display real estate to accommodate the data from each attached device.

The term "and/or" herein has its broadest least limiting meaning which is the disclosure includes A alone, B alone, both A and B together, or A or B alternatively, but does not require both A and B or require one of A or one of B. As used herein, the phrase "at least one of" A, B, "and" C should be construed to mean a logical A or B or C, using a non-exclusive logical or.

The term "plethysmograph" includes it ordinary broad meaning known in the art which includes data responsive to changes in volume within an organ or whole body (usually resulting from fluctuations in the amount of blood or air it contains).

III. Additional Monitoring Environment Embodiments

Figure 24:
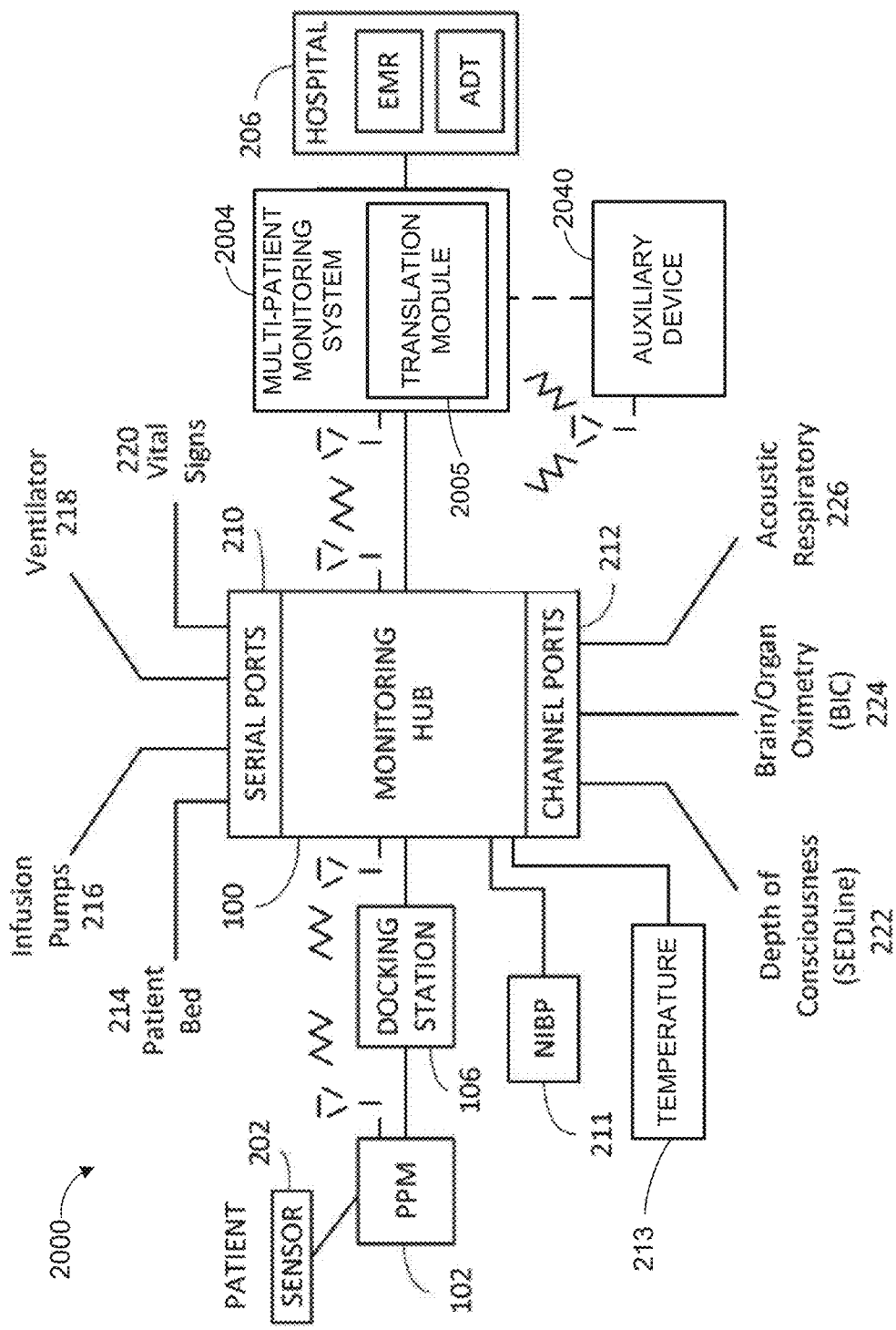
FIG. 24 illustrates another embodiment of a monitoring environment including the hub of FIG. 1.

FIG. 24 illustrates another embodiment of a monitoring environment 2000 including the hub 100 of FIG. 1. The monitoring environment 2000 may include all the features of the monitoring environment 200 of FIG. 2, as well as any of the other features described above. In addition, the monitoring environment 2000 depicts another embodiment of the multi-patient monitoring system 204, namely, the multi-patient monitoring system (MMS) 2004. The MMS 2004 includes a translation module 2005 that can receive serial data, translate the serial data into a format recognizable by the monitoring hub 100, and provide the serial data to the monitoring hub 100 (among possibly other devices). Also shown is an auxiliary device 2040 that may communicate with the MMS 2004, the monitoring hub 100, or the PPM 102, wired or wirelessly.

As described above, the hub 100 may receive serial data from a variety of medical equipment, including the patient's bed 214, infusion pumps 216, a ventilator 218, and other vital signs monitors 220. The hub 100 can pass serial data from these sources on to the MMS 2004. As described above, the MMS 2004 may then store the serial data in a caregiver backend system 206 such as an EMR system or ADT system.

The serial data may have a known data type defined, for example, based on the SDK described above. As the serial data is supplied from the medical equipment, the hub 100 or the MMS 2004 can readily identify the data type and frequencies. The example data types may include: (1) waveform data or high frequency data, (2) parameter data, and (3) event data. Advantageously, in some embodiments, rather than having a huge database which includes various data types, a database may be designed based on the known data type. The data acquisition process may be different based on the data type. For example, when the data is a waveform data or high frequency data, the hub 100 or the MMS 2004 may not attempt to recover losses as the data comes in from the medical equipment. Rather, any data received can be streamed and stored to the database as it is acquired. Parameter data can come in (to the hub 100 or the MMS 2004) at a certain frequency (for example, every 1 Hz). As a result, the hub 100 or the MMS 2004 can take a snapshot of the data at that frequency. Event data, such as patient alarms (and optionally parameter data associated with the alarms), can be generated in response to a certain event. The event data may include a timestamp which may be associated with the time the data is taken or the time of the event. Additionally or alternatively, the hub 100 or the MMS 2004 can also receive audio or video data associated with a patient.

The medical equipment providing this serial data may use a variety of different proprietary protocols, messaging infrastructure, and the like that may not be natively recognizable by the hub 100. Accordingly, the hub 100 may not have native capability to read parameter values or other data from this medical equipment, and as a result, may not have the capability to display parameter values or other data from these devices. Advantageously, however, the translation module 2005 at the MMS 2004 can receive serial data from these devices, translate the serial data into a format recognizable by the monitoring hub 100, and provide the serial data to the monitoring hub 100. The monitoring hub 100 can then read parameter values and other data from the translated information and output these values or data to a display, such as any of the displays described above.

In an embodiment, the translation module 2005 applies one or more translation rules to the serial data to translate or transform the serial data from one format to another format. The serial data may be formatted according to a Health Level Seven ("HL7") protocol in one embodiment. The HL7 protocol has been developed to provide a messaging framework for the communication of clinical messages between medical computer systems and devices. However, the HL7 standard is quite flexible and merely provides a framework of guidelines. Consequently, medical devices or clinical computer systems that are all HL7-compliant may still be unable to communicate with each other. For example, the medical equipment 214-220 may each implement a version of the HL7 protocol, but these implementations may be different from an HL7 protocol implemented by the monitoring hub 100. Accordingly, the monitoring hub 100 may not be able to parse or read messages from the medical equipment 214-220, even though both use the HL7 standard. Further, the translation module 2005 may translate between different implementations of a common standard other than the HL7 protocol implemented by the hub 100 and medical equipment 214-220 in some embodiments.

In addition to translating between different implementations of a common electronic medical communication protocol (for example, different formatting of HL7 messages), the translation module 2005 can also translate between input and output messages adhering to different communication protocols. In some embodiments, the translation module 2005 is capable of responding to and translating messages from, for example, one medical communication protocol to a separate medical communication protocol. For example, the translation module 2005 can facilitate communication between messages sent according to the HL7 protocol, the ISO 11073 protocol, other open protocols, or proprietary protocols. Accordingly, the translation module 2005 can translate an input message sent according to the HL7 protocol to an output message according to a different protocol, or vice-versa. In certain embodiments, the translation module 2005 can implement any of the translation features described below in greater detail under the section entitled "Translation Module Embodiments," as well as further in U.S. application Ser. No. 14/032,132, filed Sep. 19, 2013, titled "Medical Monitoring System," the disclosure of which is hereby incorporated by reference in its entirety.

Advantageously, in certain embodiments, the translation module 2005 can pass translated serial data back to the hub 100 or PPM 102. Since the translated data is in a format readable by the hub 100 or PPM 102, the hub 100 or PPM 102 can output the data from the medical equipment 214-220 on the display of the hub 100 or PPM 102. In addition, the translation module 2005 can provide the translated data to devices other than the hub 100, including clinician devices (such as cell phones, tablets, or pagers) and an auxiliary device 2040 that will be described below. Moreover, since the serial data provided by the medical equipment 214-220 may include alarm notifications, the translation module 2005 can pass these alarm notifications to the hub 100 or PPM 102. The hub 100 or PPM 102 can therefore generate visual or audible alarms responsive to these alarm notifications. Further, the translation module 2005 can provide the alarm notifications to clinician devices, for example, over a hospital network or wide area network (such as the Internet). In addition, the translation module 2005 can provide the alarm notifications to the auxiliary device 2040.

The translation module 2005 is shown as implemented in the MMS 2004 because it may be beneficial to maintain and update the translation rules of the translation module 2005 in a single location. However, in other embodiments, the translation module 2005 may also be (or instead be) implemented in the hub 100 or PPM 102. Accordingly, the hub 100 or PPM 102 can access an internal translation module 2005 to translate serial data for output to the display of the hub 100 or PPM 102.

The auxiliary device 2040 can be a computing device having physical computer hardware, a display, and the like. For example, the auxiliary device 2040 may be a handheld computing device used by a clinician, such as a tablet, laptop, cellphone or smartphone, personal digital assistant (PDA), a wearable computer (such as a smart watch or glasses), or the like. The auxiliary device 2040 may also be simply a display device, such as a computer monitor or digital television. In an embodiment, the auxiliary device 2040 provides second screen functionality for the hub 100, PPM 102, or MMS 2004. As such, the auxiliary device 2040 can communicate wirelessly or through a wired connection with the hub 100, MMS 2004, or PPM 102.

As a second screen device, the auxiliary device 2040 can depict a copy of at least a portion of the display of the hub 100 (or the PPM 102) or a different version of the hub 100 (or the PPM 102) display. For instance, the auxiliary device 2040 can receive physiological parameter data, trend data, or waveforms from the hub 100, PPM 102, or MMS 2040 and display the parameter data, trend data, or waveforms. The auxiliary device 2040 can output any information available to the hub 100, PPM 102, or MMS 2004. One use of the auxiliary device 2040 is as a clinician device usable by a clinician to view data from the hub 100, PPM 102, or MMS 2004 while away from a patient's room (or even while in a patient's room). A clinician can use the auxiliary device 2040 to view more detailed information about physiological parameters than is displayed on the hub 100 or PPM 102 in an embodiment (see, for example, FIG. 39). For instance, the auxiliary device 2040 may include zoom functionality or the like that enables a clinician to zoom into trends or waveforms to more closely inspect parameter activity.

One example reason for copying at least a portion of the display of the hub 100 or PPM 102 is to enable different clinicians to have the same view of the data during a surgical procedure. In some surgical procedures, for instance, two anesthesiologists monitor a patient, one anesthesiologist monitoring the brain function and brain oxygenation of the patient, while the other monitors peripheral oxygenation of the patient. A brain sensor, such as has been described above, may be attached to the patient and provide brain monitoring and oxygenation data that is output to the hub 100 or the PPM 102 for presentation to the first anesthesiologist. A finger or toe/foot optical sensor can also be attached to the patient and output data to the hub 100 or PPM 102. For example, the optical sensor can be attached to the body of the patient (such as, for example, on the finger, toe, ear lobe, forehead, and other locations). An light emitter can emit light through the body tissue and a detector can receive the light attenuated by the body tissue to measure data of a patient's blood parameters. The hub 100 or PPM 102 can transmit this data to the auxiliary device 2040, which the second anesthesiologist can monitor to observe oxygenation in the patient's peripheral limbs. The second anesthesiologist may also need to know the oxygenation at the brain to help interpret the seriousness or lack thereof of poor peripheral oxygenation values. However, in many surgical procedures, a curtain or screen is placed over the patient as part of the procedure, blocking the second anesthesiologist's view of the hub 100 or PPM 102. Accordingly, the hub 100 or PPM 102 can output a copy of at least a portion of its display to the auxiliary device 2040 so that the second anesthesiologist can monitor brain function or oxygenation.

In one embodiment, the auxiliary device has a larger display area than the display of the hub 100. For instance, the hub 100 may have a relatively smaller display, such as about 10 inches, while the auxiliary device 2040 may be a television monitor or the like that has a 40 inch or larger display (although any size display may be used for the auxiliary device 2040). In an embodiment, the auxiliary device 2040 as a television can include a hardware module that includes a processor, memory, and a wireless or wired networking interface or the like. The processor can execute programs from the memory, including programs for displaying physiological parameters, trends, and waveforms on the display of the television. Since a television monitor is larger than embodiments of the hub 100, the television monitor version of the auxiliary device 2040 can display more fine detail of patient waveforms and trends in some embodiments (see, for example, FIG. 39).

In another embodiment, the auxiliary device 2040 may display one portion of any of the displays described herein while the hub 100 displays another portion thereof. For instance, the auxiliary device 2040 may display any of the anatomical graphics described above with respect to FIGS. 19A-19J, while the hub 100 displays any of the parameter displays described above with respect to FIGS. 20A-23F (or vice versa). Likewise, the auxiliary device 2040 may display the translated data received from the translation module 2005 while the hub 100 displays channel data (or vice versa). In another embodiment, the auxiliary device 2040 can display both translated data and channel data (see, for example, FIG. 38).

In still other embodiments, the auxiliary device 2040 can perform at least some processing of physiological parameters, including any of the functionality of the monitoring hub 100. For instance, the auxiliary device 2040 may include the translation module 2005 and perform the features thereof.

Figure 25:
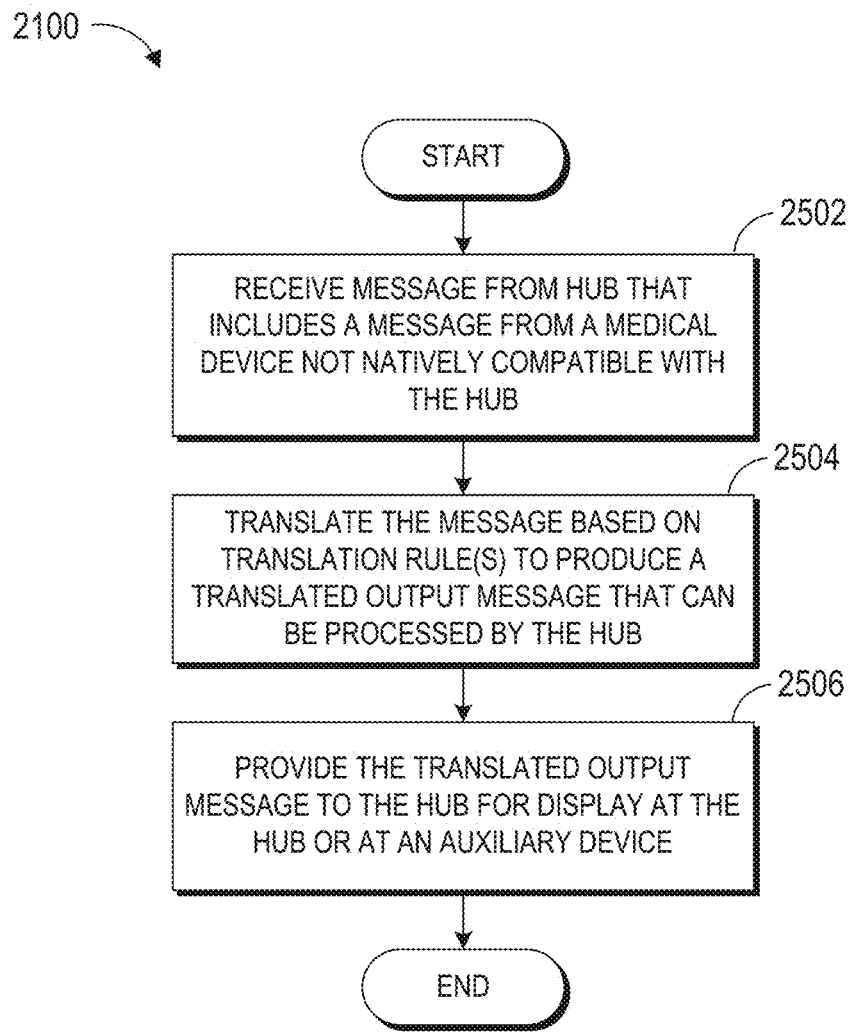
FIG. 25 illustrates an embodiment of a translation message handling process.

FIG. 25 illustrates an embodiment of a translation message handling process 2100. The process 2100 can be implemented by the translation module 2005 described above or by any other computing system. In an embodiment, at block 2502, the translation module 2005 receives a message from the hub 100 (or PPM 102) that includes a message from a medical device not natively compatible with the hub 100 (or PPM 102). At block 2504, the translation module 2005 translates the message based on one or more translation rules to produce a translated output message that can be processed by the hub 100 (or PPM 102). At block 2506, the translation module provides the translated output message to the hub 100 for display at the hub 100 (or PPM 102) or at an auxiliary device 2040. The hub 100 (or PPM 102) may route the translated data to the auxiliary device 2040, or the auxiliary device 2040 may receive the translated data directly from the translation module 2005.

For example, in one embodiment, a first medical device having digital logic circuitry receives a physiological signal associated with a patient from a physiological sensor, obtains a first physiological parameter value based on the physiological signal, and outputs the first physiological parameter value for display. The first medical device can also receive a second physiological parameter value from a second medical device other than the first medical device, where the second physiological parameter value is formatted according to a protocol not used by the first medical device, such that the first medical device is not able to process the second physiological parameter value to produce a displayable output value. The first medical device can pass the physiological parameter data from the first medical device to a separate translation module, receive translated parameter data from the translation module at the first medical device, where the translated parameter data is able to be processed for display by the first medical device, and output a second value from the translated parameter data for display. The first medical device may be, for example, the hub 100, PPM 102, or MMS 2004, and the second medical device may be the infusion pump 216 or ventilator 218 or the like.

FIGS. 26-38 and 46-71 illustrate additional example hub displays, including displays of measurement data. Each of these displays may be implemented by the auxiliary device 2040, although similar displays may also be output on the hub 100 (or PPM 102) directly. The example Figures shown are depicted as being implemented for a tablet computer that includes touchscreen functionality. Touchscreen functionality is optional and be replaced by other suitable input devices, such as keyboards, mice, track wheels, and the like.

Figure 26:
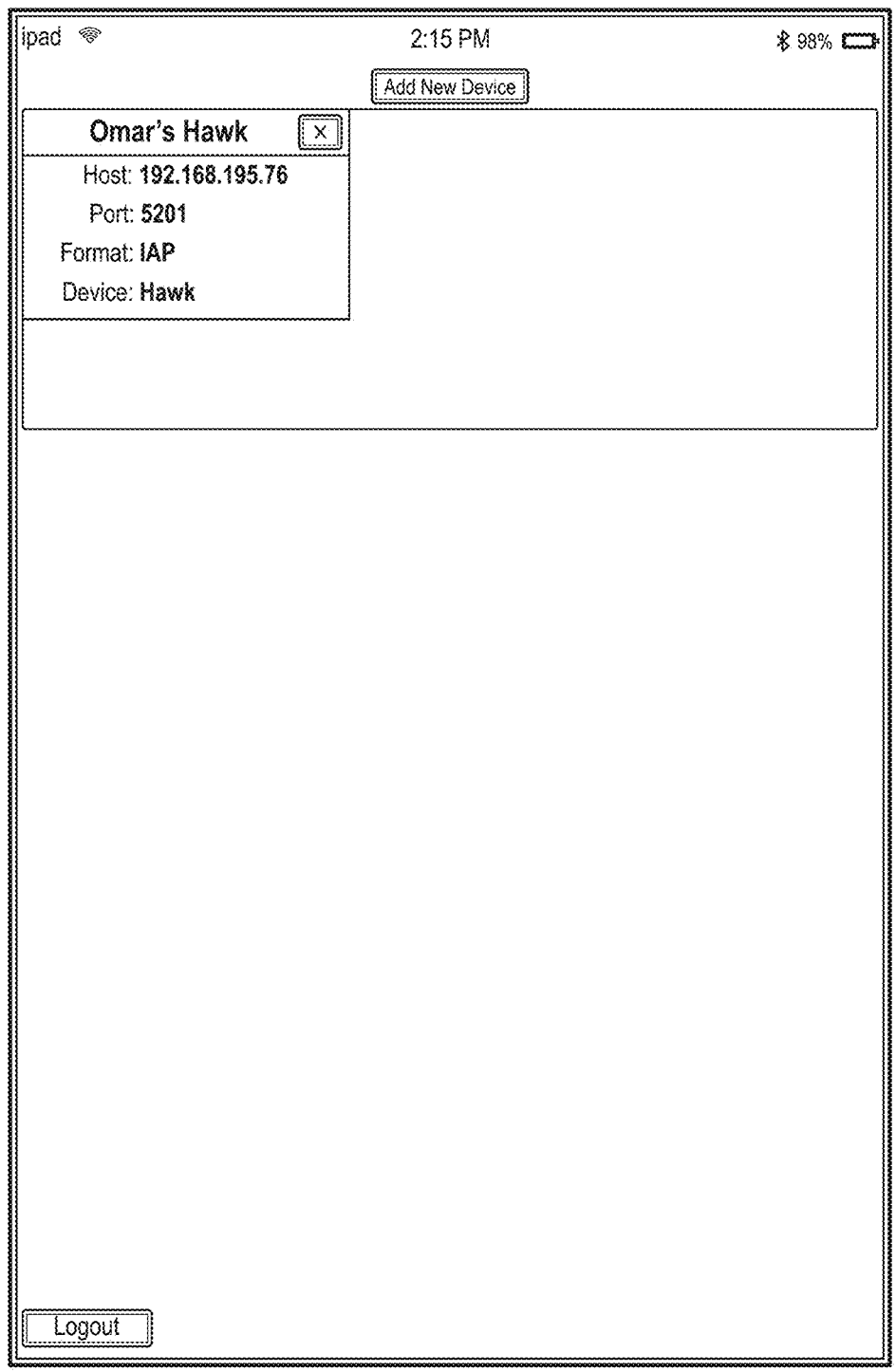
FIGS. 26-39 illustrate additional example hub displays, including displays of measurement data.

Turning to FIG. 26, the user interface shown depicts a device connected to the auxiliary device 2040. The device shown is "Omar's Hawk," which can be an embodiment of the monitoring hub 100. The auxiliary device 2040 is connected wirelessly to the hub 100 in this embodiment so as to receive data from the hub 100. The auxiliary device could also connect wirelessly to the MMS 2004 or PPM 102 in other embodiments.

Figure 27:
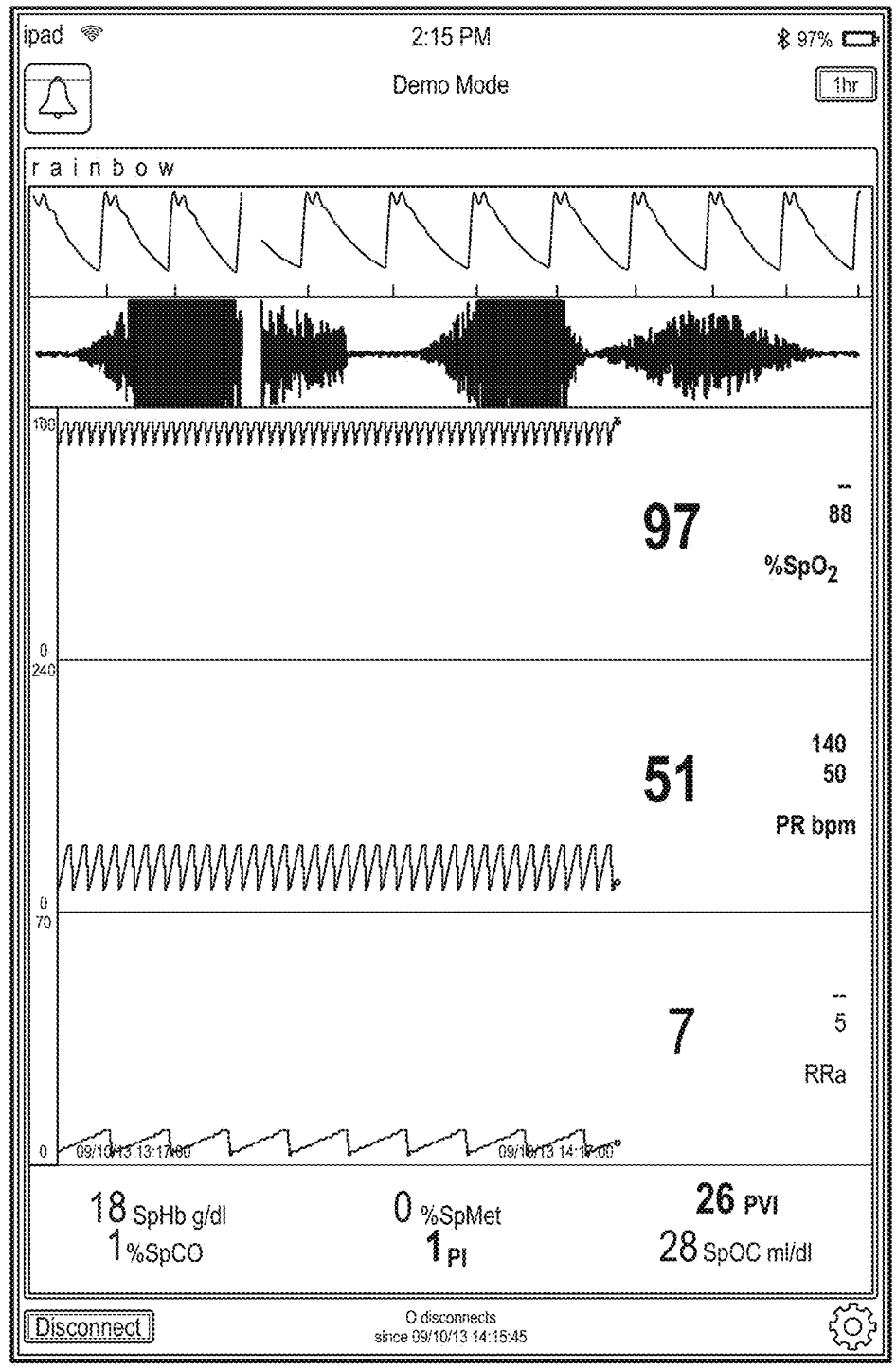
Figure 28:
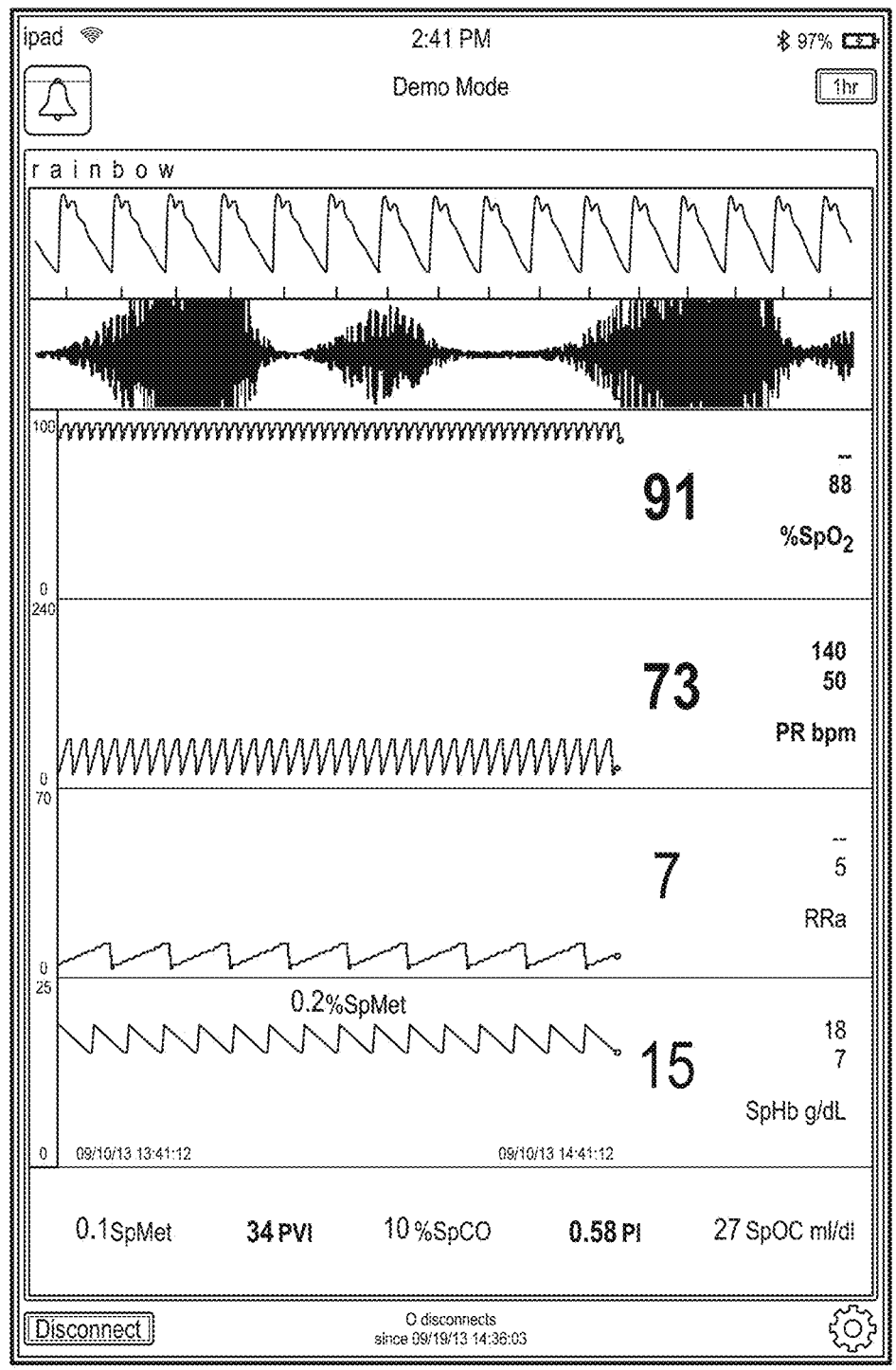

FIG. 27 depicts a default parameter view on the auxiliary device 2040. Parameter values are shown together with waveforms in an upper portion of the display, and other parameters (such as SpHb, SpMet, PVI, etc.) are shown at the bottom of the display without their corresponding waveforms. Any of these parameters at the bottom of the display may be dragged and dropped onto the upper portion of the display to cause their waveforms to be shown. For instance, FIG. 28 depicts a similar display as in FIG. 27 except that the SpHb parameter has been dragged and dropped onto the upper portion of the display, causing the SpHb waveform and additional details on alarm limits (18 and 7) to be shown. Similarly, FIG. 29 shows the same display as FIG. 28 except that the SpMet parameter has been dragged and dropped on the upper portion of the display, causing its waveform and alarm limit (3) to be shown.

Figure 29:
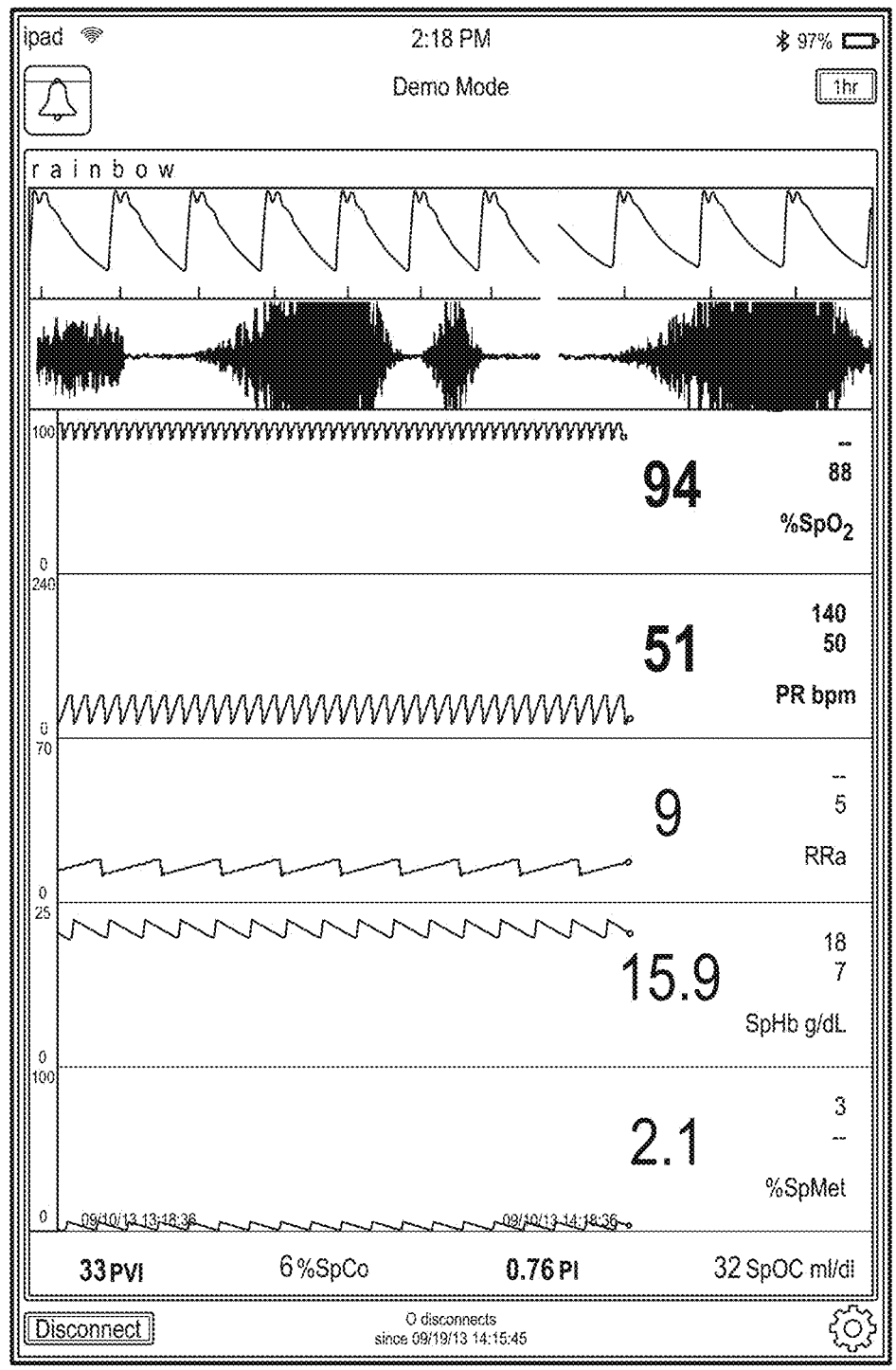
Figure 30:
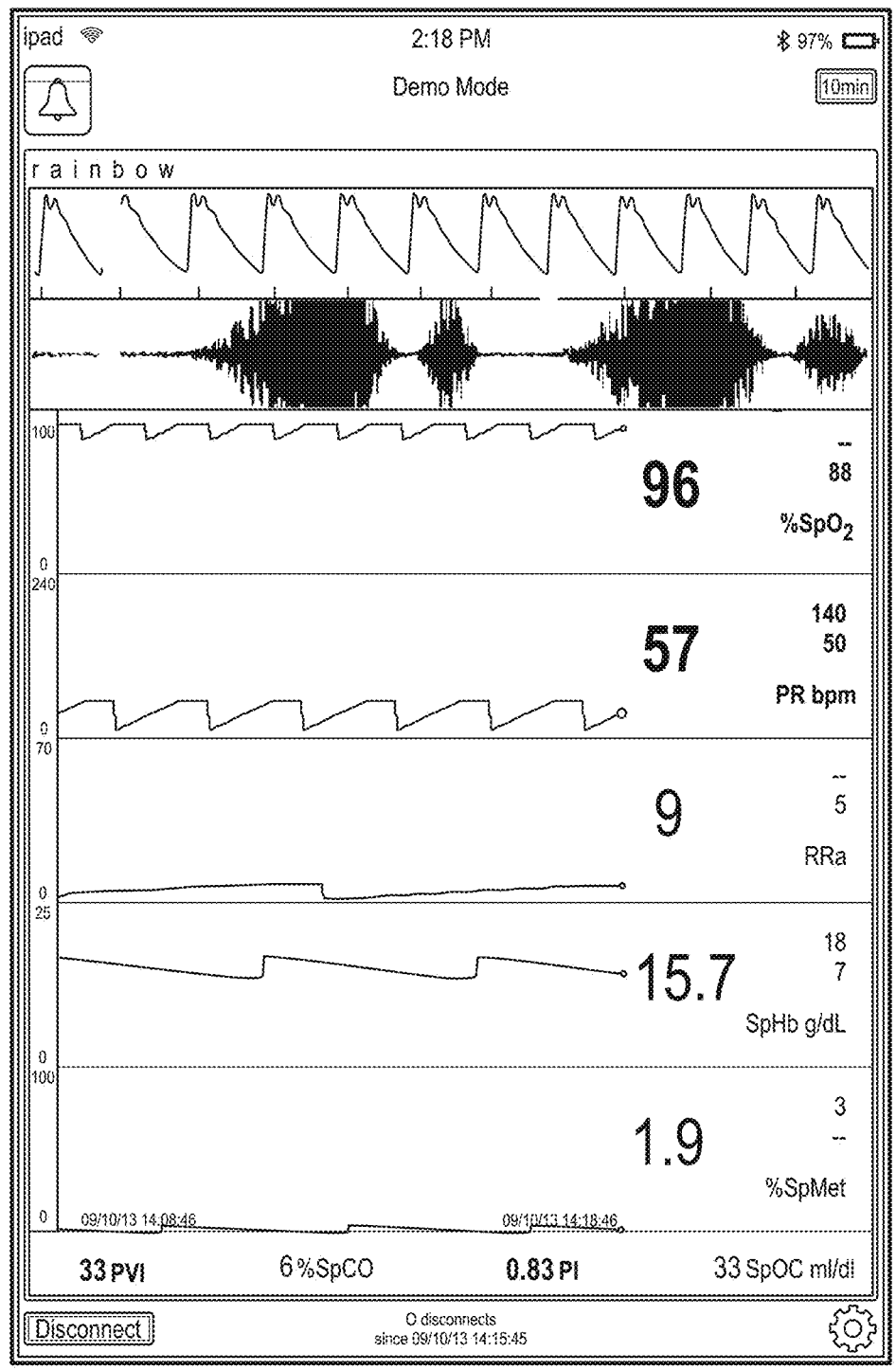

In each of the displays of FIGS. 27-29, a time window button is shown in the upper right corner. This time window button says "1 hr" in FIGS. 27-29 but may be selected by a user to change the time window, which can affect the window of trend or waveform data shown in the display. A user selection of this time window button and change to a 10 minute window is shown in FIG. 30. As can be seen, the waveforms in FIG. 30 are shown in a smaller window of time than in the previous Figures.

Figure 31:
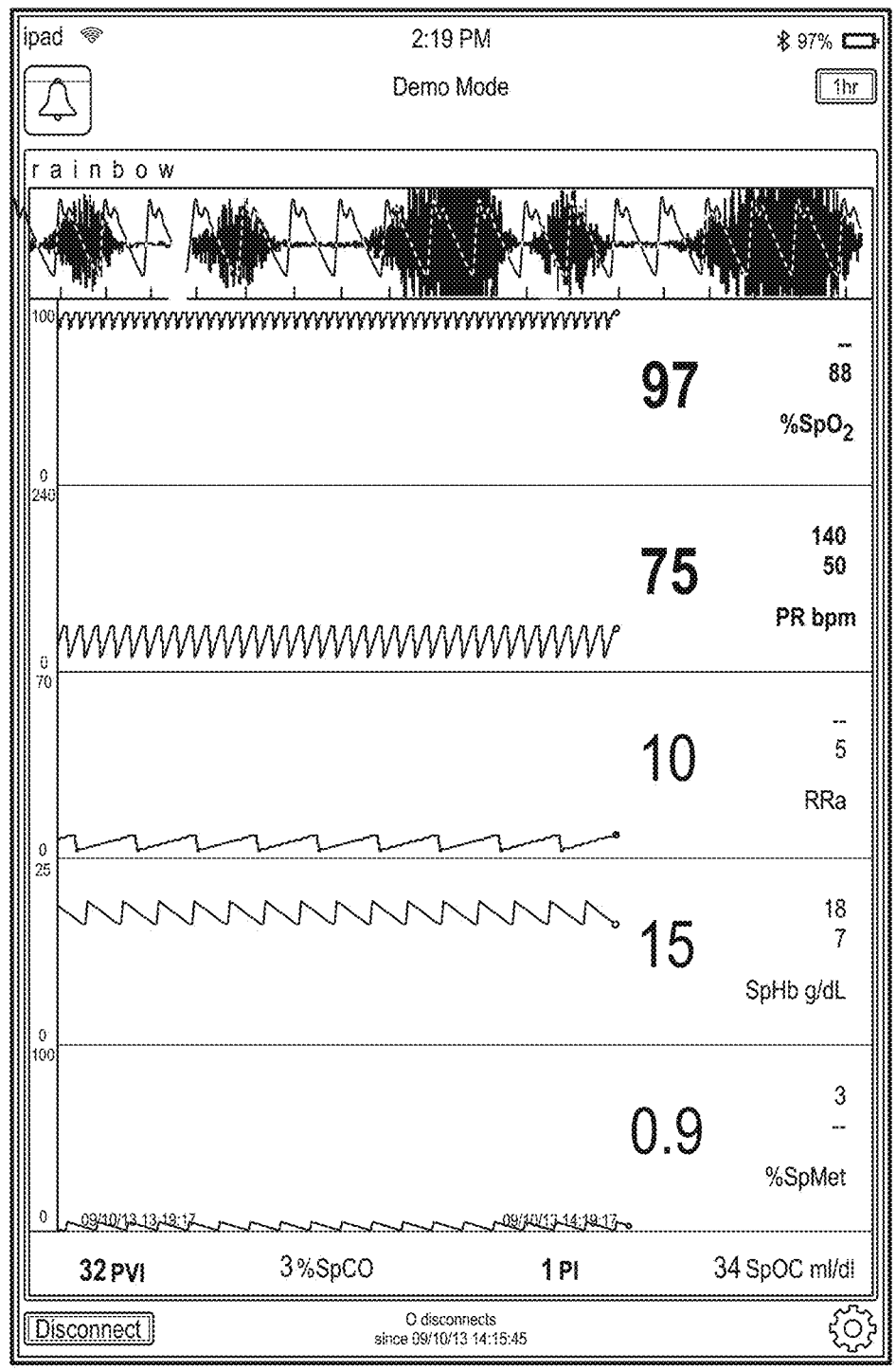
Figure 32:
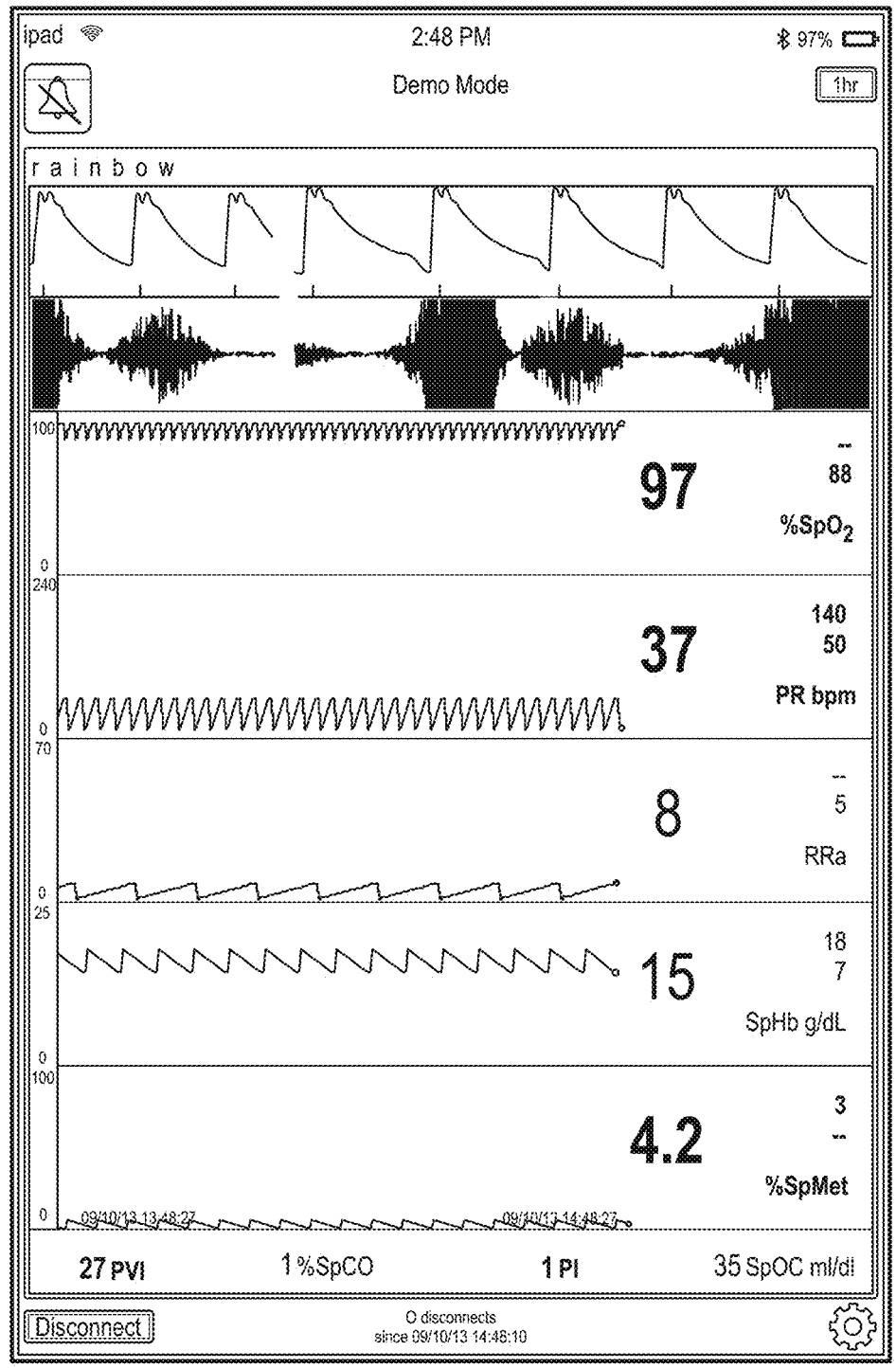

FIG. 31 shows another version of the display of FIG. 29 with stacked waveforms, including a stacked SpO2 and respiratory waveform, similar to other stacked waveforms described elsewhere herein. FIG. 32 shows a similar display to FIG. 29 with the pulse rate (PR) and SpMet (methemoglobin) parameters highlighted as being in alarm condition. The alarm condition can be represented as a red box around the parameter values and waveforms in an embodiment, or with red transparency coloring at least a portion of the box. The red box or transparency may also flash in an embodiment, and an audible alarm may sound. Other ways to represent an alarm condition are used in other embodiments.

Figure 33:
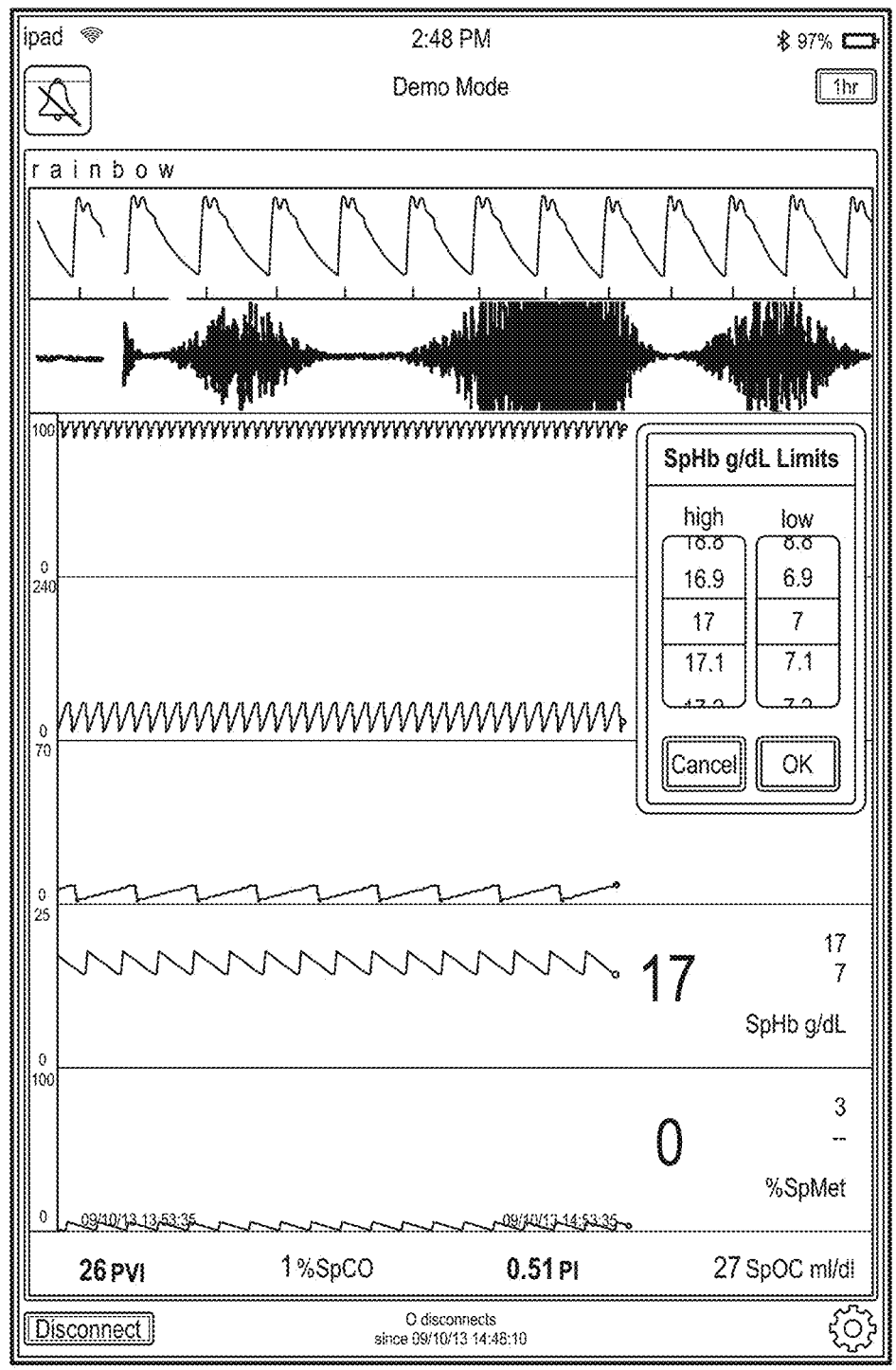

FIG. 33 shows a popup interface that enables a user to adjust alarm limits for a parameter (in this embodiment, SpHb or total hemoglobin). The popup interface includes scroll wheels that allow a user to quickly scroll among and select possible parameter limit values.

Figure 34:
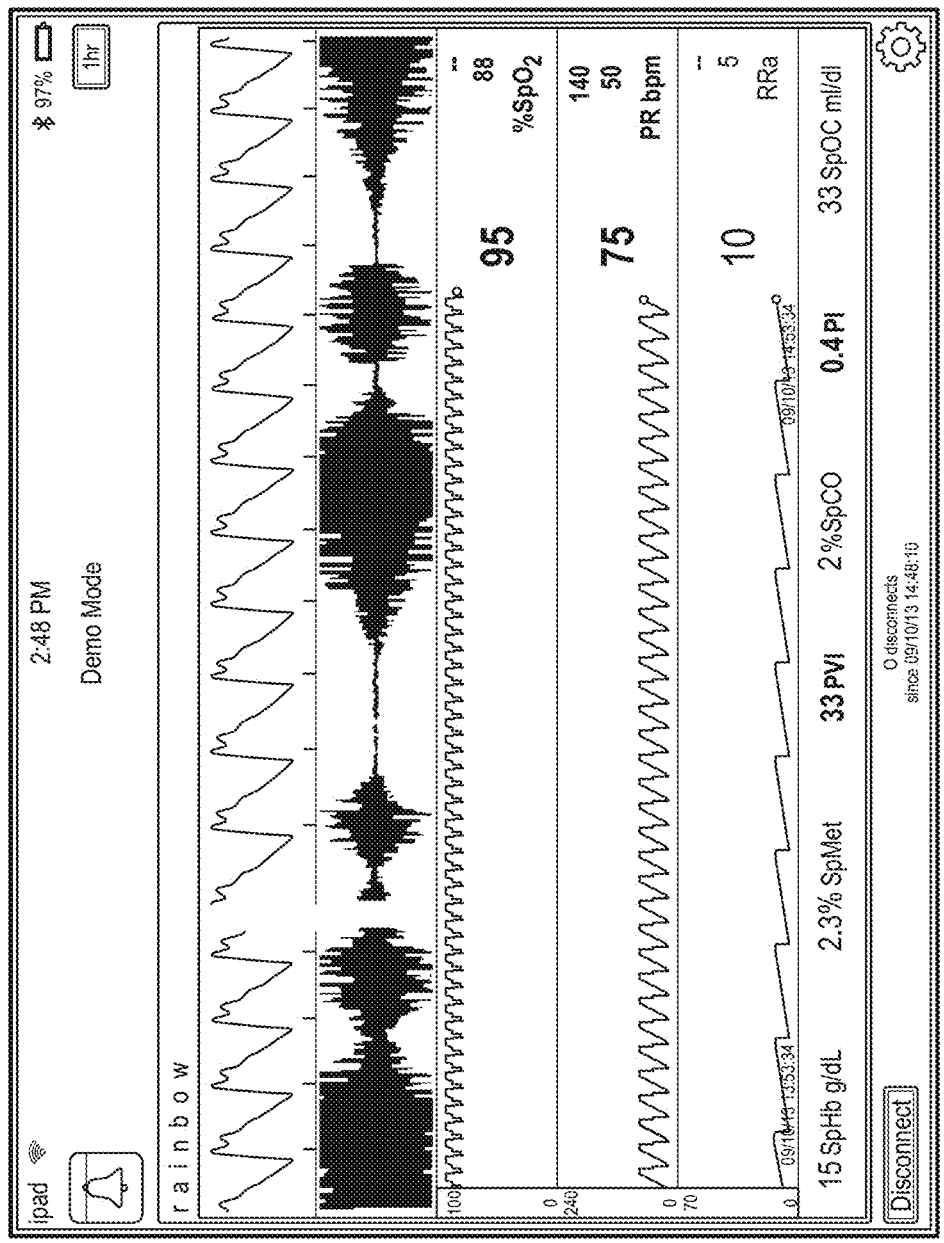
Figure 35:
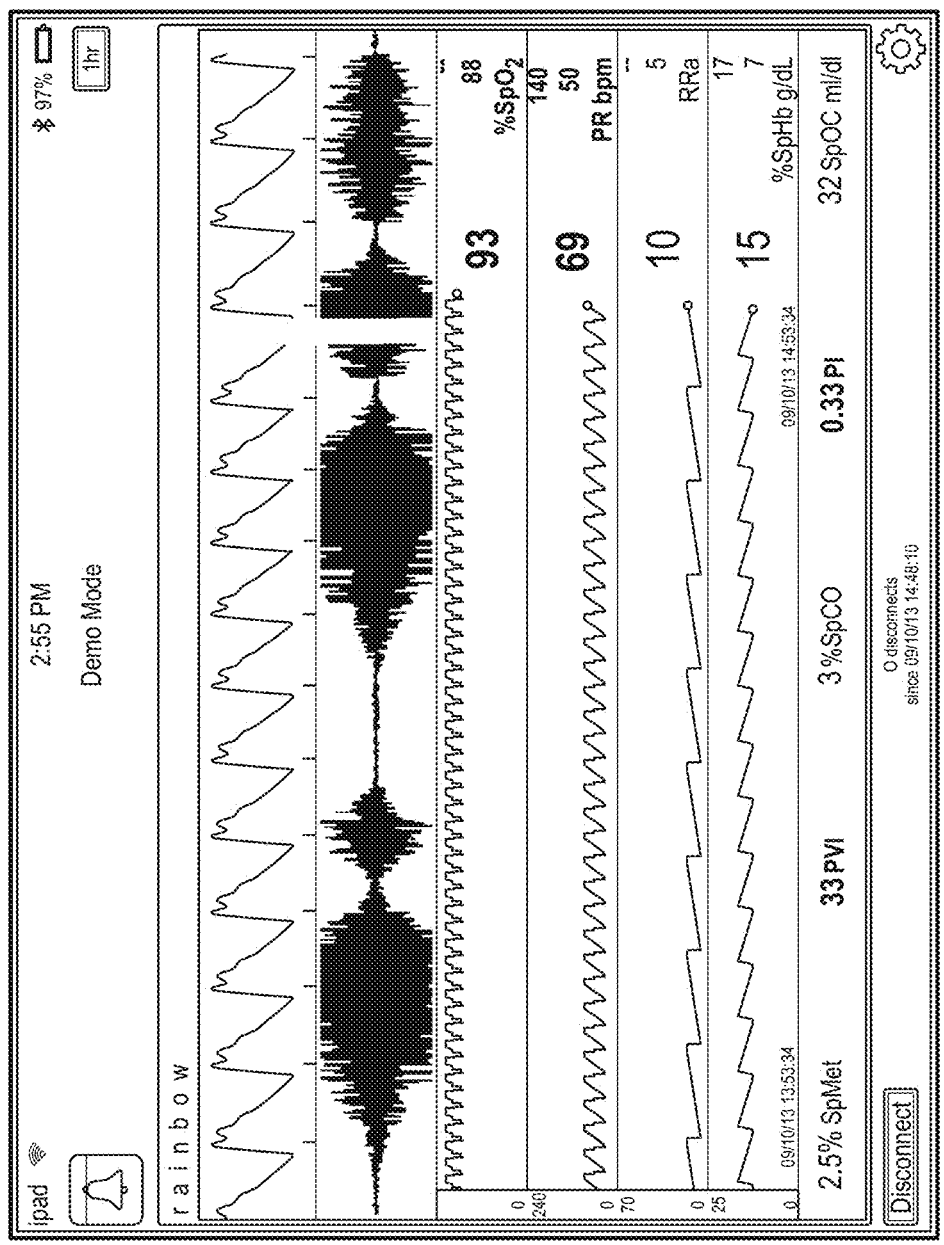
Figure 36:
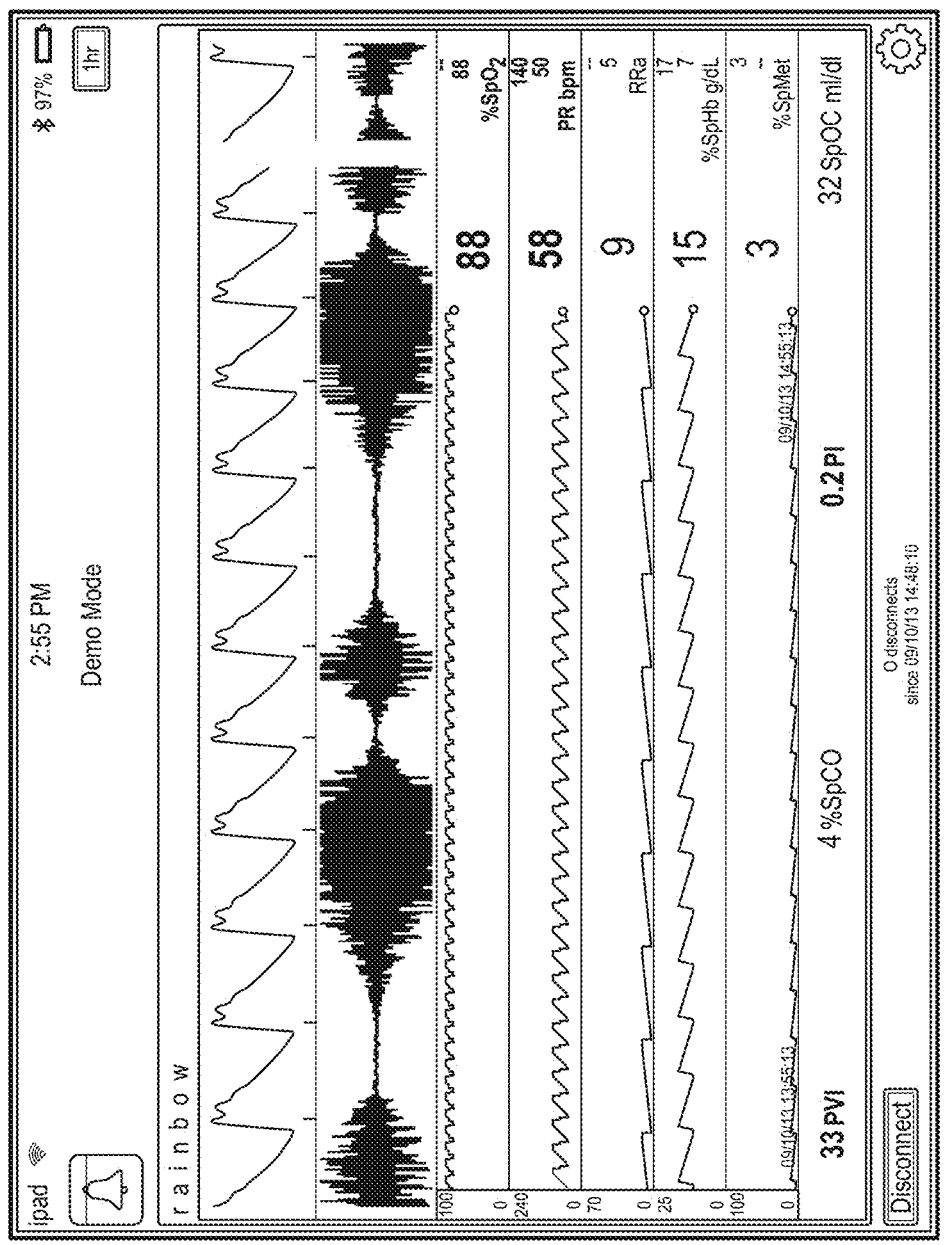
Figure 37:
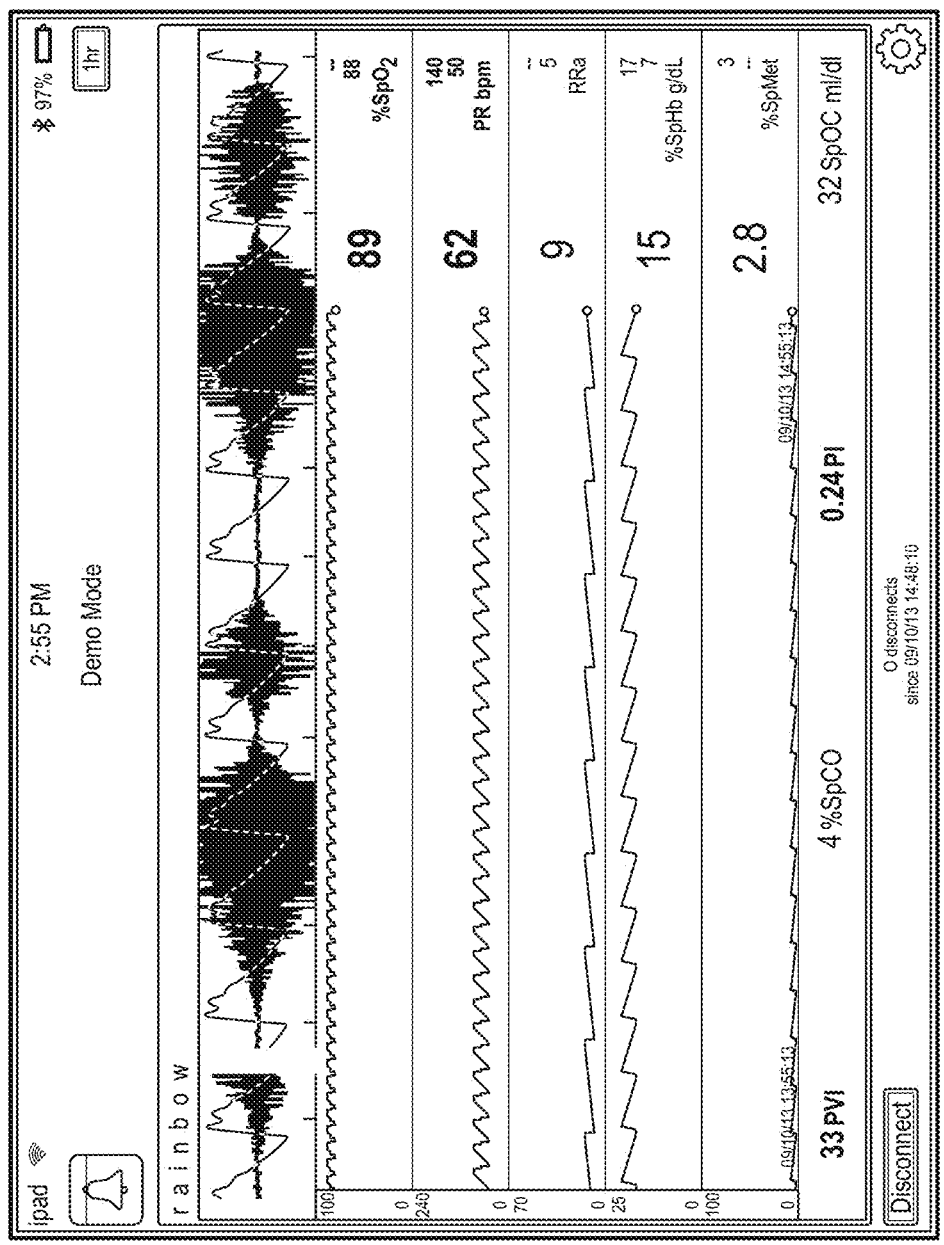
Figure 38:
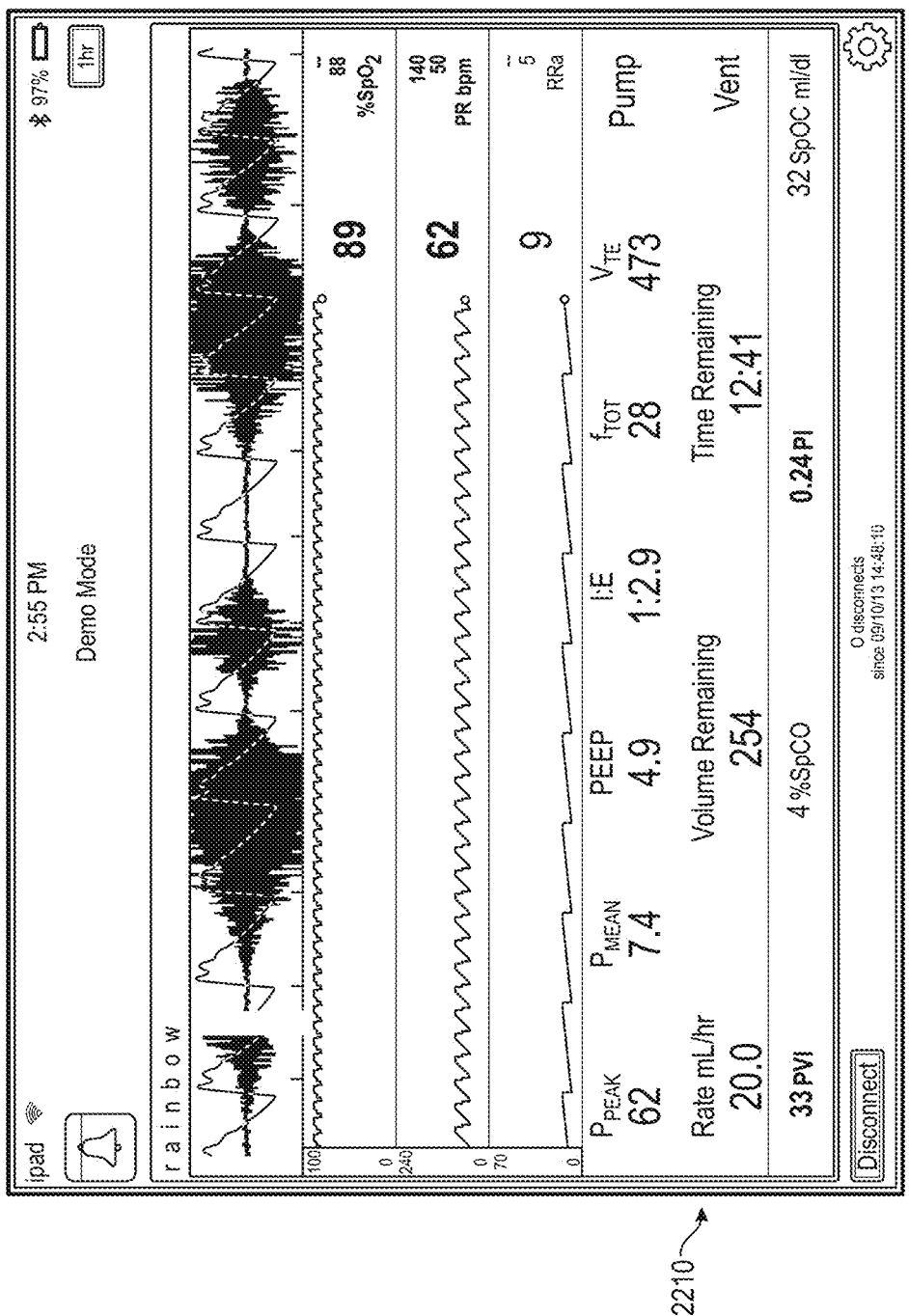

FIGS. 34-38 show landscape display views in contrast to the portrait-oriented displays of FIGS. 26-33. These landscape display views may be accessed by rotating the auxiliary device 2040 (such as tablet etc.) to a landscape orientation. FIG. 34 shows a first set of parameters, while FIGS. 35 and 36 add additional drag-and-dropped parameters with their waveforms and additional alarm limit details, similar to those described above with respect to FIGS. 27-29. FIG. 37 depicts stacked parameter waveforms, stacking SpO2 and respiratory waveforms. FIG. 38 depicts both channel parameters (such as SpO2, PR (pulse rate), and RRa (acousticly-measured respiratory rate)) while also showing translated serial data parameters 2210, including parameters from a pump and a vent. These translated serial data parameters 2210 may have been received from the translation module 2005, either through the hub 100 or directly from the MMS 2004.

Referring again to FIG. 24, as described above, the hub 100 or PPM 102 can output a copy of at least a portion of the display to the auxiliary device 2040. In other embodiments, the hub 100 or PPM 102 can output data with respect to a subset of the full parameters shown on the hub 100 or PPM 102 to the auxiliary device 2040. For instance, the hub 100 or PPM 102 may provide functionality for a clinician to select one or more of the parameters displayed thereon to see just that one or more parameters displayed on the auxiliary device 2040. Doing so may allow the auxiliary device 2040 to show more detail about the selected one or more parameters because fewer parameters may be shown on the auxiliary device's 2040 display than on the hub 100 or PPM 102.

Figure 39:
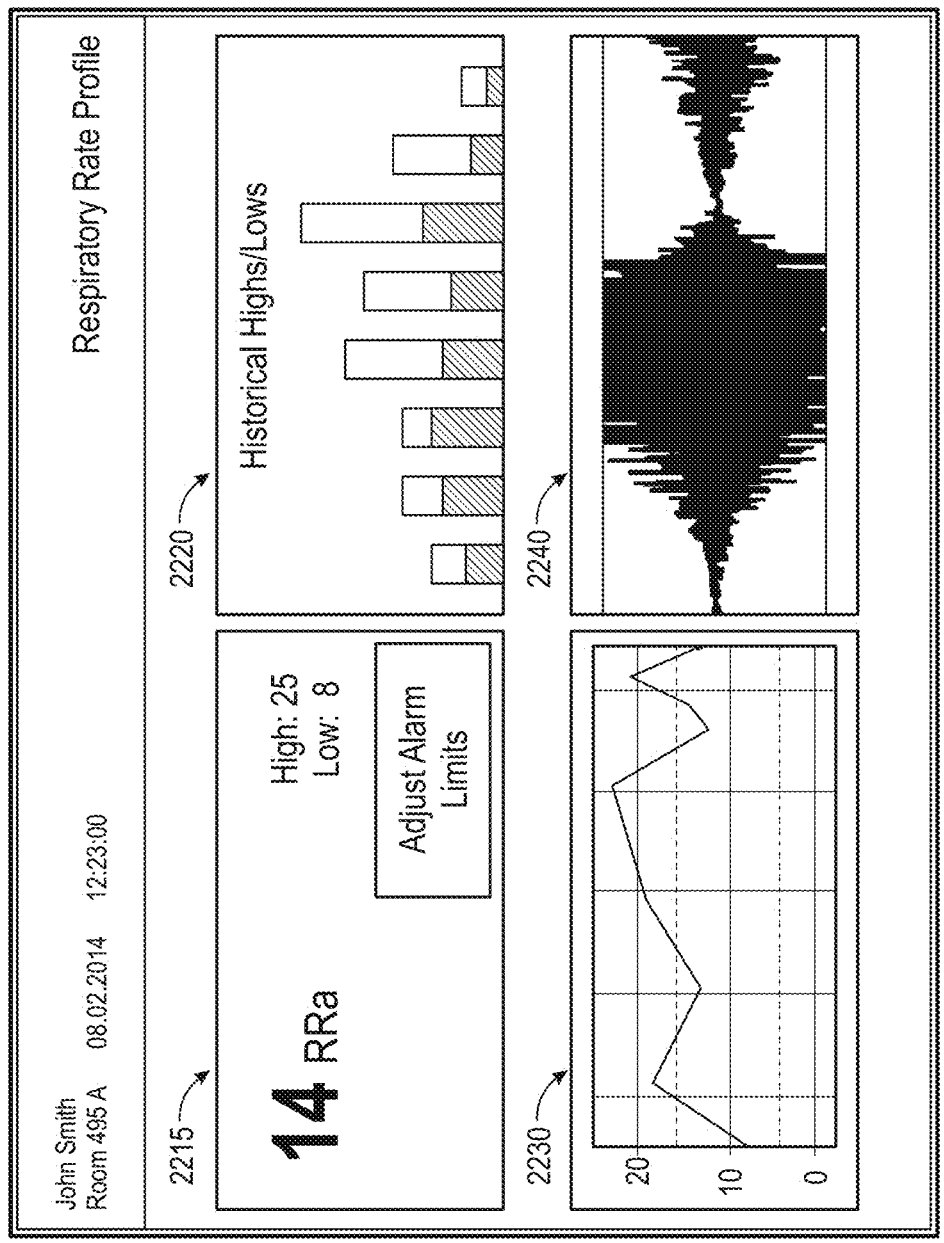

FIG. 39 depicts one example display of an auxiliary device 2040 that depicts data with respect to one parameter, respiratory rate. Unlike the main display of the hub 100 or PPM 102, the display shown in FIG. 39 includes more than just the current value 2215, a recent trend 2230, and small waveform of the respiratory rate. In addition, the display depicts a histogram 2220 of historical highs and lows (for example, for the past several days) of the patient being monitored. In addition, a detailed waveform 2240 is shown, which may be larger than the waveforms shown on the main display of the hub 100 or PPM 102, which may give the user more detailed insight into the patient's respiratory condition. A user may choose to zoom into the waveform 2240 (or other aspects of the display), causing the waveform 2242 to be enlarged to fill the display in place of the other elements of the display, or the like. Other graphs, tables, waveforms, and data may be shown for the respiratory parameter on the auxiliary device display 2040. Of course, parameters other than respiratory rate may also be selected for detailed display on the auxiliary device 2040. For example, the hub 100 or the auxiliary device 2040 can show cerebral blood flow while a doctor is performing a bypass surgery, for example, based on the output of the brain/organ oximetry (BIC) device 224. Advantageously, in some embodiments, the hub 100 or the auxiliary device 2040 can allow a doctor to easily view the cerebral blood flow and have time to validate adequate perfusion to the patient while maintaining the doctor's attention on the bypass circuit.

IV. Translation Module Embodiments

Any of the following features described with respect to FIGS. 40A through 45D can be implemented by the translation module 2005 of FIG. 24 or together with any of the devices described above with respect to FIG. 24.

Healthcare costs have been increasing and the demand for reasonably-priced, high-quality patient care is also on the rise. Health care costs can be reduced by increasing the effectiveness of hospital information systems. One factor which may affect the efficacy of a health institution is the extent to which the various clinical computer systems employed at the health institution can interact with one another to exchange information.

Hospitals, patient care facilities, and healthcare provider organizations typically include a wide variety of different clinical computer systems for the management of electronic healthcare information. Each of the clinical computer systems of the overall IT or management infrastructure can help fulfill a particular category or aspect of the patient care process. For example, a hospital can include patient monitoring systems, medical documentation and/or imaging systems, patient administration systems, electronic medical record systems, electronic practice management systems, business and financial systems (such as pharmacy and billing), and/or communications systems, etc.

The quality of care in a hospital or other patient care facility could be improved if each of the different clinical computer systems across the IT infrastructure (or even within the same hospital room; see, for example, FIGS. 1 and 24) were able to effectively communicate with each other. This could allow for the exchange of patient data that is collected by one clinical computer system with another clinical computer system that could benefit from such patient data. For example, this may allow decisions relating to patient care to be made, and actions to be taken, based on a complete analysis of all the available information.

In current practice, individual clinical computer systems can be, and often are, provided by different vendors. As a result, individual clinical computer systems may be implemented using a proprietary network or communication infrastructure, proprietary communication protocols, etc.; the various clinical computer systems used in the hospital cannot always effectively communicate with each other.

Medical device and medical system vendors sometimes develop proprietary systems that cannot communicate effectively with medical devices and systems of other vendors in order to increase their market share and to upsell additional products, systems, and/or upgrades to the healthcare provider. Thus, healthcare providers are forced to make enterprise or system-wide purchase decisions, rather than selecting the best technology available for each type of individual clinical computer system in use.

One example where this occurs is in the area of life-saving technology available for patient monitoring. For example, many different bedside devices for monitoring various physiological parameters are available from different vendors or providers. One such provider may offer a best-in-class device for monitoring a particular physiological parameter, while another such provider may offer the best-in-class device for another physiological parameter. Accordingly, it may be desirable in some circumstances for a hospital to have the freedom to use monitoring devices from more than one manufacturer, but this may not be possible if devices from different manufacturers are incapable of interfacing and exchanging patient information. Accordingly, the ability to provide reasonably-priced, high-quality patient care can be compromised. In addition, since each hospital or patient care facility may also implement its own proprietary communication protocols for its clinical computer network environment, the exchange of information can be further hindered.

As described above, the Health Level Seven ("HL7") protocol has been developed to provide a messaging framework for the communication of clinical messages between medical computer systems and devices. The HL7 communication protocol specifies a number of standards, guidelines, and methodologies which various HL7-compliant clinical computer systems can use to communicate with each other.

The HL7 communication protocol has been adopted by many medical device manufacturers. However, the HL7 standard is quite flexible, and merely provides a framework of guidelines (for example, the high-level logical structure of the messages); consequently, each medical device or medical system manufacturer or vendor may implement the HL7 protocol somewhat differently while still remaining HL7-compliant. For example, the format of the HL7 messages can be different from implementation to implementation, as described more fully herein. In some cases, the HL7 messages of one implementation can also include information content that is not included in messages according to another HL7 implementation. Accordingly, medical devices or clinical computer systems that are all HL7-compliant still may be unable to communicate with each other.

Consequently, a translation module can be provided that can improve the communication of medical messages between medical devices or systems that use different allowed implementations of an established communication protocol (for example, HL7), thereby increasing the quality of patient care through the integration of multiple clinical computer systems.

Figure 40A:
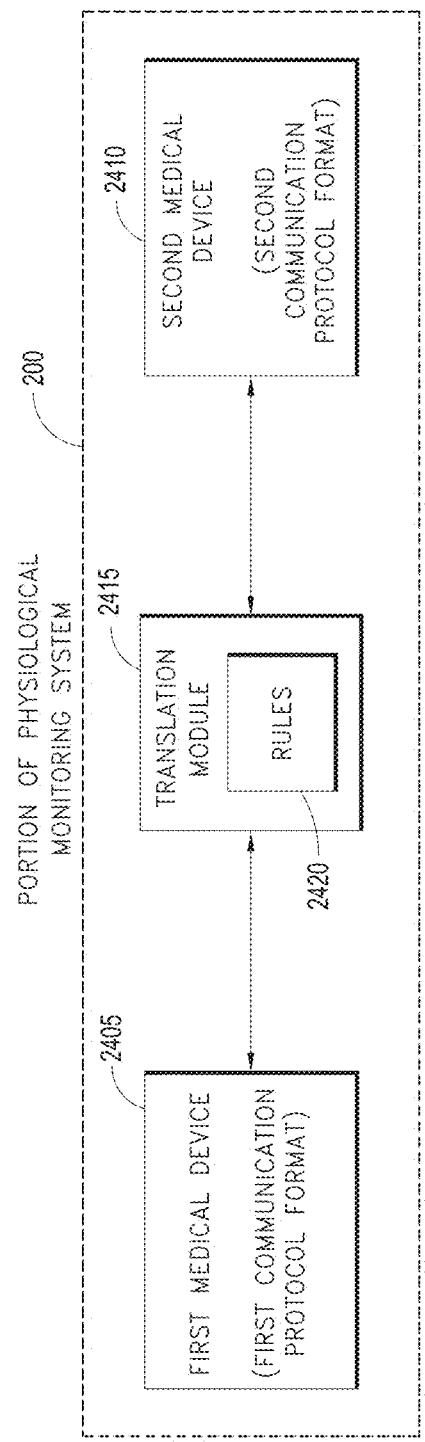
FIG. 40A illustrates an example first medical device and an example second medical device that communicate with one another via a translation module.

FIG. 40A illustrates a first medical device 2405 and a second medical device 2410 that communicate with one another via a translation module 2415. The first medical device 2405 is configured to transmit and receive messages according to a first allowed format or implementation of an accepted electronic medical communication protocol, while the second medical device 2410 is configured to transmit and receive messages according to a second allowed format or implementation of the electronic medical communication protocol. In some embodiments, the first and second protocol formats are different implementations of the HL7 communication protocol. Other electronic medical communication protocols besides HL7 can also be used.

The translation module 2415 receives input messages having the first protocol format from the first medical device 2405 and generates output messages to the second medical device 2410 having the second protocol format. The translation module 2415 also receives input messages having the second protocol format from the second medical device 2410 and generates output messages to the first medical device 2405 having the first protocol format. Thus, the translation module 2415 can enable the first and second medical devices 2405, 2410 to effectively and seamlessly communicate with one another without necessarily requiring modification to the communication equipment or protocol implemented by each device.

In certain embodiments, the translation module 2415 determines the protocol format expected by an intended recipient of the input message based on, for example, the information in the input message or by referencing a database that stores the protocol format used by various devices, and then generates the output message based on the protocol format used by the intended recipient device or system. The output message can be generated based upon a comparison with, and application of, a set of translation rules 2420 that are accessible by the translation module 2415.

The translation rules 2420 can include rules that govern how to handle possible variations between formatting implementations within a common protocol. Examples of variations in formatting implementation of an electronic medical communication protocol include, for example, the delimiter or separator characters that are used to separate data fields, whether a particular field is required or optional, the repeatability of portions of the message (for example, segments, fields, components, sub-components), the sequence of portions of the message (for example, the order of fields or components), whether a particular portion of a message is included, the length of the message or portions of the message, and the data type used for the various portions of the message.

In certain embodiments, the translation rules 2420 define additions, deletions, swappings, and/or modifications that should be performed in order to "translate" an input message that adheres to a first HL7 implementation into an output message that adheres to a second HL7 implementation. The output message can have, for example, different formatting than the input message, while maintaining all, or a portion of, the substance or content of the input message.

In addition to translating between different implementations of a common electronic medical communication protocol (for example, different formatting of HL7 messages), the translation module 2415 can also translate between input and output messages adhering to different communication protocols. In some embodiments, the translation module 2415 is capable of responding to and translating messages from, for example, one medical communication protocol to a separate medical communication protocol. For example, the translation module 2415 can facilitate communication between messages sent according to the HL7 protocol, the ISO 11073 protocol, other open protocols, and/or proprietary protocols. Accordingly, an input message sent according to the HL7 protocol can be translated to an output message according to a different protocol, or vice-versa.

The operation of the translation module 2415 and the translation rules 2420 will be described in more detail below. Various embodiments of system architectures including the translation module 2415 will now be described.

In certain embodiments, the first medical device 2405, the second medical device 2410, and the translation module 2415 are communicatively coupled via connection to a common communications network or directly (via cables or wirelessly), for example, through the hub 100, PPM 102, and/or MMS 2004. In some embodiments, the translation module 2415 can be communicatively coupled between the first medical device 2405 and the second medical device 2410 (with or without a communications network) such that all messages between the first and second medical devices 2405, 2410 are routed through the translation module 2415. Other architectures are also possible.

The first and second medical devices 2405, 2410 and the translation module 2415 can be included in, for example, a portion of the monitoring environments of FIG. 1 or 24 described above. The first medical device 2405 may be, for example, the infusion pump(s) 216 or ventilator 218, while the second medical device 2410 may be, for example, the monitoring hub 100, PPM 102, MMS 2004, or auxiliary device 2040. The translation module 2415 is an example implementation of the translation module 2005.

In certain embodiments, the translation module 2415 can facilitate communication across multiple networks within a hospital environment. In other embodiments, the translation module 2415 can facilitate communication of messages across one or more networks extending outside of the hospital or clinical network environment. For example, the translation module 2415 can provide a communications interface with banking institutions, insurance providers, government institutions, outside pharmacies, other hospitals, nursing homes, or patient care facilities, doctors' offices, and the like.

In some embodiments, the translation module 2415 of FIG. 40 can be a component of, for example, the environment 2000 described above with respect to FIG. 24. For example, the translation module 2415 can be communicatively coupled with a hospital network or other networks or monitoring environments described above. In such embodiments, the translation module 2415 can facilitate the exchange of patient monitoring information, including, for example, physiological parameter measurements, physiological parameter trend information, and physiological parameter alarm conditions between bedside medical monitor devices, nurses' monitoring stations, a Hospital or Clinical Information System (which may store Electronic Medical Records), and/or many other medical devices and systems. The translation module 2415 can enable seamless communication between different medical devices and systems, each of which may use a different implementation of an electronic medical communication protocol such as, for example, the HL7 communication protocol, within a clinical or hospital network environment.

In certain embodiments, the translation module 2415 can also facilitate communication between a first medical device that is part of the patient monitoring sub-system and a second medical device that is not part of, or is external to, the patient monitoring system 200. As such, the translation module 2415 can be capable of responding to externally-generated medical messages (such as patient information update messages, status query messages, and the like from an HIS or CIS) and generating external reporting messages (such as event reporting messages, alarm notification messages, and the like from patient monitors or nurses' monitoring stations).

In another embodiment, first and second medical devices 2405, 2410 communicate with each other over a communication bus 2421. Communication bus 2421 can include any one or more of the communication networks, systems, and methods described above, including the Internet, a hospital WLAN, a LAN, a personal area network, etc. For example, any of the networks describe above can be used to facilitate communication between a plurality of medical devices, including first and second medical devices 2405, 2410, discussed above. One such embodiment is illustrated in FIG. 40B.

Figure 40B:
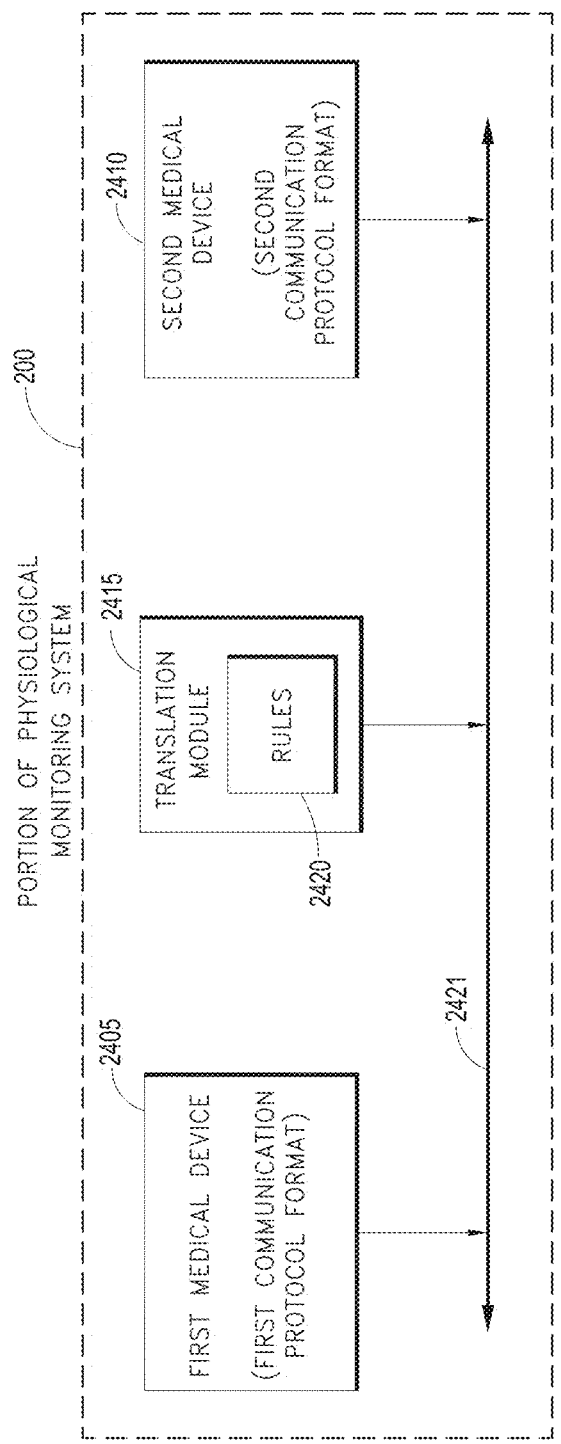
FIG. 40B illustrates an example first medical device and an example second medical device that communicate with one another via a translation module and a communication bus.

In FIG. 40B, first medical device 2405 provides a message to the communication bus 2421. The message is intended for receipt by the second medical device 2410; however, because first and second medical devices 2405, 2410 communicate according to different communication protocol format, second medical device 2410 is unable to process the message.

Translation module 2415 monitors the communication bus 2421 for such messages. Translation module receives the message and determines that first medical device 2405 is attempting to communicate with second medical device 2410. Translation module 2415 determines that message translation would facilitate communication between first and second medical devices 2405, 2410. Translation module 2415 therefore utilizes an appropriate translation rule stored in a translation module 2420. Translation module 2420 can include a memory, EPROM, RAM, ROM, etc.

The translation module 2415 translates the message from the first medical device 2405 according to any of the methods described herein. Once translated, the translation module 2415 delivers the translated message to the communication bus 2421. The second medical device 2410 receives the translated message and responds appropriately. For example, the second medical device may perform a function and/or attempt to communication with the first medical device 2405. The translation module 2415 facilitates communication from the second medical device 2410 to the first medical device 2405 in a similar manner.

The first medical device 2405 and the second medical device 2410 can be, for example, any of the medical devices or systems communicatively coupled to a hospital network or hub 100, PPM 102, and/or MMS 2004. These medical devices or systems can include, for example, point-of-care devices (such as bedside patient monitors), data storage units or patient record databases, hospital or clinical information systems, central monitoring stations (such as a nurses' monitoring station), and/or clinician devices (such as pagers, cell phones, smart phones, personal digital assistants (PDAs), laptops, tablet PCs, personal computers, pods, and the like).

In some embodiments, the first medical device 2405 is a patient monitor for communicatively coupling to a patient for tracking a physiological parameter (for example, oxygen saturation, pulse rate, blood pressure, etc.), and the second medical device 2410 is a hospital information system ("HIS") or clinical information system ("CIS"). In some embodiments, the patient monitor can communicate physiological parameter measurements, physiological parameter alarms, or other physiological parameter measurement information generated during the monitoring of a patient to the HIS or CIS for inclusion with the patient's electronic medical records maintained by the HIS or CIS.

In some embodiments, the first medical device 2405 is an HIS or CIS and the second medical device 2410 is a nurses' monitoring station, as described herein. However, the translation module 2415 can facilitate communication between a wide variety of medical devices and systems that are used in hospitals or other patient care facilities. For example, the translation module 2415 can facilitate communication between patient physiological parameter monitoring devices, between a monitoring device and a nurses' monitoring station, etc.

Using the translation module 2415, a patient monitoring sub-system, such as those described herein (for example, physiological monitoring system 200), can push data to the HIS or pull data from the HIS even if the HIS uses a different implementation of the HL7 protocol, or some other electronic medical communication protocol.

In certain embodiments, the patient monitoring sub-system can be configured to push/pull data at predetermined intervals. For example, a patient monitor or clinician monitoring station can download patient data automatically from the HIS at periodic intervals so that the patient data is already available when a patient is connected to a patient monitor. The patient data sent from the HIS can include admit/discharge/transfer ("ADT") information received upon registration of the patient. ADT messages can be initiated by a hospital information system to inform ancillary systems that, for example, a patient has been admitted, discharged, transferred or registered, that patient information has been updated or merged, or that a transfer or discharge has been canceled.

In other embodiments, the patient monitoring sub-system can be configured to push/pull data to/from the HIS only when the HIS is solicited by a query. For example, a clinician may make a request for information stored in a patient's electronic medical records on the HIS.

In still other embodiments, the patient monitoring sub-system can be configured to push/pull data to/from the HIS in response to an unsolicited event. For example, a physiological parameter of a patient being monitored can enter an alarm condition, which can automatically be transmitted to the HIS for storing in the patient's electronic medical records. In yet other embodiments, any combination of the above methods or alternative methods for determining when to communicate messages to and from the HIS can be employed.

Example system architectures and example triggers for the communication of messages involving the translation module 2415 have been described. Turning now to the operation of the translation module, FIGS. 25A-25D illustrate an example medical message at different phases or steps of a translation process. The translation process will be described in more detail below in connection with FIGS. 26, 27A and 27B.

FIG. 41A illustrates an example ADT input message 2505 received by the translation module 2415 from an HIS. The ADT input message 2505 is implemented according to the HL7 communication protocol and contains information related to the admission of a patient to a hospital. The ADT message 2505 includes multiple segments, including a message header segment 2506, an event segment, a patient identification segment, a patient visit segment, role segments, a diagnosis segment, and multiple custom segments.

In some embodiments, the message header ("MSH") segment 2506 defines how the message is being sent, the field delimiters and encoding characters, the message type, the sender and receiver, etc. The first symbol or character after the MSH string can define the field delimiter or separator (in this message, a "caret" symbol). The next four symbols or characters can define the encoding characters. The first symbol defines the component delimiter ("~"), the second symbol defines the repeatable delimiter ("|"), the third symbol defines the escape delimiter ("\"), and the fourth symbol defines the sub-component delimiter ("&"). All of these delimiters can vary between HL7 implementations.

In some embodiments, the example header segment 2506 further includes the sending application ("VAFC PIMS"), the receiving application ("NPTF-508"), the date/time of the message ("20091120104609-0600"), the message type ("ADT~A01"), the message control ID ("58103"), the processing ID ("P"), and the country code ("USA"). As represented by the consecutive caret symbols, the header segment also contains multiple empty fields.

FIG. 41B illustrates the message header segment 2506 after it has been parsed into fields or elements based on an identified field delimiter (the caret symbol). In certain embodiments, the parsed input message comprises an XML message that is configured to be transformed according to extensible stylesheet language transformation (XSLT) rules.

In certain embodiment, the parsed input message can be encoded. FIG. 41C illustrates the parsed message header segment of the input message after being encoded (for example, using a Unicode Transformation Format-8 ("UTF-8") encoding scheme).

The encoded message header segment shows some of the various data types that can be used in the message. For example, the sending application ("VAFC PIMS") of the third parsed field and the receiving application ("NPTF-508") of the fifth parsed field are represented using a hierarchic designator ("HD") name data type. The date/time field (the seventh parsed field) is represented using the time stamp ("TS") data type. The processing ID field (the eleventh parsed field) is represented using the processing type ("PT") data type. The fields that do not include a data type identifier are represented using the string ("ST") data type. Other possible data types include, for example, coded element, structured numeric, timing quantity, text data, date, entry identifier, coded value, numeric, and sequence identification. The data types used for the various fields or attributes of the segments can vary between formatting implementations.

FIG. 41D illustrates an example output message 2510 from the translation module 2415 based on the example input message 2505 of FIG. 41A. The output message 2510 includes a message acknowledgement segment 2512.

Turning to the operation of the translation module, the translation module 2415 can, for example, create, generate, or produce an output message that is reflective of the input message based on an application of the set of translation rules 2420. In some embodiments, the translation module 2415 can, for example, translate, transform, convert, reformat, configure, change, rearrange, modify, adapt, alter, or adjust the input message based on a comparison with, and application of, the set of translation rules 2420 to form the output message. In some embodiments, the translation module 2415 can, for example, replace or substitute the input message with an output message that retains the content of the input message but has a new formatting implementation based upon a comparison with, and application of, the set of translation rules 2420.

Figure 42:
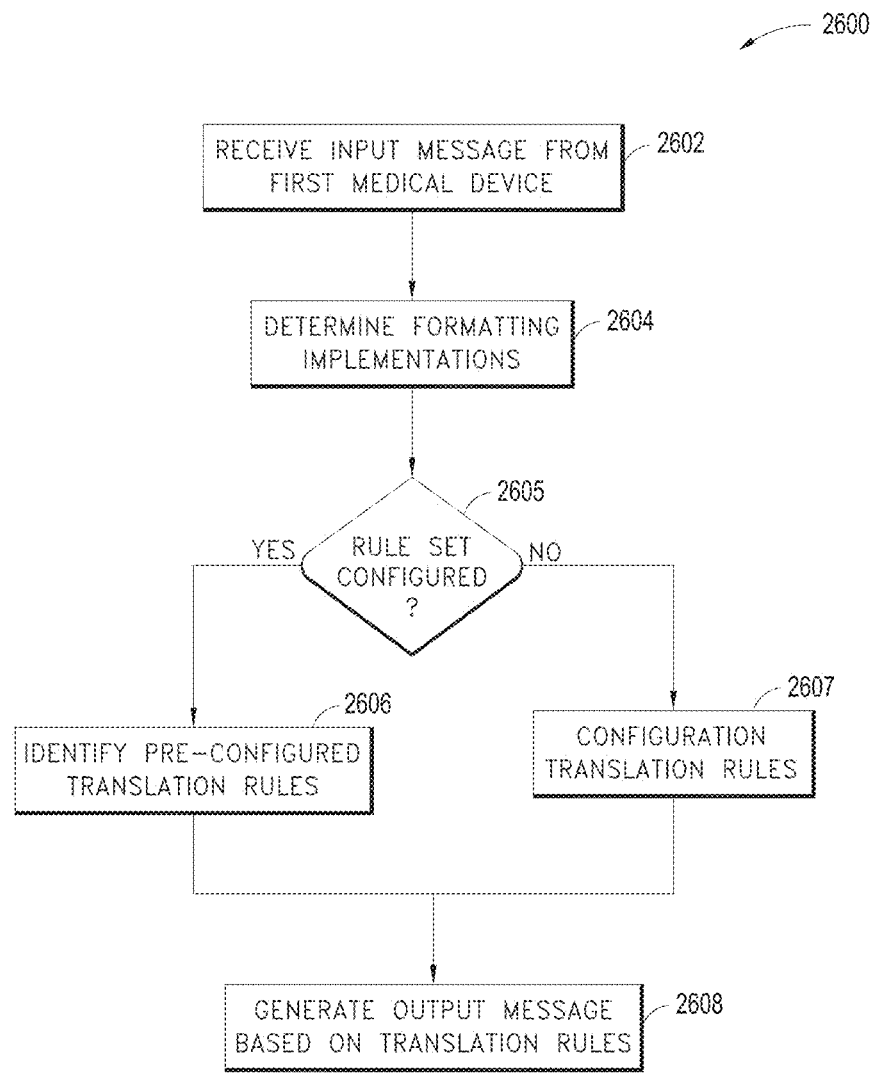
FIG. 42 illustrates an example translation process for generating an output message based on an input message and a comparison with translation rules associated with the translation module.

FIG. 42 illustrates a translation process 2600 for generating an output message based on an input message and a comparison with the set of translation rules 2420 associated with the translation module 2415. The translation process 2600 starts at block 2602 where the translation module 2415 receives an input message from a first medical device.

At block 2604, the translation module 2415 determines the formatting implementation of the input message and the formatting implementation to be used for the output message. In certain embodiments, the input message can include one or more identifiers indicative of the formatting implementation. In some embodiments, the determination of the formatting implementation can be made, for example, by analyzing the message itself by identifying the delimiter or encoding characters used, the field order, the repeatability of segments, fields, or components, the data type of the fields, or other implementation variations. In certain embodiments, the translation module 2415 can separate or parse out the formatting from the content of the message (as shown in FIG. 41B) to aid in the determination of the formatting implementation. In some embodiments, the translation module 2415 determines the formatting implementation of the input message by referencing a database that stores the implementation used by each device with which the translation module 2415 has been configured to interface.

In certain embodiments, the determination of the formatting implementation used by the output message can also be determined from the input message. For example, the input message can include a field that identifies the intended recipient application, facility, system, device, and/or destination. The input message can alternatively include a field that identifies the type of message being sent (for example, ADT message) and the translation module 2415 can determine the appropriate recipient from the type of message being sent and/or the sending application, device, or system. The translation module 2415 can then determine the formatting implementation required by the intended recipient of the input message.

At decision block 2605, the translation module 2415 determines whether a rule set has been configured for the translation from the identified formatting implementation of the input message to the identified formatting implementation to be used for the output message. The rule set may have been manually configured prior to installation of the translation module software or may have been automatically configured prior to receipt of the input message. If a rule set has already been configured, then the translation process 2600 continues to block 2606. If a rule set has not been configured, then a rule set is configured at block 2607. The configuration of the rule set can be performed as described below in connection with FIGS. 44 and 45A-2459D. The translation process 2600 then continues to block 2608.

At block 2606, the translation module 2415 identifies the pre-configured rules from the set of translation rules 2420 that govern translation between the determined formatting implementation of the input message and the formatting implementation of the output message. In some embodiments, the identification of the pre-configured rules can be made manually.

At block 2608, the translation module 2415 generates an output message based on the configured rule set(s) of the translation rules 2420. In certain embodiments, the output message retains all, or at least a portion of, the content of the input message but has the format expected and supported by the intended recipient of the input message.

The translation rules 2420 can include, for example, unidirectional rules and/or bidirectional rules. A unidirectional rule can be one, for example, that may be applied in the case of a message from a first medical device (for example, 2405) to a second medical device (for example, 2410) but is not applied in the case of a message from the second medical device to the first medical device. For example, a unidirectional rule could handle a difference in the delimiters used between fields for two different formatting implementations of, for example, the HL7 communication protocol. The translation module 2415 can apply a field delimiter rule to determine if the field delimiter is supported by the intended recipient of the input message. If the field delimiter of the input message is not supported by the intended recipient, the field delimiter rule can replace the field delimiter of the input message with a field delimiter supported by the intended recipient.

For example, an input message from an input medical device can include a formatting implementation that uses a "caret" symbol (""") as the field delimiter or separator. However, the formatting implementation recognized by the intended recipient medical device may use a "pipe" symbol ("|") as the field delimiter. The translation module 2415 can identify the field delimiter symbol used in the formatting implementation recognized by the intended recipient medical device from the set of translation rules 2420 and generate an output message based on the input message that uses the pipe field delimiter symbol instead of the caret field delimiter symbol used in the input message. The rule to substitute a pipe symbol for a caret symbol would, in this case, only apply to messages that are sent to a recipient device that recognizes the pipe symbol as a field delimiter. This rule could be accompanied by a complementary rule that indicates that a caret symbol should be substituted for a pipe symbol in the case of a message that is intended for a recipient device that is known to recognize the caret symbol as the field delimiter.

Another unidirectional rule can handle the presence or absence of certain fields between different formatting implementations. For example, an input message from an input medical device can include fields that would not be recognized by the intended recipient medical device. The translation module 2415 can generate an output message that does not include the unrecognized or unsupported fields. In situations where an input message does not include fields expected by the intended recipient medical device, the set of translation rules 2420 can include a rule to insert null entries or empty " " strings in the fields expected by the intended recipient medical device and/or to alert the recipient device of the absence of the expected field. The sender device may also be notified by the translation module 2415 that the recipient device does not support certain portions of the message.

Other unidirectional rules can facilitate, for example, the conversion of one data type to another (for example, string ("ST") to text data ("TX") or structured numeric ("SN") to numeric ("NM")), and the increase or decrease in the length of various portions of the message. Unidirectional rules can also be used to handle variations in repeatability of portions of the message. For example, the translation module 2415 can apply a field repeatability rule to repeated instances of a segment, field, component, or sub-component of the message to determine how many such repeated instances are supported by the recipient device, if any, and deleting or adding any repeated instances if necessary. For example, a phone number field of a patient identification segment can be a repeatable field to allow for entry of home, work, and cell phone numbers.

Bidirectional rules can also be used. Such rules may apply equally to messages between first and second medical devices (for example, 2405, 2410) regardless of which device is the sender and which is the recipient. A bidirectional rule can be used to handle changes in sequence, for example. In certain implementations, an input message from an input medical device can include a patient name field, or fields, in which a first name component appears before a last name component. However, the intended recipient medical device may be expecting an implementation where the last name component appears before the first name component. Accordingly, the set of translation rules 2420 can include a bidirectional rule to swap the order of the first and last name components when communicating between the two medical devices, or between the two formatting implementations. In general, field order rules can be applied to determine whether the fields, components, or sub-components are in the correct order for the intended recipient and rearranging them if necessary. Other bidirectional rules can be included to handle, for example, other sequential variations between formatting implementations or other types of variations.

The translation rules 2420 can also include compound rules. For example, a compound rule can include an if-then sequence of rules, wherein a rule can depend on the outcome of another rule. Some translation rules 2420 may employ computations and logic (for example, Boolean logic or fuzzy logic), etc.

Figure 43A:
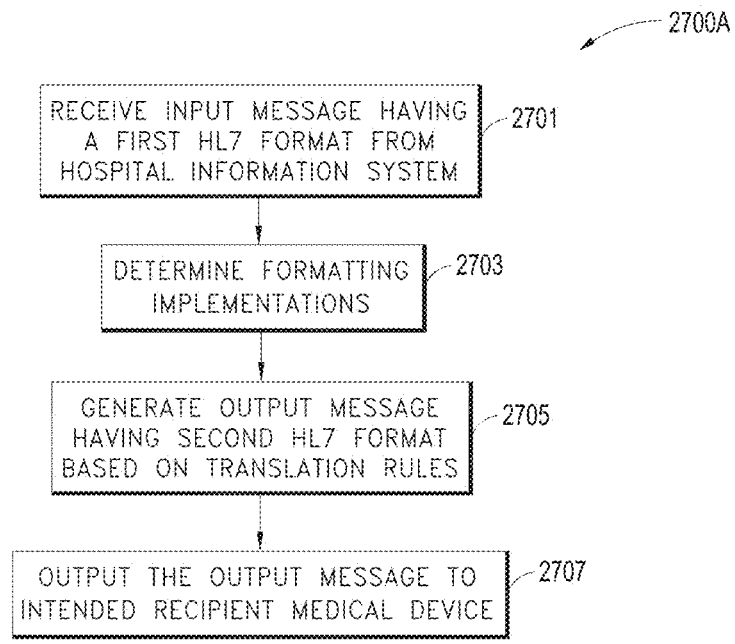
FIG. 43A illustrates an example translation process in which the translation module facilitates communication of an HL7 message from a Hospital Information System ("HIS") having a first HL7 format to an intended recipient medical device having a second HL7 format.
Figure 43B:
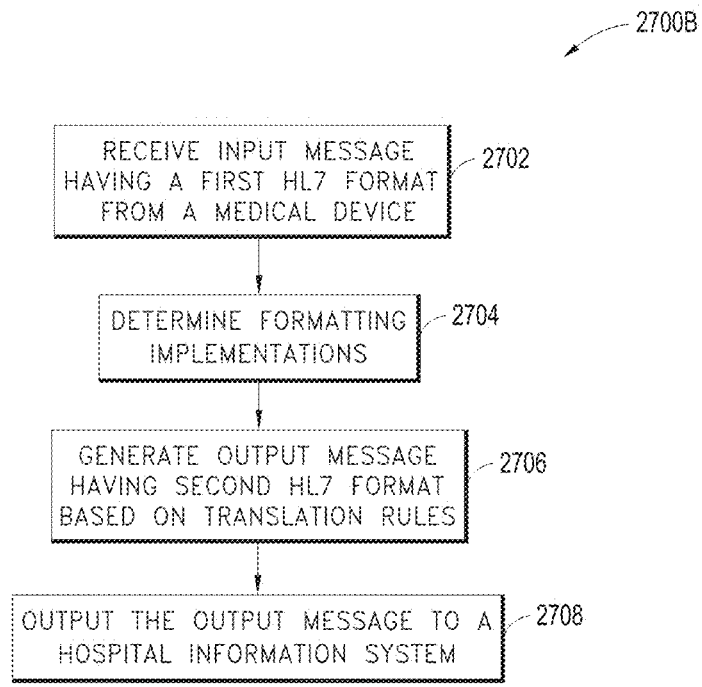
FIG. 43B illustrates an example translation process in which the translation module facilitates communication of an HL7 message from a medical device having a first HL7 format to a HIS having a second HL7 format.

As discussed above, the messages communicated over the hospital-based communication network can employ the HL7 protocol. FIGS. 43A and 43B illustrate translation processes 2700A, 2700B in which HL7 messages are communicated between a HIS and a medical device over a hospital-based communications network or a clinical network. The translation processes 2700A, 2700B will be described with the assumption that the rules governing "translation" between the first and second HL7 formats have already been configured.

FIG. 43A illustrates a translation process 2700A in which the translation module 2415 facilitates communication of an HL7 message, such as the ADT message of FIG. 41A, from an HIS having a first HL7 format to an intended recipient medical device, such as a patient monitor or a clinician monitoring station, having a second HL7 format.

The translation process 2700A starts at block 2701, where the translation module 2415 receives an input message having a first HL7 format from the HIS. In certain embodiments, the input message includes information regarding, for example, the admission of a patient and/or patient identification and patient medical history information from an electronic medical records database.

At block 2703, the translation module 2415 determines the formatting implementation of the input message and the formatting implementation to be used for the output message. These determinations can be made in a similar manner to the determinations discussed above in connection with block 2604 of FIG. 42.

At block 2705, the translation module 2415 identifies the rules that govern translation between the determined HL7 format of the input message and the HL7 format of the output message and generates an output message having the second HL7 format based on the identified rules. In certain embodiments, the output message retains the content of the input message sent by the HIS but has the format expected and supported by the intended recipient of the input message.

At block 2707, the translation module 2415 can output the output message to the intended recipient over the hospital-based communications network. In certain embodiments, the intended recipient can transmit an acknowledgement message back to the hospital information system acknowledging successful receipt or reporting that an error occurred.

FIG. 43B illustrates a translation process 2700B in which the translation module 2415 facilitates communication of an HL7 message from a medical device, such as a patient monitor, having a first HL7 format to an HIS having a second HL7 format. For example, the patient monitor can transmit reporting event data m such as patient alarm data, to the HIS to store in the patient's electronic medical records.

The translation process 2700B starts at block 2702, where the translation module 2415 receives an input message having a first HL7 format from the medical device. In certain embodiments, the input message includes patient monitoring data or alarm data regarding one or more physiological parameters of the patient being monitored for storage in an electronic medical records database associated with the HIS.

At block 2704, the translation module 2415 determines the formatting implementation of the input message and the formatting implementation to be used for the output message. These determinations can be made in a similar manner to the determinations discussed above in connection with block 2604 of FIG. 42.

At block 2706, the translation module 2415 identifies the rules that govern translation between the determined HL7 format of the input message and the HL7 format of the output message and generates an output message having the second HL7 format based on the identified rules. In certain embodiments, the output message retains the content of the input message sent by the medical device but has the format expected and supported by the HIS.

At block 2708, the translation module 2415 can output the output message to the hospital information system over the hospital-based communications network. In certain embodiments, the HIS can transmit an acknowledgement message back to the medical device acknowledging successful receipt or reporting that an error occurred.

FIGS. 42, 43A and 43B described the operation of the translator module 2415. FIGS. 44 and 45A-45D will be used to illustrate the description of the configuration of the translation rules 2420.

The translation rules 2420 can be implemented as one or more stylesheets, hierarchical relationship data structures, tables, lists, other data structures, combinations of the same, and/or the like. In certain embodiments, the translation rules 2420 can be stored in local memory within the translation module 2415. In other embodiments, the translation rules 2420 can be stored in external memory or on a data storage device communicatively coupled to the translation module 2415.

The translation module 2415 can include a single rule set or multiple rule sets. For example, the translation module 2415 can include a separate rule set for each medical device/system and/or for each possible communication pair of medical devices/systems coupled to the network or capable of being coupled to the network. In some embodiments, the translation module 2415 can include a separate rule set for each possible pair of formatting implementations that are allowed under a medical communication protocol such as, for example, the HL7 protocol.

Figure 44:
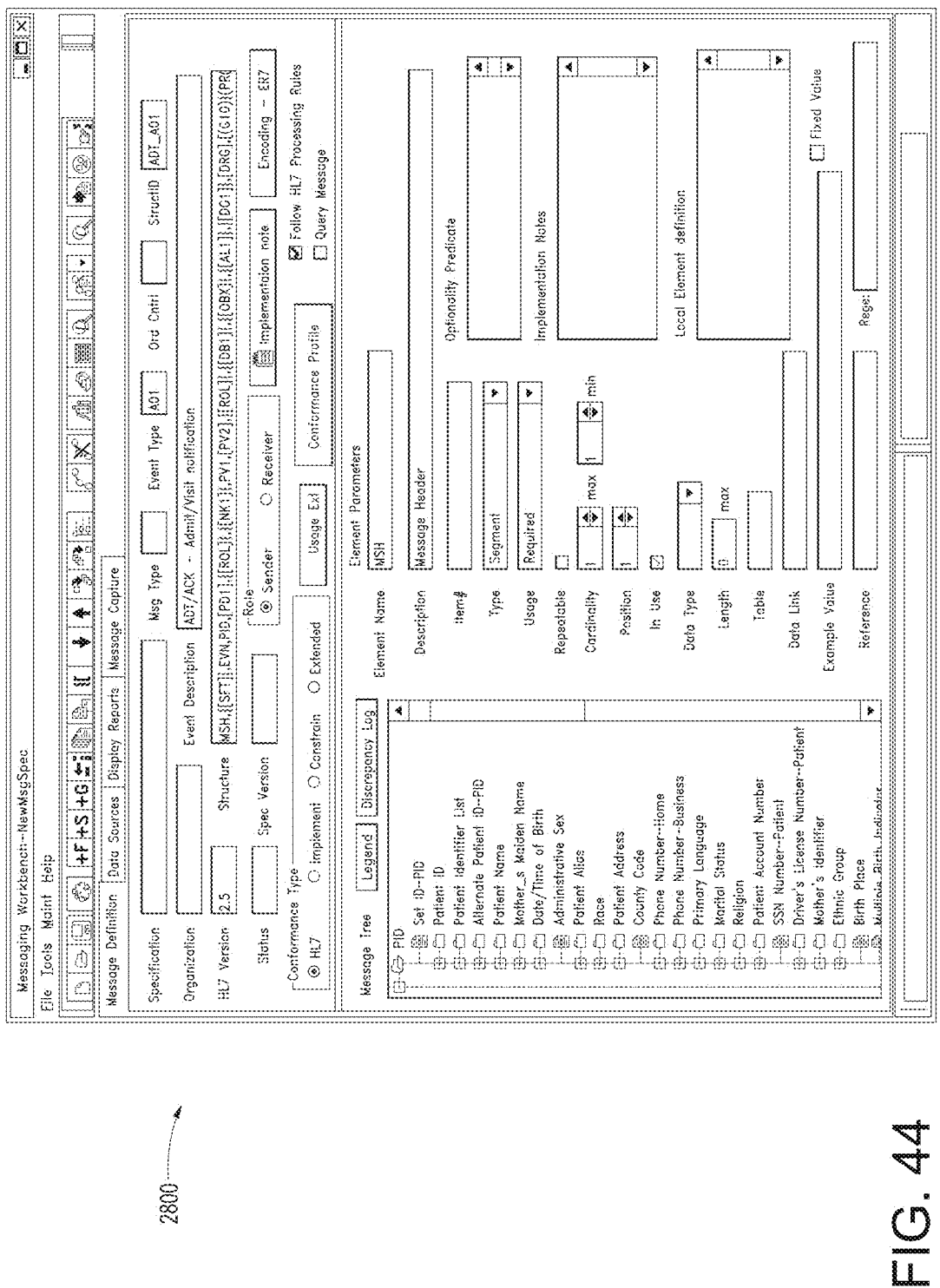
FIG. 44 illustrates an example screenshot from a messaging implementation tool for manually configuring translation rules to be used by the translation module.

In certain embodiments, the translation rules 2420 can be manually inputted using, for example, the messaging implementation software tool 2800 illustrated in FIG. 44. For example, the software developer for a particular hospital network can determine the protocol message formats used by the devices and/or systems that are or can be coupled to the hospital network and then manually input rules to facilitate "translation" between the various protocol message formats supported or recognized by the devices and/or systems.

FIG. 44 illustrates an example screenshot from a messaging implementation software tool 2800 for manually configuring translation rules 2420 to be used by the translation module 2415. The screenshot from the messaging implementation software tool 2800 illustrates various parameters that may differ between formatting implementations of an electronic medical communication protocol, such as HL7. The screenshot also includes areas where a user can input information that defines, or is used to define, translation rules for converting between different HL7 implementations. In some embodiments, the messaging implementation software tool 2800 stores a variety of pre-configured rule sets based, for example, on known communication protocol implementations of various medical devices. In such embodiments, a user may configure one or more translation rules 2420 to be used in communications involving such devices by entering identification information, such as the device manufacturer, model number, etc. Based on this identification information, the messaging implementation tool 2800 can identify a pre-configured set of translation rules for communication with that device.

In other embodiments, the translation rules 2420 can be automatically generated. For example, the automatic generation of a new set, or multiple sets, of rules can be triggered by the detection of a newly recognized "communicating" medical device or system on a network. In certain embodiments, the automatic generation of a new set or multiple sets of rules can occur at the time a first message is received from or sent to a new "communicating" medical device or system coupled to the network. In still other embodiments, the automatic generation of rule sets includes updating or dynamically modifying a pre-existing set of rules.

The automatic generation of translation rule sets can be carried out in a variety of ways. For example, in some embodiments, the translation module 2415 can automatically initiate usage of a pre-configured set of translation rules 2420 based upon, for example, the make and model of a new device that is recognized on the network. In certain embodiments, the translation module 2415 can request one or more messages from the new device or system and then analyze the messages to determine the type of formatting being implemented, as illustrated by the automatic rule configuration process 2900A of FIG. 45A. The automatic rule configuration process 2900A starts at block 2901, where the translation module 2415 receives one or more messages from a detected medical device or system on the network. The messages can be received upon transmission to an intended recipient medical device or system or in response to a query sent by the translation module 2415 or another medical device or system coupled to the network.

At block 2903, the translation module 2415 determines the protocol of the one or more received messages by, for example, analyzing the message or by consulting a database that indicates what communication protocol/format is implemented by each medical device or system on the network. In certain embodiments, the translation module 2415 is configured to handle medical messages implemented using a single common protocol, such as HL7. Accordingly, if a determination is made that the received messages are implemented using a non-supported or non-recognized protocol, the translation module can ignore the messages received from the detected medical device or system, output an alert or warning, or allow the messages to be sent without being translated.

At block 2905, the translation module 2415 determines the formatting implementation of the received message(s). In certain embodiments, the received messages can include one or more identifiers indicative of the formatting implementation. In other embodiments, the determination of the formatting implementation can be made, for example, by analyzing the message itself by checking field order, the delimiter or encoding characters used, or other implementation variations. In certain embodiments, the translation module 2415 can separate or parse out the formatting from the content of the message to aid in the determination of the formatting implementation.

At block 2907, the translation module 2415 configures one or more rules or rule sets to handle messages received from and/or sent to the detected medical device or system. In certain embodiments, the configuration of the rules involves the creation or generation of new rules. In other embodiments, the configuration of the rules involves the alteration or updating of existing rules. The configured rules or rule sets can be included with the translation rules 2420. If a set of rules already exists for the formatting implementation used by the new device or system, then the configuration of new translation rules may not be required. Instead, existing translation rules can be associated with the new device or system for use in communication involving that device or system. In other embodiments, the translation module 2415 can create a new set of rules geared specifically for the new device or system or can modify an existing set of rules based on subtle formatting variations identified.

In other embodiments, the translation module 2415 can generate test message(s) that may be useful in identifying the communication protocol and implementation used by a device or system. For example, the translation module can generate test messages to cause the newly detected device or system to take a particular action (for example, store information) and then query information regarding the action taken by the newly detected device to determine whether or how the test message was understood. This is illustrated by the automatic rule configuration process 2900B of FIG. 45B.

The automatic rule configuration process 2900B starts at block 2902, where the translation module 2415 transmits one or more test, or initialization, messages to a remote device or system detected on a network. The test messages can be configured, for example, to instruct the remote device or system to take a particular action (for example, store patient information). In certain embodiments, the test messages can be configured to generate a response indicative of the type of formatting recognized or supported by the remote device or system. In other embodiments, the test messages can be configured such that only devices or systems supporting a particular formatting implementation will understand and properly act on the test messages.

At block 2904, the translation module 2415 queries the remote device or system to receive information regarding the action taken based on the test message sent to the remote device or system to determine whether the test message was understood. For example, if the test message instructed the remote device or system to store patient information in a particular location, the translation module 2415 can query the information from the location to determine whether the test message was understood. If the test message was not understood, the translation module 2415 can, for example, continue sending test messages of known formatting implementations until a determination is made that the test message has been understood.

At block 2906, the translation module 2415 determines the protocol and formatting implementation based on the information received. As an example, in certain embodiments, the test message can include an instruction to store patient name information. The test message can include a patient name field having a first name component followed by a surname component. The translation module 2415 can then query the remote device or system to return the patient surname. Depending on whether the patient surname or the first name is returned, this query can be useful in determining information about the order of fields in the formatting implementation being used by the remote device or system. As another example, the test messages can instruct the detected device or system to store repeated instances of a component. The translation module 2415 can then query the device or system to return the repeated instances to see which, if any, were stored. This repeatability information can also be useful in determining whether certain fields are allowed to be repeated in the formatting implementation being used by the remote device for system, and, if so, how many repeated instances are permitted.

At block 2908, the translation module 2415 configures one or more rules to handle messages received from and/or sent to the detected medical device or system. For example, the rules can convert messages from the message format used by a first medical device to that used by a second medical device, as described herein. In certain embodiments, the configuration of the rules involves the creation or generation of new rules. In other embodiments, the configuration of the rules involves the alteration or updating of existing rules. If a set of rules already exists for the formatting implementation used by the new device or system, then the configuration of new translation rules may not be required. Instead, existing translation rules can be associated with the new device or system for use in communication involving that device or system.

FIGS. 29C and 29D illustrate automatic rule configuration processes performed by the translation module 2415 for messages utilizing the HL7 protocol. The HL7 protocol can be used, for example, to communicate electronic messages to support administrative, logistical, financial, and clinical processes. For example, HL7 messages can include patient administration messages, such as ADT messages, used to exchange patient demographic and visit information across various healthcare systems.

Figure 45A:
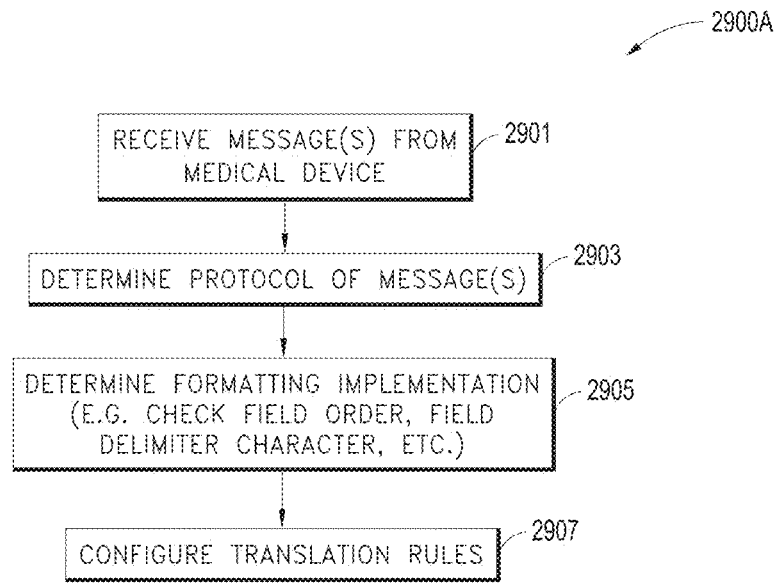
FIGS. 45A and 45B illustrate example automatic rule configuration processes that can be performed by the translation module.
Figure 45B:
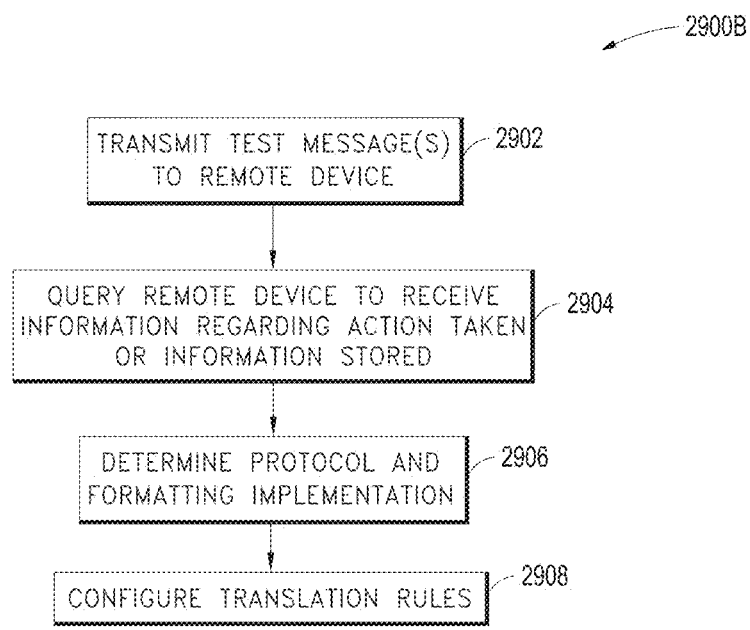
Figure 45C:
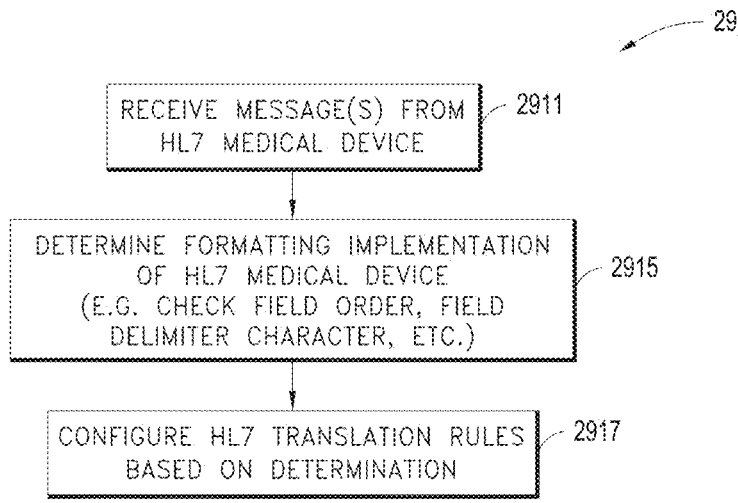
FIGS. 45C and 45D illustrate example automatic rule configuration processes that can be performed by the translation module for messages utilizing the HL7 protocol.

The automatic rule configuration process 2900C illustrated in FIG. 45C is similar to the process 2900A illustrated in FIG. 45A. At block 2911, the translation module 2415 receives one or more messages from an HL7 medical device. At block 2915, the translation module 2415 determines the formatting implementation of the HL7 medical device from the one or more messages received. As discussed above, the determination of the formatting implementation can be made, for example, by checking field order or sequence, field delimiter characters, repeatability, cardinality, and other HL7 implementation variations.

At block 2917, the translation module 2415 configures one or more rules to handle messages received from and/or sent to the HL7 medical device. In certain embodiments, the configuration of the rules involves the creation or generation of new rules for the detected formatting implementation. In other embodiments, the configuration of the rules involves the dynamic alteration or updating of existing rules. If a set of rules already exists for the formatting implementation used by the new HL7 medical device, then the configuration of new translation rules may not be required. Instead, existing translation rules can be associated with the new HL7 medical device for use in communication involving that device.

Figure 45D:
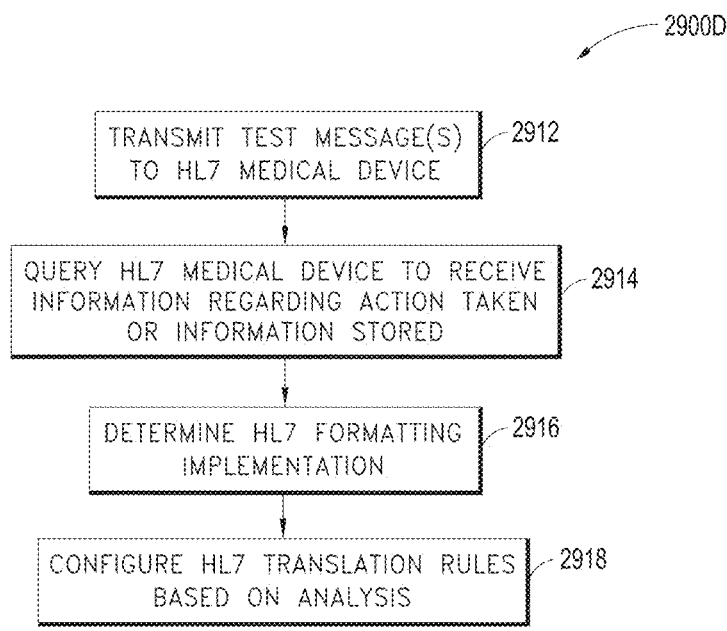
Figure 46:
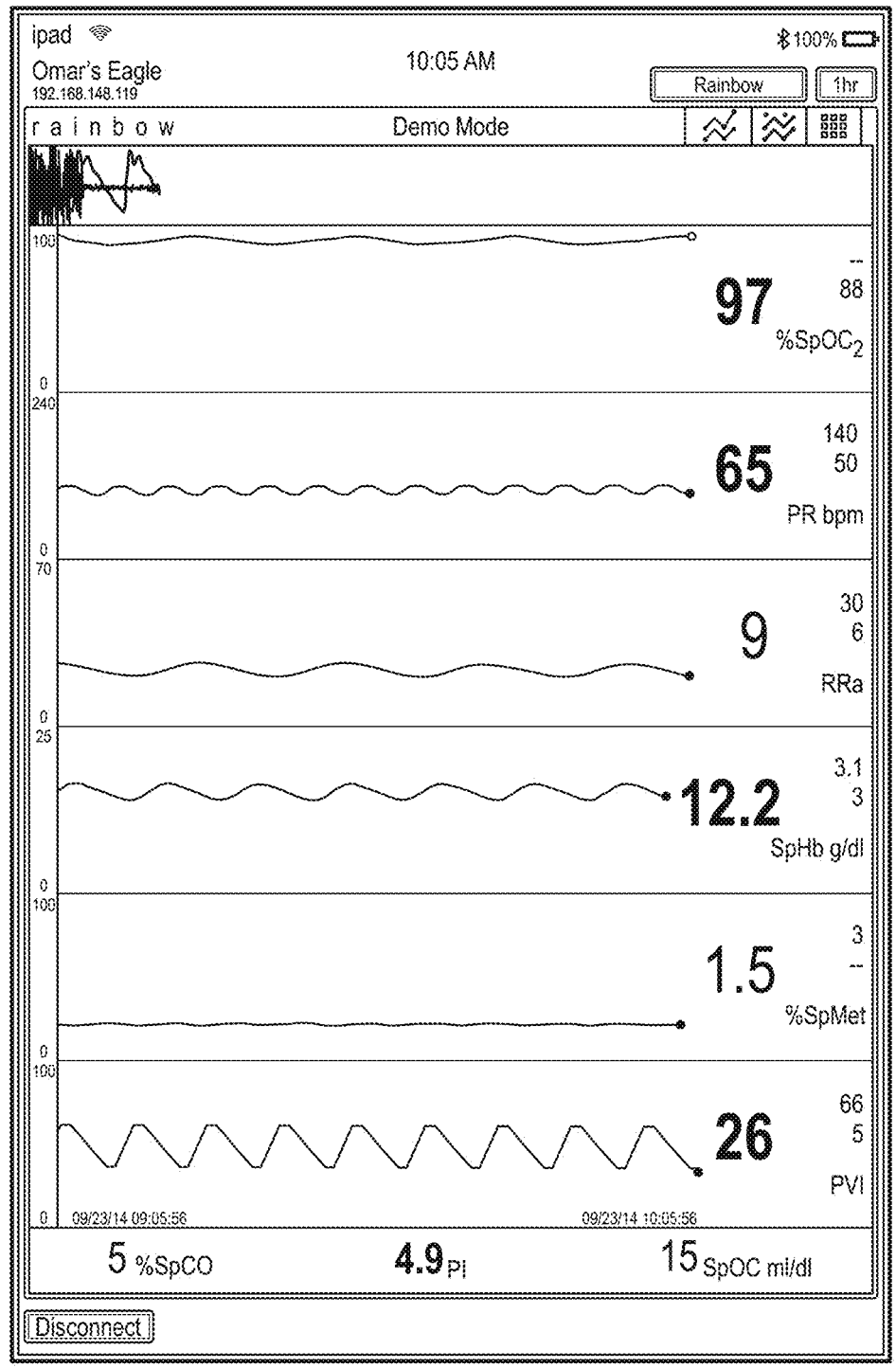
FIGS. 46-71 illustrate additional example hub displays, including displays of measurement data.
Figure 47:
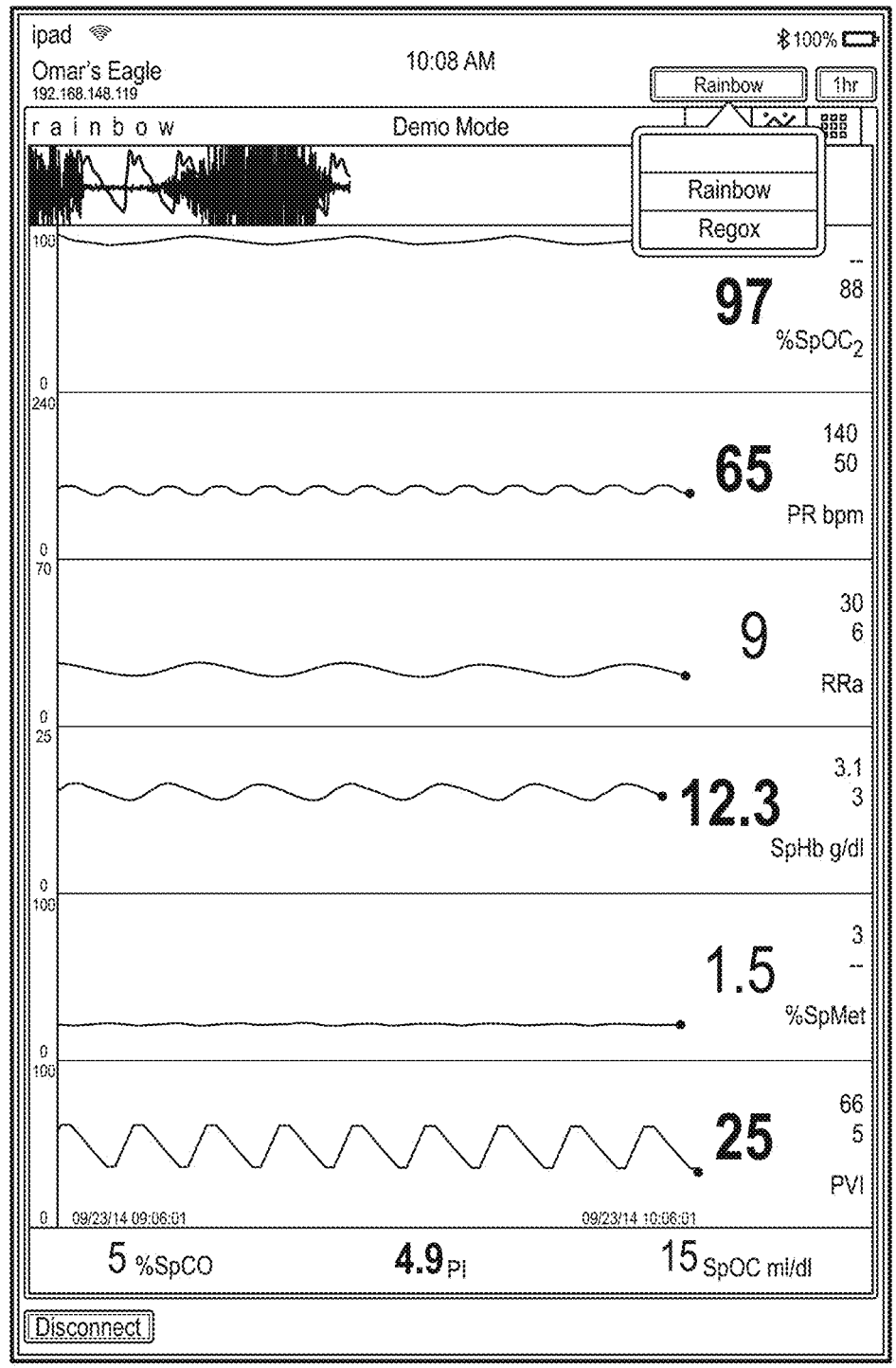
Figure 48:
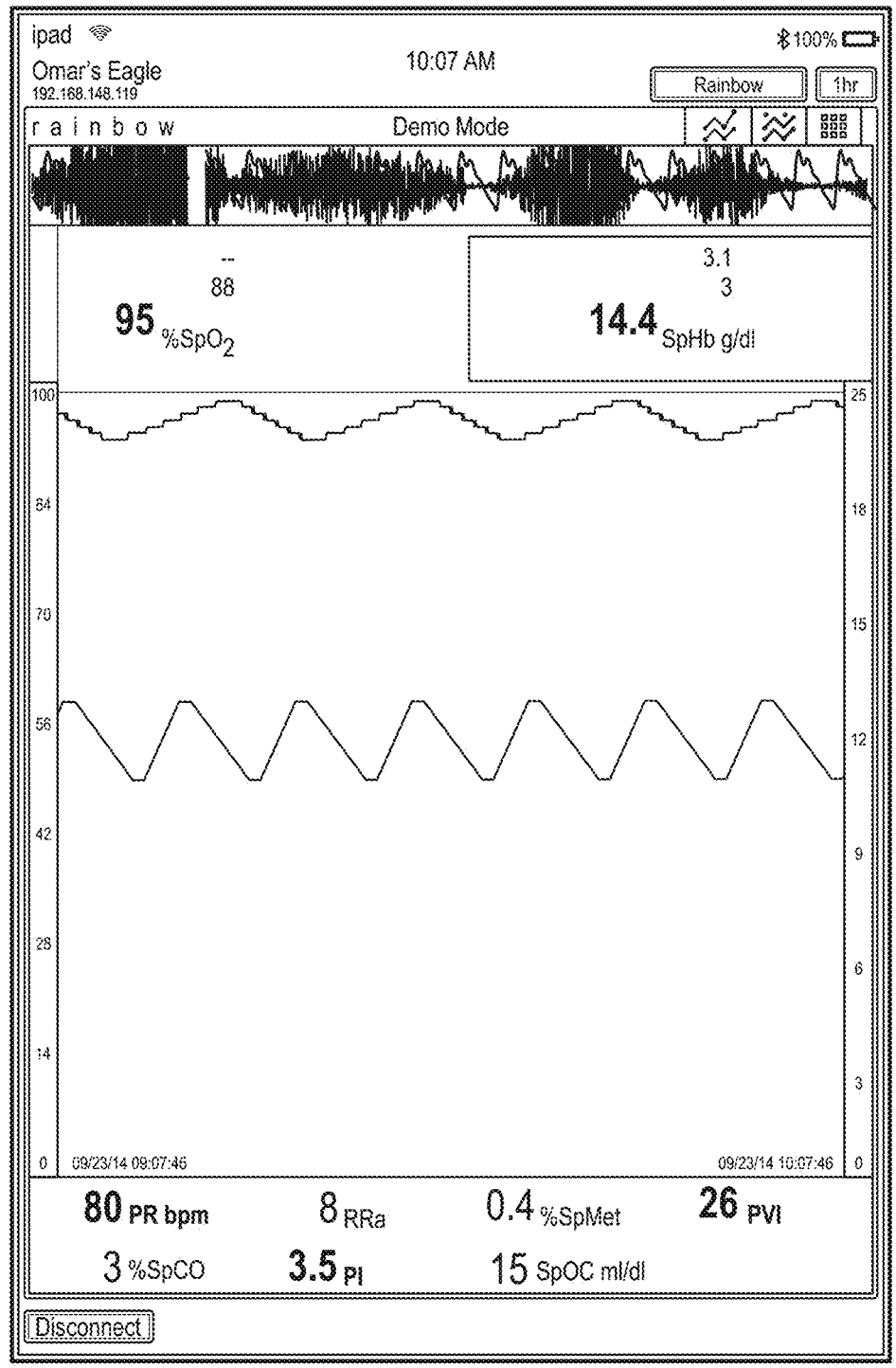
Figure 49:
Figure 50:
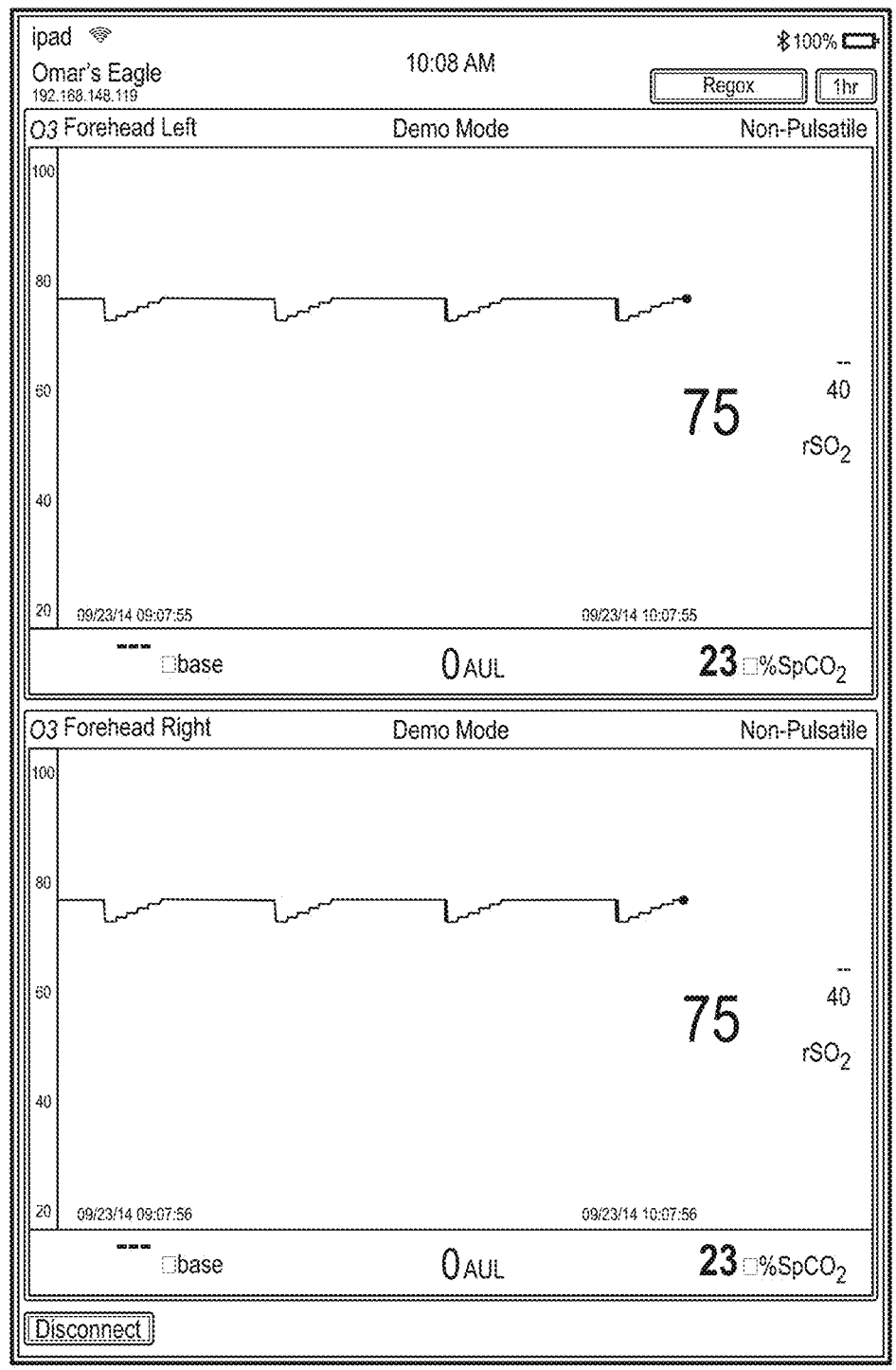
Figure 51:
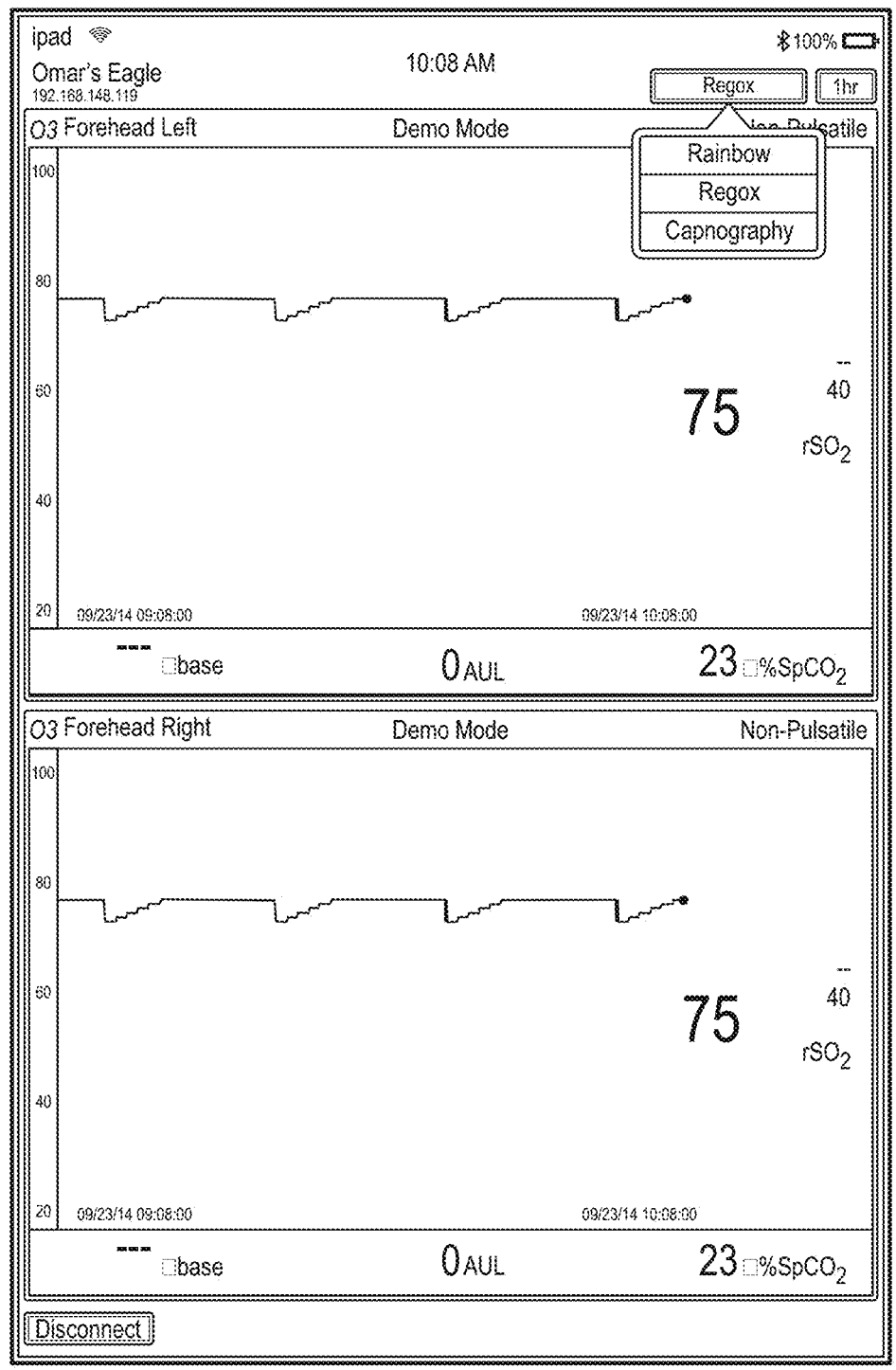
Figure 52:
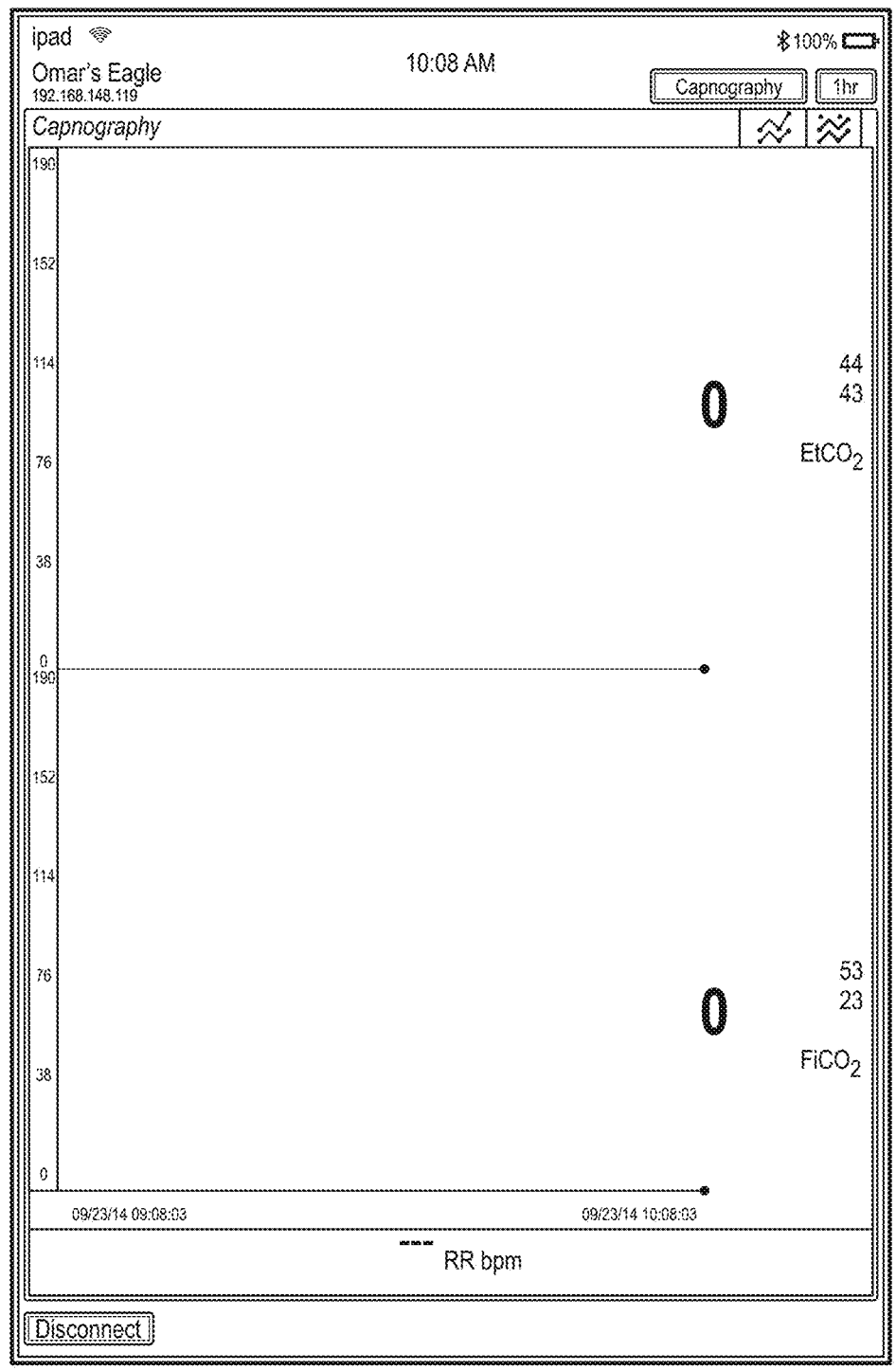
Figure 53:
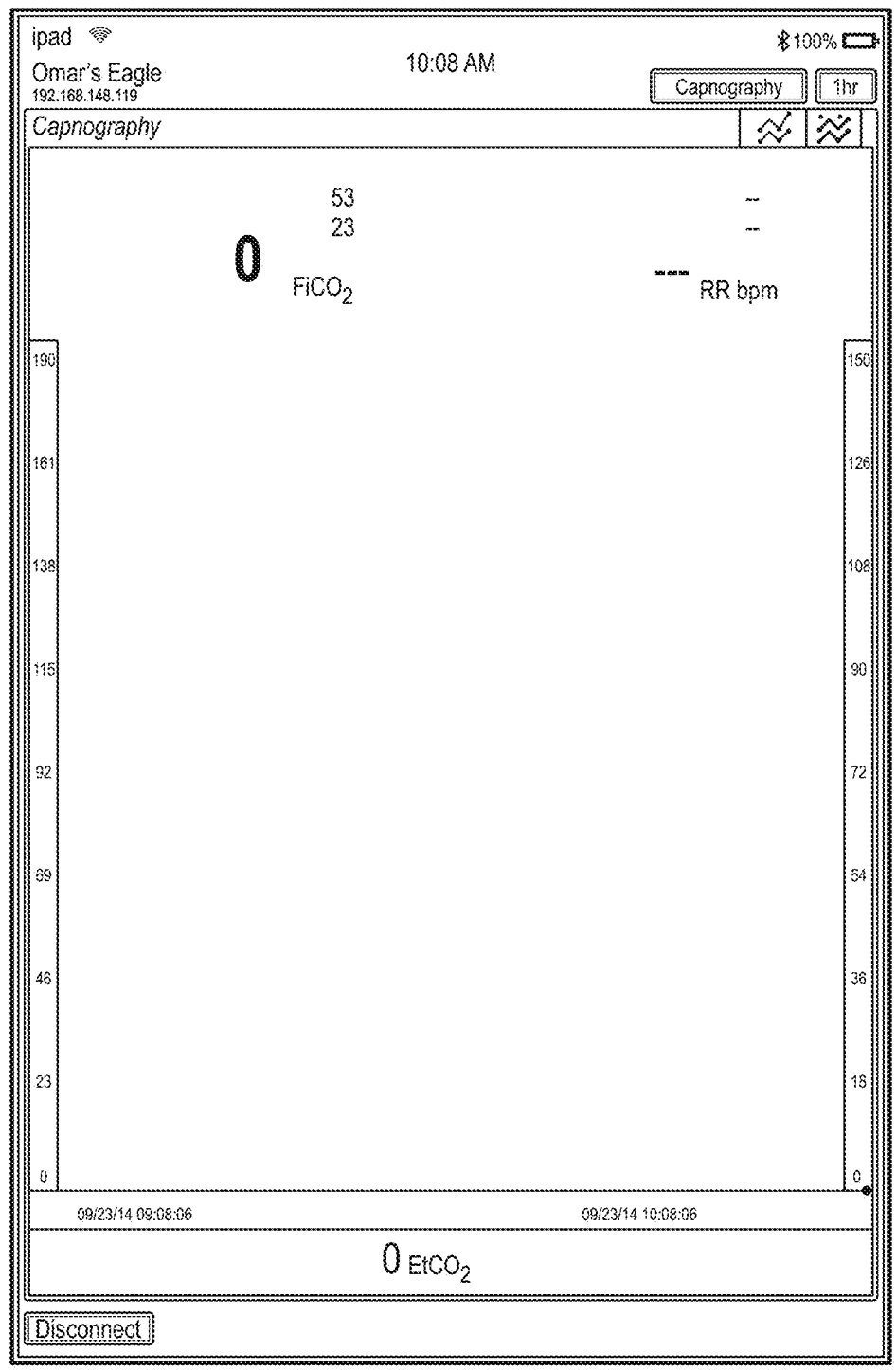
Figure 54:
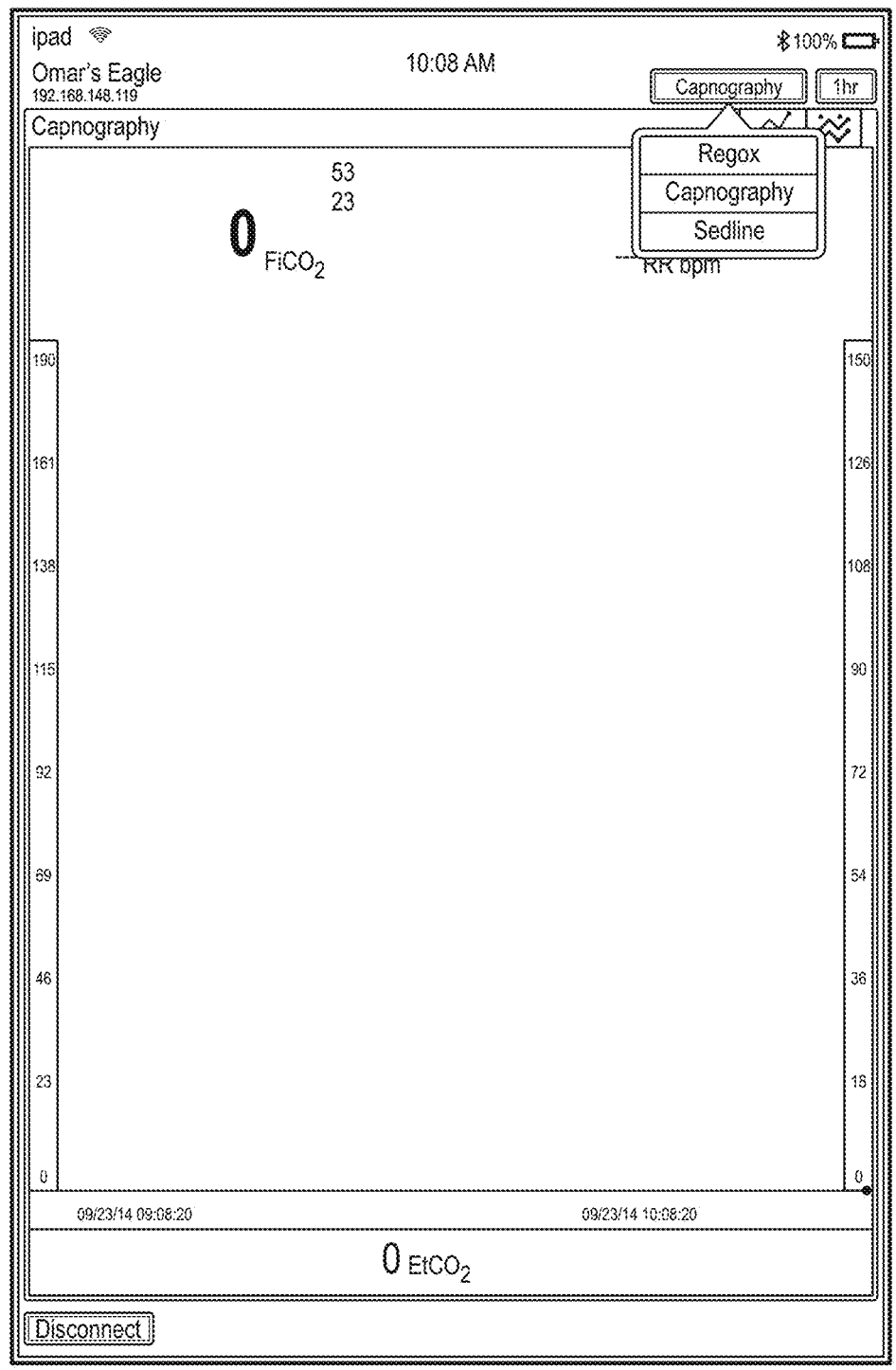
Figure 55:
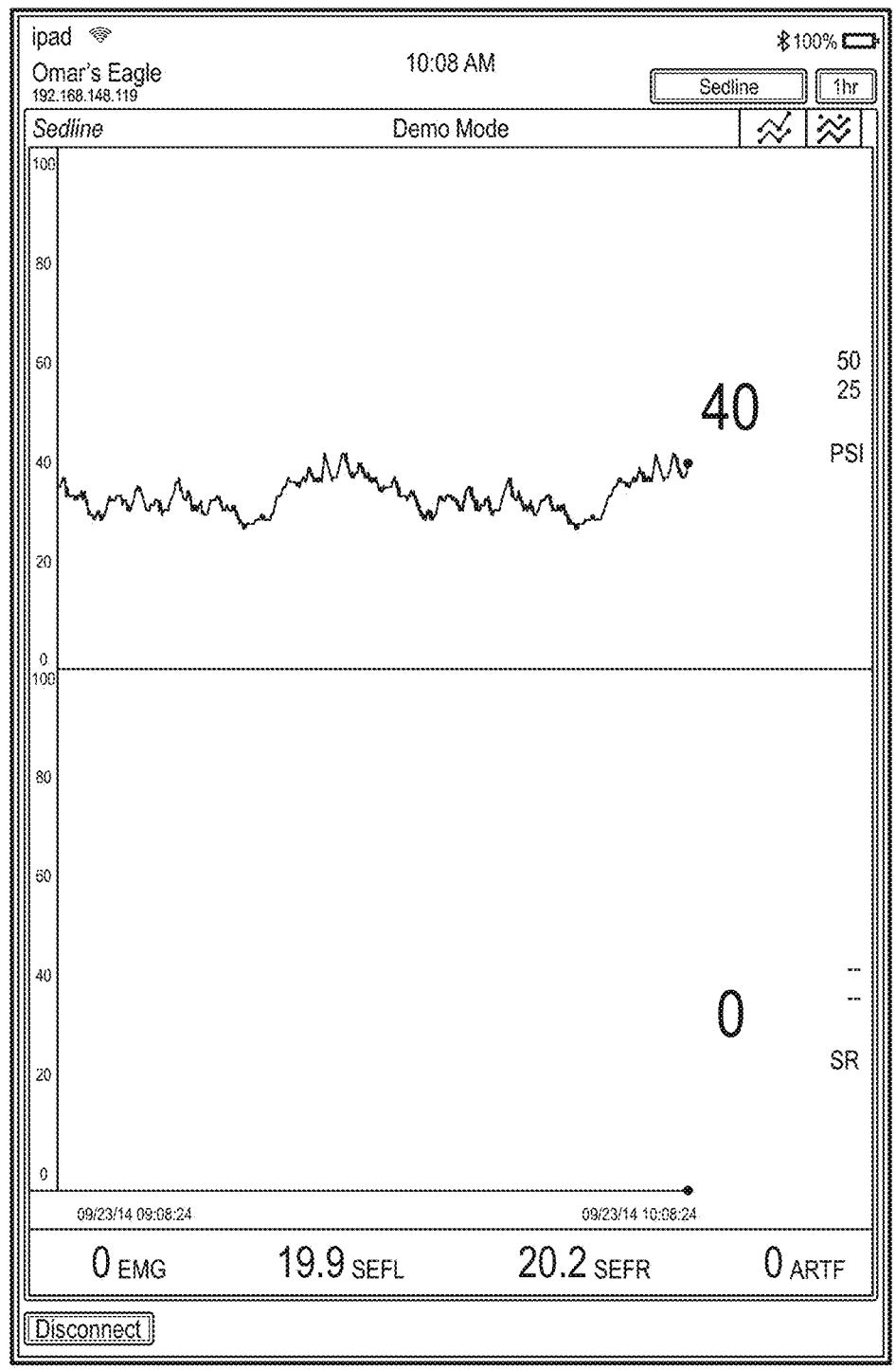
Figure 56:
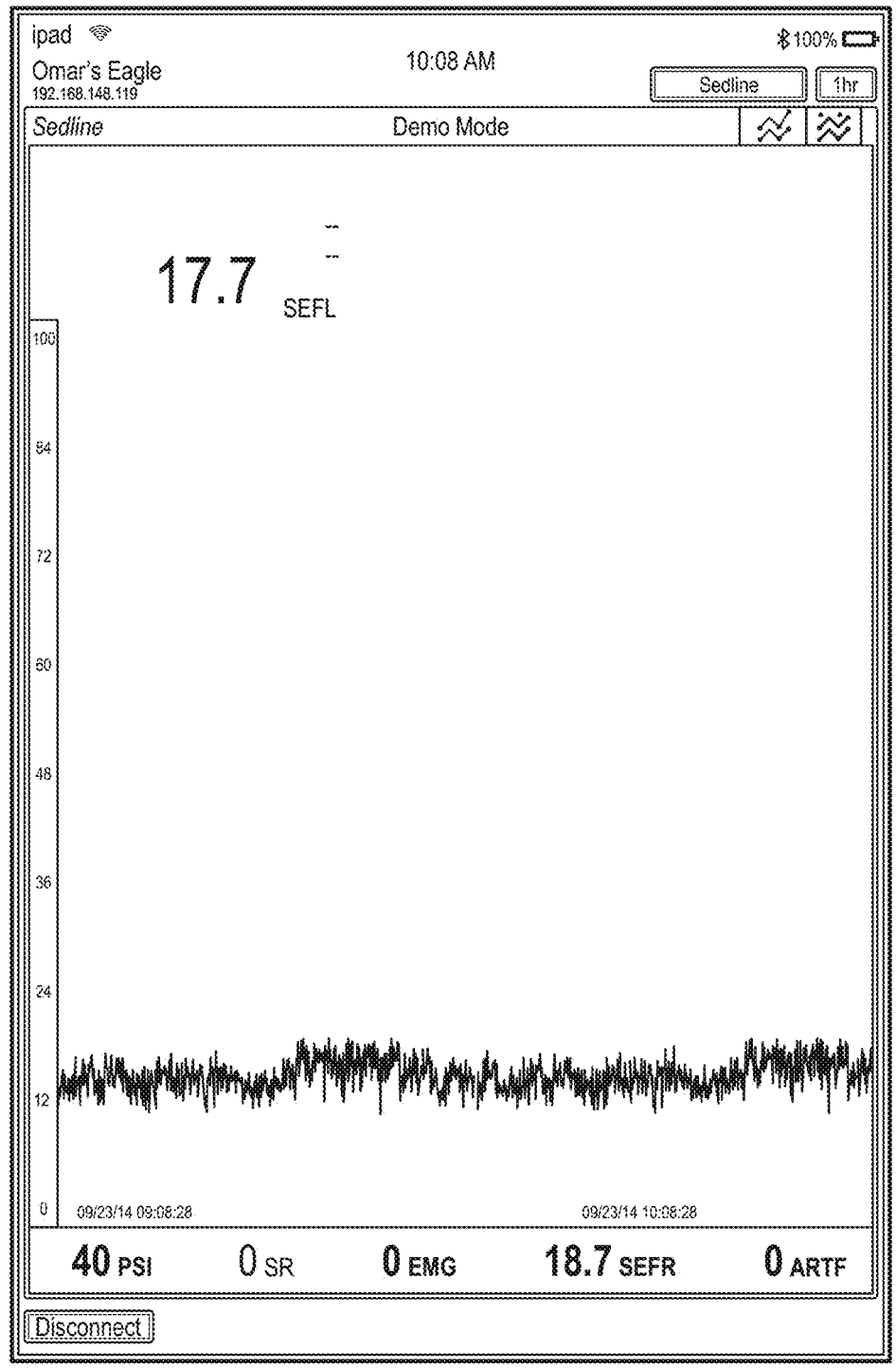
Figure 57:
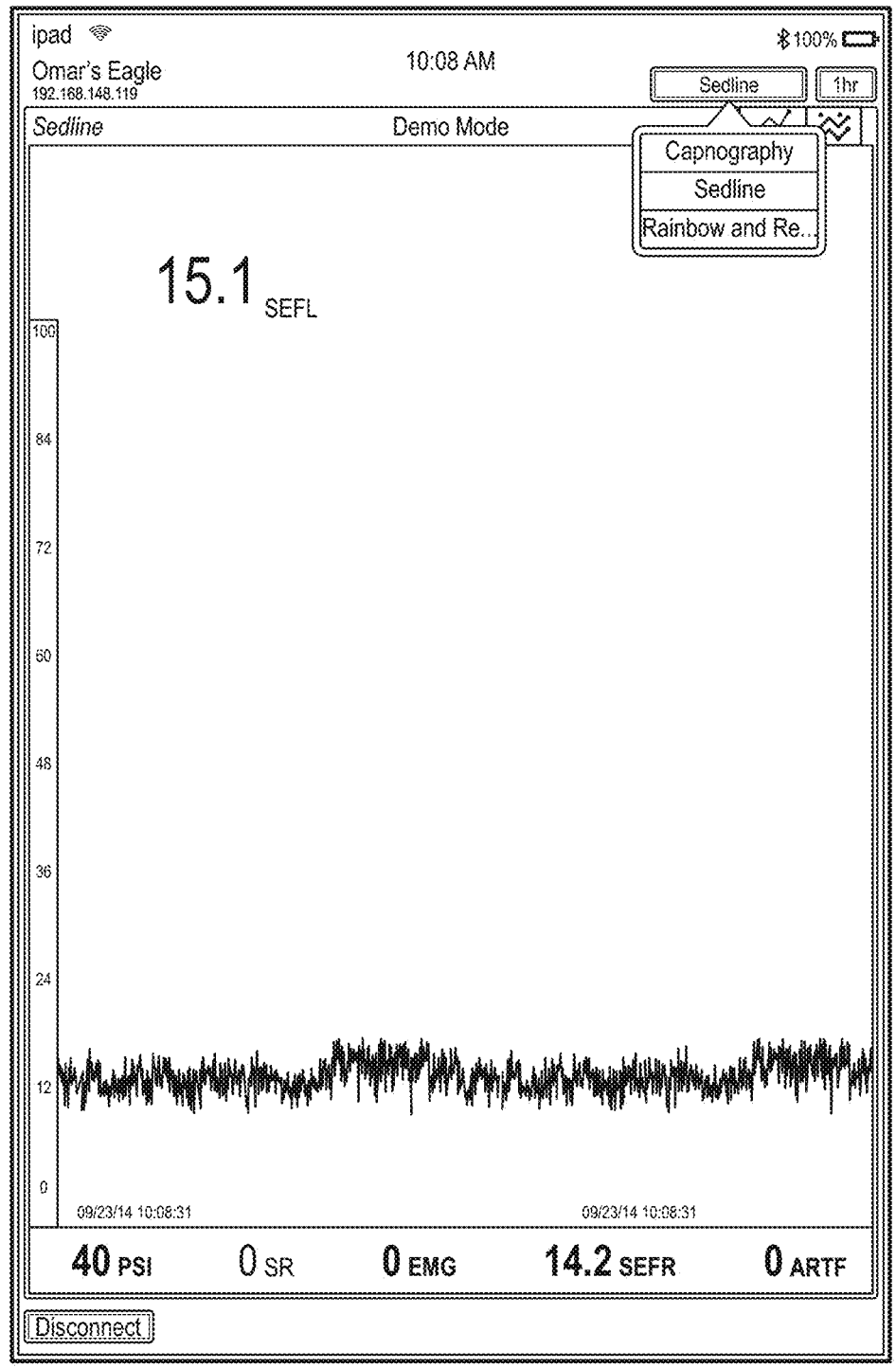
Figure 58:
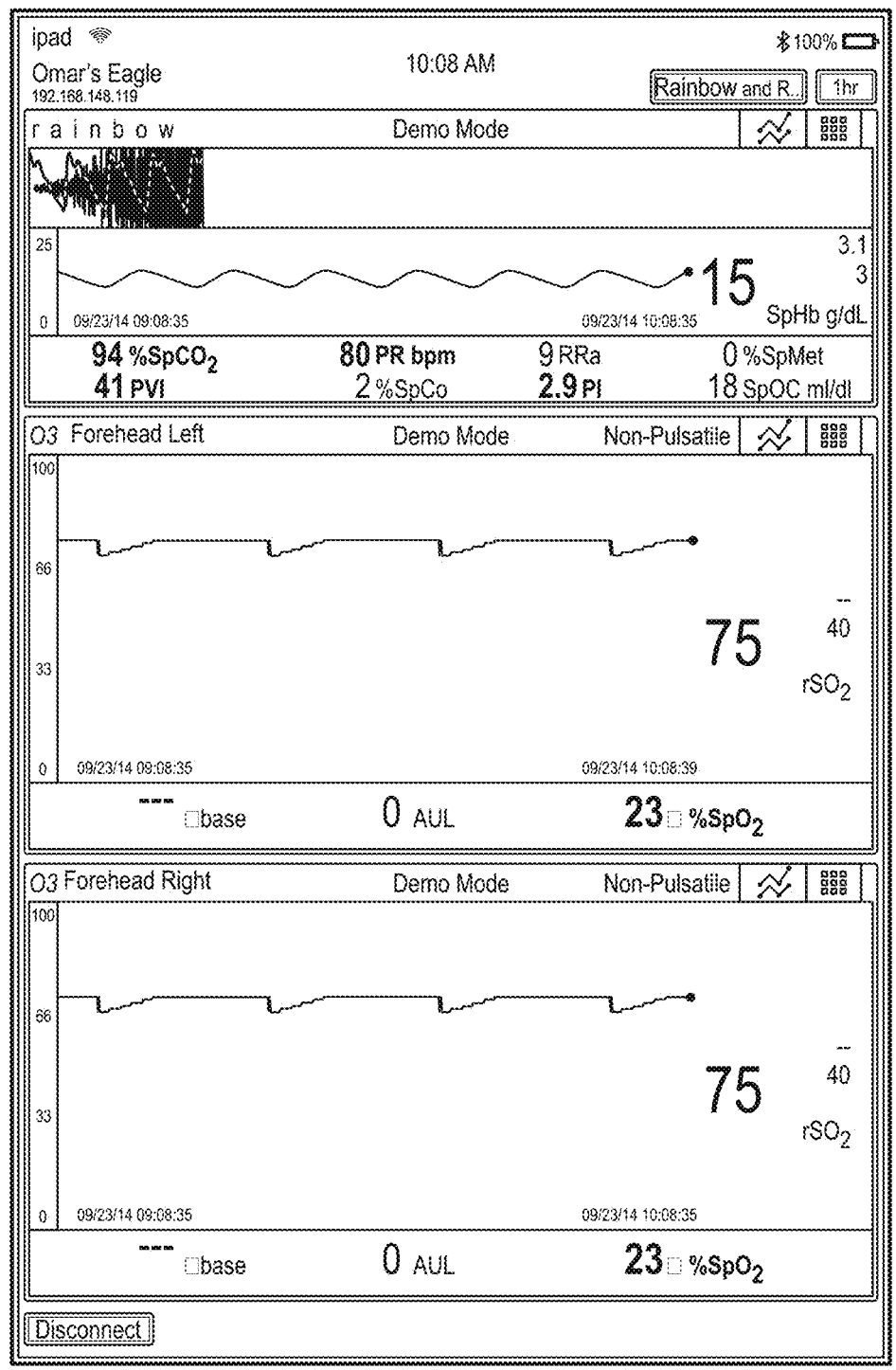
Figure 59:
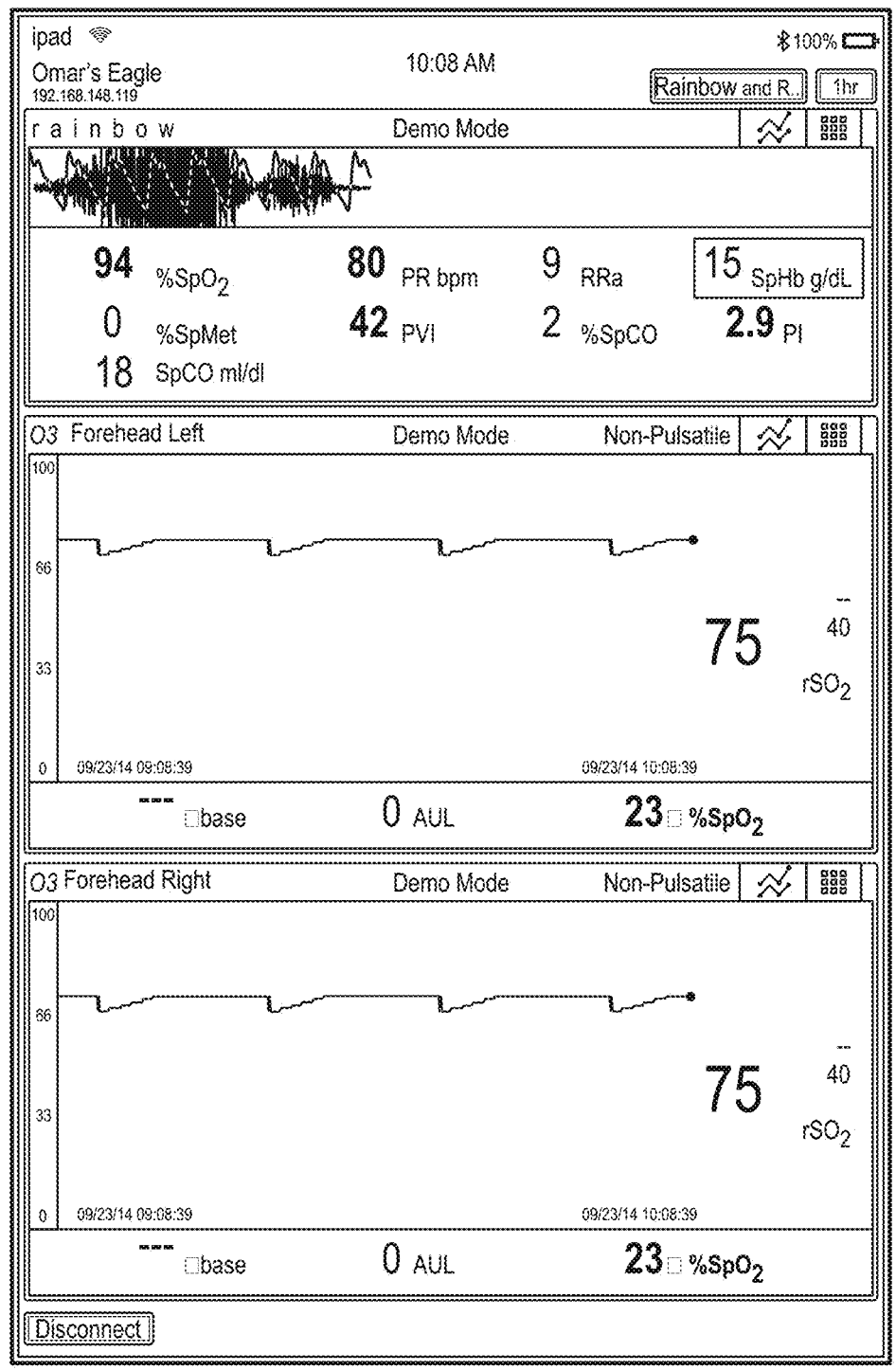
Figure 60:
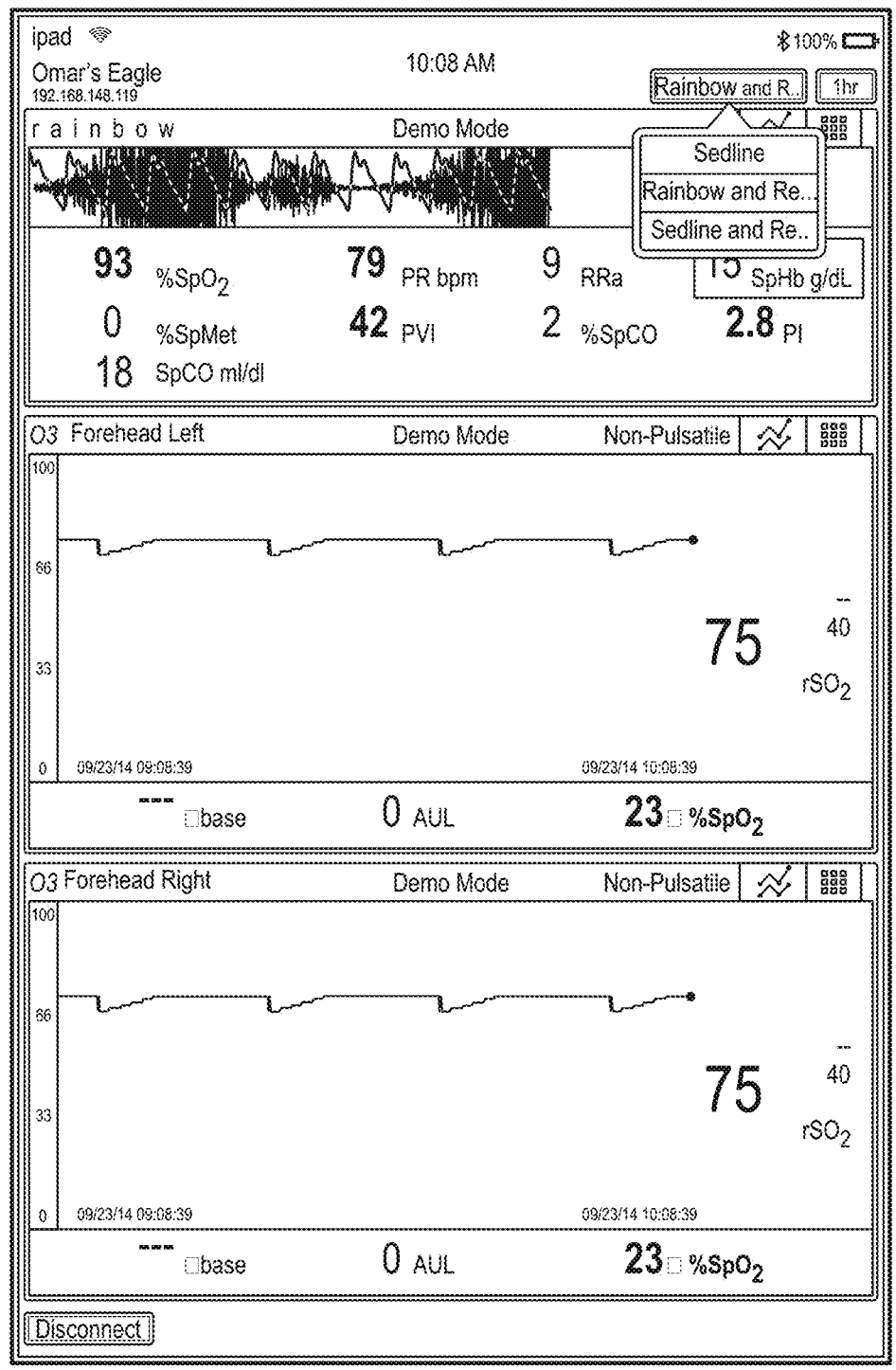
Figure 61:
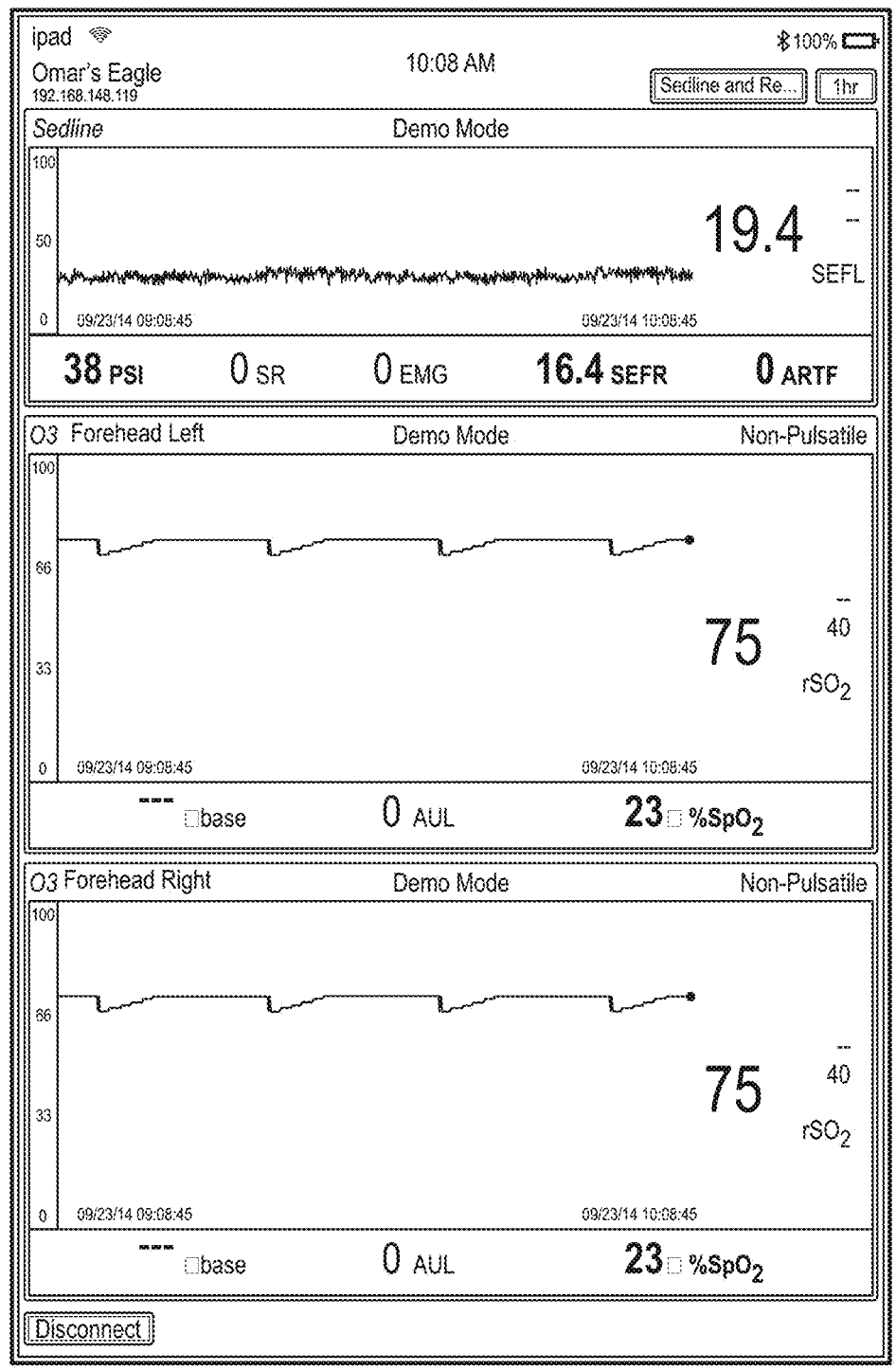
Figure 62:
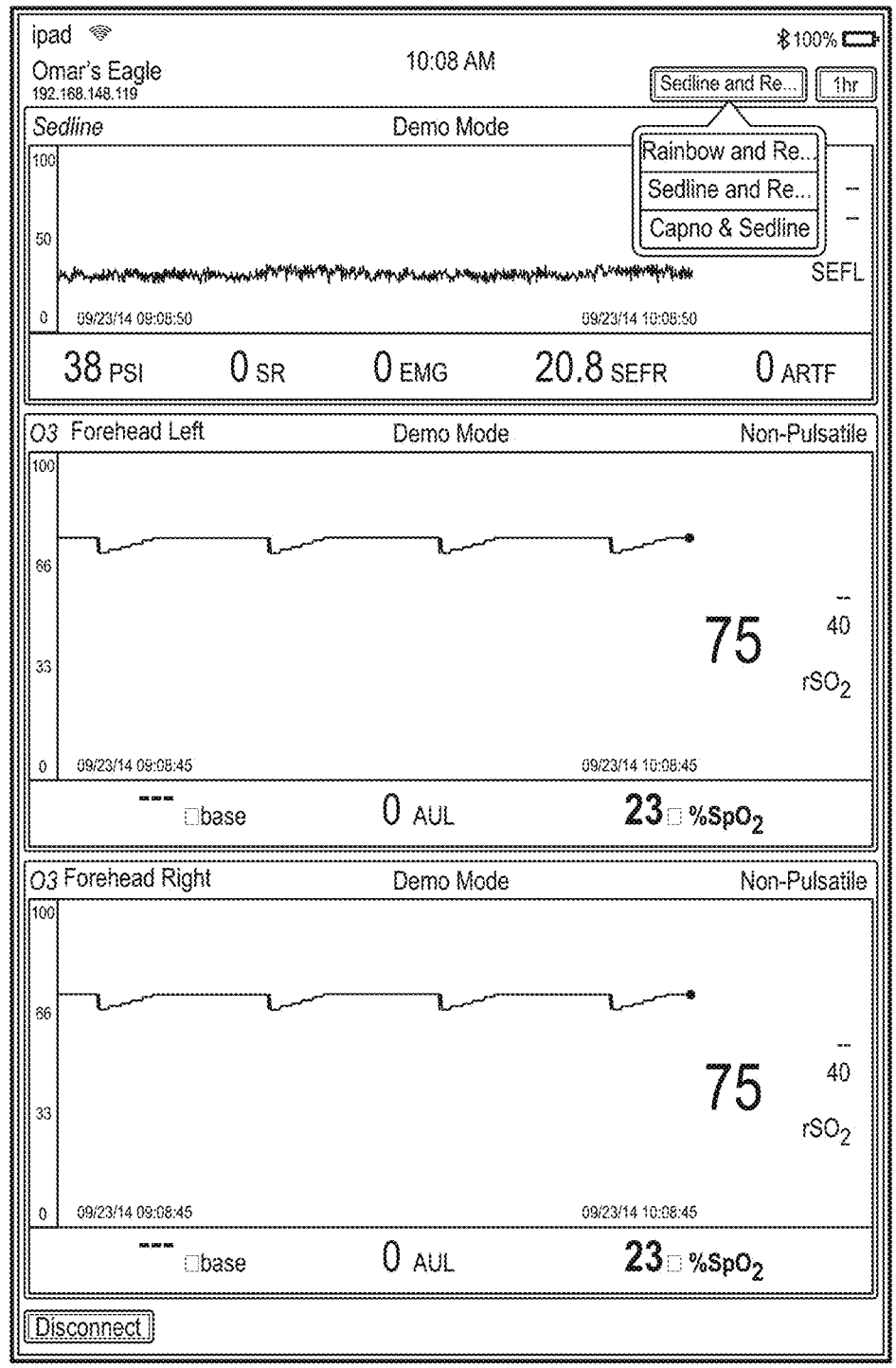
Figure 63:
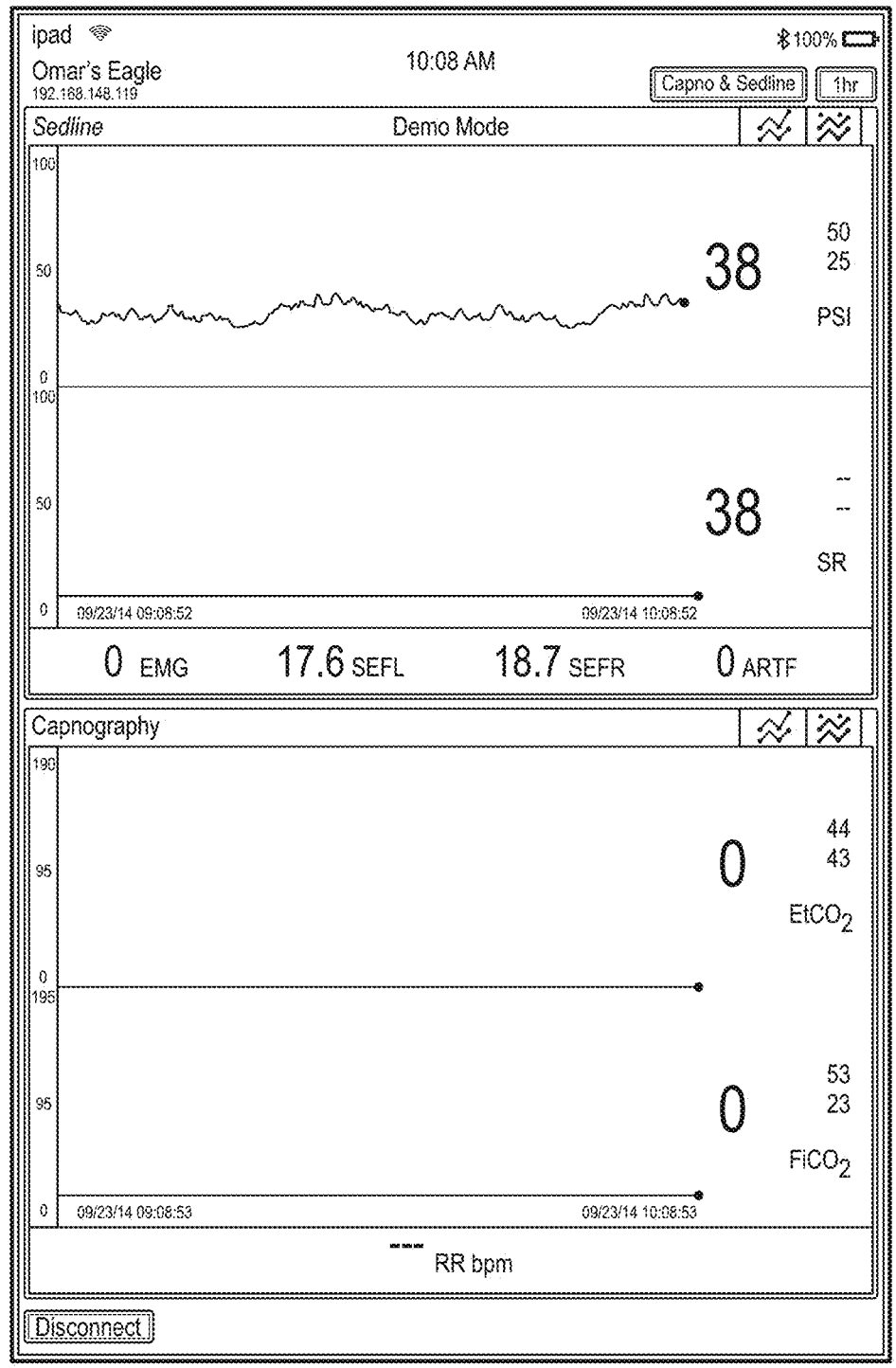
Figure 64:
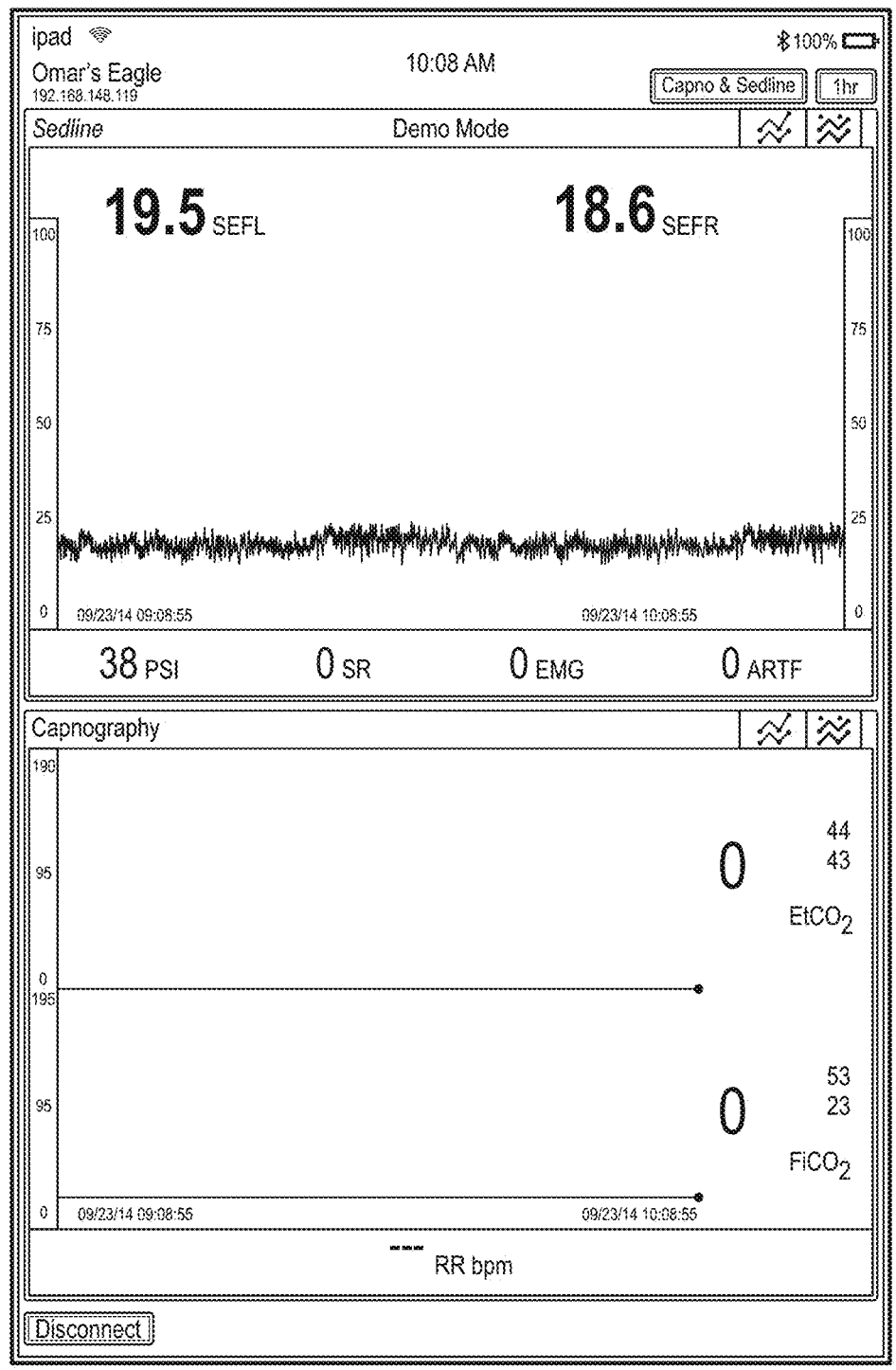
Figure 65:
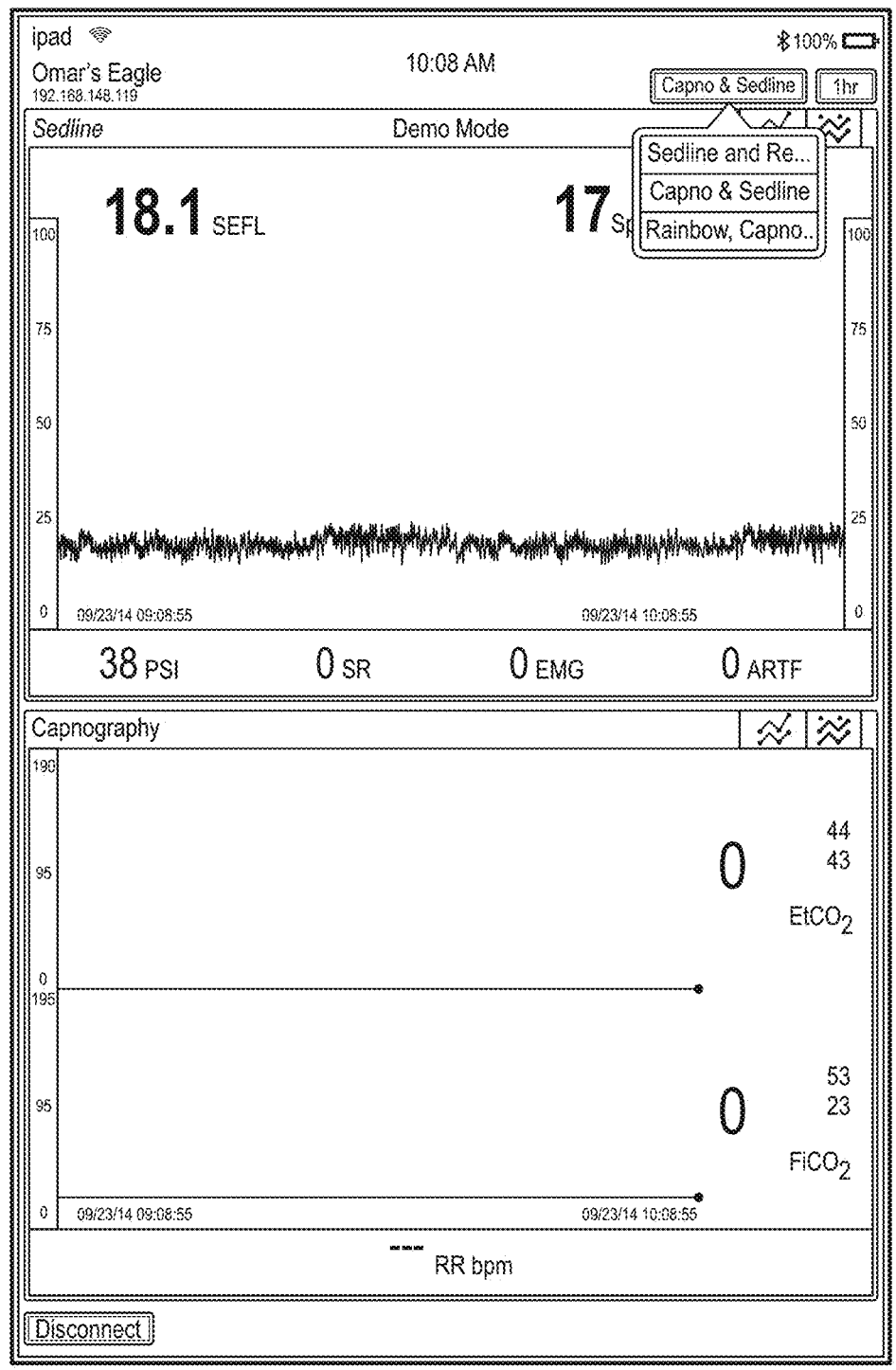
Figure 66:
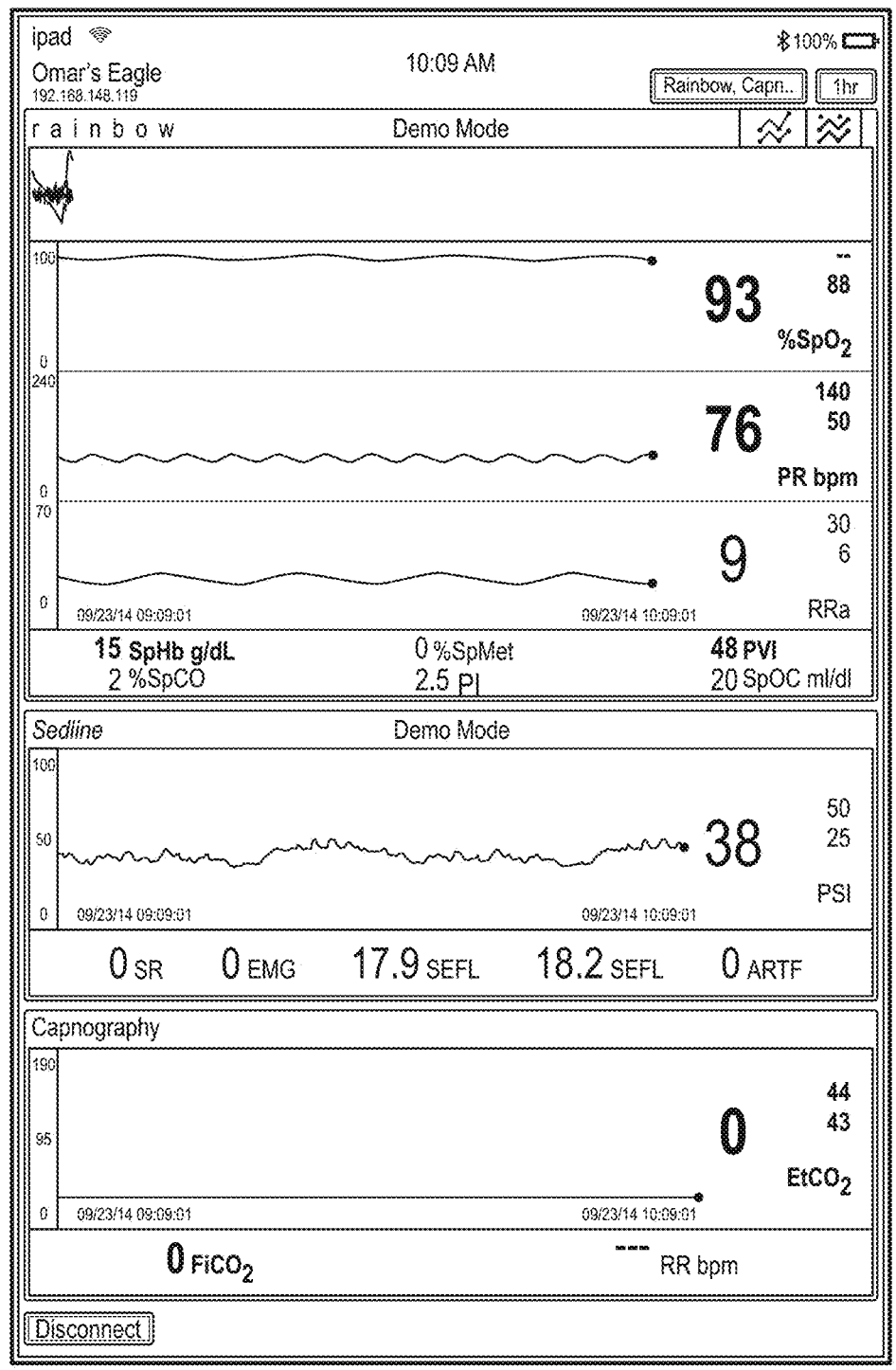
Figure 67:
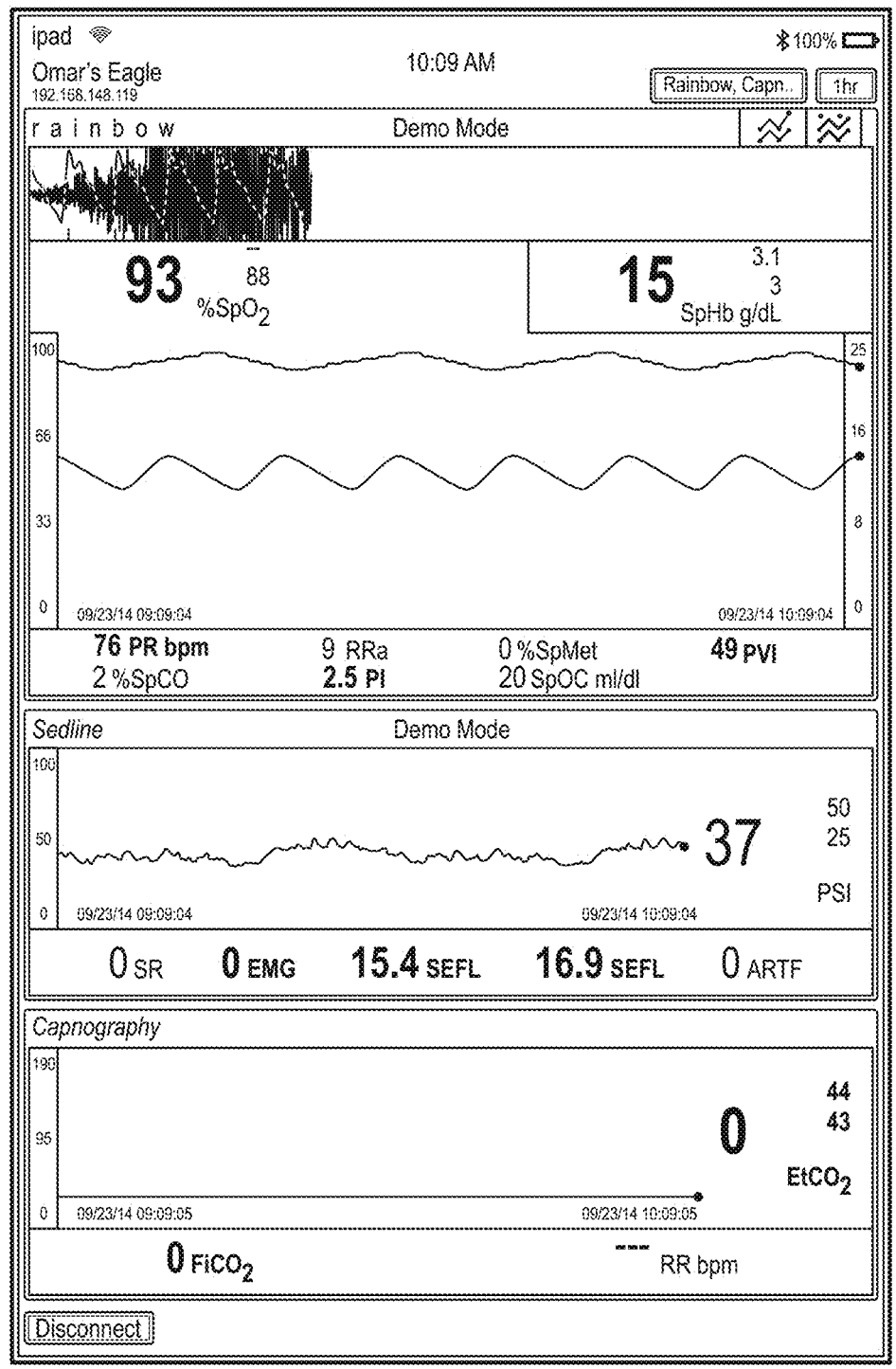
Figure 68:
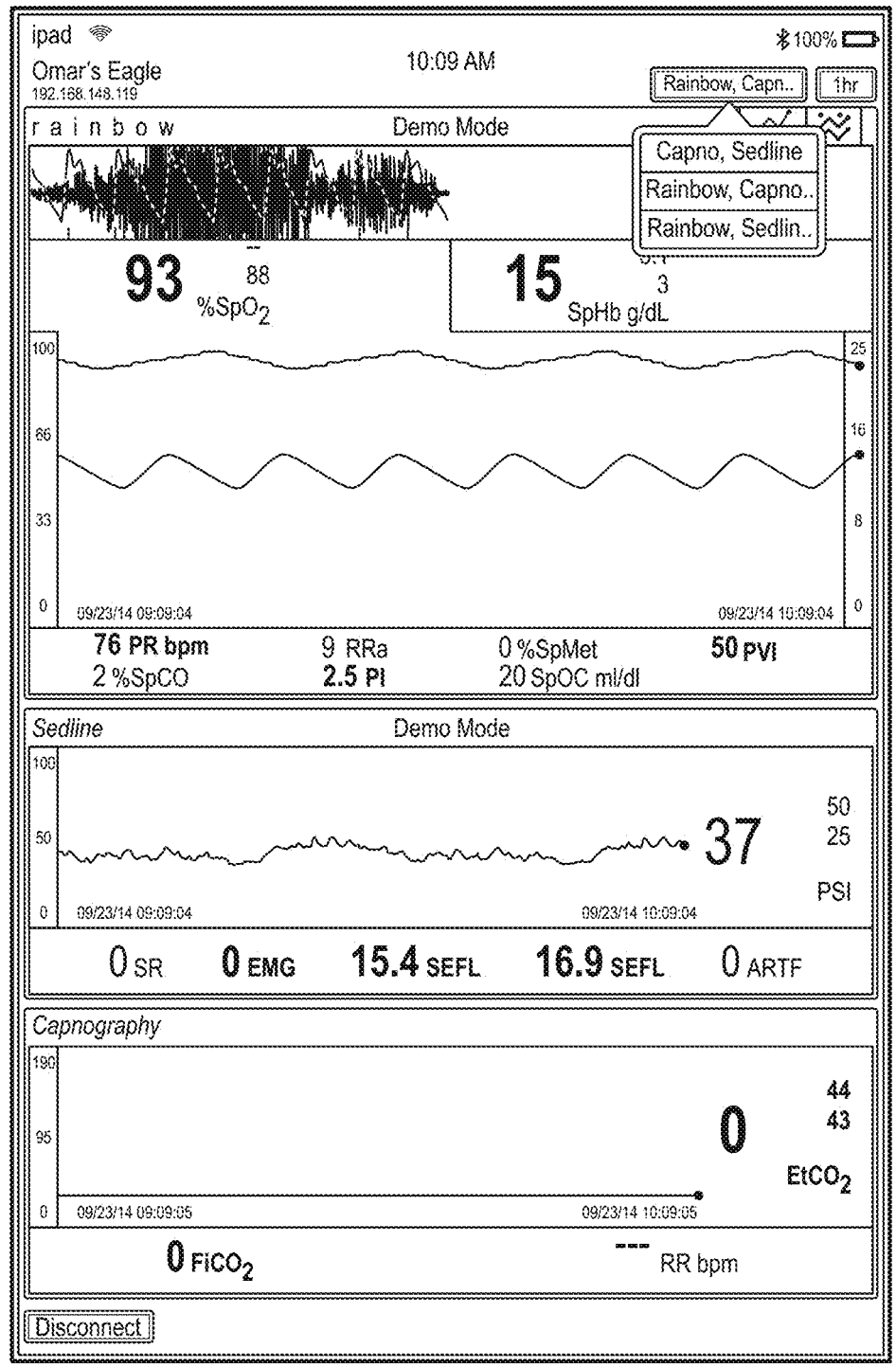
Figure 69:
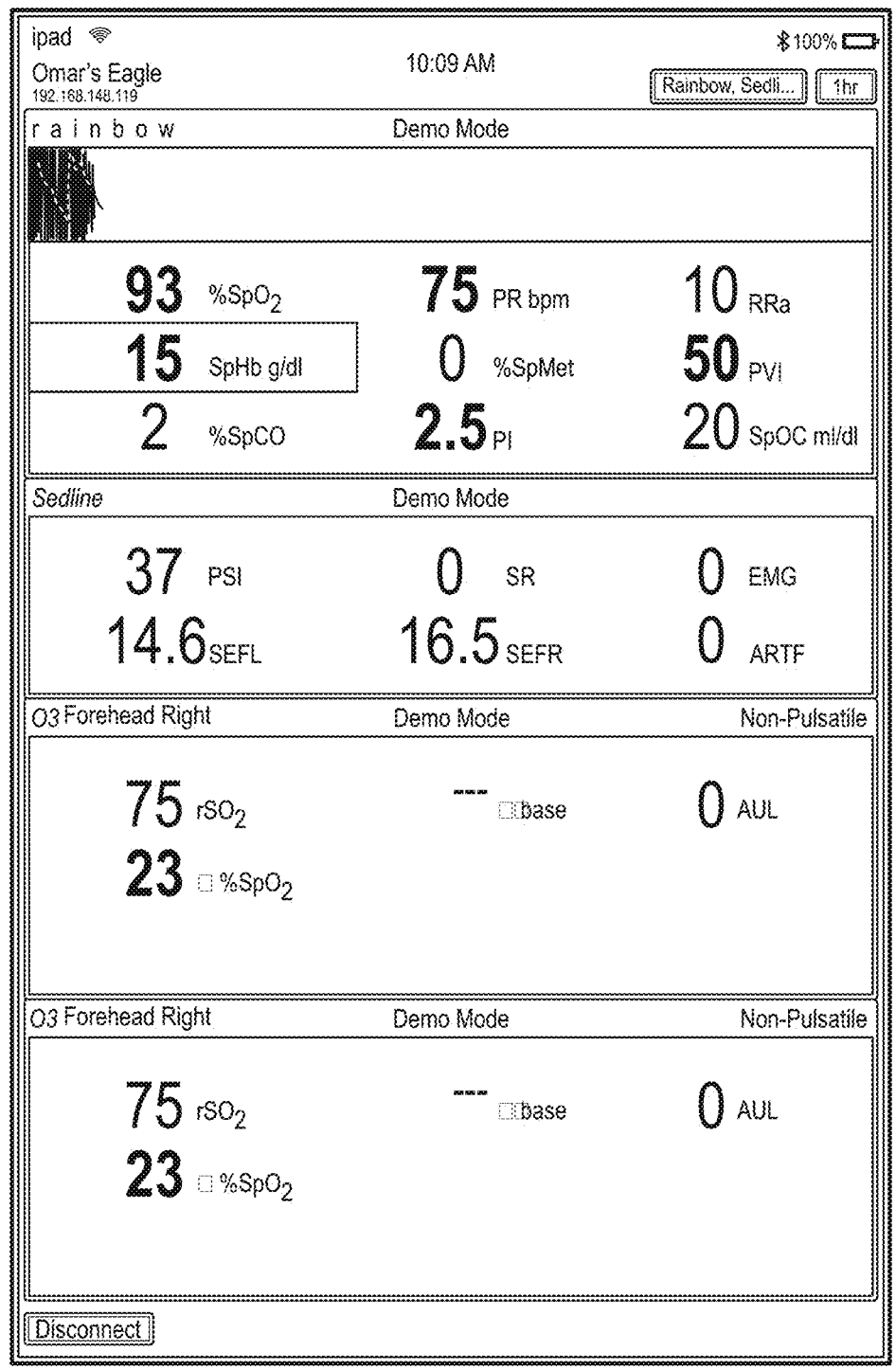
Figure 70:
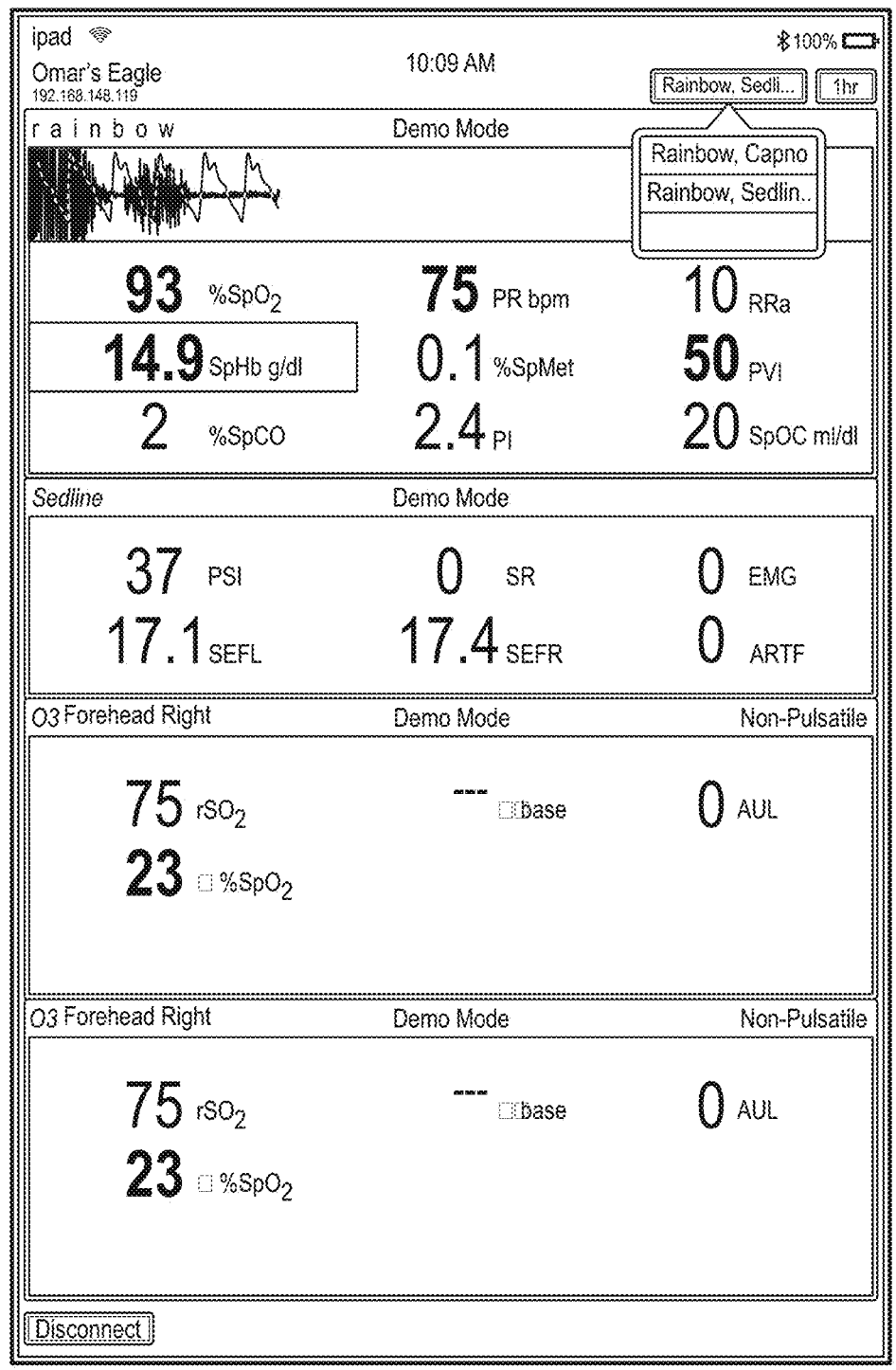
Figure 71:
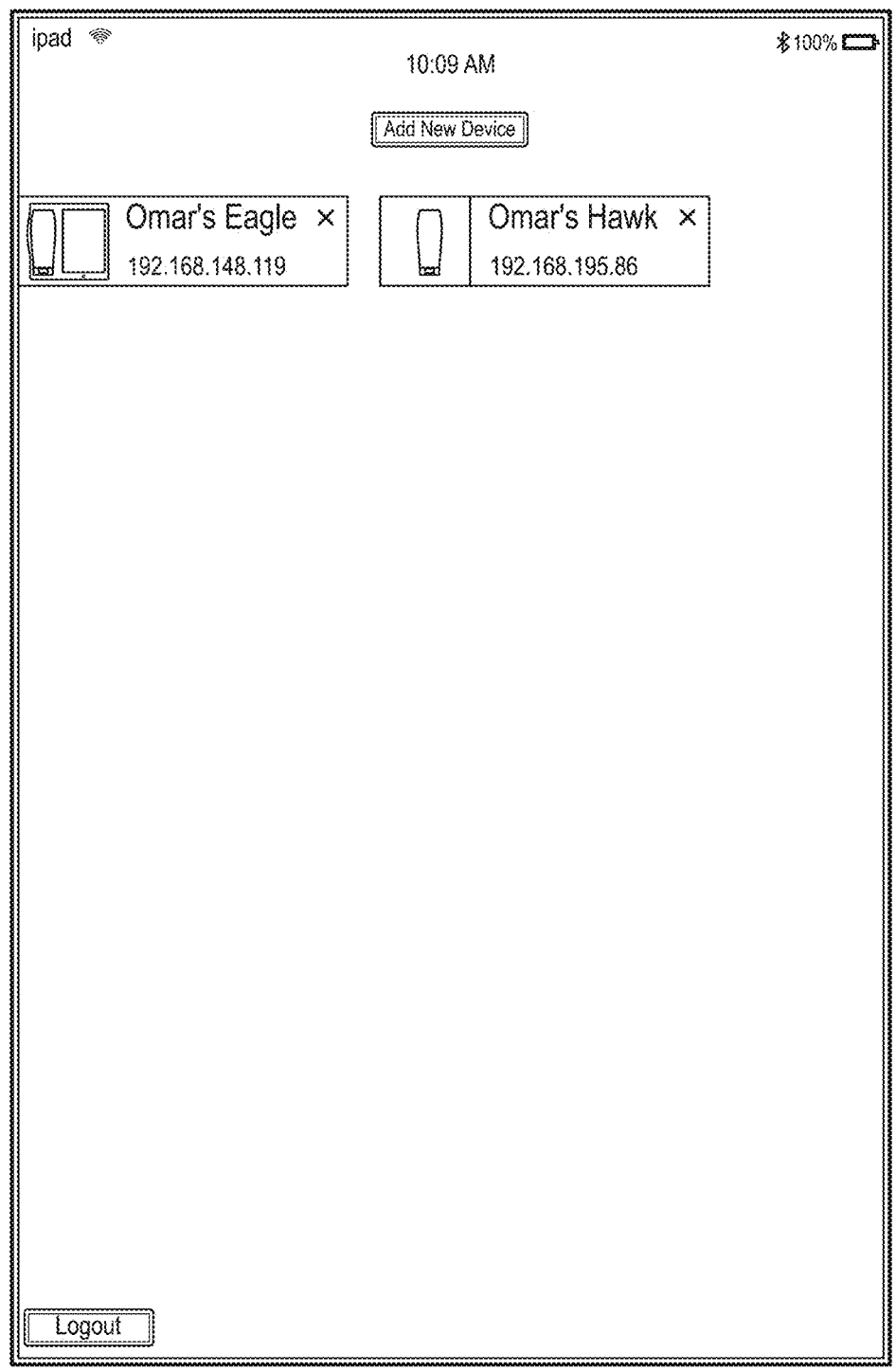

The automatic rule configuration process 2900D illustrated in FIG. 45D is similar to the process 2900B illustrated in FIG. 45B. At block 2912, the translation module 2415 transmits one or more test, dummy, or initialization messages to an HL7 medical device. In other embodiments, the translation module 2415 can cause one or more test messages to be transmitted to the new HL7 medical device from another HL7 medical device. As described above, the test messages can include messages having known HL7 formats configured to determine whether the HL7 device understands the test messages. The test messages can include test ADT messages, for example.

At block 2914, the translation module 2415 queries the HL7 medical device to receive information regarding an action taken or information stored in response to the test message. At block 2916, the translation module 2415 determines the formatting implementation of the HL7 device based on the information received. In certain embodiments, the translation module 2415 can analyze the information received to determine whether the test message or messages were properly understood. If none of the test messages were properly understood, the translation module 2415 can send additional test messages having other known HL7 formats and repeat blocks 2914 and 2916.

At block 2918, the translation module 2415 configures one or more translation rules to handle messages received from and/or sent to the detected HL7 medical device. In certain embodiments, the configuration of the translation rules involves the creation or generation of new translation rules. In other embodiments, the configuration of the rules involves the alteration or updating of existing rules. If a set of translation rules already exists for the formatting implementation used by the new HL7 medical device, then the configuration of new translation rules may not be required. Instead, existing translation rules can be associated with the new HL7 medical device for use in communication involving that HL7 medical device.

The automatic rule configuration processes described above can be triggered by the detection of a network device or system by the translation module 2415. The medical devices referred to in FIGS. 45A-45D can include any of the devices or systems illustrated in FIG. 1 or 24.

In some embodiments, the automatic generation of translation rules can advantageously occur post-installation and post-compilation of the messaging sub-system software, which includes the translation module 2415. In certain embodiments, the automatic generation or dynamic modification of the translation rules 2420 can occur without having to recompile or rebuild the translation module software. This feature can be advantageous in terms of efficiently complying with U.S. Food and Drug Administration ("FDA") requirements regarding validation of software used in healthcare environments.

Take, for example, a situation where a medical device manufacturer plans to use the translation module 2415 to facilitate communication between a particular medical device or system that is to be installed in a hospital (for example, a patient monitoring system, as described herein), or other patient care facility, and other devices or systems that are already installed at the hospital (for example, the HIS or CIS). Any software required for the operation of the new medical device to be installed may be at least partially validated for FDA compliance prior to installation at the hospital despite the fact that, for example, the HL7 implementations of other existing devices or systems at the hospital may still be unknown. For example, any aspects of the software for the new medical device that are dependent upon receiving messages from other hospital devices can be validated pre-installation as being capable of fully and correctly operating when the expected message format is received. Then, once the medical device is installed at the hospital, the validation of the software can be completed by showing that the translation module 2415 is able to provide messages of the expected format to the newly installed device. In this way, FDA validation tasks can be apportioned to a greater extent to the pre-installation timeframe where they can be more easily carried out in a controlled manner rather than in the field.

In addition, the translation module 2415 can further help streamline FDA validation, for example, when a medical device or system is expected to be installed at different hospitals whose existing devices use, for example, different implementations of the HL7 protocol. Normally, this type of situation could impose the requirement that the entire functionality of the software for the new medical device be completely validated at each hospital. However, if the translation module 2415 is used to interface between the new medical device and the hospital's existing devices, then much of the software functionality could possibly be validated a single time prior to installation, as just described. Then, once installed at each hospital, the software validation for the medical device can be completed by validating that correct message formats are received from the translation module (the translation rules for which are field-customizable). This may result in making on-site validation procedures significantly more efficient, which will advantageously enable more efficient FDA compliance in order to bring life-saving medical technology to patients more quickly by the use of field-customizable translation rules.

V. Example Embodiments

In certain embodiments, a system for providing medical data translation for output on a medical monitoring hub can include a portable physiological monitor comprising a processor that can: receive a physiological signal associated with a patient from a physiological sensor, calculate a physiological parameter based on the physiological signal, and provide a first value of the physiological parameter to a monitoring hub for display. The monitoring hub can include a docking station that can receive the portable physiological monitor. The monitoring hub can: receive the first value of the physiological parameter from the portable physiological monitor; output the first value of the physiological parameter for display; receive physiological parameter data from a medical device other than the portable physiological monitor, the physiological parameter data formatted according to a protocol other than a protocol natively readable or displayable by the monitoring hub; pass the physiological parameter data to a translation module; receive translated parameter data from the translation module, where the translated parameter data can be readable and displayable by the monitoring hub; and output a second value from the translated parameter data for display.

The system of the preceding paragraph can be combined with any subcombination of the following features: the monitoring hub is further configured to output the first value of the physiological parameter and the second value from the translated parameter data on separate displays; the monitoring hub is further configured to output the second value from the translated parameter data to an auxiliary device having a separate display from a display of the monitoring hub; the auxiliary device is selected from the group consisting of a television, a tablet, a phone, a wearable computer, and a laptop; the physiological parameter data comprises data from an infusion pump; the physiological parameter data comprises data from a ventilator; and the translation module is configured to translate the physiological parameter data from a first Health Level 7 (HL7) format to a second HL7 format.

In certain embodiments, a method of providing medical data translation for output on a medical monitoring hub can include: under the control of a first medical device comprising digital logic circuitry, receiving a physiological signal associated with a patient from a physiological sensor; obtaining a first physiological parameter value based on the physiological signal; outputting the first physiological parameter value for display; receiving a second physiological parameter value from a second medical device other than the first medical device, where the second physiological parameter value is formatted according to a protocol not used by the first medical device, such that the first medical device is not able to process the second physiological parameter value to produce a displayable output value; passing the physiological parameter data from the first medical device to a separate translation module; receiving translated parameter data from the translation module at the first medical device, the translated parameter data able to be processed for display by the first medical device; and outputting a second value from the translated parameter data for display.

The method of the preceding paragraph can be combined with any subcombination of the following features: further including translating the message by at least translating the message from a first Health Level 7 (HL7) format to a second HL7 format; the message can include data from a physiological monitor; the message can include data from an infusion pump or a ventilator; and the message can include data from a hospital bed.

In certain embodiments, a system for providing medical data translation for output on a medical monitoring hub can include a first medical device including electronic hardware that can: obtain a first physiological parameter value associated with a patient; output the first physiological parameter value for display; receive a second physiological parameter value from a second medical device other than the first medical device, the second physiological parameter value formatted according to a protocol not used by the first medical device, such that the first medical device is not able to process the second physiological parameter value to produce a displayable output value; pass the physiological parameter data from the first medical device to a translation module; receive translated parameter data from the translation module at the first medical device, the translated parameter data able to be processed for display by the first medical device; and output a second value from the translated parameter data for display.

The system of the preceding paragraph can be combined with any subcombination of the following features: the first medical device can also output the first value of the physiological parameter and the second value from the translated parameter data on the same display; the first medical device can also output the first value of the physiological parameter and the second value from the translated parameter data on separate displays; the first medical device can also output the second value from the translated parameter data to an auxiliary device; the auxiliary device can be a television monitor; the auxiliary device can be selected from the group consisting of a tablet, a phone, a wearable computer, and a laptop; the first medical device can include the translation module; the first medical device can also pass the physiological parameter data to the translation module over a network; and the physiological parameter data can include data from an infusion pump or a ventilator.

VI. Augmented Reality Embodiments

Today's patient monitoring environments provide one more traditional displays or screens for clinicians that present data from one or more electronic medical devices associated with a wide variety of monitoring, treatments, or procedures for a patient. Thus, during such patient monitoring, treatments, or procedures a clinician typically reviews one or more traditional displays to gather information about a patient. However, while a clinician looks at the one or more traditional displays their attention may be diverted away from the patient, such as a clinician looking away from the patient to a traditional display during a surgical procedure. For example, during particular surgical procedures, such as an endoscopy or an epidural, it is common for the operating clinician to look at the patient to see where a probe is going but the clinician has to look away from the patient to view a traditional display, which is inefficient.

The systems and methods described herein advantageously may, in certain embodiments, improve the presentation of data or provide improved interactive user interfaces using augmented reality. For example, a clinician using an augmented reality device, such as wearing augmented reality glasses, is presented with medical monitoring data that may be received from the medical monitoring hub, as described herein. In some embodiments, an advantage of augmented reality is that the augmented reality display overlays real world visual information. Accordingly, a clinician can remain visually focused on a patient while simultaneously receiving augmented reality information. In some embodiments, an advantage of augmented reality is that the display area for an augmented reality user interface may be larger than traditional displays, such as device screens. For example, an augmented reality display area may be ten times larger than a traditional display area. The following are examples of improved augmented reality user interfaces.

An example augmented reality device presents one or more user interfaces. Example user interfaces that may be presented on the augmented reality device include any of the user interfaces described herein. Further, augmented reality user interfaces can improve the efficiency of surgical procedures. For example during certain procedures, such as an endoscopy or an epidural, the clinician can efficiently maintain their view of the patient to see where a probe is going and simultaneously view an overlay user interface that includes data that would have previously only been available on a traditional display. In some embodiments, an augmented reality user interface may be pinned to a particular area within a three-dimensional space or the patient room. For example, a clinician interacts with the augmented reality device to pin an augmented reality user interface to a physical device, a location, or to the patient. Continuing with the example, the clinician using the augmented reality device views the pinned augmented reality user interface when looking near the physical device or the location that was pinned; however, if the clinician looks away from the physical device or the location then the augmented reality user interface is not presented. In some embodiments, the auxiliary device 2040 may be optional or any information displayed on the auxiliary device 2040 may be presented through the augmented reality device.

Another example of improved user interfaces using augmented reality is the presentation of analog display indicia as superimposed on a patient. Example analog display indicia that may be presented on the augmented reality device include any of the analog display indicia described herein. The example analog display indicia, such as a two-dimensional or three-dimensional lungs, heart, brain, or circulatory system, can be superimposed on a patient. Accordingly, a clinician looking at the patient would see the superimposed analog display indicia. In some embodiments, the analog display indicia is pinned to the patient such that if the clinician looks away from the patient then the analog display indicia is no longer presented. As described herein, the analog display indicia can present health indicators of various physiological parameters. Example health indicators include color-coded analog display indicia, such as green, yellow, or red indicia, which may indicate nominal, cautionary, or severe situations, respectively, which is described in further detail herein.

In some embodiments, improved augmented reality user interfaces enable a user to configure or interact with the user interface. For example, the augmented reality user interface may be a dashboard where a user can add or remove particular virtual display panels or change the arrangement or the location of the augmented reality panels or objects. The augmented reality device may receive user input corresponding to user interactions. Example user interactions include voice input or commands, visual or eye commands, touch input, or movement, such as head movement or hand gestures. Example head gestures include head tilt, bobbing, or nodding. As another example, a clinician may receive augmented reality patient data when outside of the patient's room or area. In the example, a clinician walking past a patient's room interacts with the augmented reality device to receive data regarding the patient or from the electronic medical devices within the patient's room. Continuing with the example, the clinician executes a hand gesture that virtually grabs the patient's data and causes presentation of the data in their augmented reality device without entering the patient room. As another example, patient data may be virtually posted outside of rooms. Additionally or alternatively, in some embodiments, the patient data may be available anywhere within a healthcare facility or even remotely, such as a clinician being tens or hundreds of miles away from the physical location of the patient.

Additional example user interfaces and systems for patient monitoring and notifications are disclosed in U.S. patent application Ser. No. 14/511,972 by the assignee of the present disclosure and is incorporated by reference herein.

Figure 72A:
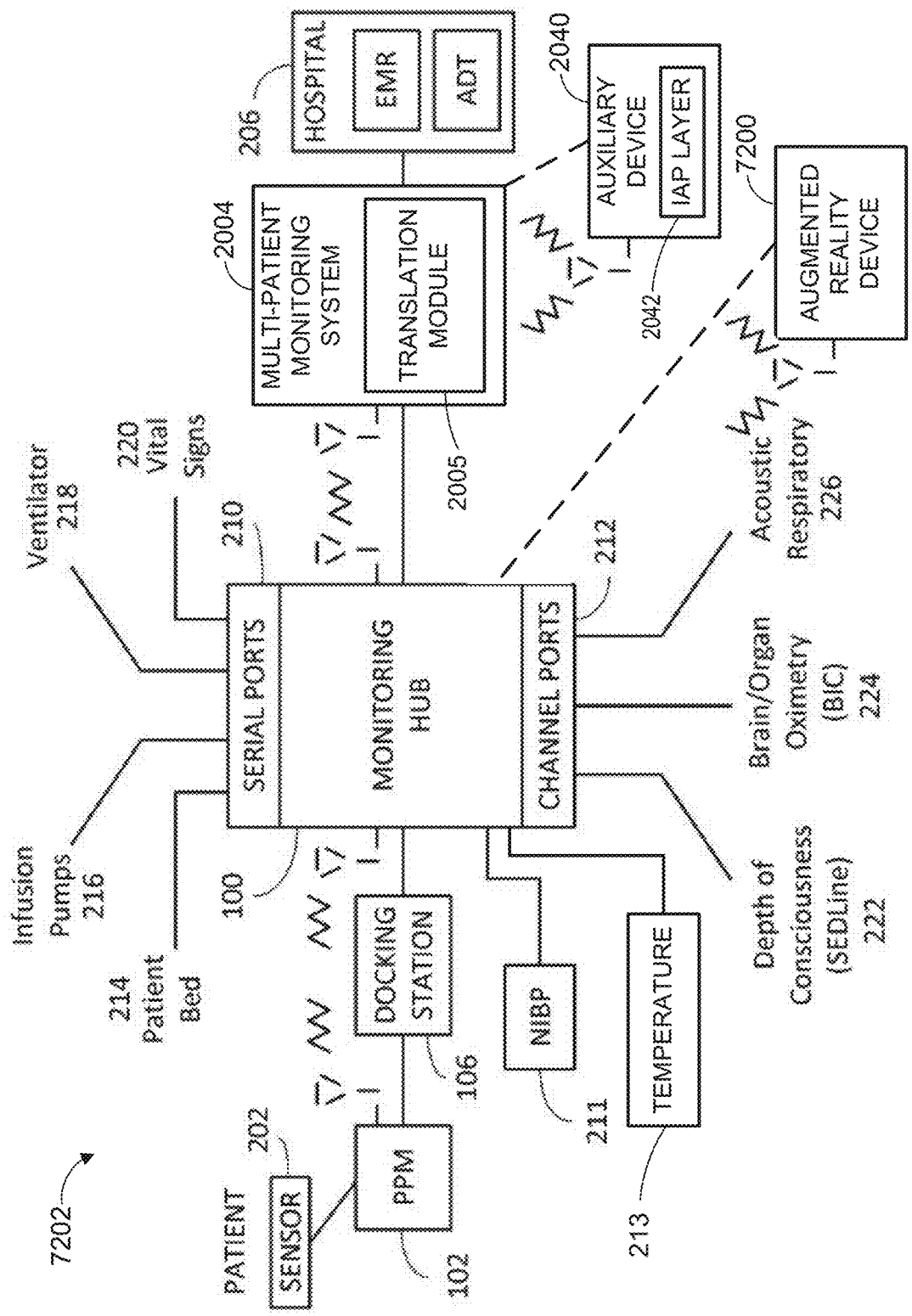
FIG. 72A illustrates another embodiment monitoring environment including an augmented reality device.

FIG. 72A illustrates another embodiment of a monitoring environment 7202 including the hub 100 of FIG. 1 and the devices of FIG. 24. The monitoring environment 7202 may include all or some of the features of the monitoring environment 200 of FIG. 2 or the monitoring environment 2000 of FIG. 24, as well as any of the other features described above. In addition, the monitoring environment 7202 depicts the multi-patient monitoring system (MMS) 2004. The MMS 2004 includes a translation module 2005 that can receive serial data, translate the serial data into a format recognizable by the monitoring hub 100, and provide the serial data to the monitoring hub 100 (among possibly other devices). Also shown is an auxiliary device 2040 that may communicate with the MMS 2004, the monitoring hub 100, or the PPM 102, wired or wirelessly. Similarly, the augmented reality device 7200 may communicate with the MMS 2004, the monitoring hub 100, or the PPM 102, wired or wirelessly.

The example augmented reality device 7200 includes augmented reality glasses, head-mounted displays, head-up displays, contact lenses, a smartphone, or a tablet. The augmented reality device 7200 may include some combination of one or more hardware processors, displays, sensors, or input devices. For example, the augmented reality device 7200 can include a camera, an accelerometer, gyroscope, a GPS device, or a solid state compass. The augmented reality device 7200 may include one or more wired or wireless devices that enable communication over Bluetooth, USB, wired networks, or one or more wireless networks, such as a Global System for Mobile Communications (GSM) network, a Code Division Multiple Access (CDMA) network, a Long Term Evolution (LTE) network, Wi-Fi, or some other type of wireless network. In some embodiments, the augmented reality device 7200 may communicate with an augmented reality server (not illustrated), which may handle some augmented reality processing. Accordingly, the example augmented reality device can offload some or all of the augmented reality processing to be performed by the augmented reality server in a distributed manner.

Figure 72B:
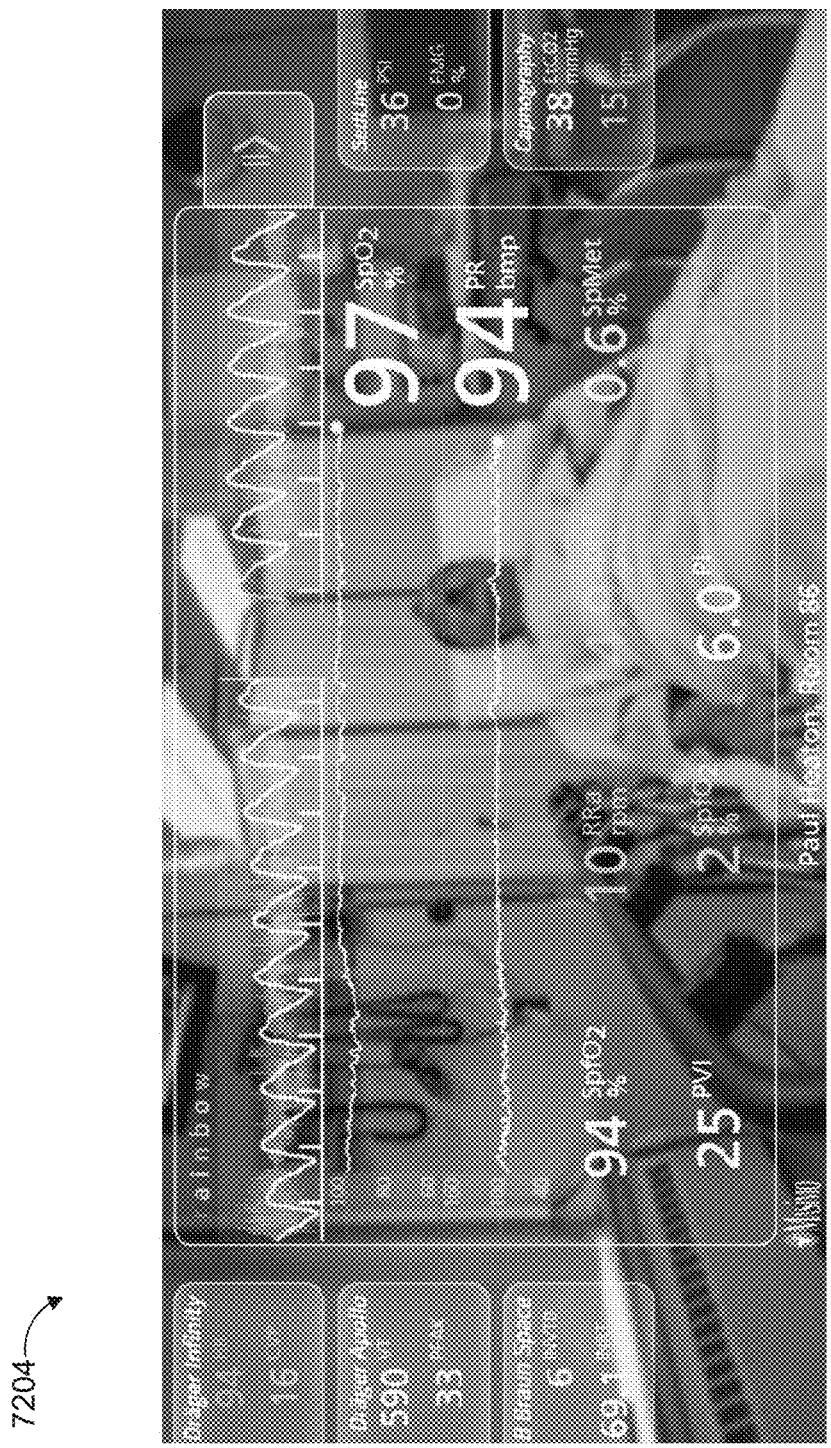
FIGS. 72B-72E illustrates example augmented reality user interfaces.

FIG. 72B depicts an example augmented reality user interface 7204. The example augmented reality user interface 7204 includes one or more augmented reality user interface objects. As described herein, the medical monitoring system may receive one or more physiological signals associated with a patient that is being monitored via one or more physiological sensors. The medical monitoring system may calculate physiological parameters based on the physiological signals. The augmented reality device 7200 or another device of the medical monitoring environment may generate the one or more augmented reality user interface objects from the physiological monitoring data that includes the physiological parameters. As described herein, the physiological monitoring data may update in a real-time or near-time manner; accordingly, the augmented reality user interface objects displaying the physiological monitoring data may update in a real-time or near-time manner. In some embodiments, the clinician using the augmented reality device may configure the augmented reality user interface. For example, the augmented reality device may receive user input corresponding to user interactions that configure the augmented reality user interface. Example user configuration of the augmented reality user interface includes additions or removals of augmented reality objects, a change in the position of augmented reality objects, selections to cycle through different augmented reality user interfaces, or a selection of a particular augmented reality user interface. For example, a first augmented reality user interface corresponds to a first collection of augmented reality objects for monitoring patient physiological data, a second augmented reality user interface corresponds to a second collection of augmented reality objects for presenting patient medical history, or a third augmented reality user interface corresponds to a third collection of augmented reality objects for presenting patient demographics data.

Figure 72C:
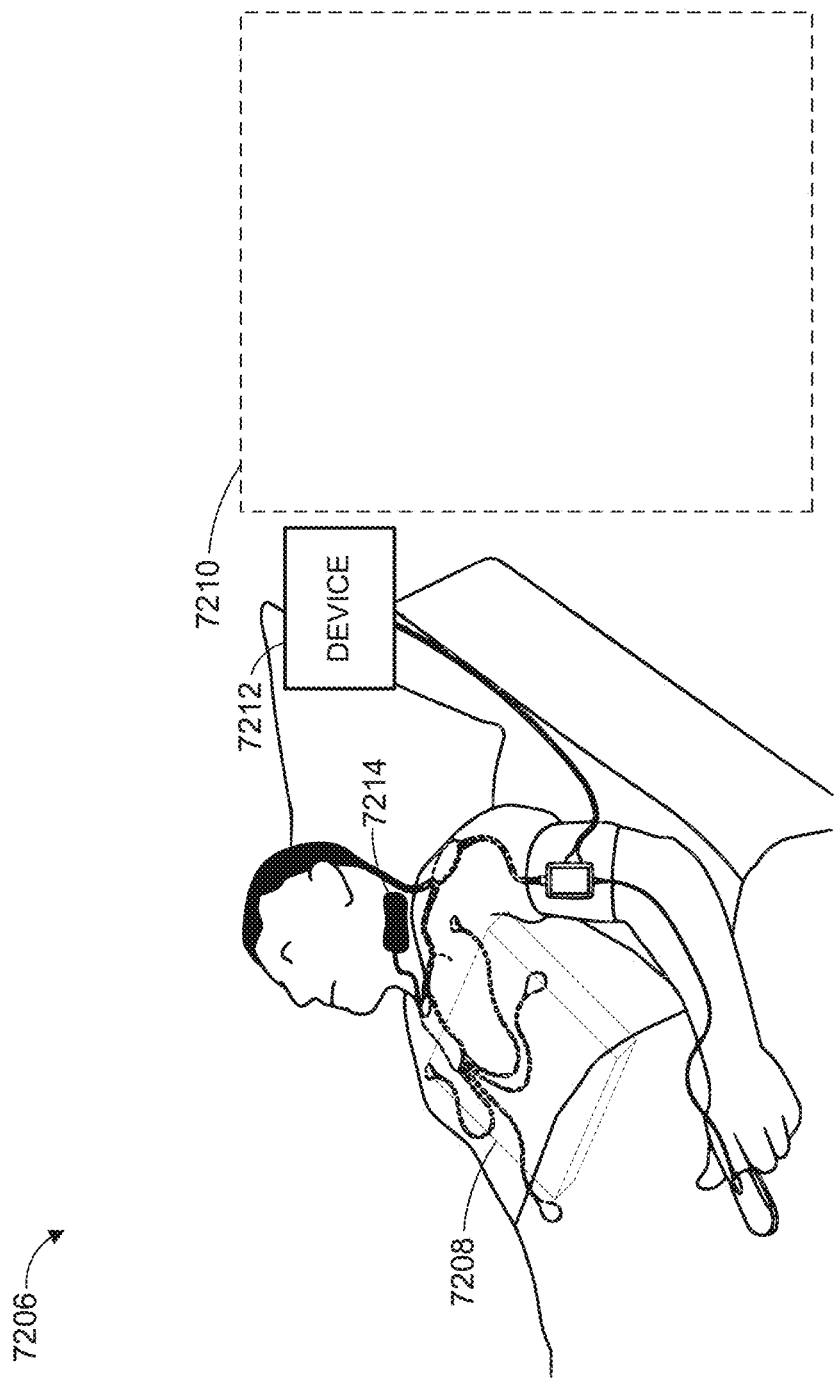

FIG. 72C depicts another example augmented reality user interface 7206. The example augmented reality user interface 7206 includes one or more augmented reality objects 7208 and an augmented reality display area 7210. As described herein, the example augmented reality object 7208 includes analog display indicia that are superimposed on the patient. For example, the augmented reality object 7208 corresponds to a color-coded visual representation of lungs that indicates the status of the patient's lungs. The patient may be connected to or may be wearing one or more devices 7214, which is further connected to another device 7212 that may correspond to the hub, the monitoring system, or a traditional display, for example. In some embodiments, an augmented reality system, such as the augmented reality device 7200 or an augmented reality server, determines the position of the augmented reality object 7208 based on positional information derived from the one or more devices 7214. For example, the one or more devices 7214 may include tracking sensors, such as accelerometers, GPS, gyroscopes, solid state compasses, RFID, or wireless sensors.

Additionally or alternatively, the one or more devices 7214 may include visual markers that can be detected by the augmented reality device 7200 for image registration or the patient may be wearing one or more visual markers for image registration. In some embodiments, the clinician using the augmented reality device 7200 may pin the augmented reality display area 7210 to the device 7212. The augmented reality display area 7210 may include any of the example user interfaces described herein.

Similar to the visual markers or tracking sensors associated with the patient or the one or more devices 7214, the augmented reality system may determine the position of the augmented reality display area 7210 based on visual markers or tracking sensors associated with the device 7210. As described herein, the example augmented reality system determines the position of the augmented reality display area 7210 by identifying a reference object, here the device 7212, determining a reference position for the reference object, and calculating a positional offset from the reference position. In some embodiments, the positional offset may be calculated as a predetermined or configurable distance and direction from the reference object. Continuing with the example, the clinician using the augmented reality device may change or update the positional offset of the augmented reality display area 7210.

Figure 72D:
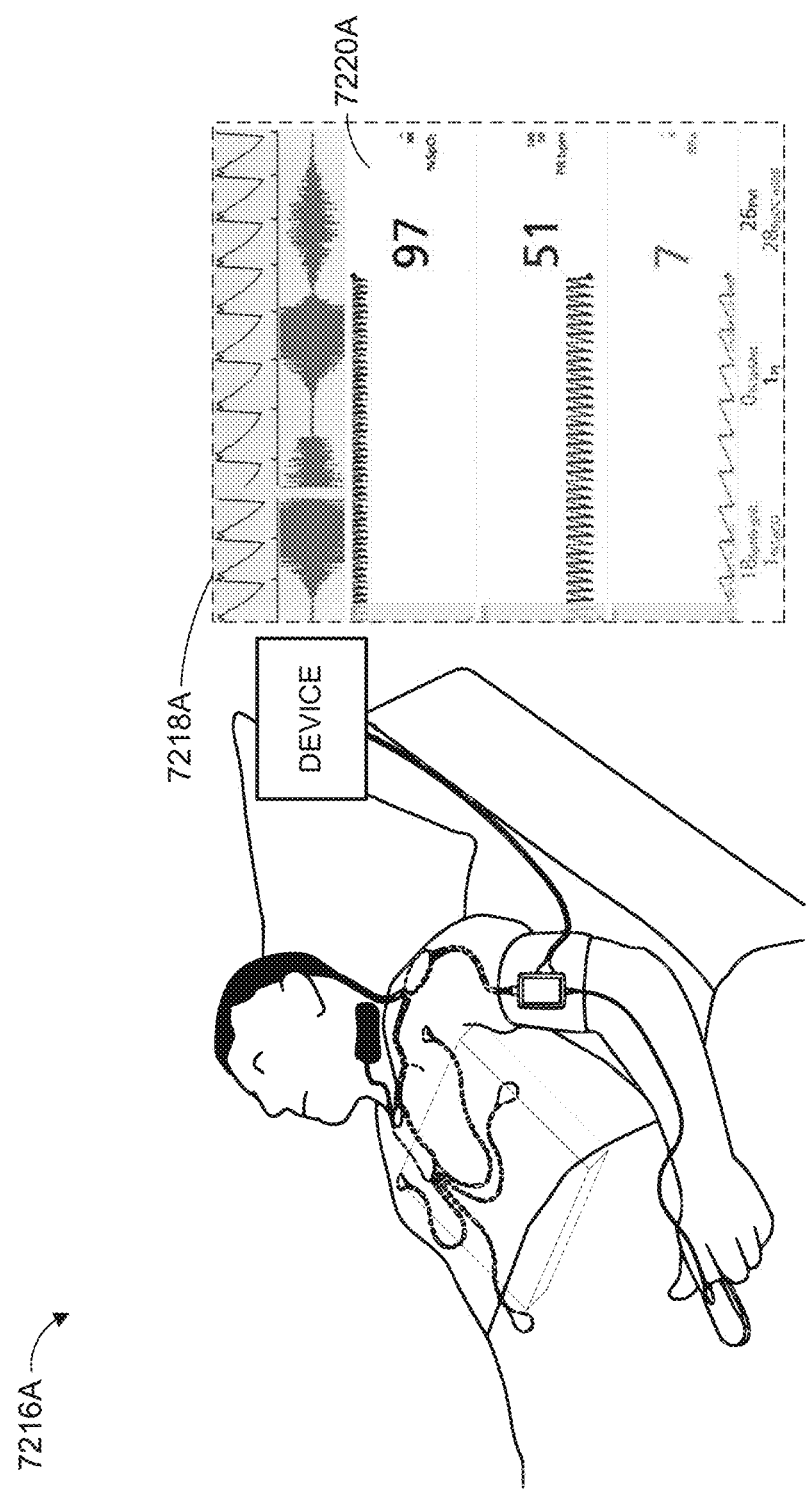
Figure 72E:
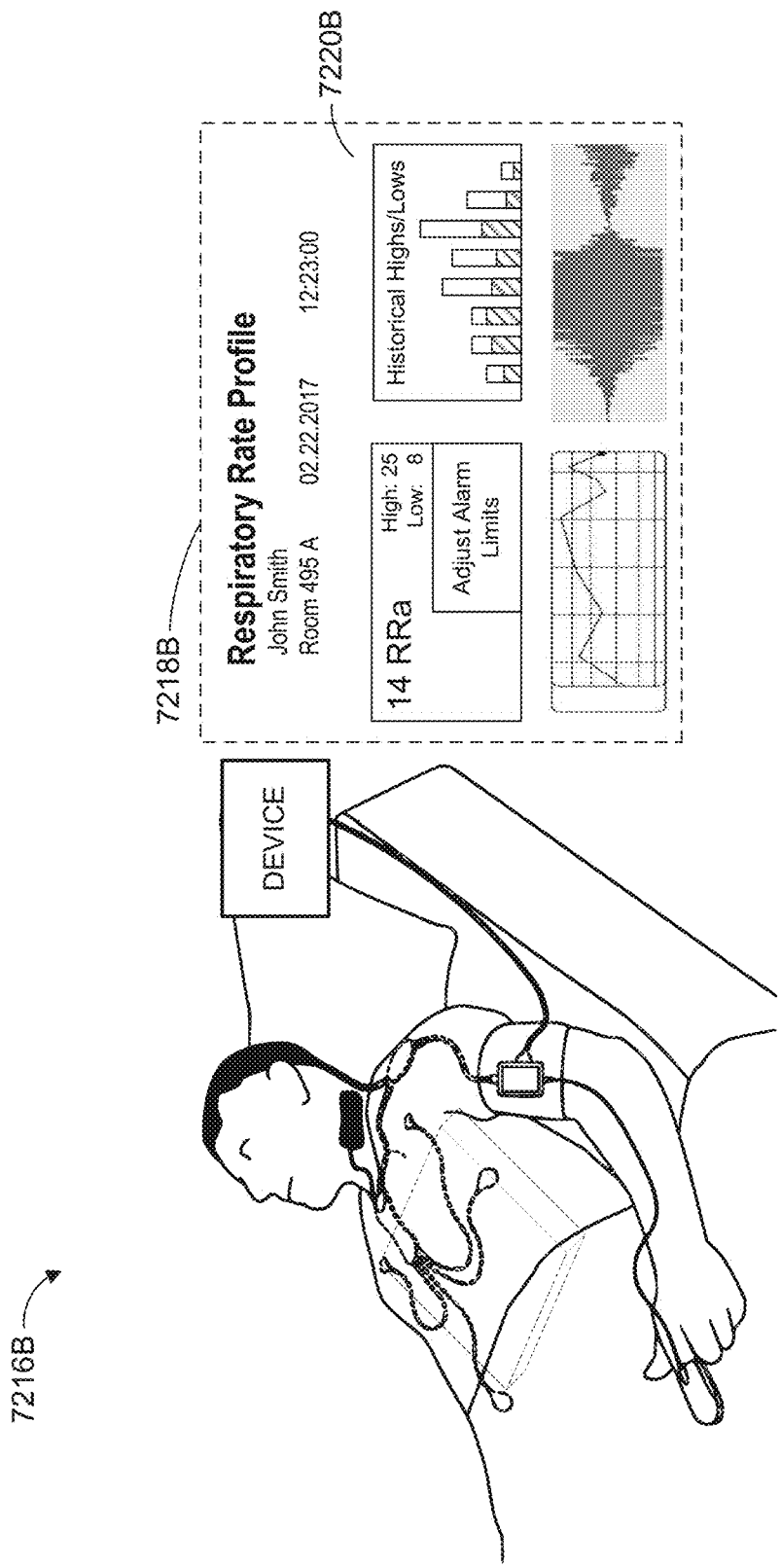

FIGS. 72D and 72E depict additional example augmented reality user interfaces 7216A and 7216B, respectively. The example augmented reality user interfaces 7216A and 7216B may be similar to the augmented reality user interface 7206 of FIG. 72C. As illustrated, the example augmented reality user interfaces 7216A and 7216B include user interface display areas 7218A and 7218B, respectively, which include user interface objects 7220A and 7220B, respectively. The example user interface objects 7220A and 7220B may correspond to the example user interfaces described herein.

Figure 72F:
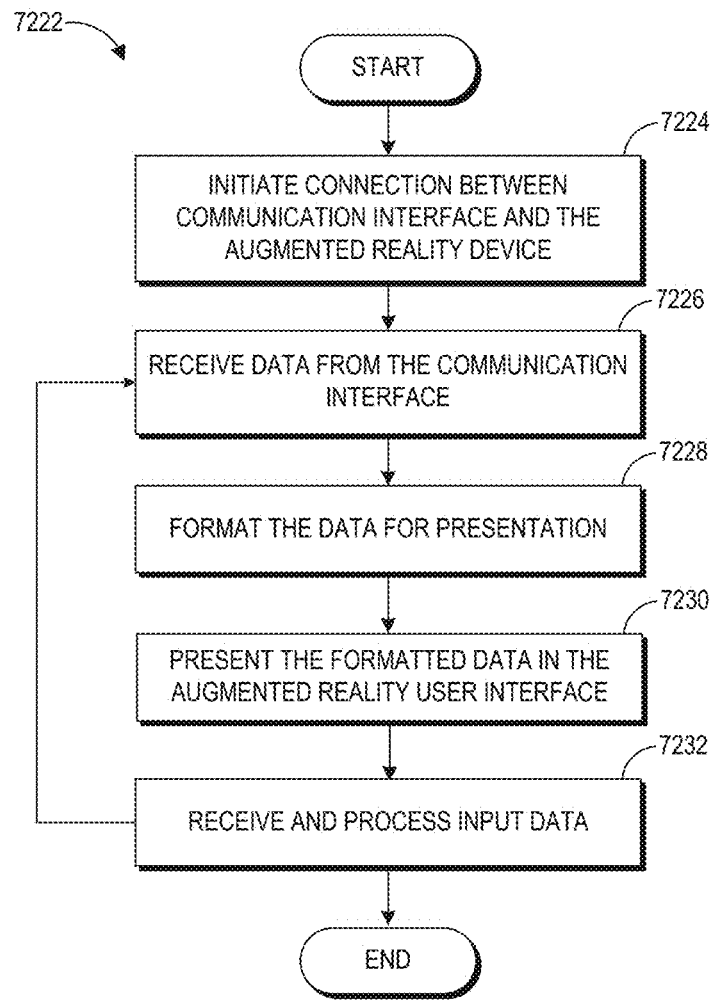
FIG. 72F illustrates an embodiment of an augmented reality display generation process.

FIG. 72F depicts an augmented reality display generation process 7222. The process 7222 illustrates an example mode of operation of the environment 7202 of FIG. 72A and may be implemented by the various components shown in the environment 7202, such as the augmented reality device 7200 or by an augmented reality server separate from the augmented reality device 7200. For convenience, process 7222 is described in the context of the environment 7202 (such as being implemented by the augmented reality device 7200 or by an augmented reality server, which will be referred to herein as an augmented reality system) but may instead be implemented by other systems described herein or other computing systems not shown. Further, the process 7222 provides an example approach by which the augmented reality device 7200 or by an augmented reality server can generate an augmented reality display. Depending on the embodiment, the process of FIG. 72F may include fewer or additional blocks or the blocks may be performed in order different than is illustrated.

At block 7224 the augmented reality system server initiates a connection with a communication interface. For example, the augmented reality device 7200 may connect to a communication interface of the MMS 2004, the monitoring hub 100, or the PPM 102, wired or wirelessly. In some embodiments, the augmented reality device 7200 must be authenticated via one or more security protocols before a connection with the communication interface can be established.

At block 7226, the augmented reality system receives data from the communication interface. As described herein, example data includes physiological monitoring data, which may include physiological parameter data from a patient that is calculated from physiological signals that are captured by physiological sensors monitoring the patient.

At block 7228, the augmented reality system formats the received data for presentation. For example, the augmented reality system may access user interface configuration data that indicates which augmented reality objects should be displayed or the arrangement of the augmented reality objects. In some embodiments, a clinician using the augmented reality device 7200 may update or modify the user interface configuration data via one or more user interactions with the augmented reality device 7200, as described herein. Accordingly, the augmented reality system can format the received data, such as the physiological monitoring data, into user interface display data according to the user interface configuration data. For example, the augmented reality system generates one or more augmented reality objects from the physiological monitoring data according to the user interface configuration data that specifies which objects are to be generated or where the objects should be presented on the augmented reality device display.

At block 7230, the augmented reality system presents the formatted data in a display of the augmented reality device. Example augmented reality user interfaces are shown and described in further detail with reference to FIGS. 72B-72E.

At block 7232, the augmented reality system receives and processes input data. Example input data includes user interaction data that is received from the augmented reality system. For example, a clinician may interact with the augmented reality user interface to modify the user interface. Accordingly, the augmented reality system may return to block 7226 to receive additional data to continue processing user interaction data, display data, or monitoring data to present updated augmented reality user interfaces. For example, the augmented reality user interfaces may update in near-time a real-time based on the physiological sensors capturing updated data from the patient or from new data received from the MMS 2004, the monitoring hub 100, or the PPM 102.

Figure 72G:
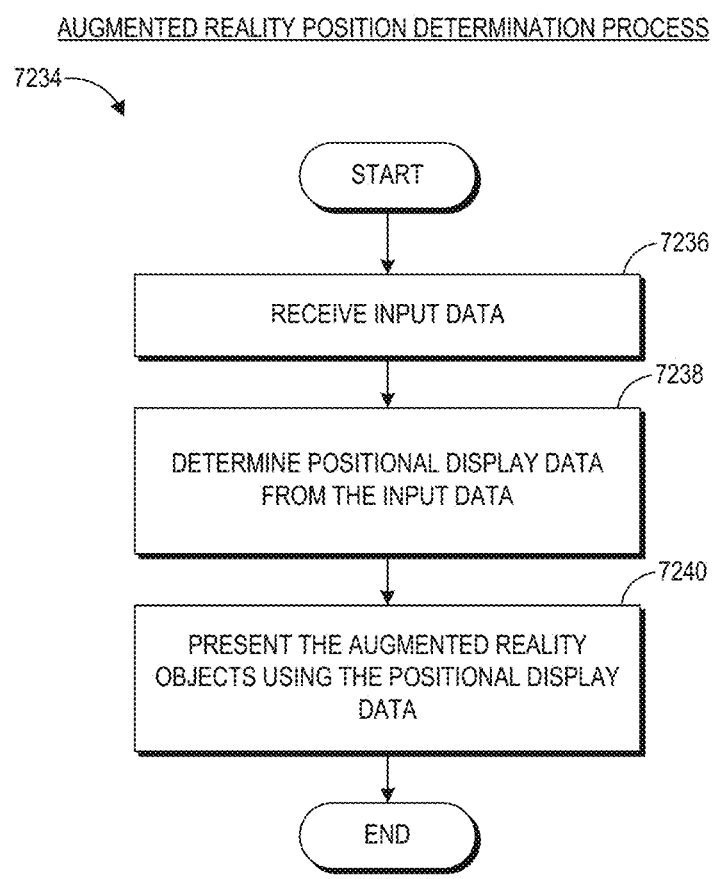
FIG. 72G illustrates an embodiment of an augmented reality position determination process.

FIG. 72G depicts an augmented reality position determination process 7234. The process 7234 illustrates an example mode of operation of the environment 7202 of FIG. 72A and may be implemented by the various components shown in the environment 7202, such as the augmented reality device 7200 or by an augmented reality server separate from the augmented reality device 7200. For convenience, process 7234 is described in the context of the environment 7202 (such as being implemented by the augmented reality system) but may instead be implemented by other systems described herein or other computing systems not shown. Further, the process 7234 provides an example approach by which the augmented reality system determines positions for one or more augmented reality objects. Depending on the embodiment, the process of FIG. 72G may include fewer or additional blocks or the blocks may be performed in order different than is illustrated. Further, the blocks of the process 7234 may correspond to one or more blocks of the process 7222 of FIG. 72F, such as blocks 7226, 7228, 7230, or 7232.

At block 7236, the augmented reality system receives input data. Example input data includes a tagged or pinned reference object or location. An example tagged pinned reference object may correspond to one or more physical objects, such as an auxiliary display, a device of the monitoring system, or a patient. Additionally or alternatively, the example input data includes positional or positional-related data, such as image data, video data, accelerometer data, GPS data, gyroscopic data, solid state compass data, RFID data, or wireless data. Example positional or positional-related data may correspond to data captured by the augmented reality device or one or more devices of the monitoring system, such as the auxiliary display or one or more devices attached to the patient. As another example, the image or video data may capture a known visual marker (also known as or referred to as a fiducial marker as used herein) that is attached to a patient or device of the monitoring system.

At block 7238, the augmented reality system determines positional display data from the input data. For example, the augmented reality system determines or calculates a reference position for the reference object from the image data, video data, accelerometer data, GPS data, gyroscopic data, solid state compass data, RFID data, or wireless data. Typically GPS data is accurate within several meters. Accordingly, the augmented reality system may use other positional-related data, such as image or video data, accelerometer data, gyroscopic data, solid state compass data, RFID data, or wireless data to determine a more accurate position for a reference object. In a computer vision example, the augmented reality system executes an image registration process to identify known visual markers through one or more feature detection techniques such as corner detection, blob detection, edge detection, thresholding, or other image processing techniques. Additionally or alternatively, the augmented reality system determines a three-dimensional position for the reference object using a pose estimation technique. In some embodiments, the augmented reality system generates a real world coordinate system from the obtained or generated positional data. An example real world coordinate system at least includes three-dimensional coordinates.

The example augmented reality system generates positional display data from the obtained or generated positional data. In the pinning example, the augmented reality system determines a positional offset from a reference object, such as a patient or a display or device of the monitoring system. The augmented reality system may calculate a position offset from a predefined or configurable distance and direction from the reference object. An example predefined distance includes five or ten centimeters to the right or left of the reference object. In some embodiments, user interaction input received from a clinician may update the position offset. For example, a clinician can interact with the augmented reality objects by moving them, such as with push, pull, or hand wave gestures. In the direct overlay or superimposed example, the augmented reality system may display one or more augmented reality objects at the reference position for the reference object. For example, the reference position of the patient may correspond to a particular coordinate within the coordinate system and the augmented reality system presents the object at the coordinate. As described herein, the augmented reality system can present analog display indicia at the reference position that corresponds to the patient, such as the coordinate position of the lung, heart, or brain areas of the patient. Accordingly, if the reference object moves, the one or more pinned augmented reality objects may move with the reference object.

VII. Additional Example Aspects of the Augmented Reality Embodiments

In a first aspect, a method for presenting augmented reality data from a medical monitoring system, the method comprising: under control of a hardware processor, receiving physiological monitoring data comprising physiological parameter values associated with a patient from a monitoring hub; accessing user interface configuration data; generating, from the physiological monitoring data, a plurality of augmented reality objects according to the user interface configuration data; and causing presentation of the plurality of augmented reality objects in an augmented reality display.

In a second aspect, the method of aspect 1, further comprising: receiving user interaction data from a user input sensor of an augmented reality device; and generating the user interface configuration data from the user interaction data.

In a third aspect, the method according to any of aspects 1 or 2, further comprising: receiving user interaction data from a user input sensor of an augmented reality device; determining, from the user interaction data, a reference object; determining a reference position for the reference object; and calculating a positional offset from the reference position, wherein the plurality of augmented reality objects are presented relative to the reference position according to the positional offset.

In a fourth aspect, the method according to any of aspects 1-3, further comprising: determining, from the user interface configuration data, whether to present a direct overlay; determining, from the user interface configuration data, a reference object; determining a reference position for the reference object, wherein an overlay object of the plurality of augmented reality objects is presented at the reference position.

In a fifth aspect, the method of aspect 4, wherein the reference object corresponds to the patient.

VIII. Additional Auxiliary Device Embodiments

Several additional embodiments associated with the auxiliary device 2040 will now be described, including authentication features (see FIG. 73), features for controlling devices that send data to the auxiliary device 2040 (see FIGS. 74 and 76), and features for controlling outputs to the auxiliary device 2040 (see FIG. 75).

In general, as described above, the auxiliary device 2040 can provide second screen functionality for the hub 100, PPM 102, or MMS 2004. Further, as described above, the translation module 2005 can be implemented in any device, including the hub 100 or the MMS 2004. Data set by the translation module 2005 (or from another device shown in FIG. 24 or 72A) to the auxiliary device 2040 may be sent in a format suitable for the auxiliary device 2040 to determine how to display it on the display of the auxiliary device 2040. In other words, devices can feed data to the auxiliary device 2040 independent of any specific user interface formatting, and the auxiliary device 2040 can determine how to format and display that data on its display. For example, a software module installed on the auxiliary device 2040 (not shown) can format received data into any desirable user interface format. In one embodiment, the data received by the auxiliary device 2040 is in XML format or another similar format, and software running in a hardware processor of the auxiliary device 2040 parses the XML (or similar) data and generates a display based on the data.

Figure 73:
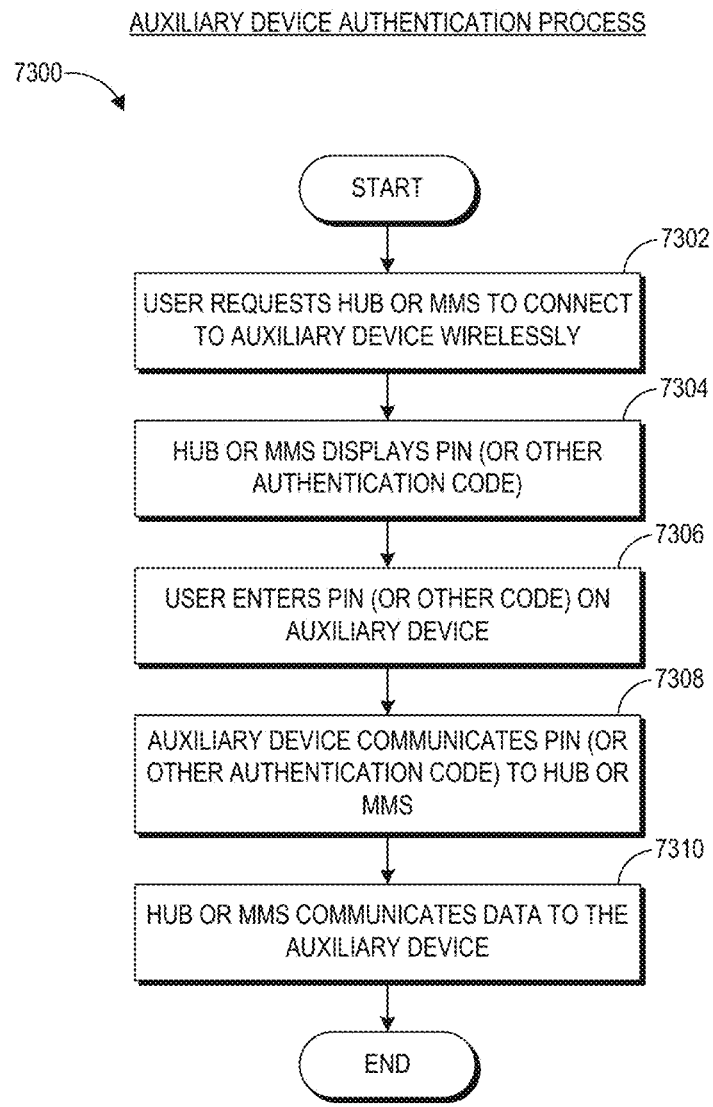
FIG. 73 illustrates an embodiment of an auxiliary device authentication process.

Turning to FIG. 73, an embodiment of an auxiliary device authentication process 7300 is shown. The process 7300 can be implemented using components of the systems described above with respect to FIGS. 24 and 72A. In general, the process 7300 can be implemented by software or firmware executing on a hardware processor. The process 7300 can enable the auxiliary device 2040 to authenticate to the hub 100, MMS 2004, or PPM 102. (For convenience, the remainder of this disclosure will refer to communications between the auxiliary device 2040 and the hub 100, although it should be understood that any of these communications may also take place between the auxiliary device 2040 and the MMS 2004 or the PPM 102.)

It may be desirable to authenticate the auxiliary device 2040 to the hub 100 so that communications may take place between the two devices. Viewed another way, the process 7300 can be considered a process for pairing the auxiliary device 2040 with the hub 100. Multiple auxiliary devices 2040 can be paired or otherwise authenticated to the hub 100 at one time. This may be useful, for instance so that multiple clinicians can each have a tablet or other auxiliary device 2040, instead of and/or in addition to a TV auxiliary device 2040 being present in the hospital room. Further, in some embodiments the augmented reality device 7200 described above can be an example of one of the auxiliary devices 2040, and multiple clinicians may have augmented reality devices 7200 that they wish to use together with the hub 100 (for example, so that each one may have a different heads-up display with a set of views customized to that particular clinician).

At block 7302, a user requests the hub 100 (or MMS 2004 etc.) to connect to the auxiliary device 2040 wirelessly (wired connectivity is also possible in other embodiments). For example, the user can access the settings menu on the hub 100 to begin pairing or authentication of an auxiliary device 2040. At block 7304, the hub 100 displays a PIN number or other authentication code (for example, a number of alphanumeric digits/letters) on its display. At block 7306, a user enters the PIN or other authentication code on the auxiliary device. At block 7308, the auxiliary device communicates the PIN or other authentication code to the hub or MMS. At block 7310, the hub or MMS communicates data gathered from patient monitors to the auxiliary device. Block 7310 can be implemented either before, during, or after the process 7300.

Figure 74:
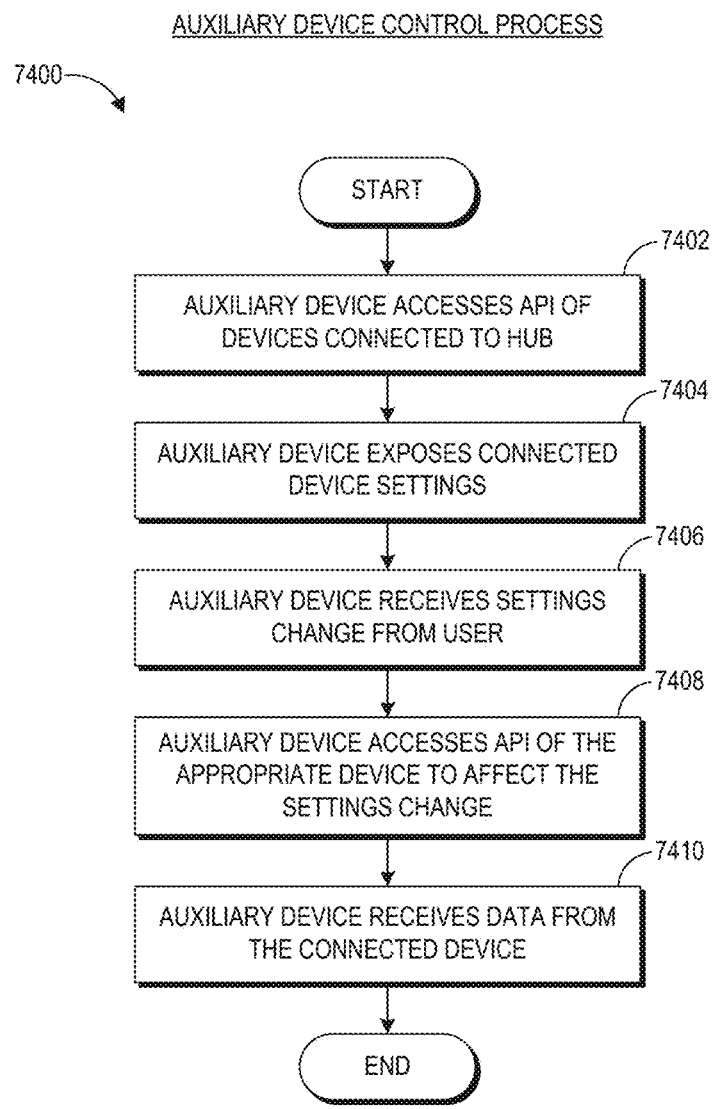
FIG. 74 illustrates an embodiment of an auxiliary device control process.

Turning to FIG. 74, an embodiment of an auxiliary device control process 7400 is shown. The process 7400 can be implemented using components of the systems described above with respect to FIGS. 24 and 72A. In general, the process 7400 can be implemented by software or firmware executing on a hardware processor. The process 7400 can enable the auxiliary device 2040 to control the hub 100 (and/or MMS 2004, etc.). Thus, for example, the auxiliary device 2040 may not just receive data, but it may also be able to send data to the hub 100 or other devices described above. This data can include control data that enables the auxiliary device 2040 to not just passively receive and display data but also to control the settings of any of the devices described above, including both third-party monitors (for example, 214-220) connected serially or otherwise to the hub 100 and first party monitors (for example, 222-226) connected via channels or otherwise to the hub 100.

For example, the auxiliary device 2040 can control any option or setting that is able to be controlled on any of the patient monitors or hub 100. For example, alarms, layouts of user interfaces, settings, etc. may be controlled via the auxiliary device 2040. The auxiliary device 2040 may output a user interface that enables control of these settings. For instance, turning to FIG. 76, an example user interface 7600 is shown that include settings 7610 for controlling an infusion pump, patient bed, and a ventilator, as well as displaying parameter values from multiple devices. Thus, with a single auxiliary device 2040, a clinician can control some or even all devices in a hospital room (for example, that are in communication with the hub 100 or MMS 2004).

In one embodiment, the manufacturer of the hub 100 can provide a software development kit (SDK) for third-party patient monitor manufacturers to use so that an auxiliary device 2040 can communicate with their hardware. Using the SDK, for instance, a third-party monitor manufacturer can install software libraries on a third-party patient monitor (for example, 214-220) so that the auxiliary device 2040 can communicate changes to settings or other parameters directly to those devices. The software library or libraries may, for instance, include an application programming interface (API) defining routines or functions and associated parameters that the auxiliary device 2040 can call or invoke to set different settings within the third-party devices. A similar library or libraries may be installed on first party devices, such as the channel devices (222-226). In one embodiment, the auxiliary device 2040 includes a set of instructions or libraries that it can invoke to send settings changes to the hub 100 (or the MMS 2004), which the hub 100 passes on to the third-party devices or first party devices. The hub 100 may also translate the settings request changes from the auxiliary device 2040 into more complex instructions provided to the individual patient monitors. In one embodiment, the manufacturer of the hub 100 can certify medical devices that are capable of control by the auxiliary device 2040. In another embodiment, any of the functions for controlling the third-party and first party devices can be implemented directly by the hub 100 instead of or in addition to by the auxiliary device 2040.

Thus, either the hub 100 or the auxiliary device 2040 can essentially become the monitor itself as it enables full control over a variety of patient monitoring equipment. Thought of another way, auxiliary device 2040 or the hub 100 can include a unified display for managing a plurality of patient devices.

Turning again to FIG. 74, an example process of how the auxiliary device 2040 can perform settings changes for medical devices connected to the hub 100 is shown. At block 7402, and auxiliary device accesses an API of devices connected to the hub, either directly or through the hub itself. At block 7404, the auxiliary device exposes connected device settings, for example on a user interface (see, for example, FIG. 76) that a user may access. At block 7460, the auxiliary device receives a settings change from a user through the user interface. At block 7408, the auxiliary device accesses the API of the appropriate medical device, either directly or through the hub, to affect the setting change. And at block 7410, the auxiliary device receives data from the connected device. Of course, block 7410 may operate in parallel with the process 7400, such that data is received before, during, and/or after the setting is changed.

Figure 75:
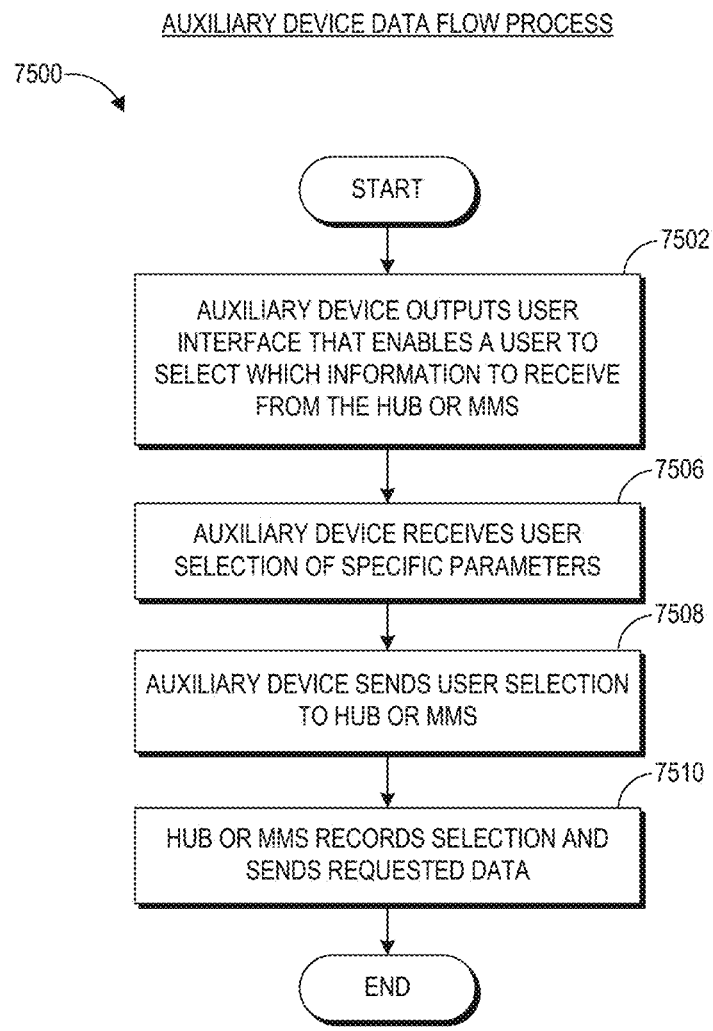
FIG. 75 illustrates an embodiment of an auxiliary device data flow process.
Figure 76:
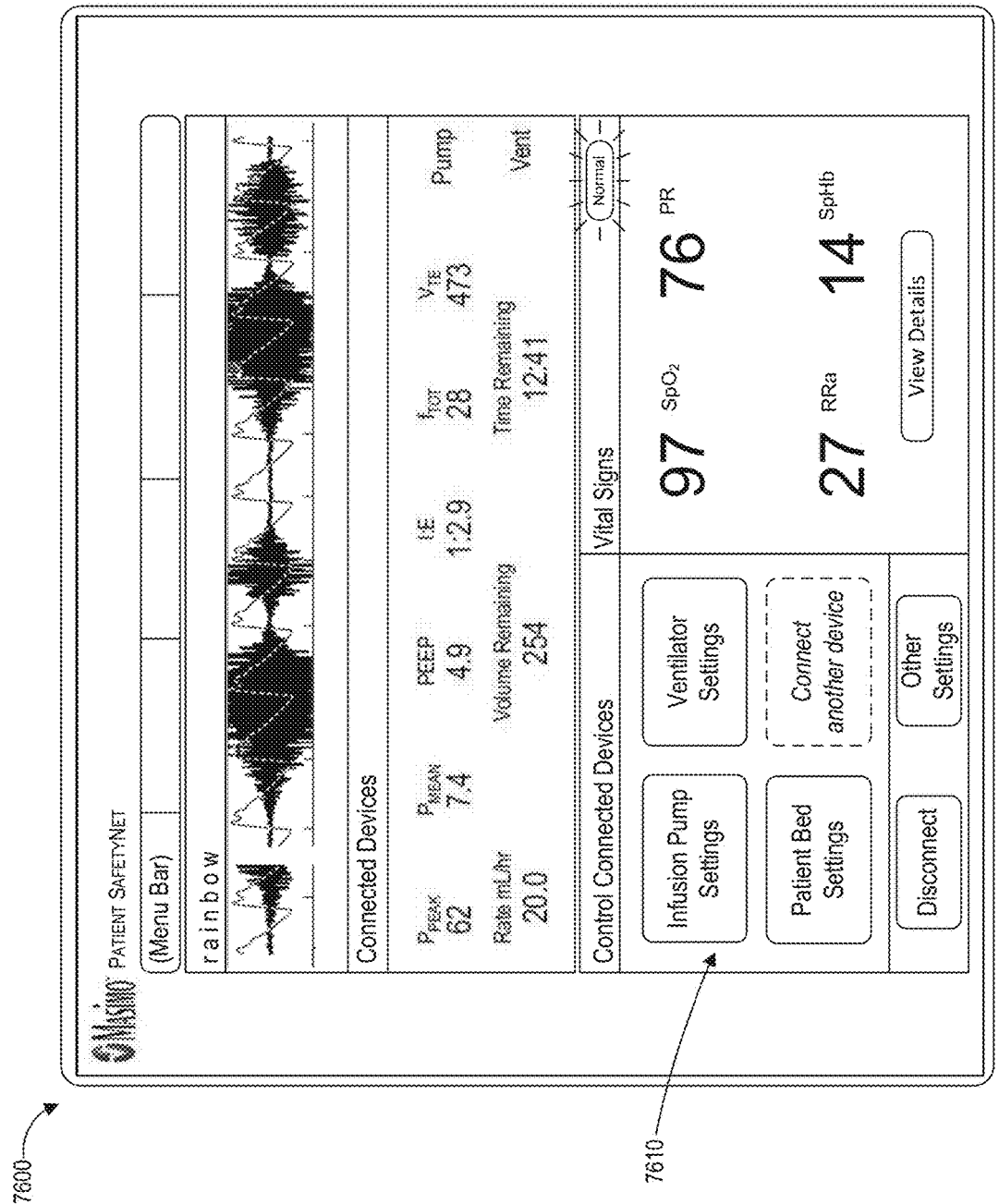
FIG. 76 illustrates an embodiment of a user interface for auxiliary device control.

Turning to FIG. 75, an embodiment of an auxiliary device data flow process 7500 is shown. The process 7500 can be implemented using components of the systems described above with respect to FIGS. 24 and 72A. In general, the process 7500 can be implemented by software or firmware executing on a hardware processor. The process 7500 can enable the auxiliary device 2040 or the hub 100 to control the flow of data to the auxiliary device 2040.

In some current implementations, the translation module 2005 pushes most or all of the data it receives from most or all the devices connected to the hub 100 on to the auxiliary device 2040. For some auxiliary devices 2040 with lower computing resources (for example, reduced processing capability, lower memory, lower battery and power capability, lower bandwidth connection, etc.), this can mean that those devices may be overwhelmed with the received data. As a result, these devices may crash or get bad or incomplete results.

One way to solve this problem is to have the auxiliary device 2040 request that the translation module 2005 send data less frequently, for example, by lowering the frequency with which it receives data. Another way is for the auxiliary device 2040 to have a module that reduces the firehose effect of all the data it receives by requesting instead a specific subset of information from the translation module 2005 or hub 100. An example of such a module is shown in FIG. 72A, an IAP (instrument auxiliary protocol) layer 2042. This layer 2042 can automatically request that a subset of information be provided to the auxiliary device 2040. In one embodiment, the IAP layer 2042 exposes a user interface on the axillary device 2040 that enables a user to control what data is to be provided to the auxiliary device 2040. Similarly, in other embodiments, the layer 2042 may be implemented as a module on the MMS 2004 or directly in the hub 100.

In another embodiment, instead of being fully flexible, the IAP layer 2042 may have a predefined capability for receiving data at the auxiliary device 2040. This capability may be determined, for example, by a level of service paid for by a clinical facility using the auxiliary device 2040, or the like. For instance, greater levels of service can enable a larger number of parameters or different variety of parameters to be provided to the auxiliary device 2040.

Turning specifically to the process 7500 shown in FIG. 75, at block 7502, an auxiliary device outputs a user interface that can enable a user to select which information to receive from the hub or MMS. At block 7506, the auxiliary device receives a user selection of specific parameters from the interface. For instance, the user may request to view ventilator or pump data to the exclusion of other data. At block 7508, the auxiliary device sends the user selection to the hub or MMS. And at block 7510, the hub or MMS records the selection and sends the requested data.

IX. Additional Example Aspects of the Auxiliary Device Embodiments

In a first aspect, a method for authenticating an auxiliary device to a medical monitoring hub, the method comprising: under control of a medical monitoring hub comprising a hardware processor: receiving a request to connect an auxiliary device wirelessly to the medical monitoring hub; outputting, on a display of the medical monitoring hub, an authentication code for a user to input into the auxiliary device; receiving an indication from the auxiliary device that the authentication code has been entered at the auxiliary device; and sending data to the auxiliary device from one or more patient monitors coupled to a patient.

In a second aspect, a method for controlling an auxiliary device in communication with a medical monitoring hub, the method comprising: under control of an auxiliary device comprising a hardware processor, the auxiliary device in communication with a medical monitoring hub: accessing a software library corresponding to a medical device connected to the medical monitoring hub; outputting a setting associated with the medical device on a display of the auxiliary device; receiving a change of the setting from the display; and using the software library to communicate the changed setting to the medical device through the medical monitoring hub.

In a third aspect, a method for controlling data flow to an auxiliary device in communication with a medical monitoring hub, the method comprising: under control of an auxiliary device comprising a hardware processor, the auxiliary device in communication with a medical monitoring hub: outputting a user interface comprising functionality for a user to select specific types of information to receive from the medical monitoring hub; receiving a user selection of a first type of information for the auxiliary device to receive from the medical monitoring hub; transmitting the user selection to the medical monitoring hub; and receiving data corresponding to the first type of information at the auxiliary device.

X. Medical Network Interface Embodiments

While the hub 100 described above beneficially provides a functionality for standalone devices (such as beds, pumps, ventilators, and other monitors) to connect to the hub 100, this functionality is included together with significant other patient monitoring functionality in the same box. Namely, in some embodiments, the hub 100 can compute physiological parameters obtained from sensors (202), receive and process channel data from various sensors (see, for example, FIGS. 2, 24, and 74A), and can also receive serial data from standalone devices. The functionality of the hub beneficially can enable the channel devices (for example, 222, 224, 226) and standalone (serial) devices to supply patient data to the MMS 2004 for storage in the EMR, as well as optionally display data from channel or serial devices at the hub 100. However, the functionality of enabling standalone patient devices to communicate data for storage in the EMR entails including the seller functionality of the hub 100. It would be desirable to provide this functionality separately in instances when usage of the hub 100 is not desired, or where the hub 100 is unavailable, or where lower-functionality monitoring equipment is used.

This section describes embodiments of a medical network interface that can advantageously provide the network connection functionality of the hub 100 without including other functionality of the hub 100. For example, the medical network interface may be a network device that receives data from standalone patient devices and then forwards this data on to the MMS 2004. As discussed below, the MMS 2004 can also perform other functions using this data. The medical network interface may function as a networking hub (for example, a network device without patient monitoring functionality as distinguished from the hub 100), switch, router, or network bridge without necessarily performing any patient monitoring itself. One medical network interface may be used for a single patient, or devices servicing multiple patients may connect to a single medical network interface (for example, two patients in one hospital room can connect to a single interface). The medical network interface can advantageously provide network conductivity for the standalone patient devices, which may not have native capability for connecting to the hospital network (for example, other than having a hardware port for connecting to a network, these devices may not be configured with software configured with information needed to connect to the MMS 2004). The medical network interface can be an information technology (IT) appliance in some implementations.

Further, as discussed in detail below, a wireless pairing system may be used to pair the medical network interface with standalone patient devices so that these devices may wirelessly transmit patient data to the medical network interface. The pairing system can include connecting a wireless dongle to the medical network interface to obtain an identifier and/or security key, and then connecting the wireless dongle to a standalone patient device to enable the standalone patient device to transmit data wirelessly—and optionally securely—to the medical network interface. Advantageously, in certain embodiments, this pairing system can be simple and quick for clinicians to use, enabling clinicians to spend less time on configuring devices and return to patient care more quickly.

Figure 77A:
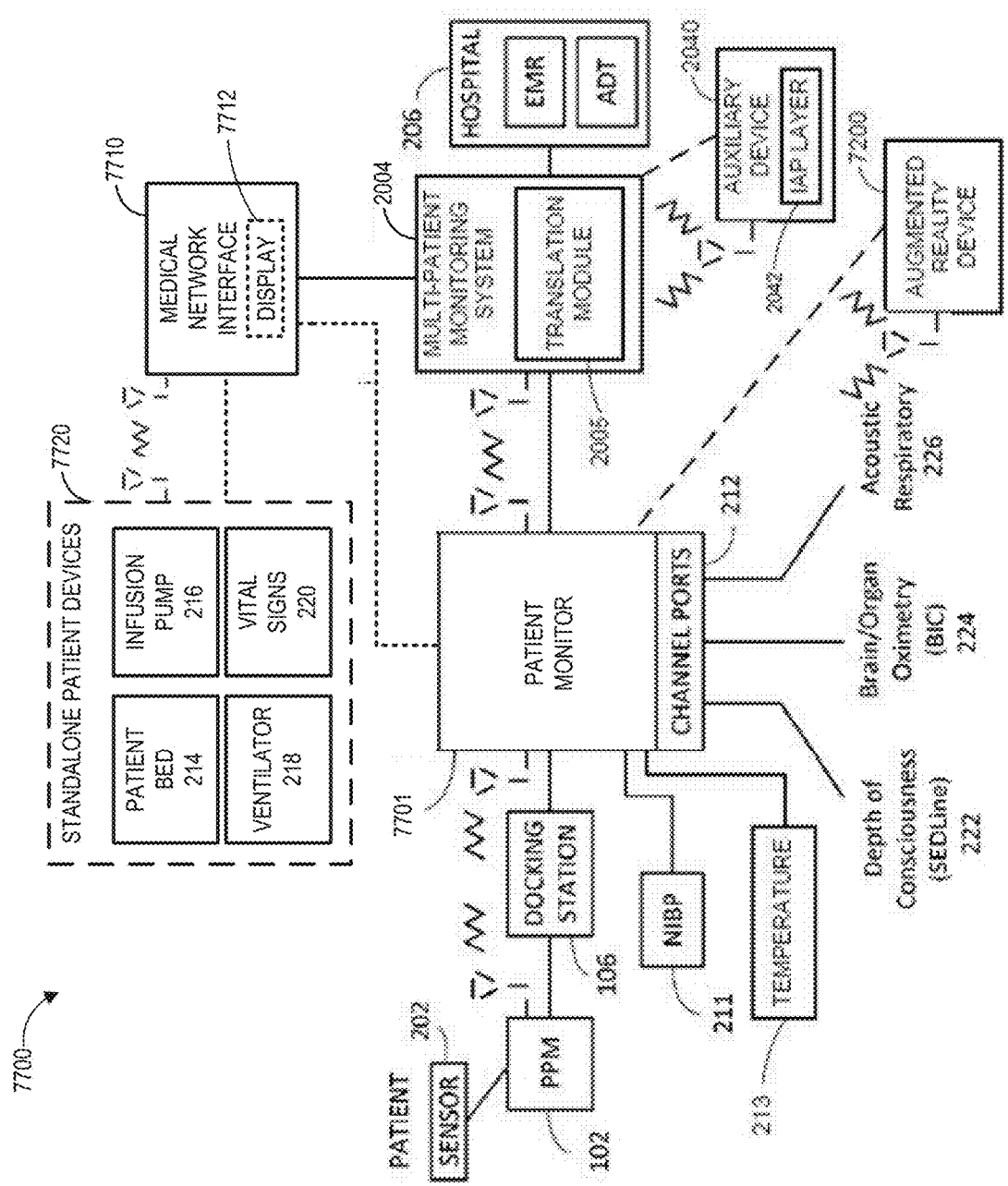
FIGS. 77A and 77B illustrate additional embodiments of a monitoring environment.

FIG. 77A illustrates another embodiment of a monitoring environment 7700 including a medical network interface 7710, a patient monitor 7701, and devices and systems of FIGS. 24 and 72A. The monitoring environment 7700 may include all or some of the features of the monitoring environment 200 of FIG. 2, the monitoring environment 2000 of FIG. 24, or the monitoring environment 7202, as well as any of the other features described above. In addition, the monitoring environment 7700 depicts the medical network interface 7710, which is an embodiment of the medical network interface described previously.

The medical network interface 7710 can support various wired or wireless connections via, for example, universal medical connectors, Ethernet ports, USB ports, Bluetooth, Wi-Fi, or other types of wired or wireless connections described herein. The medical network interface 7710 can be connected to the MMS 2004 using wired or wireless network connections. In certain embodiments, the medical network interface 7710 is also configured to be connected to devices such as, for example, the patient monitor 7701, the auxiliary device 2040, the augmented reality device 7200, standalone devices and sensors 7720 (including the patient bed 214, the infusion pumps 216, the ventilator 218, the PPM 102), or other devices and sensors described herein. In certain implementations, the medical network interface 7710 can be paired with one or more devices prior to a data transmission via a wired or wireless connection, as discussed in detail below.

Advantageously, in certain embodiments, the medical network interface 7710 provides connectivity for standalone patient devices 7722 to communicate with the MMS 2004. The medical network interface 7710 can provide this connectivity when the monitoring hub 100 is not available, or in addition to a monitoring hub in the same hospital room. However, in the embodiment shown, the hub 100 has been replaced with a patient monitor 7701 that does not connect directly to the standalone patient devices 7720. The patient monitor 7701 (complete with docking station, PPM 102, channel ports, augmented reality, etc.) may also be omitted in other embodiments, in favor of other types of patient monitors (including less full-featured monitors) that can connect to the medical network interface 7710, like standalone patient devices 7720 (see, for example, FIG. 77B).

The medical network interface 7710 can pass data acquired from a medical device to the MMS system 2004. During this process, the medical network interface 7710 can automatically discover the communication protocol used by a device connected to the medical network interface 7710. The medical network interface 7710 can further update a message comprising one or more data packets from the medical device to include an identifier of the medical network interface 7710 prior to transmissions to the patient monitor 7701 or the MMS 2004. The patient monitor 7701 and the MMS 2004 can accordingly identify that the message is from the medical network interface 7710. Further, the medical network interface 7710 may include a display 7712 to facilitate pairing with the standalone patient devices 7720 (or for other reasons), as discussed in greater detail below.

To simplify discussion and not to limit the present disclosure, FIG. 77A illustrates only one medical network interface 7710, though multiple medical network interfaces may be used for connections to the patient monitor 7701, the MMS 2004, and other devices, sensors, or systems. As one example, two medical network interfaces 7710 may be connected to each other, thereby expanding the ports available on one medical network interface. As another example, two or more medical network interfaces 7710 may be connected to the MMS 2004 where each medical network interface is associated with a patient. The MMS 2004 can accordingly process data associated with more than one patient. Further, although the examples of medical network interfaces 7710 herein are described as connected to the MMS 2004, in various embodiments, the medical network interface 7710 can also be connected via wired or wireless connections with the patient monitor 7701 (or the hub 100). For example, the medical network interface 7710 can pass data obtained from medical equipment to the patient monitor 7701 or hub 100 in addition to or in alternative to the MMS 2004. The patient monitor 7701 or hub 100 can for this data onto the MMS 2004. Thus, for example, the medical network interface 7710 can expand the functionality of the hub 100 by connecting to a port of the hub 100 instead of directly to the medical network. Detailed example descriptions of the medical network interface 7710 are described below with reference to FIGS. 78A, 78B, and 80.

Figure 77B:
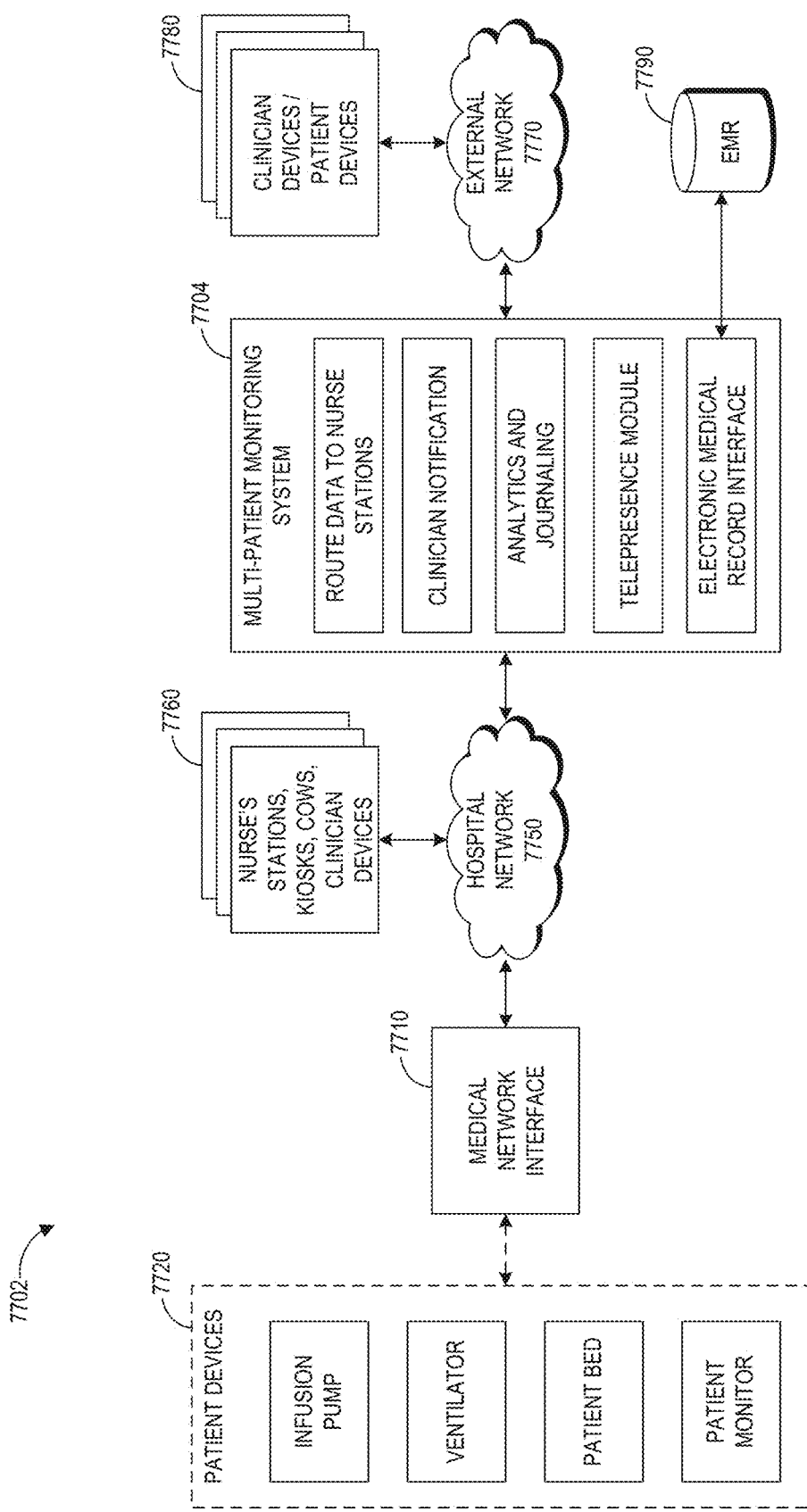

FIG. 77B depicts another example of a monitoring environment 7702 in which the medical network interface 7710 is shown. As in FIG. 77A, standalone patient devices 7720 connect with the medical network interface 7710, which provides network connection functionality for these devices by connecting to the hospital network 7750. Also connected to the hospital network 7750 is an MMS 7704 and other hospital devices 7760, such as, for example, nurses station computers, kiosk, computers on wheels (COWs), and clinician devices (such as phones, pagers, tablets, and the like). The MMS 7704 can also be in communication with an external network 7770 which may also communicate with clinician devices or patient devices 7780 remote from the hospital. The MMS 7704 also interfaces with an EMR 7790. Thus, in certain embodiments, the medical network interface 7710 enables data from the stand location devices 7720 to be communicated to any of the other components shown in FIG. 77B, among possibly others.

The MMS 7704 may have all the functionality of the MMS 2004 described elsewhere herein. Specific functionality shown may also be possessed by the MMS 2004. This functionality includes the ability to route data to nurses' stations (sometimes referred to as central stations). Data received from standalone patient devices 7720 of the medical network interface 7710 may be provided to their stations, central stations, and clinician devices, among others. The MMS 7704 may also perform clinician notification, for example, by routing alarms obtained from the patient devices 7720 to the devices 7760, 7780. Further, the MMS 7704 may perform analytics and journaling, for example, as disclosed in U.S. Pat. No. 9,142,117, filed Sep. 22, 2015, titled "Systems and Methods for Storing, Analyzing, Retrieving and Displaying Streaming Medical Data,", and U.S. App. No. 62/463,262, filed Feb. 24, 2017, titled "Systems and Methods for Storing, Analyzing, Retrieving and Displaying Streaming Medical Data,", the disclosures of which are hereby incorporated by reference in their entirety. Further, the MMS 7704 may include telepresence module that performs telepresence monitoring of patients by clinicians remotely, for example, as described in U.S. Pub. No. 2014/0077956, filed Sep. 18, 2013, titled "Intelligent Medical Network Edge Router," the disclosure of which is hereby incorporated by reference in its entirety. Further, the MMS 7704, like the MMS 2004, may be expandable and can supply data to other software engines and databases, including the EMR 7790.

The data obtained by the medical network interface 7710 from standalone patient devices 7720 (or from the patient monitor 7701 in FIG. 77A) may come in one or more of the following forms: waveform data, parameter data, or event data. Waveform data can include trend data, which may be high-frequency data. The network interface 7710 and/or the MMS 7704 may treat this data akin to video streaming data, such that if there are losses (for example, due to buffer overruns), those losses are ignored. Parameter data (for example, physiological parameter measurement such as oxygen saturation values), may come at a set frequency such as once every second (1 Hz). The medical network interface 7710 may combine parameter data into a patient snapshot and provide this snapshot to the MMS 7704 or to other devices shown. Event data can include event driven data, such as alarms (for example, parameter values going out of bounds) and alerts (for example, a progress fallen off or alarm settings were change on a device 7720). Events may be supplied asynchronously, when they occur, and the medical network interface 7710 may apply a time stamp to any events received from the patient devices 7720 before supplying the event data to other devices on the network.

XI. Examples of a Medical Network Interface

Figure 78A:
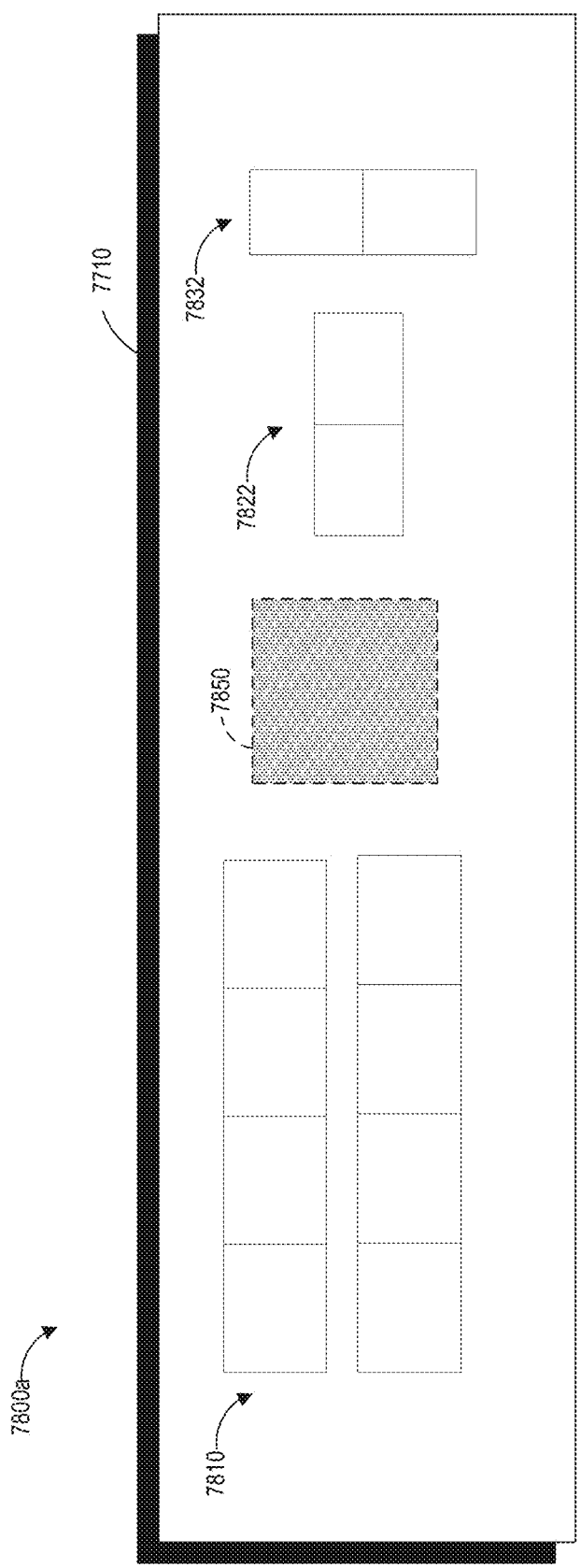
FIGS. 78A and 78B schematically illustrate an example embodiment of a medical network interface.
Figure 78B:
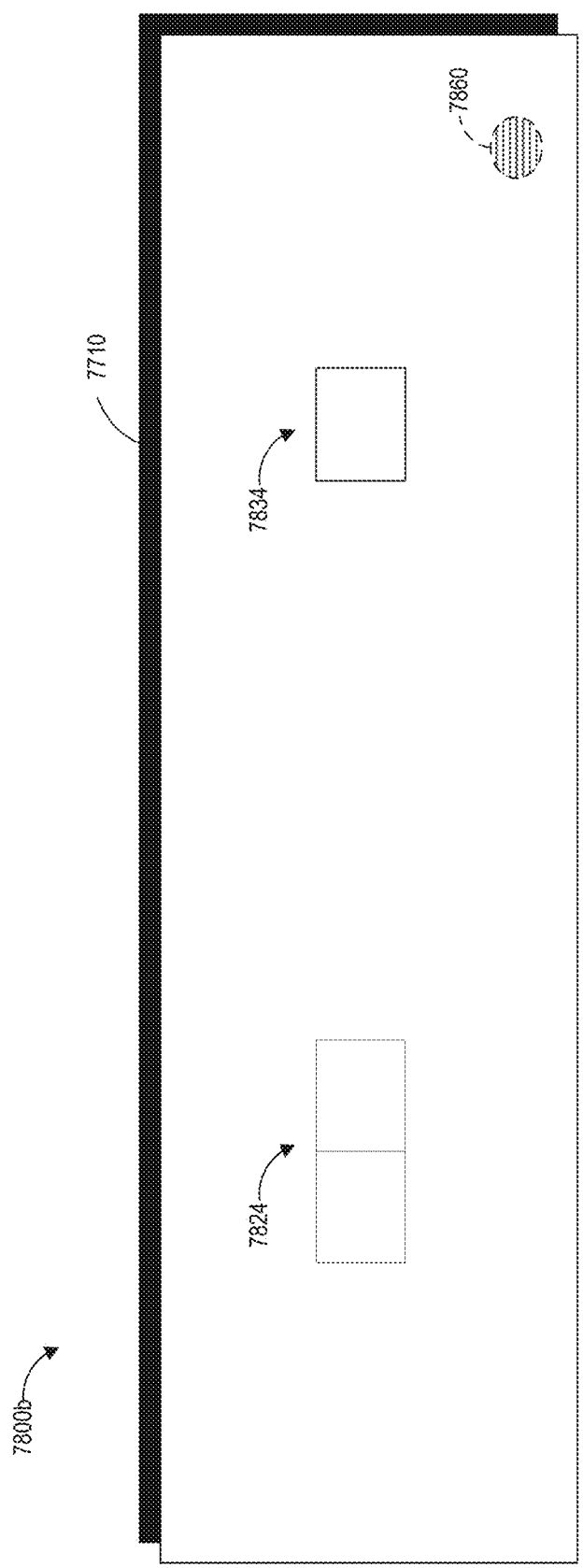

FIGS. 78A and 78B schematically illustrate an example embodiment of a medical network interface 7710 described above. FIG. 78A schematically illustrates a front perspective view 7800a while FIG. 78B schematically illustrates a back perspective view 7800b of the example medical network interface 7710.

The front side of the example medical network interface 7710 as shown in FIG. 78A can include Ethernet ports 7810, channel ports 7822, and USB ports 7832 (among others, not shown). The medical network interface 7710 can also include an optional display screen 7850 and a label 7840. The backside of the medical network interface 7710 as shown in FIG. 78B can include two USB ports 7824 and one Ethernet port 7834. The backside of the medical network interface 7710 can also include a power port 7860 which can receive a power cord. The power cord can connect the medical network interface 7710 to an AC outlet (for example, on a wall of a patient's room).

The Ethernet ports 7810 may be an example of the "Ethernet" port shown in FIG. 16. The Ethernet ports 7810 may also be an embodiment of the serial ports 210 shown in FIGS. 24 and 74A. The channel ports 7822 are embodiments of the ports 113 shown in FIG. 1B, the channel ports 212, or the universal connector ports shown in FIGS. 11E and 11F. The channel ports 7822 can be configured to mate with a proprietary connector, which can connect to a device (for example, illustrated in FIG. 77A) via a cable. Advantageously, in certain embodiments, the medical network interface 7710 can include more ports than the hub 100. For example, the hub 100 can include four Ethernet ports 7810 while the medical network interface 7710 can include eight (or more) Ethernet ports 7810. As a result, the medical network interface 7710 can expand the number of devices that can communicate (for example, via the medical network interface 7710) with the MMS 2004 (and other devices; see FIG. 77B). Alternatively, the medical network interface 7710 may have the same number or fewer ports than the hub 100.

The medical network interface 7710 can also include USB ports for connection with other devices in the patient's room. The USB ports may be configured to support type-A, type-A superspeed, type-B, type-B superspeed, type-C, mini or micro USB (for example, mini-A, mini-AB, mini-B, micro-AB, micro-B, micro-B superspeed), or other types of USB connectors known by a skilled artisan.

In certain embodiments, the medical network interface 7710 can also support wireless connections. The wireless connections may involve Bluetooth, Wi-Fi, ZigBee, or other types of wireless connections. As further described below in detail with reference to FIG. 81, the medical network interface 7710 can use a dongle to pair the medical network interface 7710 with a device that can communicate with the medical network interface 7710. For example, the dongle can be plugged into one of the USB ports 7832. The dongle may receive information from the medical network interface 7710 via the connector port 7832. A user may then disconnect the dongle from the medical network interface 7710 and plug the dongle into one of the standalone devices. The standalone device can then communicate with the medical network interface 7710 using wireless capability of the dongle, which can leverage the information the dongle obtained from the medical network interface 7710.

This information received may be security information. For instance, the dongle may receive a permission key from the medical network interface 7710. The key may be a cryptographic key, which may be used in an asymmetric or symmetric encryption algorithm (such as the private or public key). The dongle may then be plugged into a medical device such that the medical device will also receive, or generate, the permission key. The medical network interface 7710 can interrogate devices in its environment and identify the medical device that has the permission key. In one embodiment, once the medical network interface 7710 has identified the medical device and authenticated the permission key, the medical network interface 7710 can communicate with the medical device wirelessly.

The medical network interface 7710 can also receive a signal (for example, an RFID, Wi-Fi, or Bluetooth) signal emitted by a medical device seeking to pair with the medical network interface 7710 directly. Thus, in one embodiment, a dongle is not needed to pair with a standalone patient device. The medical network interface 7710 can reply back with the pairing protocols (or permission keys) to establish a connection for transferring the patient's data.

Another possible approach is for the medical network interface 7710 to interrogate the medical device to determine what protocol the medical device uses to communicate. For example, the medical network interface 7710 can attempt to communicate (for example, wirelessly) with the medical device using a first protocol, and if that protocol does not work, then with a second protocol, and so on until the medical network interface 7710 selects a correct protocol with which to communicate with the medical device. The protocol can refer to the network communications protocol, the message format used by the medical device, and/or the data format used by the medical device. For instance, the protocol can refer to whether messages used by the medical device have a fixed or dynamic length, whether a checksum or CRC (cyclic redundancy check) code is used, framing parameters, and so on. Further, the medical network interface 7710 may communicate with the medical device using standard protocols such as TCP/IP, optionally plus a custom application layer unique to the medical device. For example, the medical device may format its application-layer messages in a manner that is unique to that medical device. The medical network interface 7710 can cycle through different possible protocols—including different message formats—until it finds the correct message format to understand the messages sent by the medical device.

The message format may, for instance, include key-value pairs (sometimes called tag-value pairs) where keys define types or categories of data (such as parameter types, alarms, and so on) and the values are instances of the types or categories (such as specific parameter values, alarm states, and so on). The protocol or message format used by the medical device may also be self-defining, so that the medical network interface 7710 can inspect messages received from the medical device and thereby automatically determine what message format or protocol is used by the medical device. The message format used by the medical device may be formatted according to XML, so that tag-value pairs are machine-readable by the medical network interface 7710 directly from the XML. The medical network interface 7710 can include libraries of different protocols or message formats for different medical devices, so that the medical network interface 7710. In an example implementation, the medical network interface 7710 identifies the type of device that is connecting wirelessly to the medical network interface 7710 based on analyzing the message format from the medical device, comparing the message format to known message formats in its library of protocols, and identifying the correct medical device from the library.

The medical network interface 7710 can associate one or more identifiers with data obtained from the patient devices. The medical network interface 7710 may have its own identifier, for instance. Each standalone patient device may have its own identifier, either supplied by the device or generated by the medical network interface 7710. Further, each patient may have an identifier. The patient identifier may be obtained by optically scanning a machine-readable code, such as a QR (quick response) code or bar code, which may be in the form of a tag or sticker on the patient's wrist bracelet. An optical scanner may be included with the medical network interface 7710 for this purpose, or the clinician may use his or her phone, tablet, or other device to perform the scanning function. The scanning functionalities described in greater detail in U.S. application Ser. No. 14/511,972, filed Oct. 10, 2014, titled "Alarm Notification System,", the disclosure of which is hereby incorporated by reference in its entirety. The features in the '972 application may be used in conjunction with the features described herein, for example by using these features to perform scanning of patient or device identifiers.

In certain embodiments, the medical network interface 7710 tags or associates data it receives from the patient devices with the patient identifier, device identifier, and medical network interface identifier. The medical network interface 7710 can supply the data together with this identification data to the MMS 2004 or 7704 (for convenience, when the remainder of this document refers to one of the MMS 2004 or 7704 individually, it may be considered to also refer to the other).

Optionally, the medical network interface 7710 can include a display 7850. The display 7850 can show which patient the medical network interface 7710 is associated with, and which devices are currently in communication with the medical network interface 7710. The display 7850 can also provide an indication of a pairing status. For example, in some embodiments, the display 7850 can show information of a medical device during or right after a pairing (and optionally any of the identification information described above). The display 7850 can also illuminate a light pattern to show that a medical device has been paired with the medical network interface 7710.

In addition to or in alternative to the ports shown in the front perspective view 7800*a*, the medical network interface 7710 can also include various ports on the back as shown in the back perspective view 7800*b* in FIG. 78B. For example, the medical network interface 7710 can include two USB ports 7824 and one Ethernet port 7834. One of the USB ports 7824 can connect the medical network interface 7710 to the patient monitor 7701 while the other USB port can connect the medical network interface 7710 to a display device which can show the patient's data in aggregation. The medical network interface can also be connected to a hospital's main network using the Ethernet port 7834. The medical network interface 7710 can pass the data acquired from medical devices to the MMS 2004 via the Ethernet port 7834.

The medical network interface 7710 can also include a power port 7860. A power cord can be used to connect the AC outlet in the environment to the patient's monitoring box 7710 (via the power port 7860). In some embodiments, the medical network interface 7710 has a power cord fixedly attached to the power port 7860. The medical network interface 7710 can also have a backup battery (such as an uninterruptible power supply (UPS)) in case the power goes out. In certain implementations, power port 7860 (or the power cord) is optional. The medical network interface 7710 may be powered by battery.

A medical network interface 7710 may be assigned to a specific patient such that the medical network interface 7710 can acquire data from medical devices (for example, pump, ventilator, other devices or sensors) associated with the patient. The medical network interface 7710 can also be configured to gather data from more than one patient. Advantageously, in some embodiments, a portion of the medical network interface 7710 may be color coded to indicate from which patient a port is receiving data. For example, the top four ports of the Ethernet ports 7810 may be color coded to yellow while the bottom four ports of the Ethernet ports 7810 may be color coded to blue. (More generally, some of the ports on the device may be color to represent one patient while others of the ports on the device or collect represent another patient.) Where the color yellow represents data coming from devices associated with patient A while color blue represents data coming from devices associated with patient B. As another example, the left side of the front surface of the medical network interface 7710 may be color coded to yellow indicating that the ports on this side of the medical network interface 7710 should be connected to medical devices of the patient A. The right side of the front surface of the medical network interface 7710 may be color coded to blue indicating that the ports on this side of the medical network interface 7710 should be connected to medical devices of the patient B. The display 7850 can also provide an indication as to which patient the medical network interface 7710 is collecting data from. For example, the display 7850 can provide the patient ID associated with the patient A on one row and the patient ID associated with the patient B on the next row. The display may be a touch screen or otherwise.

More generally, data received on a certain colored port for one patient may be associated with that patient's ID automatically in the medical network interface, while data received on the other colored port for the other patient may be associated with that patient's ID automatically in the medical network interface.

In certain embodiments, pairing using the dongle does not require a passcode to be entered into either the dongle or the patient device or the medical network interface. By avoiding this requirement, the clinician can rapidly pair a patient device with the network interface without having to be distracted by entering a pairing code, which can take away time from caring for patient. This hands-free operation (other than plugging in the dongle) can enable clinicians to quickly return to patient care and more quickly obtain data from the patient devices. However, in other embodiments pairing codes are used.

The example components including the ports 7810, 7822, 7824, 7832, 7834, 7860, display 7850, and label 7840 merely schematic illustrations. The medical network interface 7710 can include fewer or more components as illustrated. Further, the positions of these components in FIGS. 78A and 78B are for illustrations only, these components are not required to be located at the positions illustrated in these drawings. For example, one or more of the ports in the view 7800a may be moved to the backside of the medical network interface 7710. Further, the size of these example components is not illustrated to scale. In addition, some ports may be located on a side of the device instead of or in addition to front or back portions.

XII. Examples of a Dongle

FIG. 79 illustrates an example embodiment of a dongle 7900 used to pair the medical network interface 7910 with another device. The dongle 7900 may be used in pairings for Bluetooth, Wi-Fi, or other types of wireless communication. Advantageously, in some embodiments, employing wireless communications among medical devices can result in a cleaner hospital environment, fewer infections (due, for example, to less sharing of cables), and easier user interactions with the medical devices. As an example, by employing wireless communications, an operating room no longer needs to employ long Ethernet cables to connect various medical devices.

The dongle 7900 can be equipped with an antenna 7920 (or a beacon), a location tag 7930, a battery 7940, and a processing unit 7910. The processing unit 7910 can include a processor 7912, a memory 7914, and a network interface 7916. The processing unit 7910 can include an embodiment of the core board 312. The dongle 7900 can also include an optional display 7952 and/or a light 7954. In various embodiments, the dongle 7900 can include fewer or more components as illustrated in FIG. 79. For example, the dongle 7900 may include either the beacon 7920 or the location tag 7930 but not both.

The dongle 7900 can be used to pair a medical network interface 7710 to a medical device seeking to communicate with the medical network interface 7710. A clinician may insert the dongle 7900 into the one of the USB ports 7822 or the Ethernet ports 7810 to obtain the permission key. For example, the processing unit 7910 can be programmed to communicate with the medical network interface 7710 to receive a permission key from the medical network interface 7710 once the dongle 7900 has been plugged into the medical network interface. The permission key can include a device identifier of the medical network interface 7710. Additionally or alternatively, the permission key can be a password, a token, or an encryption/decryption key for establishing a communication with the medical network interface 7710.

The clinician can plug the dongle into the patient device. To establish the pairing between the medical network interface 7710 and the patient device once the dongle is inserted, the dongle 7900 can pass the permission key received from the medical network interface 7710 to the medical device, for example, by plugging into a USB port of the medical device. In some embodiments, the medical device might not have a compatible port that the dongle 7900 can plug in. As a result, the dongle 7900 may use a connector which can adapt the dongle 7900 to connect to a port of the medical device.

The medical device can retrieve the permission key from the dongle 7900. The medical device can search for the medical network interface 7710 using the device ID (of the medical network interface 7710) received from the dongle 7900. As discussed above, to speed up pairing, the medical device can optionally avoid requiring a password to be provided for connection with the medical network interface. In some embodiments, the medical network interface 7710 interrogates the devices in its surroundings for the permission key. The medical network interface 7710 can establish a connection and receive patient data from a medical device if the medical device can provide the permission key in response to medical network interface's 7710 interrogation.

In some embodiments, the permission key is supplied and shared to multiple medical devices seeking connections to the medical network interface 7710. For example, the dongle 7900 can be plugged into the medical device A so that the medical device A can receive the permission key from the dongle 7900. The dongle 7900 can also be plugged into the medical device B and pass the permission key to the medical device B. In certain implementations, the dongle 7900 stores more than one permission key, where medical devices may receive different permission keys. For example, the dongle 7900 can store permission keys A and B in its memory 7914 where the permission key A may be used to pair the medical network interface 7710 with the patient bed 214 and the permission key B may be used to pair the medical network interface 7710 with the ventilator 218. The permission keys A and B may have a different expiration time. For example, the permission key A (for the patient bed 214) may include a longer expiration time than the permission key B (for the ventilator 218). Further, in some situations, the permission keys A and B can originate from two different medical network interfaces.

In certain embodiments, the medical network interface 7710 can update the permission key periodically or based on a triggering event to reduce the likelihood that a malicious device gains the connection to the medical network interface 7710. For example, the permission key may automatically expire when a period of time (for example, 24 hours, 1 week, 1 month, etc.) has elapsed. The permission key may also be automatically updated, for example, when the medical network interface 7710 becomes associated with a new patient. The permission key may be stored in the memory 7914 for later passing to another device. Once the old permission key expires, the medical network interface 7710 may need to be paired with other devices again.

In addition to or in alternative to pairing using the dongle 7900, other techniques can also be used to pair the medical network interface 7710 with another medical device. For example, the medical network interface 7710 and the other device can be paired using a label (such as, for example, a bar code or an RFID) on the medical network interface 7710 or the other device. Furthermore, a system administrator can add a device identifier of a medical device to a whitelist of the medical network interface 7710. Accordingly, the medical network interface 7710 can start communicating with the medical device if the medical device is within a communication range of the medical network interface 7710. In certain implementations, the dongle 7900 can obtain the permission key via a wireless connection. For example, the dongle 7900 may establish a connection with the medical network interface 7710 wirelessly and can subsequently receive the permission key from the medical network interface 7710 using the network interface 7916.

Advantageously, in some embodiments, a position of the dongle can be tracked by the location tag 7930 in addition to or in alternative to the antenna 7920. The location tag 7930 may be an RFID tag or the like. The location tag 7930 or the antenna 7920 can emit a signal which can be picked up by another device. For example, a patient monitor 7701 can automatically discover the dongle 7900. The patient monitor 7701 can determine the location (for example, which room the dongle 7900 is in) based on the signal emitted by the location tag or the antenna 7920. In certain implementations, more than one patient monitor 7701 can pick up the signal of the dongle 7900. Accordingly, the location of the dongle 7900 may be identified by triangulation using the locations of the patient monitors 7701, or by triangulation using access points in the hospital. In some embodiments, a map of the hospital room may be accessed electronically at any of the devices shown in FIG. 77A or 77B to determine a location of the dongle in the hospital room. The map can show the location of the dongle as determined, for example, based on this triangulation or RFID tag locating. If the connection between the dongle and the patient monitor is not working, the dongle can attempt to wirelessly communicate with a nearby patient monitor, which may be in a nearby hospital room. The dongle can wirelessly transmit data to the nearby patient monitor, so that this data can be sent to a remote server or electronic medical record for subsequent retrieval by the patient monitor in the room with the dongle.

The dongle 7900 can also include a battery 7940. The battery 7940 may be charged while the dongle 7900 is plugged into one of the USB ports 7822 or the Ethernet ports 7810. For example, once the dongle 7900 has obtained the permission key from the medical network interface 7710, the dongle 7900 may remain plugged-in for charging.

The dongle 7900 can include an optional display 7952 and an optional light component 7954. The display 7952 and the light component 7954 can provide an indication of the pairing status or the status of the dongle 7900. For example, once the dongle 7900 is fully charged, the light component 7954 may illuminate a specific color or pattern (for example, a flashing green) to indicate that the battery is full. As another example, the display 7952 can display a device ID of the device that the dongle 7900 is currently plugged-in. As yet another example, the light component 7954 may illuminate or the display 7952 may provide an alert when the medical network interface 7710 is paired with a medical device using the permission key stored in the dongle 7790. In this example, assuming the medical network interface 7710 is paired with the patient monitor 7701, the display 7952 can show the hub ID (for example, 1162) and state "paired". In addition to or in alternative to visual indication provided by the display 7952 and the light component 7954, the dongle can also include a speaker which will play a tone indicating the status of the pairing or the status of the dongle 7900. A color, pattern, tone, or display can be easily for a clinician to see and be readily identifiable.

Advantageously, in some embodiments, the dongle 7900 may be hot swapped without interrupting the functions of the device in which the dongle 7900 is plugged. For example, a dongle may be plugged into a patient medical device 7720 (either directly or via a dongle socket). The dongle can consume its battery power to communicate with the medical network interface 7710 while being plugged into the patient medical device 7720. However, a physician may notice that the battery power of the dongle has become low because the light component 7954 becomes amber in color. The physician can unplug the dongle from the patient medical device 7720 and swap the low battery dongle with a fully charged dongle that is currently plugged into the medical network interface 7710. Accordingly, the physician can plug the fully charged dongle into the patient medical device 7720 while re-plugging the low battery dongle into the medical network interface 7710 for charging. During this swapping process, the communications between the patient medical device 7720 and the medical network interface 7710 can remain uninterrupted. For example, to avoid interruptions of data transmissions, the patient medical device 7720 may not require a pairing process to be performed with the fully charged dongle because the fully charged dongle carries the same permission key (for the same medical network interface 7710) as the low battery dongle and the fully charged dongle is plugged into the patient medical device 7720 within a certain threshold time period from when the low battery dongle is unplugged.

Example Components of a Medical Network Interface

Figure 80:
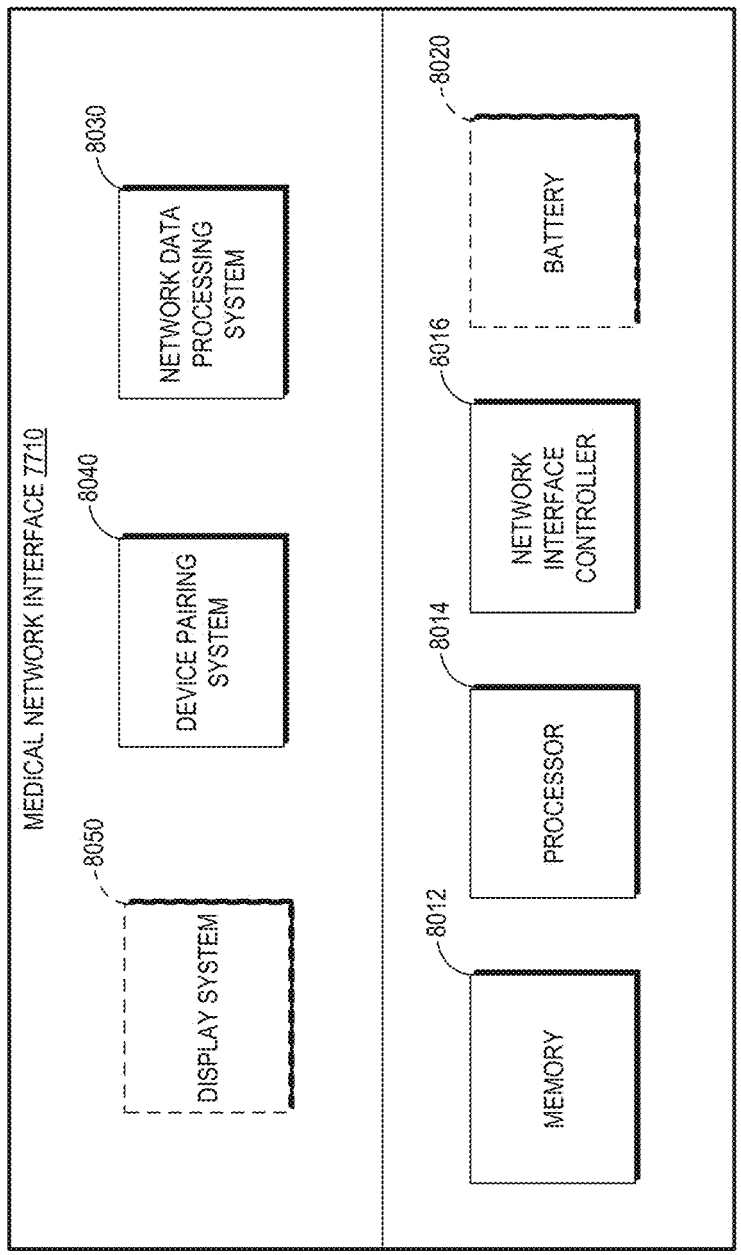
FIG. 80 illustrates an example embodiment of components of a medical network interface.

FIG. 80 illustrates an example embodiment of components of a medical network interface. These components are for illustrative purposes only, and the medical network interface 7710 can include fewer or more components as shown in FIG. 80.

The medical network interface 7710 can include hardware components such as, for example, a memory 8012, a processor 8014, a network interface 8016, and an optional backup battery 8020. In some embodiments, the hardware components can include a coreboard where the main processor 8014 (or a separate processor) can act as a network bridge. The network interface controller 8016 can be configured to receive communications from various devices via a wired or wireless connection, such as, for example, via Ethernet, Wi-Fi, Bluetooth, or other types of connections. The network interface controller 8016 can be configured to pass the data to another device, such as, for example, the patient monitor 7701, the MMS 2004, a multi-parameter monitor, and so on. As further described with reference to the network data processing system 8030, the processor 8014 and the memory 8012 can facilitate this data transfer together with the network interface controller 8016. For example, the memory can store instructions associated with the network data processing system 8030 while the processor 8014 can execute the instructions to identify a patient identifier and a device identifier of the device from which the network interface controller 8016 receives the communication. The processor 8014 can also associate the device identifier of the medical network interface 7710 with the data packet received from the device and pass the data packet (updated with the device identifier of the medical network interface 7710) to the patient monitor 7701 and the MMS 2004. In one embodiment, the network interface controller 8016 can act as a network bridge.

As described above with reference to FIG. 78A, the medical network interface 7710 can include a power port 7860 to obtain electricity from an AC outlet. The optional backup battery 8020 can supply battery in case the medical network interface 7710 cannot obtain electricity from other sources (such as for example, during a power outage). Accordingly, the medical network interface 7710 can be powered entirely by a battery.

The medical network interface 7710 can also include software components such as, for example, a network data processing system 8030, a device pairing system 8040, and an optional display system 8050. At least a portion of these software components may be stored in the memory 8012. The processor 8104 may be programmed to execute these software components.

The network data processing system 8030 can be configured to process data received from one device and pass the data to another device. The network data processing system 8030 can parse the packets received to identify a device ID from which the medical network interface 7710 receives the data. The packets may include a patient ID (which may be added by the device sending the data packet) and the network data processing system 8030 can accordingly identify the patient ID in the data received from the device. The network data processing system 8030 can also add the device ID of the medical network interface 7710 to the data received form the device and route the data to another device. Alternatively, the medical network interface 7710 may have previously stored the patient ID based on a scan of the patient's wrist bracelet, as discussed above. Thus, the medical network interface 7710 can associate the patient ID, the interface 7710 ID, and the patient device ID together with the data obtained from the patient device and send this data on to the MMS 2004 or to another device (such as the hub 100 or another interface 7710).

Although the network data processing system 8030 can recognize the source of packets by parsing the packets, in some embodiments, the network data processing system 8030 does not process the content (such as, for example, parameter values of a measure of the patient) in the packets. As an example of passing data, the medical network interface 7710 can be connected to the patient monitor 7701 and can receive packets from a pump. The packets can indicate a device ID for the pump and a patient ID. The network data processing system 8030 can append the device ID of the medical network interface 7710 to the header without altering the parameter values obtained by the pump. The network data processing system 8030 can then communicate these marked or tagged packets to the MMS 2004.

Optionally, the network data processing system 8030 can prioritize packets based on a variety of factor such as, for example, a patient ID, a source of the data (for example, which from device the packets comes from), a destination of the data, or based on alarms. Additional details on routing and prioritizing packets by a device such as, for example, the MMS 2004, the patient monitor 7701, the medical network interface 7710, or another device (and which may be implemented herein) are described in application Ser. No. 14/030, 360, filed Sep. 18, 2013, titled "Intelligent Medical Network Edge Router,", now U.S. Pat. No. 9,749,232 ("the '232 patent"), the disclosure of which is hereby incorporated by reference in its entirety. Further, the medical network interfaces described herein can perform the functionality of the edge router described in the '232 patent. For instance, the medical network interface can prioritize alarms over other data, or prioritize parameters over other data (except possibly alarms).

The device pairing system 8040 can control permission keys, identify devices in the environment for pairing with the medical network interface 7710, and establish connections between the devices in the environment and the medical network interface 7710. For example, the device pairing system 8040 can periodically generate or update a permission key for a dongle 7900. The device pairing system 8040 can also receive and process signals from the dongle 7900 or a medical device seeking to pair with the data gathering system 7710. The device pairing system 8040 can also authenticate a request to connect to the medical network interface based on whether the request includes the correct permission key.

The optional display system 8050 can generate user interface instructions for the optional display 7850 (shown in FIG. 78A). For example, when a medical device is paired with the medical network interface 7710, the device pairing system 8040 can instruct the display system 8050 to generate an instruction showing the device identifier of the medical device on the display 7850. As another example, the display system 8050 can communicate with the network data processing system 8030 or the device pairing system 8040 to obtain a status of a device (for example, disconnected, connected, pairing, in repair mode, etc.) connected to the medical network interface 7710. The display system 8050 can accordingly instruct the display 7850 to present the status of the device.

XIII. Example Processes for Pairing a Medical Network Interface

Figure 81:
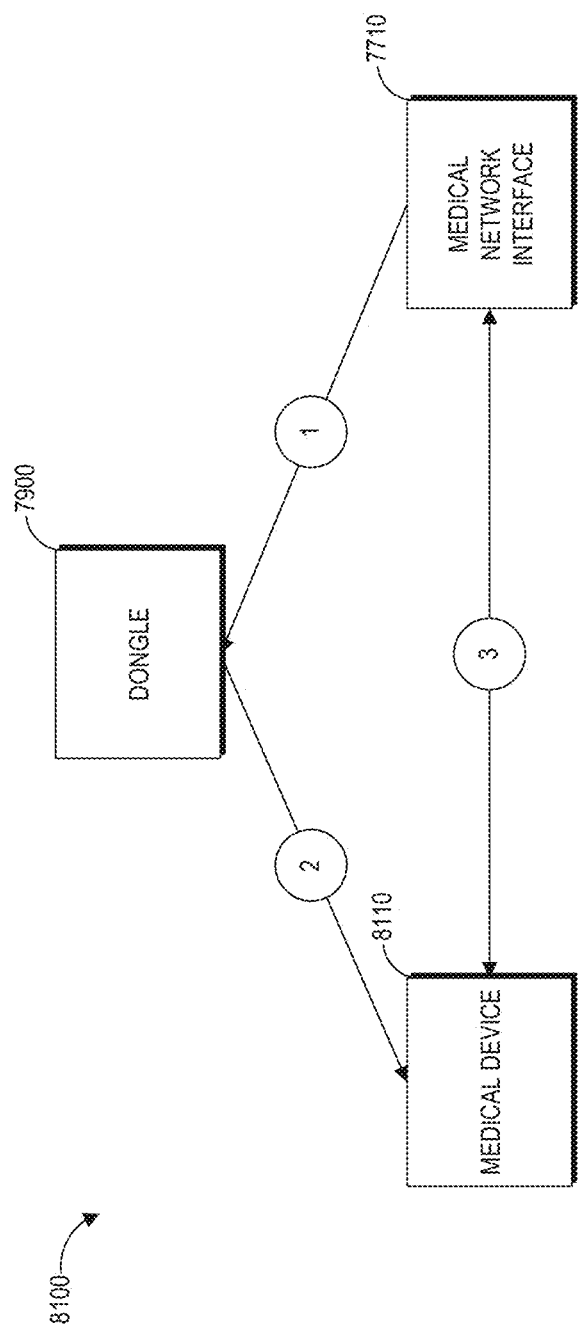
FIG. 81 illustrates an example embodiment of a flow diagram for pairing a medical network interface with a medical device.

FIG. 81 illustrates an example embodiment of a state flow diagram for pairing a medical network interface with a medical device. The example environment 8100 in FIG. 81 can be a portion of the environment 7700 shown in FIG. 77. The example environment 8100 can involve a medical device 8110, a medical network interface 7710, and a dongle 7900. The medical device 8110 can be any devices illustrated in FIG. 77 or other devices described herein.

At state (1), the dongle 7900 can receive a permission key and optionally identifier (of the interface 7710) from the medical network interface 7710. The dongle 7900 can receive the permission key (and optionally ID) when it is plugged-into the medical network interface 7710. The dongle 7900 can be plugged into an USB port, a medical port, an Ethernet port, or another port on the medical network interface 7710. The dongle 7900 can also receive the permission key (and optionally ID) from the medical network interface 7710 using other techniques, such as, for example, via wireless (for example, Bluetooth) pairing between the dongle 7900 and the medical network interface 7710.

At state (2), the dongle 7900 can pass the permission key (and optionally ID) to the medical device 8110. For example, the dongle 7900 can be unplugged from the medical network interface 7710 and re-plugged into the medical device 8110. The medical device 8110 can detect that the dongle 7900 has been connected and can automatically access the permission key (and optionally ID) stored in the dongle 7900.

At state (3), the medical device 8110 can establish a connection with the medical network interface 7710. For example, the medical network interface 7710 can interrogate devices in its proximity and requests the permission key to initiate the connection. As another example, the medical device 8110 can contact the medical network interface 7710 with the permission key to gain access to the medical network interface 7710.

The medical device 8110 can communicate with the medical network interface 7710 to pass patient data (and optionally ID) from the medical device 8110 to the medical network interface 7710. The medical network interface 7710 can further pass the patient data to another device such as, for example, the patient monitor 7701 or the MMS 2004. The packets communicated from the medical device 8110 may include a patient ID and a device ID of the medical device 8110 (or the patient ID is not in the packets and instead is inserted into the data stream by the interface 7710). The medical network interface 7710 can also associate another device ID of the medical network interface 7710 to the data packet before the data is passed to the other device. In certain implementations, the medical network interface 7710 can automatically link its device ID with the device ID of the medical device 8110 (and the patient ID).

In some embodiments, the medical network interface 7710 can also receive data from the other device (for example, from the patient monitor 7701 or the MMS 2004) and pass this data to the medical device 8110. For example, medical network interface 7710 may receive an instruction from the patient monitor 7701 to adjust a parameter of the medical device 7710 (for example, to increase the frequency of measurements, or to adjust the delivery rate of the infusion pump(s) 216). The medical network interface 7710 can pass the instruction received from the patient monitor 7701 to the medical device 7710 to cause the medical device 7710 to implement the instruction. In some embodiments, the connection between the medical device 8110 and the medical network interface is maintained while the dongle 7900 is plugged in to the medical device 8110. Once the dongle 7900 is removed from the medical device 8110, the communication between the medical device 8110 and the medical network interface 7710 may terminate.

Figure 82:
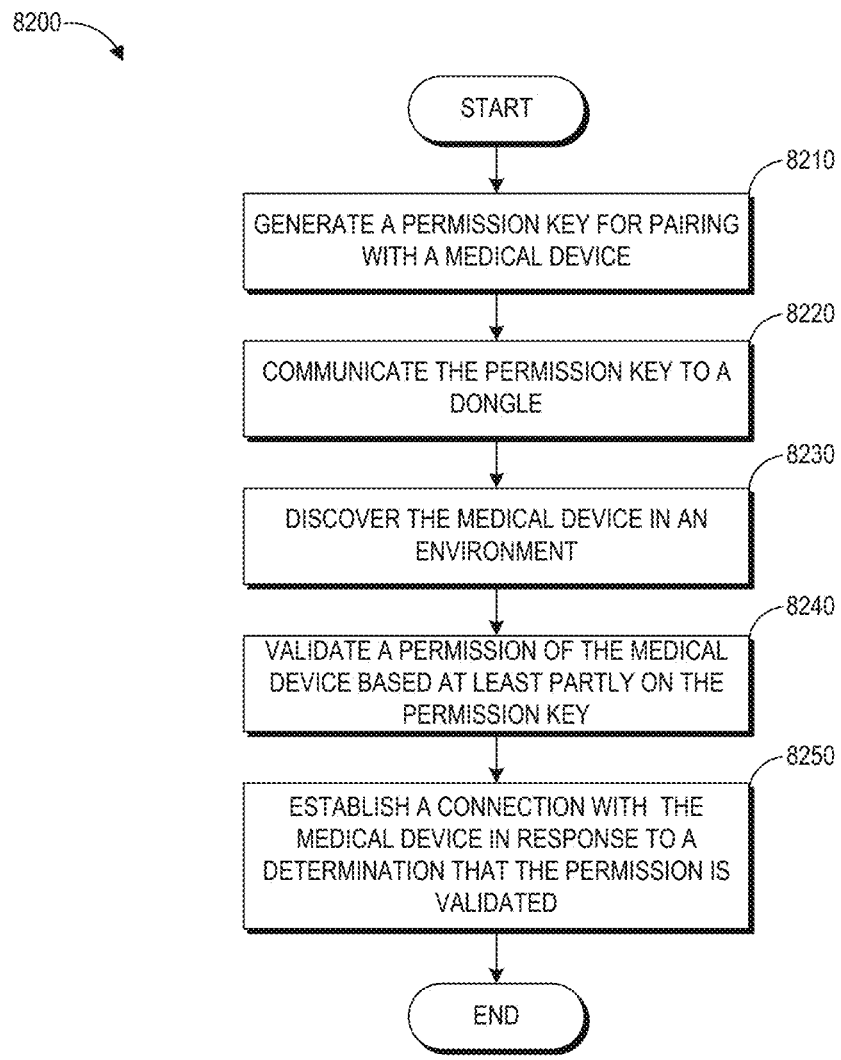
FIG. 82 illustrates an example embodiment of a process for pairing a medical network interface with a medical device.

FIG. 82 illustrates an example embodiment of a process for pairing a medical network interface with a medical device. The process 8200 can be performed by the medical network interface 7710.

At block 8210, the medical network interface can generate a permission key for pairing with a medical device. The permission key may be a randomly generated alpha-numeric string. The permission key may also encode device information or a password associated with the medical network interface. The permission key may be periodically updated after the initial pairing to reduce the likelihood that an unauthorized device or user obtains the access to the medical network interface.

At block 8220, the medical network interface can communicate the permission key to a dongle (such as, for example, the dongle 7900). For example, when a dongle is plugged-into a port of the medical network interface, the medical network interface can send the permission key to the dongle or receive a request (from the dongle) to download the permission key.

At block 8230, the medical network interface can discover the medical device in an environment of the medical network interface. For example, the medical network interface can send interrogation signals to surrounding devices and can request the surrounding devices to provide the permission key. As another example, the medical device may initiate a contact with the medical network interface (for example based on the device ID of the medical network interface) and furnish the permission key to the medical device.

At block 8240, the medical network interface can validate a permission of the medical device based at least partly on the permission key. For example, the medical network interface can determine whether the permission key provided by the medical device is a valid. In certain embodiments, the device pairing occurs in a wired connection. For example, the medical network interface can be connected to the MMS 2004 via a USB connection. The medical network interface and the MMS 2004 may be paired by receiving and recognizing the device identifier of the MMS 2004 via the USB connection. In other embodiments, the medical network interface can be paired with another device using a wireless connection, without requiring the dongle. For example, the medical network interface can be paired with the patient monitor 7701 via Wi-Fi. In this example, the device identifier of medical network interface may be added to a whitelist of allowed devices for the patient monitor 7701. The patient monitor 7701 can use the device identifier of the medical network interface to find and connect with the medical network interface.

At block 8250, the medical network interface can establish a connection with the medical device in response a determination that the permission is validated. The medical network interface can pass the data received from the medical device to another device such as, for example, the patient monitor 7701, the MMS 2004, a multi-parameter monitor, the augmented reality device 7200, and so on.

XIV. Example Processes for Data Processing by a Medical Network Interface

Figure 83:
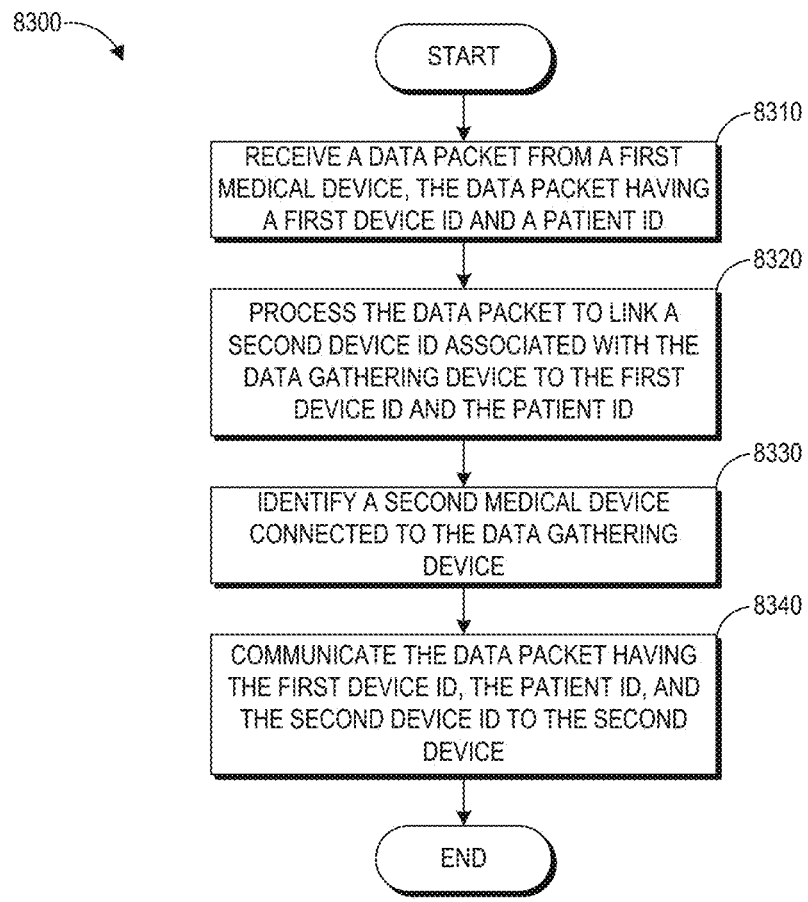
FIG. 83 illustrates an example embodiment of a process for data processing by a medical network interface.

FIG. 83 illustrates an example embodiment of a process 8300 for data processing by a medical network interface 7710.

At block 8310, the medical network interface can receive a data packet from a first medical device. The first medical device may be medical equipment (such as, for example, other devices and sensors 7720 in FIG. 77) that can acquire patient data. The patient data acquired by the first medical device can be associated with a patient ID identifying from which patient the data is acquired. The patient data can also be associated with a first device ID which may be the device identifier of the first medical device.

The medical device can pass the patient data to the medical network interface via wired or wireless connection as described with reference to FIG. 78A. The first device ID and the patient ID may be part of a header file for the patient data. At block 8320, the medical network interface can process the data packet to link a second device ID associated with the medical network interface to the first device ID and the patient ID. In certain embodiments, the medical network interface can link the second device ID to the first device ID when the medical network interface is paired with the first medical device. Therefore, the linking of the first and second device IDs may occur before the first medical device communicates patient measurements to the medical network interface. In certain embodiments, once the medical network interface has linked the first device ID and the patient device ID, the medical network interface can automatically stamp the data packet with the device ID of the medical network interface.

At block 8330, the medical network interface can identify a second medical device connected to the medical network interface 8330. The second medical device may be a patient monitor 7701, MMS 2004, a display (such as, for example, a multi-parameter monitor), or another device described herein. The medical network interface can identify the second medical device by determining which devices are plugged-into its ports. The medical network interface can also review a list of devices that are connected wirelessly to identify the second medical device.

At block 8340, the medical network interface can communicate the data packet to the second device. The data packet may include the first device ID identifying the first medical device (which acquires the patient data), the patient ID, and the second device ID (which may be stamped by the medical network interface). The second device can further process the data packet such as by routing the data packet to another device or system, perform data analysis, or display the patient data.

Further, it should be understood that passing the identifier of the medical network interface along with the patient data can enable troubleshooting of the medical network interface.

Moreover, in another embodiment, the wireless dongle includes two pieces—a first piece that stays connected to the medical network interface, and a second piece that disconnects from the first piece. The second piece connects in a corresponding first piece of a similar dongle in the medical device. The example dongles in FIGS. 77A-83 are referred to as wireless connectors in FIGS. 84A-88 as described below.

XV. Example Techniques for Connecting a Medical Network Interface with a Patient Monitor As described with reference to FIG. 77A-78B, the medical network interface 7710 can be communicatively coupled to a patient monitor 7701 or a hub 100 via wired or wireless connections. The medical network interface 7710 can also be mechanically coupled to the patient monitor 7701 or the hub 100 in addition to or in alternative to the wired or wireless connections. For example, the medical network interface 7710 can be mechanically coupled to the patient monitor 7710 by mounting the top or bottom surface of the medical network interface 7710 to a surface (for example, a top, bottom, or side surface) of the patient monitor 7701 or the hub 100. In some embodiments, the mounting of the medical network interface 7710 to the patient monitor 7701 or the hub 100 is not permanent so that the patient monitor 7701 or the hub 100 can be detached from the medical network interface 7710. In other embodiments, the medical network interface 7710 is integrally formed with the hub 100 as part of the hub 100.

Figure 84A:
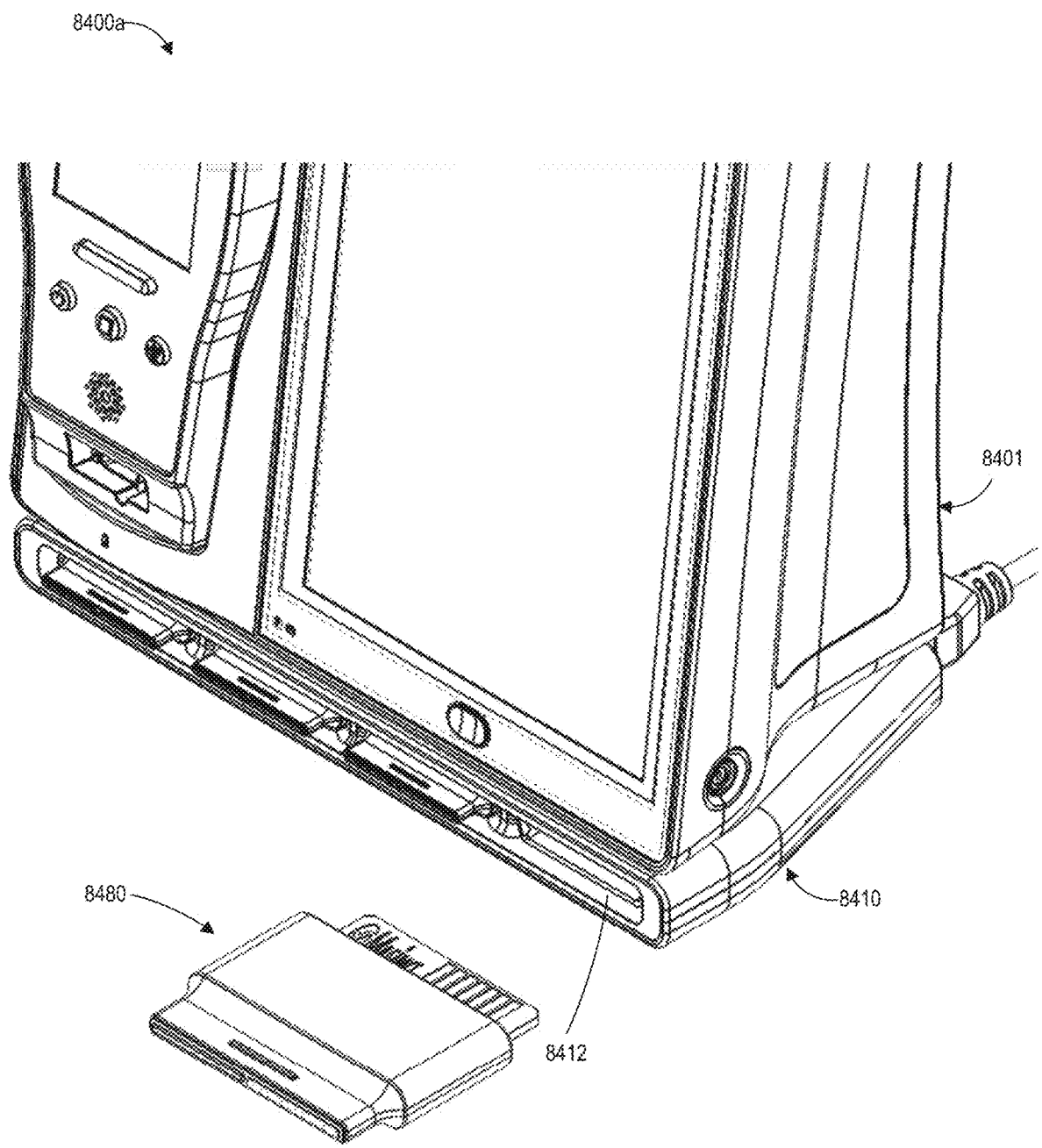
FIGS. 84A and 84B illustrate an example of a medical network interface where the medical network interface is removably mounted to a bottom surface of a hub.
Figure 84B:
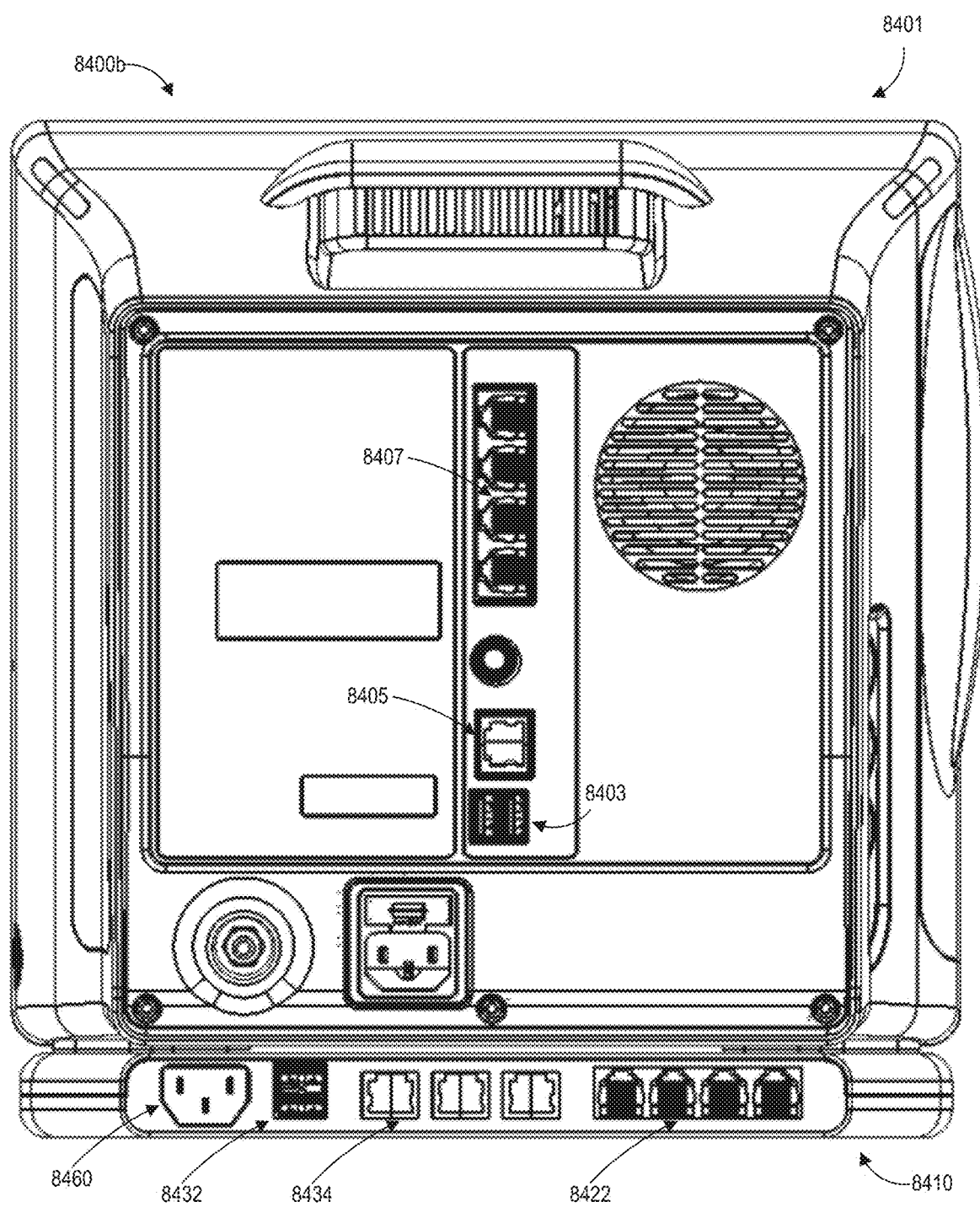

FIGS. 84A and 84B illustrate an example embodiment of a medical network interface where the medical network interface is removably mounted to a bottom surface of a hub. The hub 8401 can be an embodiment of the patient monitoring hub 100 or the patient monitor 7701 described herein. The medical network interface 8410 may be an embodiment of the medical network interface 7710 in FIGS. 77A-78B, and 80.

FIG. 84A shows a perspective view 8400a of the hub 8401 and the medical network interface 8410. The front side of the medical network interface 8410 can include various ports for interfacing with devices, such as, for example, patient devices 7720 or other devices shown in the computing environment 7700. In FIG. 84A, the front side of the medical network interface 8410 includes (as an example) four interface ports 8412. More or fewer ports may be included in other embodiments. An interface port 8412 can be configured to connect with the wireless connector 8480. The wireless connector 8480 may be an embodiment of the dongle 7900 described in FIG. 79. As illustrated in FIG. 84A, three wireless connectors 8480 are currently plugged into three out of the four interface ports 8412. The interface port 8412 may be an embodiment of the USB port 7832. In certain implementations, the wireless connector 8480 is a proprietary connector and the interface port 8412 can be customized to receive the wireless connector 8480.

The medical network interface 8410 can be attached to the bottom of the hub 8401 using various mounting types or standards, such as GCX® slide-in tracks, VESA mount, tub-mounting, universal mount, and so on. The medical network interface 8410 and the hub 8401 can also be attached together using other techniques such as clamps or adhesives. As an example, one side of the hub 8401 may include one or more clamps, which can be used to hold the medical network interface 8410. In some embodiments, the hub 8401 includes one or more holes on its bottom surface. The top surface of the medical network interface 8410 can include corresponding protrusions for insertion into the holes on the hub's 8401 bottom surface.

Although FIG. 84A illustrates four interface ports, other types of ports can be included in the front side of the medical network interface 8410. For example, as described with reference to FIG. 78A, the medical network interface 8410 can also include Ethernet ports 7810, channel ports 7822, or USB ports 7832. The medical network interface 8410 can also include fewer and more interface ports 8412, such as, for example, two, three, six, eight, or other numbers of interface ports 8412. Further, although the four interface ports 8412 are arranged in the same row in FIG. 84A, the layout of the interface ports 8412 may vary in different embodiments. For example, the medical network interface 8410 can include multiple rows of interface ports 8412 (such as two), optionally with each row having the same number of interface ports.

The number and layout of the interface ports 8412 on the medical network interface 8410 can be determined based on the size of the medical network interface 8410. For example, where the medical network interface 8410 is designed to be a thin housing that fits underneath the patient monitor 8401, such as in the example shown in FIG. 84A, the medical network interface 8410 may include one row of interface ports 8412 to keep the height of the medical network interface 8410 small. On the other hand, if the medical network interface 8410 is designed to be mounted to the either side (left or right side) of the hub 8401, the medical network interface 8410 may have a larger height while a having a shorter length. Accordingly, the medical network interface 8410 can include 4 rows of interface ports 8412 with each row having one interface port 8412.

The number and layout of the interface ports 8412 may also depend on the size and shape of the wireless connector 8480. For example, where the wireless connector 8480 is a USB A-Type connector, the medical network interface 8410 may include more interface ports 8412 than where the wireless connector 8480 is in the shape shown in FIG. 84A because the USB A-Type port may not take as much space as the port configured to receive the wireless connector 8480 in the shape shown in FIG. 84A. However, one benefit of the wireless connector configuration shown and discussed in greater detail below is greater battery capacity than USB-sized devices. This greater battery capacity may allow the wireless connector 8480 to be inserted in a standalone medical device longer than a USB-sized device (which may be useful, for example, when the medical device does not supply power to the wireless connector).

FIG. 84B illustrates a back view 8400b of the hub 8401 and the medical network interface 8410. As illustrated, the back side of the hub 8401 can include two USB ports 8403, one Ethernet port 8405, and four channel ports 8422. The two USB ports 8403, one Ethernet port 8405, and four channel ports 8422 can be embodiments of the USBs, Ethernet, and RJ ports, respectively, in FIG. 16. The back side of the medical network interface 8410 can include one battery port 8460, two USB ports 8432, three Ethernet ports 8434, and four channel ports 8422. With reference to FIGS. 78A and 78B, the battery port 8460 can be an embodiment of the battery port 7860; the USB ports 8432 can be embodiments of the USB ports 7832; the Ethernet ports 8434 can be embodiments of the Ethernet ports 7810 and 7834; and the channel ports 8422 can be embodiments of the channel ports 8422.

Although the medical network interface 8410 is shown with ports below the hub 8401, in some implementations, the medical network interface 8410 may be omitted. Rather, the hub 8401 itself may include ports such as the ports 8422, for example, in the front, back, side, or top of the hub 8401. Thus, some or all of the functionality of the medical network interface 8410 can be incorporated into the hub 8401 or into another monitor or medical device. For instance, an anesthesia machine (such as the Draeger Apollo™ or the like) could incorporate the features of the medical network interface 8410. Further, any of the medical network interfaces described herein could communicate with the hub 8410 through one of the hub's channel ports, for example, using the Masimo Open Connect (MOC) protocols, for example, as described in U.S. patent application Ser. No. 15/902,193, filed Feb. 22, 2018, titled "System for Displaying Medical Monitoring Data," the disclosure of which is hereby incorporated by reference in its entirety.

Figure 84C:
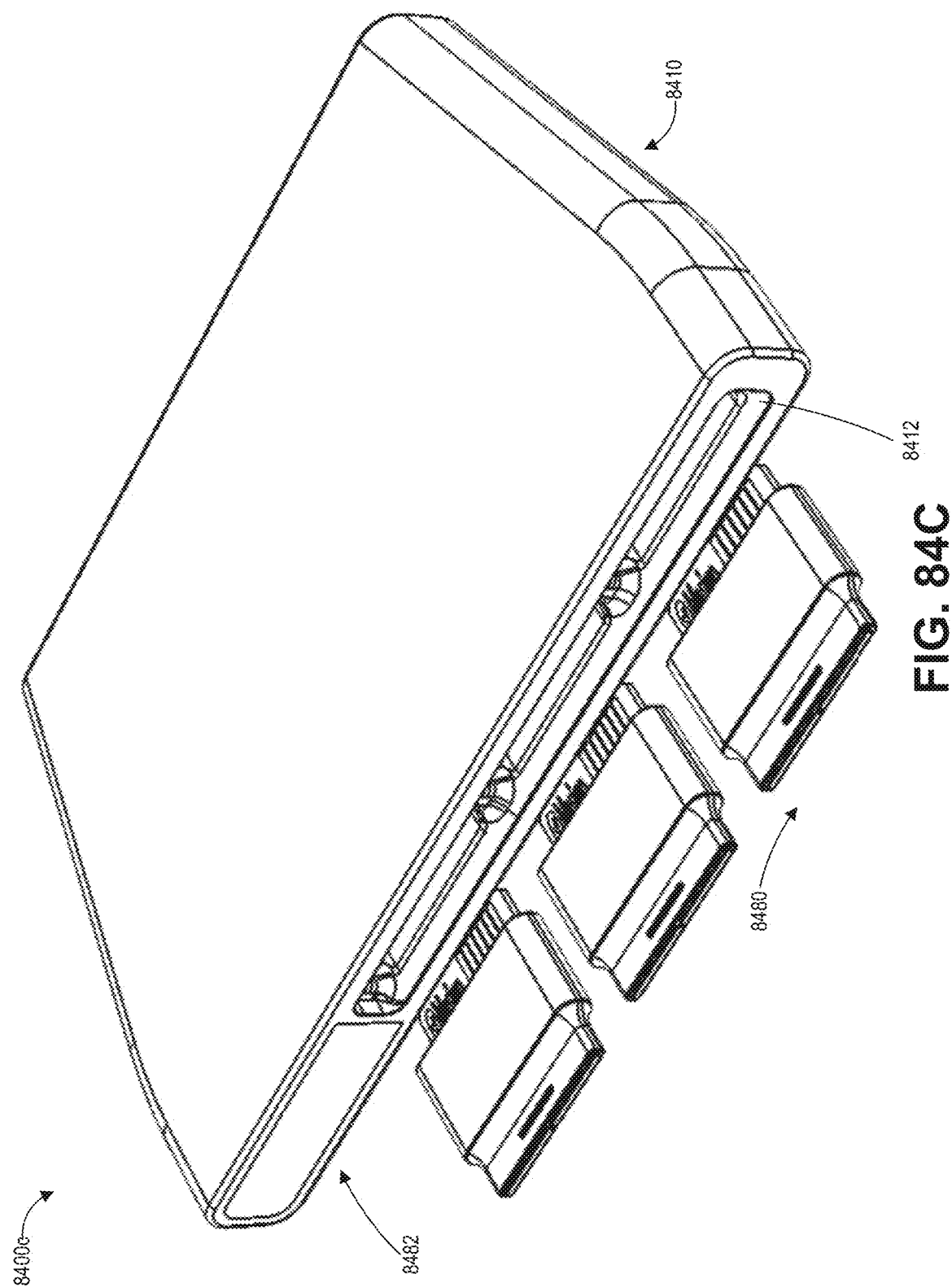
FIGS. 84C and 84D illustrate another example of the medical network interface.
Figure 84D:
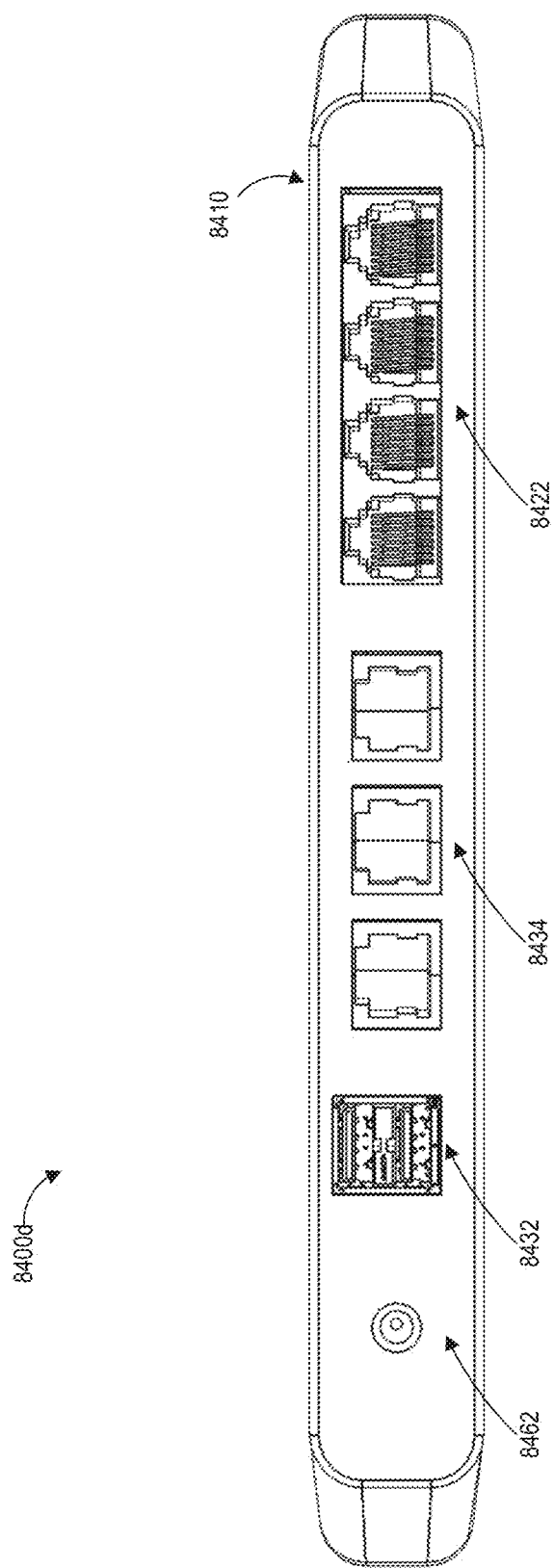

FIGS. 84C and 84D illustrate another example of the medical network interface 8410. The medical network interface 8410 can be connected to the monitoring hub 8401 as described with reference to FIGS. 84A and 84B.

FIG. 84C shows a front perspective view 8400c of the medical network interface 8410. Similar to FIG. 84A, the front side of the medical network interface 8410 can include various ports for interfacing with devices, such as, for example, patient devices 7720 or other devices shown in the computing environment 7700. In contrast with FIG. 84A, the front side of the medical network interface includes, for example, three interface ports 8412 and a display 8482. As described herein, an interface port 8412 can be configured to connect to a wireless connector 8480.

The display 8482 can be an example of the display 7850 shown in FIG. 78A. The display 8482 can be located at the left most region of the front side of the hub as shown in FIG. 84C. The medical network interface 8410 can replace one interface port 8412 with the display 8482 (as compared to FIG. 84A). The display 8482 can show various information related to medical network interface 8410, the hub 8401, and other devices that are connected to the network interface 8410. For example, the medical network interface 8410 can be connected to the hub 8401, and the one or more medical devices via the wireless connector 8480. The display 8480 can provide indications of the connection status for the hub 8401 and the medical devices 8480. The display 8480 can also show information of a patient (for example, patient identifier, parameters being monitored, etc.) that the medical network interface is connected to, via the hub 8401 or other medical devices. The display 8482 can also show information showing status or battery charging status for the wireless connectors. The display 8480, or any display herein, can also output patient data, such as waveforms, trends, and/or physiological parameter values. Thus, the medical network interfaces described herein can also act as patient monitors based on the data received through the interface ports.

FIG. 84D illustrates a back view 8400d of the medical network interface 8410. Similar to the view 8400b in FIG. 84B, the back side of the medical network interface 8410 can include two USB ports 8432, three Ethernet ports 8434, and four channel ports 8422. The medical network interface 8410 can also include a battery port 8462. The battery port 8462 may be a example of the battery port 7860 shown in FIG. 78B. The battery port 8462 can be configured to connect the medical network interface 8410 to a AC power outlet in the environment via a power connector. In this example view 8400d, the battery port 8462 accepts a different power connector as the battery port 8460 shown in FIG. 84B.

As described in FIGS. 77A-78B, the medical network interface 8410 can be connected to various medical devices, such as patient devices 7720, the hub 7801, multi-patient monitoring system 2004, and so on, using the ports 8432, 8434, 8422, or 8412. For example, one of the USB ports 8432 may be connected to one of the USB ports 8403 on the hub 7801. The other USB port 8432 of the medical network interface 8410 may be connect to a physician's computer. In addition to using the USB ports 8432, the hub 7801 and the medical network interface 8410 can connect to each other via other techniques, such as, for example, the channel ports 8422 and 8407, the Ethernet ports 8432 and 8405, or a proprietary port (not shown). In some embodiments, the proprietary port may be located on the top surface of the medical network interface 8410 and the connector to the proprietary port may be attached to the hub 8401. As another example, the proprietary port may be located on the hub 8401 (for example, on the bottom surface or the left/right surface) and the connector may be on the medical network interface 8410.

In some embodiments, the medical network interface 8410 can serve as a docking station for the hub 8401. The medical network interface 8410 can replicate existing ports that are already on the hub 8401 or offer additional ports, alone or in combination. Advantageously, in some embodiments, the medical network interface 8410 can offer a greater number of ports than is physically present on the hub 8401. This allows the hub 8401 to have fewer physical ports (or no such ports) while still providing the same range of features. For example, the Ethernet ports 8434 can increase the number of Ethernet connection from one (as offered by the Ethernet port 8405) to three. Similarly, the USB ports 8432 can offer two additional USB connections and four additional channel ports for the hub 8401 to allow more devices to communicate with the hub 8401 (via the medical network interface 8410).

As described with reference to FIG. 78B, the medical network interface 8410 can be powered by battery or be connected to an AC outlet when a power cord is plugged into the port 8460. In certain embodiments, when the hub 8401 is connected to the medical network interface 8410, both the hub 8401 and the medical network interface 8410 can be powered when the port 8460 is connected to an outlet via a power cord. As another example, when the hub 8401 is connected to a power source, the power source can also be used to power both the hub 8401 and the network interface 8410.

As shown in FIGS. 84A and 84B, the medical network interface 8410 can be mechanically attached to the hub 8401. For example, the top housing of medical network interface 8410 can be mounted to the bottom of the hub 8401. In various other embodiments, the top housing of the medical network interface 8410 can also be mounted to a side or the back of the hub 8401. The hub 8401 can also be mechanically attached to the surface of physical structure in the hospital environment. For example, the bottom surface of the hub 8401 can be mounted to a wall, a door, or a table in a patient's room. In some embodiments, the medical network interface 8410 is mounted to the physical structure and the hub 8401 at the same time, such that the medical network interface is sandwiched between the physical structure and the hub 8401. In other embodiments, the medical network interface 8410 is mounted on one side on either the physical structure or the hub 8401 but not both. The medical network interface 8410 can also be mounted to the hub 8401 using other mechanisms, such as, for example via magnetic attraction where a portion of the medical network interface 8410 (for example, the top portion of the medical network interface 8410), a portion of the hub 8401, or both comprises a magnet.

Figure 85A:
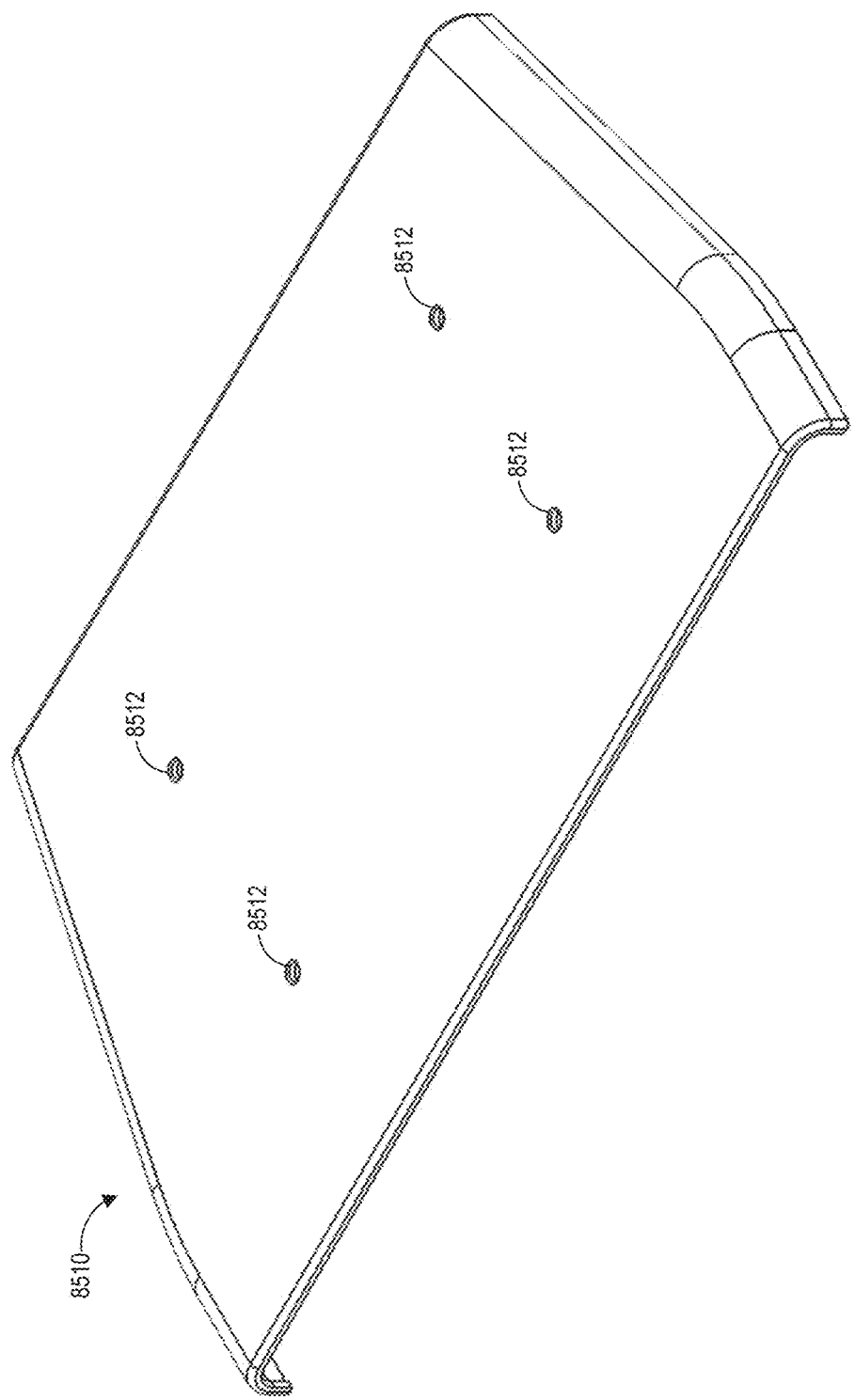
FIGS. 85A, 85B, and 85C illustrate example structures for mechanically mounting a medical network interface.
Figure 85B:
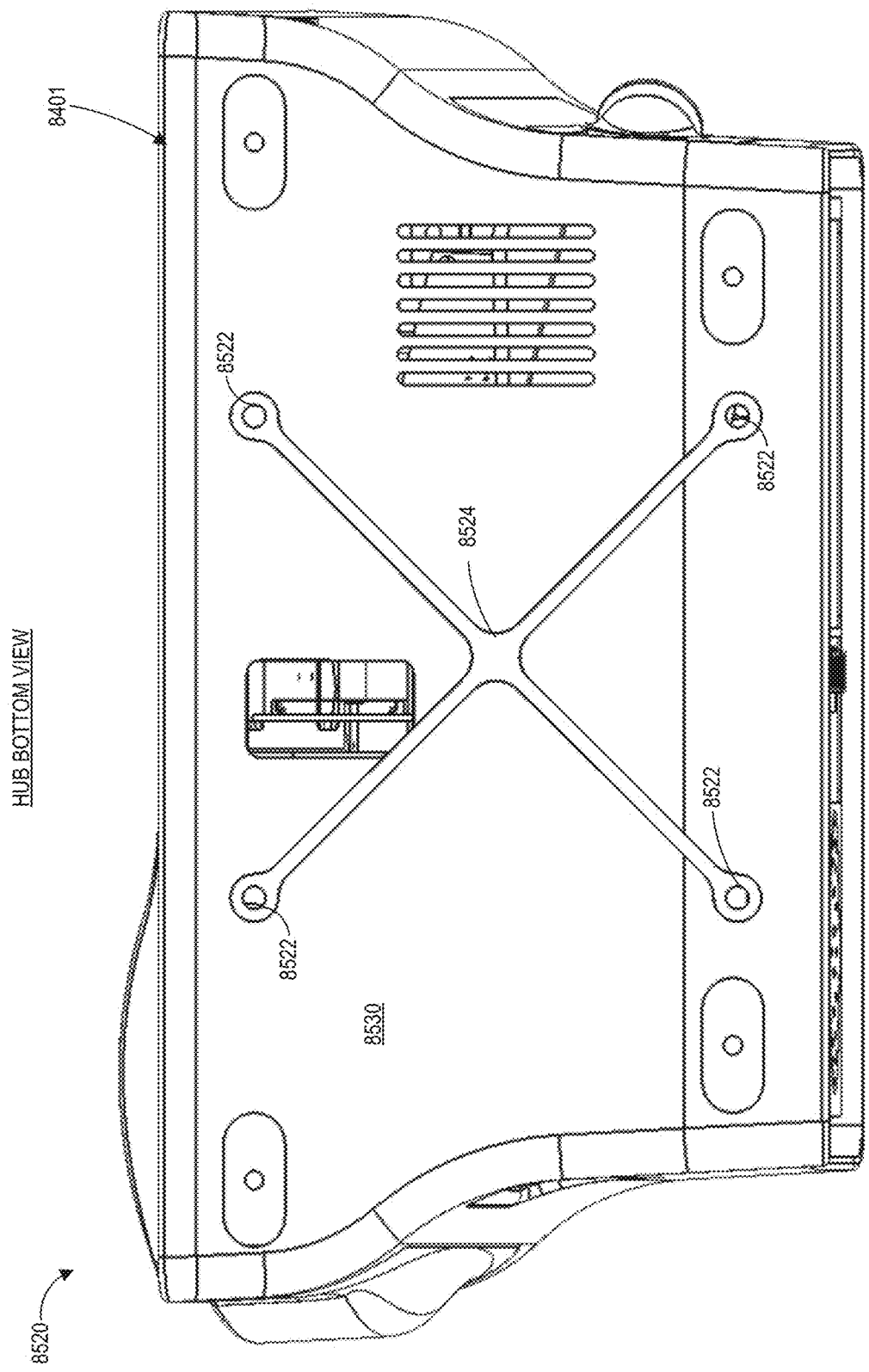
Figure 85C:
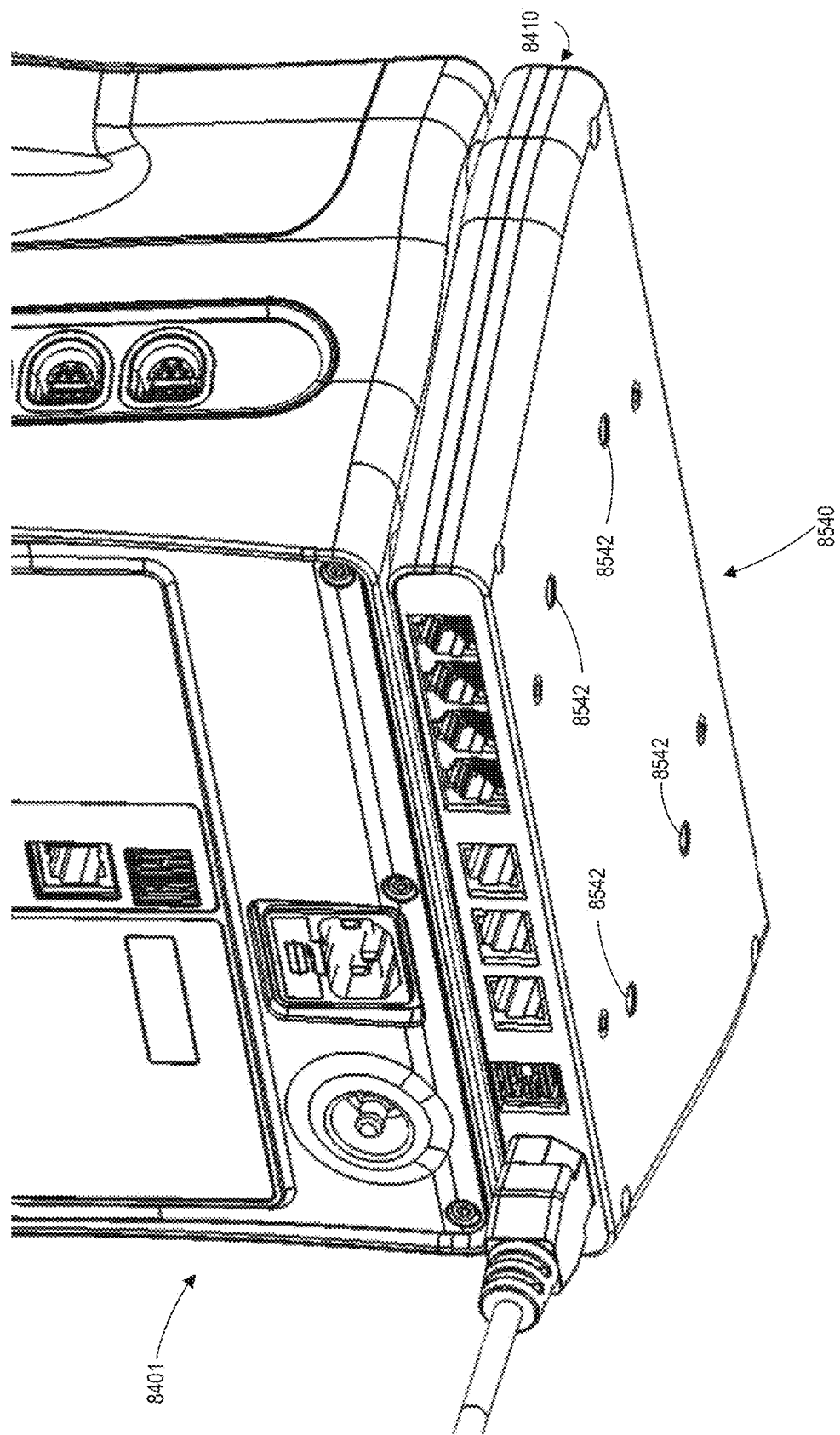

FIGS. 85A, 85B, and 85C illustrate example structures for mechanically mounting a medical network interface. FIG. 85A shows an example top housing 8510 of the medical network interface 8410. The top housing 8510 can include 4 holes for mounting to the hub 8401 or the physical structure. FIG. 85B shows a bottom view 8520 of the hub 8401. The bottom surface 8530 can include a connecting plate 8524. The connecting plate 8424 includes 4 slots 8522 as illustrated in FIG. 85B. The connecting plate 8424 can be a VESA Standard 75/100 connecting plate which can be equipped with a 100×100 mm or 75×75 mm square hole pattern. The connecting plate 8524 in FIG. 85B shows an 100×100 mm square hole pattern, even though in other examples, the connecting plate 8524 can have a 75×75 mm square hole pattern or a combination of 75×75 mm and 100×100 mm square hole pattern (where the connecting plates 8524 has eight slots 8522). Other configurations are also possible.

The top housing 8510 of the medical network interface 8410 can be mounted to the bottom of the hub 8410 using screws. For example, four M4 screws may be used to attach the slots 8522 of the connecting plate 8524 to the holes 8512 on the top housing 8510.

Although in this example, the connecting plate 8524 is located on the bottom surface of the hub 8401, the connecting plate 8524 is not required to be on the hub 8401. For example, the connecting plate 8524 may be located on the medical network interface 8410 while the bottom surface of the hub 8401 may include 4 holes for attaching the medical network interface 8410.

FIG. 85C illustrates a bottom perspective view of the medical network interface 8410 after the medical network interface 8410 is mounted to the hub 8401. The bottom surface 8540 can include holes 8542. The holes 8542 may also follow the a 100×100 mm or 75×75 mm square hole pattern. The medical network interface 8410 may be mounted to a wall using a wall mount. For example, one end of the wall mount may be fixedly attached to the wall while the other end of the wall mount may include a connecting plate which has the same hole pattern as that of the holes 8542. Accordingly, the medical network interface 8410 can be attached to the wall mount by attaching the wall mount with bottom surface 8540 using screws.

Although a VESA mount is used as an example in FIGS. 85A-85C, other types of mounting interfaces may also be used on the top housing 8510 of the medical network interface 8410, the bottom surface 8540 of the hub 8401, or the bottom surface 8540 of the of the medical network interface 8410. For example, the hole pattern may also reflect a universal mount. As another example, the medical network interface 8410 and the hub 8401 can be mounted using a GCX® slide-in mount. Further, the top surface and the bottom surface of the medical network interface 8410 do not have to have the same hole pattern. For example, the bottom surface of the medical network interface 8410 may have a hole pattern for a universal mount (which can facilitate wall mounting) while the top surface of the medical network interface 8410 may have a VESA mount. As another example, where the medical network interface 8410 can be mounted on one side, the medical network interface 8410 does not have to have holes on both the top surface and the bottom surface. In one embodiment, the holes are located on the top surface of the medical network interface 8410. While the top surface is mounted to the hub 8401, the bottom surface may sit on a tabletop. The medical network interface 8410 can also be mounted to the wall (for example, via the top surface) by itself, without the hub 8401 being attached to the bottom surface.

The medical network interface 8410 is not required to be mounted to the hub 8401 in the same fashion as illustrated in FIGS. 85A-85C. The medical network interface 8410 can be mounted to the left side, right side, or back side using the techniques described herein. For example, the back side of the hub 8401 may include a connecting plate for mounting the medical network interface 8410 using a VESA standard. Furthermore, it is not required that the medical network interface 8410 attaches to the hub 8401 using the top surface of the medical network interface 8410. For example, the bottom surface, left surface, or the right surface can also be used to mount the medical network interface 8410 to the hub 8401.

In addition to or in alternative to mounting to the hub 8401, similar techniques can also be used to mount the medical network interface 8410 with other medical devices, such as patient devices 7720, devices 7760, or other devices illustrated in the computing environments 7700 and 7702. For example, the medical network interface 8410 may be mounted to patient bed using the techniques described herein.

XVI. Example Mechanical Structures of a Wireless Connector and a Dongle Socket

As described herein, the medical network interface 8410 can be communicatively coupled to various devices and systems, such as the hub 8401, MMS 2004, patient devices 7720, or another medical network interface 8410 using wired or wireless connections. The medical network interfaces 8410 can include interface ports 8412 configured to receive a wireless connector 8480. Wireless connector 8480 can be used to pair the medical network interface 8410 with another device to achieve communications wirelessly. Interface ports 8412 may be a proprietary port, a USB port, or another type of port as described with reference to FIG. 84A.

Figure 86A:
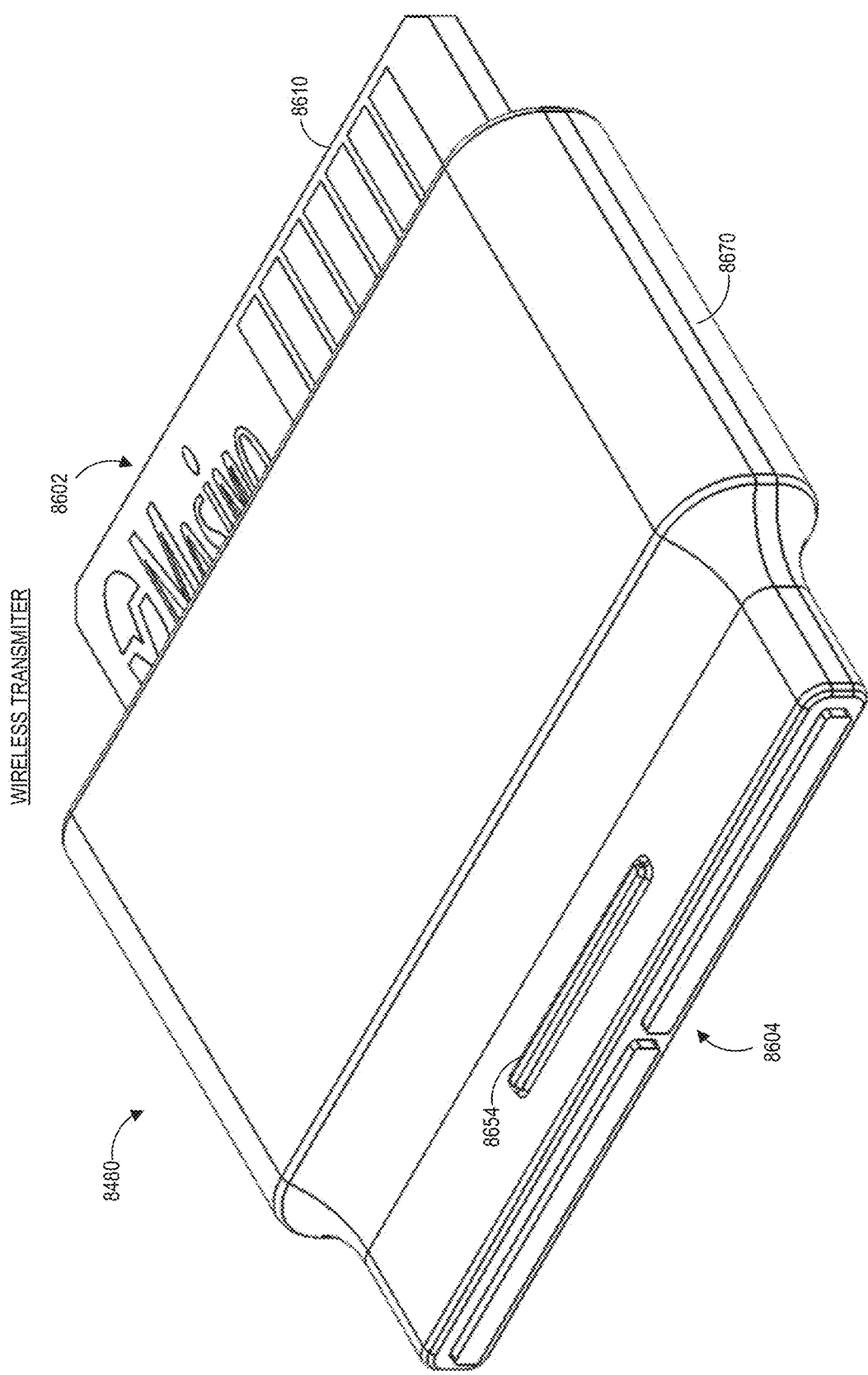
FIGS. 86A and 86B illustrate an example of hardware components of a wireless connector.
Figure 86B:
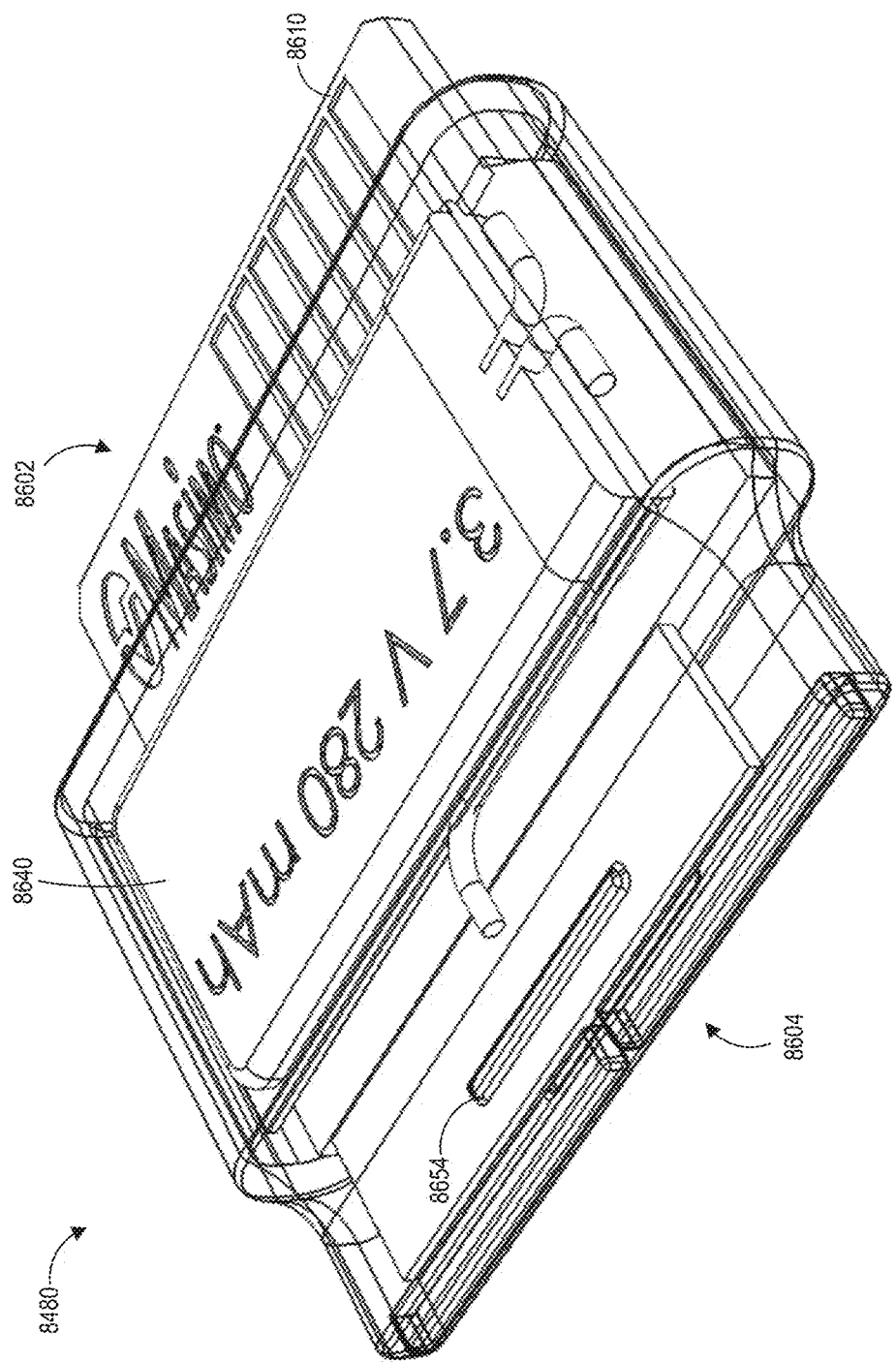

The wireless connector 8480 can include various software and hardware components to achieve the functionalities described above, for example, with reference to FIGS. 77A-83. FIGS. 86A and 86B illustrate an example embodiment of hardware components of a wireless connector. The wireless connector 8480 can be an embodiment of the dongle 7900 described in FIG. 79. The dongle 8480 in FIG. 86A can include a housing 8670, a data storage and processing component 8610, optionally one or more lights 8654 (for example, elongate light-emitting diodes (LEDs)).

The housing 8670 can include various hardware components inside. For example, a portion of the data storage and processing component 8610 and a battery 8640 are positioned inside the housing 8670 as shown in FIG. 86B. The battery may be a 3.7V, 280 mAh battery although other specifications are also possible. In some embodiments, there are two batteries 8640 inside the housing 8670. As an example, one battery may be positioned on top of the data storage and processing component 8620 while the other battery may be positioned underneath the data storage and processing component 8620. The battery 8640 may be charged when the wireless connector 8480 is plugged into the medical network interface 8410 (for example via an interface port 8412) as described in FIG. 79 or when the wireless connector is plugged into a standalone patient device 7720 as described with reference to FIGS. 87A-88.

The data storage and processing component 8610 can include the processing unit 7910. Accordingly, the data storage and processing components 8610 can perform functions, such as pairing, data receiving and transmission, and various other functions as described in FIGS. 77A-83. Where the wireless connector 8480 includes a battery 8640, the data storage and processing component 8610 can also include the antenna 7920 in addition to the processing unit 7910. The antenna 7920 can be located inside the housing 8670.

The light 8654 can be an embodiment of the light component 7954 shown in FIG. 79. The light 8654 can include a strip of LEDs or an elongated LED. As described in FIG. 79, the light pattern illuminated by the light 8654 can indicate a status of the wireless connector 8480. The status may include a connection status (for example, whether a medical device is paired with the medical network interface 8410), handshake status (which can be part of connection status), or a battery status, among other options. As an example of indicating the battery status, the light 8654 may illuminate a green light when the battery is full while illuminating an amber light when the battery is about to die. Multiple lights may be provided, such as one to indicate battery charge status and one to indicate connection status, data transfer status, or the like.

Although not illustrated in FIGS. 86A and 86B, the housing 8670 can also include other components inside. For example, the housing 8670 can also house the location tag 7930, which can facilitate another device (such as the hub 8401) to determine the location of the wireless connector 8480.

The wireless connector 8480 can have a back side 8602 and a front side 8604. The front side 8604 can include the light 8654. The back side 8602 can be plugged into the interface ports 8412 to establish a communication between the wireless connector 8480 and the medical network interface 8410. The back side 8602 can also be plugged into a port in a medical device 8110 so that the medical device 8110 can communicate with the medical network interface 8410 wirelessly.

In some situations, the medical device 8110 may not have an appropriate port (for example, an interface port or an USB port) for the wireless connector 8480 to be plugged in. To enable wireless communications via the wireless connector 8480, advantageously, in some embodiments, a dongle socket can include a medical connector to connect to a port on the medical device 8110. The dongle socket can include the wireless connector 8480 and thereby allowing the wireless connector 8480 to be connected to the medical device via the medical connector.

Figure 87A:
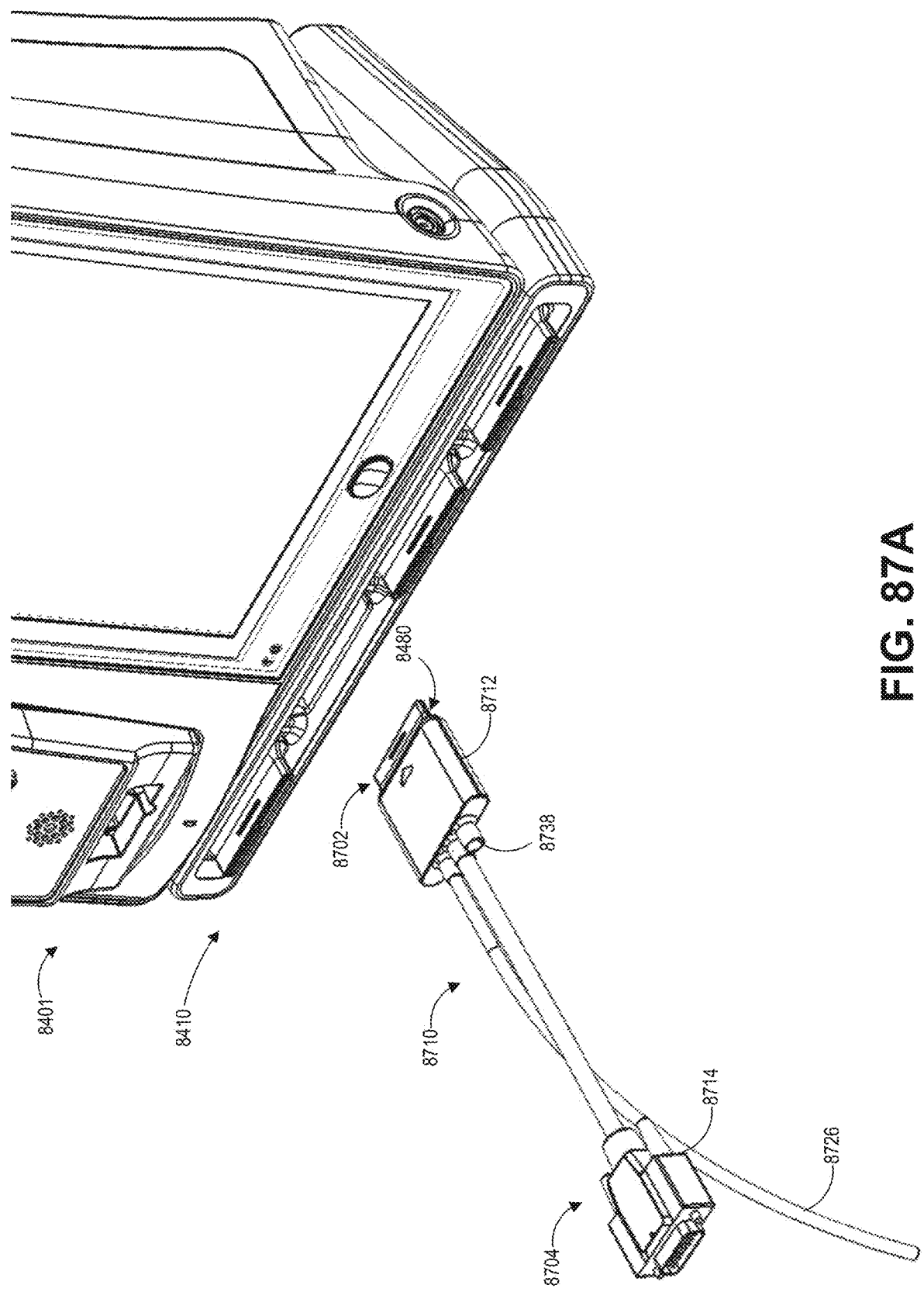
FIGS. 87A-87D illustrate an example of a dongle socket which can connect a medical device with a medical network interface via a wireless connector.

FIGS. 87A-87D illustrate an example embodiment of a dongle socket which can connect a medical device with a wireless connector. The dongle socket can be referred to as a dongle in examples described with reference to FIGS. 87A-88. FIG. 87A shows a medical network interface 8410 which is mounted to the hub 8401 and a dongle 8710 which can be connected to a medical device 8110, such as a pump or vent (see, for example, FIG. 81).

The dongle 8710 can include a front end 8702 and a back end 8704. The front end 8702 can include a socket housing 8712 which can house a wireless connector 8480.

The wireless connector 8480 may be previously plugged into the medical network interface 8410 for charging or acquisition of a permission key. The socket housing 8712 can be connected to a medical device connector 8714 located at the back end 8704 of the dongle 8710 via the wire 8724. The medical device connector 8714 can be plugged into a port of a medical device 8110. The port of the medical device 8110 can be a Video Graphics Array (VGA) port, a Digital Visual Interface (DVI) port, a High-Definition Multimedia Interface (HDMI) port, a USB port, an Ethernet port, a proprietary port, or other types of ports that are configured for electronic data transmission. Advantageously, in some embodiments, by connecting the wireless connector 8480 to the port of the medical device 8110 via the dongle 8710, the medical device 8110 can be paired with the medical network interface 8410 and wirelessly communicate data to the medical network interface 8410.

Additionally or alternatively, the pairing between the medical device 8110 and the medical network interface 8410 can be achieved by bringing the dongle 8710 close to the medical network interface 8410. The medical network interface 8410 can automatically scan for nearby devices and identify the dongle 8710 when the dongle 8710 is within range of the medical network interface 8410. A separate wireless connector 8480 may be omitted in this embodiment, such that the functionality of the wireless connector 8480 is integrated in the dongle 8710. Alternatively, the dongle 8710 can include a detachable wireless connector 8480. The back end 8704 of the dongle 8710 can be plugged into the medical device 8110. Once the wireless connector 8480 (integrated or separable) in the dongle 8710 is recognized, the medical network interface 8410 can assign and establish a connection for the medical device 8110 (via the wireless connector 8480). Advantageously, in some embodiments, by integrating the functionality of the wireless connector 8480 with the dongle 8710 (for example, by including a transceiver and battery integrated with the dongle 8710), the dongle 8710 can be paired simply by bringing the dongle 8710 within wireless range of the medical network interface 8410.

In certain embodiments, the wireless connector 8480 does not have a battery, and the medical device 8110 can supply power to the wireless connector 8480 via the dongle 8710. For example, the medical device 8110 may be plugged into a power outlet and direct the power to the dongle 8710 via the medical device connector 8714.

The wireless connector 8480 or the dongle 8710 can also be charged wirelessly, thereby reducing the need to be physically plugged into the medical device 8110 or the medical network interface 8410. The wireless charging capabilities can be enabled by any one of the medical device 8110, the medical network interface 8410, or the hub 8401. The medical device 8110, the medical network interface 8410, or the hub 8401 can include a transmitter that can be energized by alternating current to generate a magnetic field, which can in turn induce a current in a receiver in the wireless connector 8480 or the dongle 8710 to wirelessly charge the wireless connector 8480.

In some situations, the dongle 8710 may connect to a port on the medical device 8110 which is not configured for supplying power. As a result, the dongle 8710 can include a power cable 8726 for charging the wireless connector 8480 while the dongle 8710 is connected to the port on the medical device 8110. The power cable 8726 can be connected to the socket housing 8712 on one end and be connected to a power source on the other end. The power source may be obtained from another port on the medical device 8110 or from a wall socket, for example. The power cable 8726 can be implemented using various types of cables, such as a coaxial cable, ribbon cable, twisted pair cable, or shielded cable. In some embodiments, the power cable 8726 may be a USB cable. In addition to or in alternative to the power cable 8726 and the medical device connector 8714, the dongle can also include other types of cables. In other embodiments, these cables may be connected to the front end 8702 of the dongle 8710 via the socket 8738. The power cable 8726 can be useful for connecting with older devices that use RS232 (e.g., to connect to the port 8714), which does not typically have power. For devices that have a USB connection or other powered connection, the port 8714 can be a USB port, and the power cable 8726 can be omitted.

Where the wireless connector 8480 can be charged via the cable 8726 of the dongle 8710 or via the medical device 8110, the hub 8401 may not need to provide the capabilities for receiving or charging the wireless connector 8480. For example, a wafer underneath the hub 8410 may not have a slot for charging.

Although the example in FIG. 87A is described with reference to connecting the wireless connector 8480 to the medical device 8110 via the dongle 8710, the wireless connector 8480 can be connected directly to the medical device 8110 where the medical device 8110 has available interface port 8412.

Figure 87B:
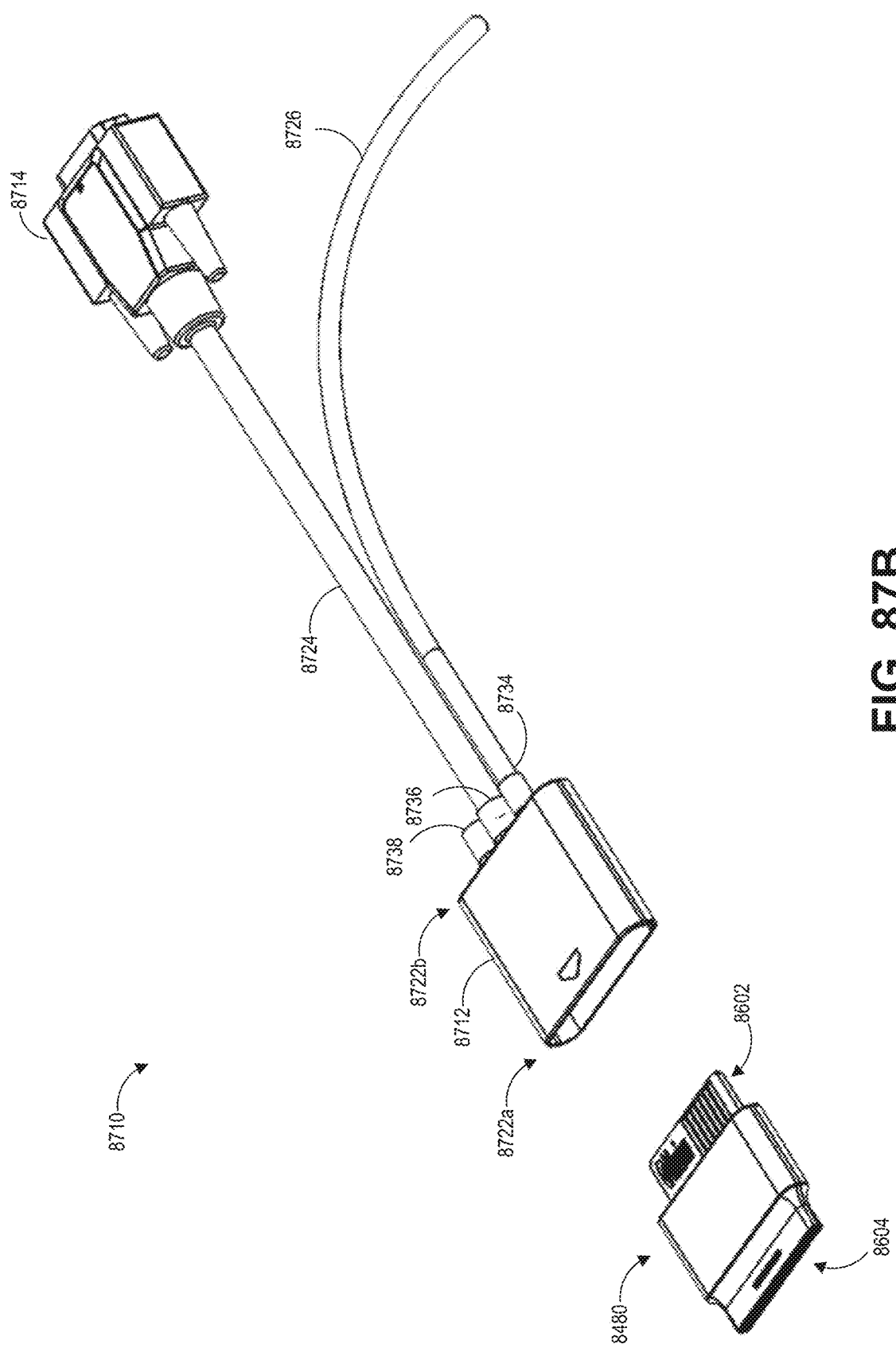

FIG. 87B illustrates example components of a dongle 8710. The dongle 8710 can include a socket housing 8712, a medical device connector 8714, a wire 8724 (for connecting the medical device connector 8714 to the housing 8712), and a power cable 8726. The socket housing 8712 can have a front end 8722a and a back end 8722b. The front end 8722a can include an opening generally shaped to receive the wireless connector 8480. Although not shown, inside the socket housing 8712 may be a connector that receives the connector on the wireless connector 8480. The back end 8722b can have three sockets 8734, 8736, and 8738 attached. The three sockets 8734, 8736, and 8738 can be attached to other cables for connection with another device or a power source. For example, the socket 8734 can connect to the power cable 8726, the socket 8736 can connect to the medical device connector 8714 via the wire 8724, and the socket 8738 can connect to a third cable.

The back end 8722 of the socket housing can include circuitry for interfacing the wireless connector 8480 and the various cables attached to the three sockets 8734, 8736, and 8738. For example, the back end 8722b can include an interface port 8412 inside the housing 8712 for receiving the wireless connector 8480. In some embodiments, the interface port 8412 is attached to the three sockets 8734.

A portion of the wireless connector 8480 can be inserted into the socket housing 8712 through the front end 8722a of the socket housing 8712. The wireless connector 8480 can include a front side 8604 and a back side 8602 as illustrated in FIGS. 86A and 86B. The back side 8602 of the wireless connector 8480 can be inserted through the front end 8722a of the socket housing 8712. A portion of the wireless connector 8480 can protrude from the socket housing 8712 to facilitate unimpeded wireless communication with the medical network interface 8410, as well as to enable a user to more easily insert and remove the wireless connector 8480 from the socket housing 8712. However, protrusion of the wireless connector 8480 from the socket housing 8712 is not necessary, and the wireless connector 8480 may be flush with the socket housing 8712 in other embodiments.

Figure 87C:
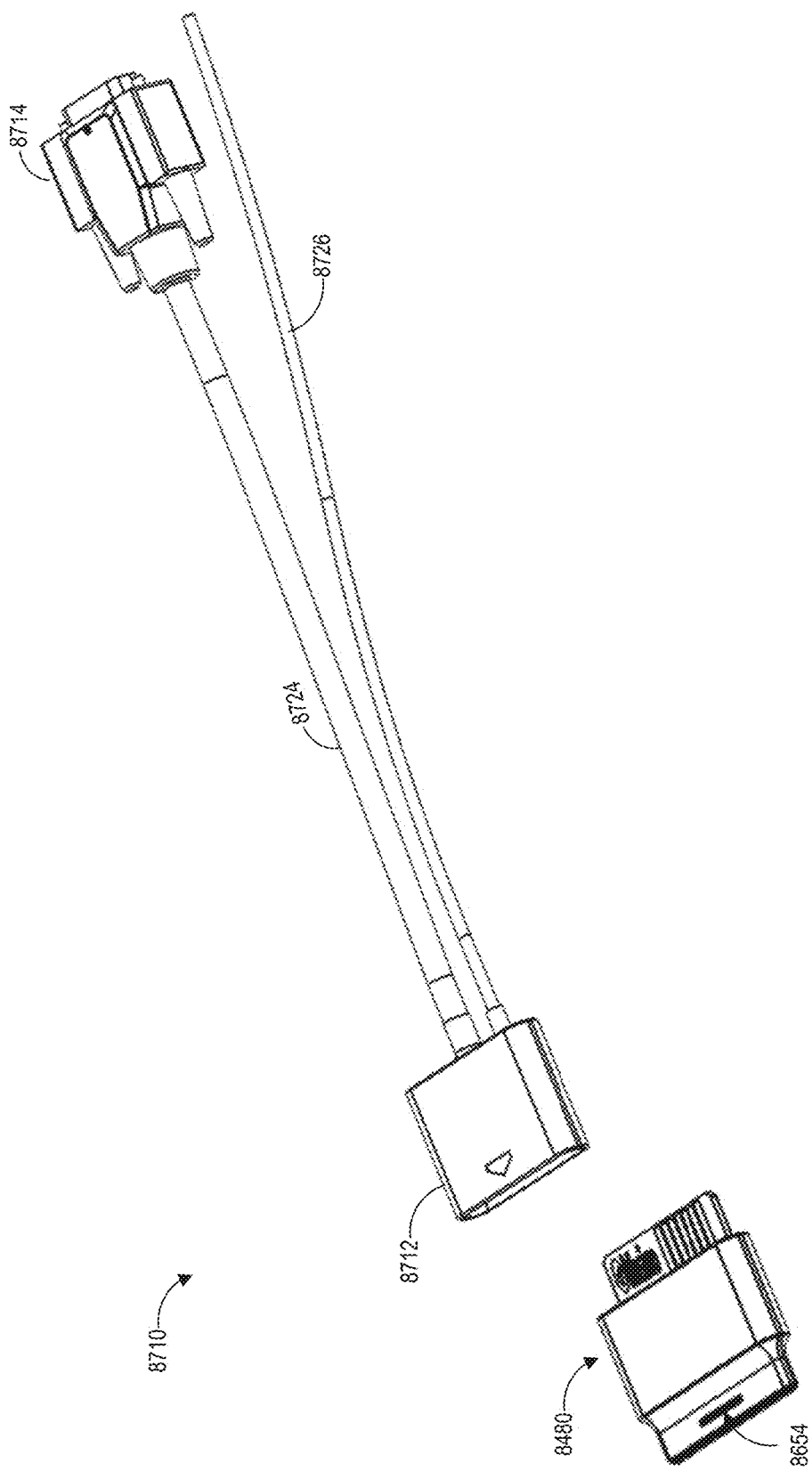

FIG. 87C illustrates another example of the dongle 8710. Similar to FIG. 87B, the dongle 8710 can include a socket housing 8712, a medical device connector 8714, and a power cable 8726. The medical device connector 8714 can be connected to the housing 8712 via the wire 8724. The power cable can connect the housing 8712 with a power outlet (for example, an AC wall outlet) to provide power to the wireless connector 8480. The wireless connector 8480 can be removably or fixedly inserted into the socket housing 8712. The socket housing 8712 can include circuitry for interfacing the wireless connector 8480 and the medical device connector 8714 and the power cable 8726, and 8738 as described with reference to FIG. 87B. In contrast to FIG. 87B, the example dongle 8710 in FIG. 87C does not have the socket 8738.

In certain implementations, the wireless connector 8480 may not have a battery. Instead, the wireless connector 8480 may be powered via the power cord 8726. The wireless connector 8480 can also be powered by the device to which it is connected in some situations, where the wireless connector 8480 is connected to a port which has power charging capacities.

As described with reference to FIG. 86A, the dongle 8480 can include a light component 8654 which can illuminate with various light patterns or colors to provide an indication associated with the wireless connector 8480 or the device connected to the wireless connector 8480. The light component 8654 can provide information on which device is connected to the wireless connector. For example, the light component 8654 may illuminate in one color when it is connected to the hub 8401 and illuminate in a different color when connected to a medical device for monitoring a patient's parameters. The light component 8654 can also indicate the power status of the wireless connector 8480. For example, when the wireless connector is connected to an AC outlet (for example, via the power cable 8726), the light component 8654 may illuminate a steady green light. When the wireless connector is on battery power, the light component 8654 may indicate the amount of the battery power remaining by illuminating one or more LEDs of the light component 8654 while not illuminate other LEDs. As another example, the light component 8654 may not illuminate when it is not connected to a power source.

Figure 87D:
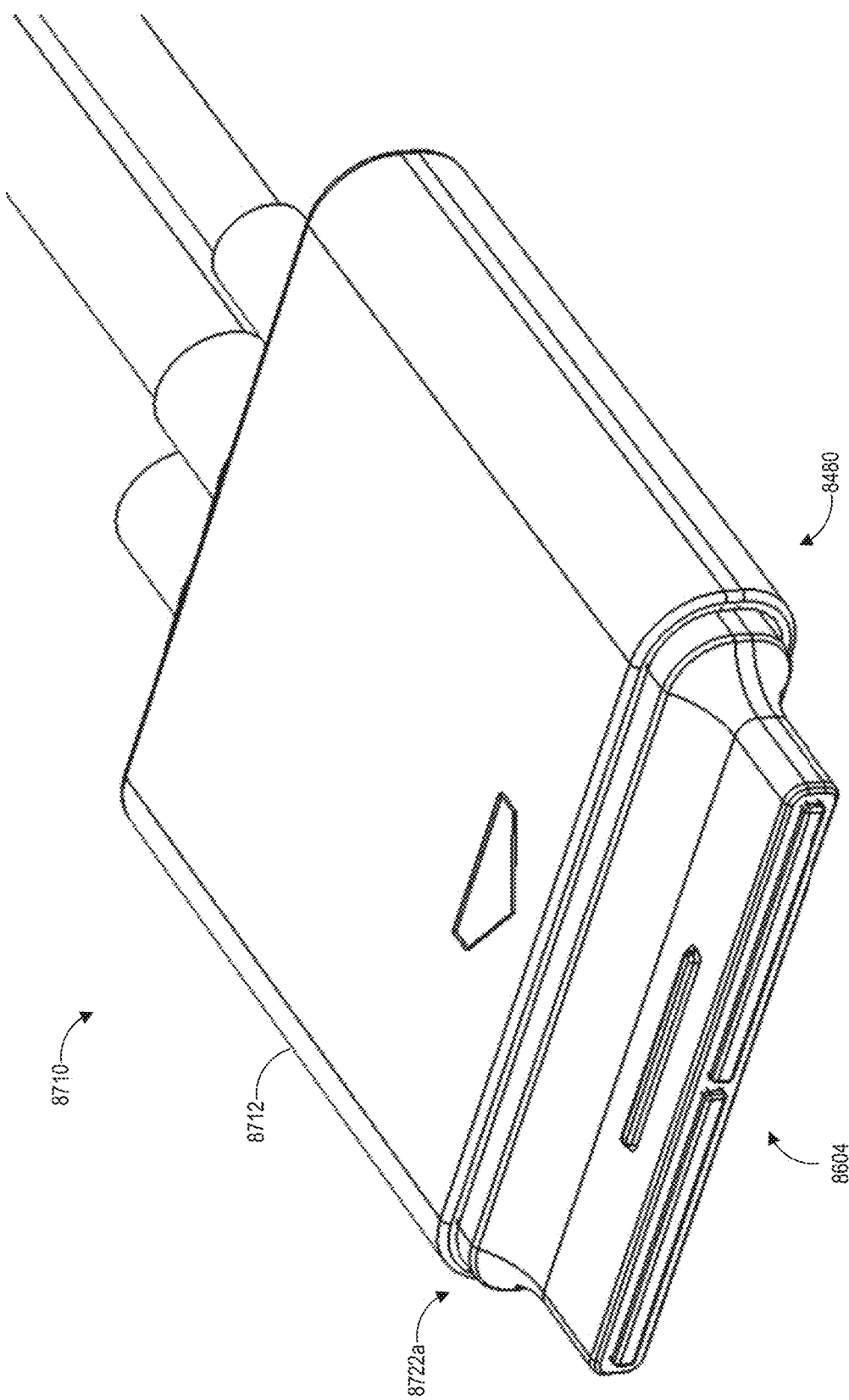

FIG. 87D illustrates an example where the wireless connector 8480 is inserted into the housing 8712. As illustrated, the front side 8604 of the wireless connector is protruding out of the front end of the socket housing 8712.

The wireless connector 8480 can be removed from the socket housing 8712 and replugged into a medical network interface 8410 or removed from the medical network interface 8410 and inserted into the socket housing 8712. For example, in some situations, the dongle 8710 may not have a power cable. As a result, when the wireless connector 8480 in the dongle 8710 is low on battery, a physician can remove the wireless connector 8480 from the socket housing 8712 and insert the wireless connector 8480 into the medical network interface 8410 for charging. As another example, a wireless connector 8480 may be removed from the medical network interface 8410 and plugged into the dongle housing 8712 to establish a wireless connection between a medical device 8110 (in which the dongle 8710 is plugged) and the medical network interface 8410.

Figure 88:
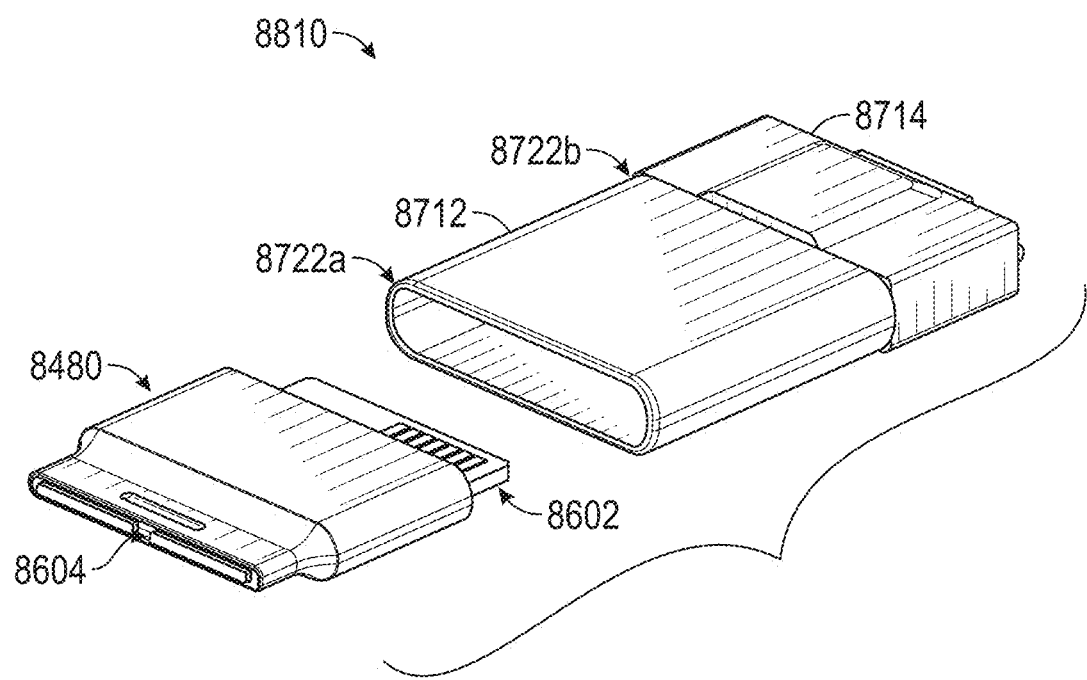
FIGS. 88 and 89 illustrate additional examples of a wireless connector and a dongle socket.

FIG. 88 illustrates another example embodiment of a wireless connector and a dongle. The example dongle 8810 can include a socket housing 8712. The socket housing 8712 can be configured to receive a medical device connector 8714 at the back end 8722b of the socket housing 8712. The socket housing 8712 can have an opening in the front end 8722a for receiving a wireless connector 8480. Although in other embodiments (such as the examples in FIGS. 87A-87D), the dongle 8810 can include a power cable for supplying directing power to the wireless connector 8480, in the example illustrated in FIG. 88, the dongle 8810 does not include a power cable. In some situations, the medical device connector 8714 can be configured to receive power from the medical device 8110 and supply the power to the wireless connector 8810. Thus, a separate power cable is not needed on the dongle 8810. In addition to or in alternative to receiving power from the medical device 8110, the wireless connector 8480 can also consume its battery power when plugged into the dongle 8810. In one embodiment, wireless connectors can be hot-swapped between the medical device 8110 and the medical network interface 8410. For example, once a first wireless connector connected to the medical device 8110 is out of battery or close to out of battery, it can be removed by a user and placed into the medical network interface 8410 for charging, while a second, charged wireless connector can be removed out of the interface 8410 and inserted into the medical device 8110 in place of the first wireless connector.

The socket housing 8712 can include circuitry for interfacing the wireless connector 8480 and the medical device connector 8714. For example, the socket housing 8712 may include an adapter which can have an interface port facing the front end 8722a for receiving the back end 8602 of the wireless connector 8480 and have another port for facing the back end 8722b for receiving the medical device connector 8714.

The medical device connector 8714 and the dongle 8710 in FIGS. 87A-88 can be modular for different medical devices. The medical device connector 8714 on the back end 8704 of the dongle 8710 can be swapped based on the type of medical device that the dongle 8710 is connected to. For example, the dongle 8710 can be removed from one medical device and plugged it into another medical device which has a different port than the previous medical device. The physician can change the medical device connector 8714 on the back end 8704 of the dongle 8710 to be compatible with the medical device that the dongle 8710 will be plugged into.

Although in the examples in FIGS. 87A-88, the wireless connector 8480 can be inserted into the housing 8712 to connect to the medical device connector 8714, in some embodiments, the wireless connector 8714 can connect directly with the medical device connector 8714. For example, the medical device connector 8714 can have an interface port 8412 on one end for receiving the wireless connector 8480 while can connect to a medical device 8110 on the other end. Further, in some embodiments, the wireless connector can include a medical device connector 8714 at the front end 8604. The wireless connector can connect to the medical network interface 8410 using the back end 8602 while connecting to the medical device 8110 using the front end 8604. The medical device 8110 can obtain a permission key or other information for achieving wireless communications through the medical device connector 8714 at the front end 8604 of the wireless connector 8480. Although the dongle 8810 of FIG. 88 does not show a power cable, one like the prior dongles described may be included. However, by eliminating the cable 8724 in the embodiment of FIG. 88, the dongle 8810 may be tidier and less prong to hang down when plugged in.

Figure 89:
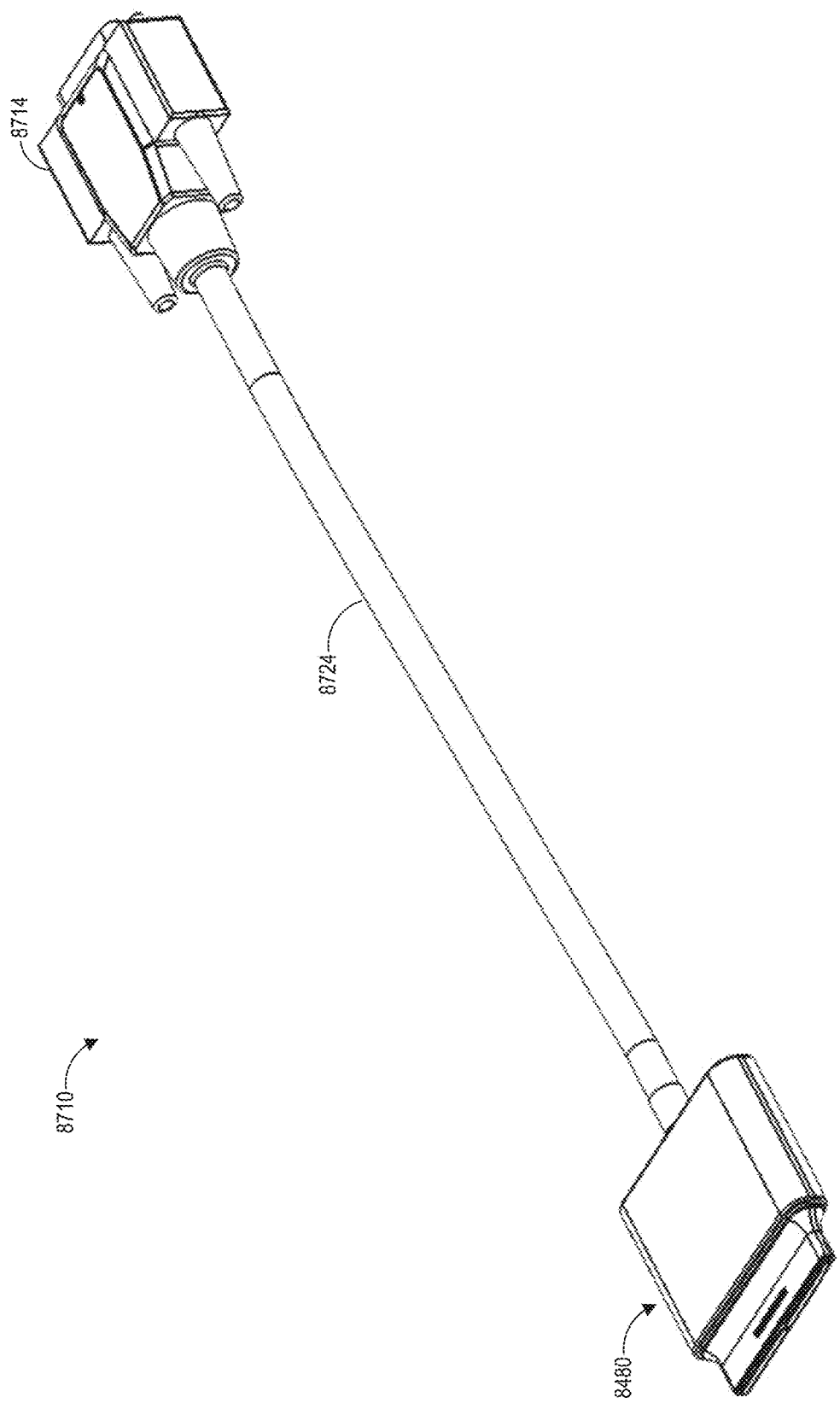

FIG. 89 illustrates another example of the dongle 8710. In this example, the wireless connector is in the socket housing 8712, which is connected to a medical device connector 8714 via the wire 8724. In this example, one end of the dongle 8710 can be plugged into a medical device whereas the other end can be plugged into the hub 100 (or the medical network interface 8410) to transfer patient data from the medical device to the hub 100. For example, the wireless connector may be plugged into the hub 100 (or the medical network interface 8410) whereas the medical device connector 8714 may be plugged into the medical device.

In this example, the medical device connector 8714 may not be able to supply power to the wireless connector 8480. As a result, the wireless connector 8480 may be powered by its battery.

XVII. Additional Aspects

In a first aspect, a medical network interface operable to provide network connectivity for a standalone medical device not natively in communication with a hospital network, the medical network interface comprising: a plurality of ports, at least one of which is configured to receive a wireless dongle; a network interface controller configured to implement a wireless communications stack; a memory configured to store processor-executable instructions; and a processor programmed to execute the instructions to: supply the wireless dongle with information sufficient to enable the wireless dongle to provide wireless connectivity to the standalone medical device; wirelessly pair with the standalone medical device in response to receiving a pairing request signal from the medical device, which occurs in response to the wireless dongle being inserted into the standalone medical device; subsequent to the pairing, wirelessly receive a data stream from the standalone medical device, the data stream comprising an identifier of the medical device and patient data associated with a patient; associate with the data stream, an identifier of the patient and an identifier of the medical network interface, to produce a modified data stream; and transmit the modified data stream across a hospital network to enable the modified data stream to be accessed by a clinician.

In a 2nd aspect, the medical network interface aspect 1, wherein the plurality of ports comprise two or more of the following: a Universal Serial Bus port, an Ethernet port, and a serial port with patient isolation hardware.

In a 3rd aspect, the medical network interface of aspect 1 or 2, wherein the processor is further configured to receive an optical scan of a patient wristband to thereby obtain the patient identifier.

In a 4th aspect, the medical network interface of any one of aspects 1-3, wherein the processor is further programmed to: generate a permission key for pairing the standalone medical device with the medical network interface; communicate the permission key to the first medical device; receive a communication from the first medical device having the permission key; and establish a communication with the first medical device in response to a determination that the permission key is authenticated.

In a 5th aspect, the medical network interface of aspect 4, wherein the permission key is set to expire after a threshold period of time.

In a 6th aspect, the medical network interface of any one of aspects 4-5, wherein in response to the determination that the permission key is authenticated, the processor is further programmed to link the patient identifier and the medical network interface identifier to the standalone medical device identifier.

In a 7th aspect, the medical network interface of any one of aspects 1-6, further comprising a display on the dongle or the medical network interface, the display configured to indicate at least one of: a status of the medical network interface, a status of the first medical device, a status of the second medical device, or a status of a pairing between the first medical device and the second medical device.

In an 8th aspect, the medical network interface of any one of aspects 1-7, further comprising a light on the dongle or the medical network interface, the light configured to indicate at least one of: a status of the medical network interface, a status of the first medical device, a status of the second medical device, a status of a pairing between the first medical device and the second medical device, or a power status associated with the dongle.

In a 9th aspect, the medical network interface of any one of aspects 1-8, wherein the plurality of ports comprise first ports of a first color and second ports of a second color.

In a 10th aspect, the medical network interface of any one of aspects 1-9, wherein data received from the first ports is automatically associated with the patient identifier and wherein data received from the second ports is automatically associated with a second patient identifier of a second patient.

In an 11th aspect, the medical network interface of any one of aspects 1-10, wherein the wireless dongle comprises two pieces.

In a 12th aspect, the medical network interface of aspect 11, wherein the two pieces comprise a first piece that stays connected to the medical network interface, and a second piece that disconnects from the first piece.

In a 13th aspect, the medical network interface of aspect 12, wherein the second piece connects in a corresponding first piece of a second dongle in the standalone medical device.

In a 14th aspect, the medical network interface of any one of aspects 1-13, wherein the processor is further programmed to: access a first identifier for pairing the standalone medical device with the medical network interface; communicate the first identifier to the first medical device; receive a communication from the first medical device having the first identifier; and establish a communication with the first medical device in response to a determination that the first identifier is authenticated.

In a 15th aspect, the medical network interface of any one of aspects 1-14, wherein the medical network interface comprises a front side and a back side, and wherein the front side comprises an interface port configured to receive the wireless dongle.

In a 16th aspect, a method for providing network connectivity for a standalone medical device not natively in communication with a hospital network, the method comprising: receiving insertion of a wireless dongle in a port of a medical network interface; in response to said insertion, supplying the wireless dongle with an identifier to enable the wireless dongle to communicate the identifier to the standalone medical device upon insertion into the standalone medical device; subsequent to removal of the wireless dongle from the port of the medical network interface, receiving, with a hardware processor, a pairing request signal from the standalone medical device, the pairing request signal comprising the identifier previously supplied to the wireless dongle; and subsequent to the pairing, supplying one or both of a visual or audible indication that the pairing has been successful, wirelessly receiving a data stream from the standalone medical device, the data stream comprising patient data associated with a patient, and associating with the data stream, an identifier of the patient and an identifier of the medical network interface, to produce a modified data stream; and transmitting the modified data stream across a hospital network to a server so as to enable distribution of the modified data stream to a plurality of devices from the server.

In a 17th aspect, the method of aspect 16, wherein said supplying comprises actuating a light.

In an 18th aspect, the method of aspect 16 or 17, wherein said supplying comprises outputting information on a display, and optionally wherein the information comprises the identifier of the standalone medical device.

In a 19th aspect, the method of any of aspects 16-18, wherein said pairing request is a modified Bluetooth pairing request that does not require input of a pin or other number or password in either the medical network device or the standalone medical device.

In a 20th aspect, the method of any of aspects 16-19, further comprising associating with the data stream an identifier of the standalone medical device.

In a 21st aspect, the method of any of aspects 16-20, further comprising obtaining the patient identifier from an optical scan of a wrist bracelet on the patient.

In a 22nd aspect, a wireless adapter for a standalone medical device, the wireless adapter comprising: a dongle comprising a socket housing configured to receive and electrically connect with a wireless dongle, and a medical device connector configured to: electrically connect with a standalone medical device; receive patient data from the standalone medical device; and pass the patient data to the wireless dongle to enable the wireless dongle to wirelessly transmit the patient data; and a power cable electrically connected to the dongle, the power cable configured to receive power and to supply the power to the wireless dongle when the wireless dongle is coupled with the socket housing.

In a 23rd aspect, the wireless adapter of aspect 22, wherein the dongle further comprises a data cable extending between the socket housing and the medical device connector, the data cable configured to pass the patient data from the medical device connector to the socket housing.

In a 24th aspect, the wireless adapter of aspect 22 or 23, further comprising the wireless dongle.

In a 25th aspect, the wireless adapter of aspect 24, wherein the wireless dongle comprises data storage, a processing unit, and a battery.

In a 26th aspect, the wireless adapter of aspect 25, wherein the wireless dongle further comprises an elongate light indicative of battery level or a power status.

In a 27th aspect, the wireless adapter of aspect 26, wherein the wireless dongle further comprises an elongate light indicative of connection status.

In a 28th aspect, a pulse oximetry system operable to measure a blood parameter of a patient and transmit the blood parameter together with third party medical device parameters to a remote device, the system comprising: a patient monitor configured to measure the blood parameter of the patient by obtaining a signal from an optical sensor coupled to the patient, wherein the signal corresponds to light attenuated by body tissue of the patient; and the patient monitor configured to communicate with a medical network interface which transmits the measured blood parameter and third party medical device parameters from a third party medical device across a hospital network, the medical network interface comprising: a plurality of ports, at least one of which is configured to receive a wireless dongle; a network interface controller configured to implement a wireless communications stack; a memory configured to store processor-executable instructions; and a processor programmed to execute the instructions to: supply the wireless dongle with information sufficient to enable the wireless dongle to provide wireless connectivity to the third party medical device; wirelessly pair with the wireless dongle in response to receiving a pairing request signal from the third party medical device, which occurs in response to the wireless dongle being inserted into the third party medical device; subsequent to the pairing, wirelessly receive a data stream from the wireless dongle, the data stream comprising an identifier of the third party medical device and the third party medical device parameters associated with the patient; associate with the data stream, an identifier of the patient, an identifier of the medical network interface, and an identifier of the patient monitor to produce a modified data stream; and transmit the modified data stream, the measured blood parameter, and the third party medical device parameters across a hospital network to enable the modified data stream and the measured blood parameter to be accessed by a clinician. Some example third party medical device parameters may include parameters measured by the standalone patient devices 7720 (shown in FIG. 77A) or other sensors or devices configured to measure the patient's physiological data.

In a 29th aspect, the pulse oximetry system of aspect 28, wherein the plurality of ports comprise two or more of the following: a Universal Serial Bus port, an Ethernet port, and a serial port with patient isolation hardware.

In a 30th aspect, the pulse oximetry system of aspect 28 or 29, wherein the processor is further programmed to receive an optical scan of a patient wristband to thereby obtain the patient identifier.

In a 31st aspect, the pulse oximetry system of aspects 28-30, wherein the processor is further programmed to: generate a permission key for pairing the third party medical device with the medical network interface; communicate the permission key to the third party medical device; receive a communication from the third party medical device having the permission key; and establish a communication with the third party medical device in response to a determination that the permission key is authenticated.

In a 32nd aspect, the pulse oximetry system of aspect 31, wherein in response to the determination that the permission key is authenticated, the processor is further programmed to link the patient identifier and the medical network interface identifier to an identifier of the third party medical device.

In a 33rd aspect, the pulse oximetry system of aspects 28-32, wherein the wireless dongle or the medical network interface further comprises a display configured to indicate at least one of: a status of the medical network interface, a status of a first medical device, a status of a second medical device, or a status of a pairing between the first medical device and the second medical device.

In a 34th aspect, the pulse oximetry system of aspects 28-33, wherein the wireless dongle or the medical network interface further comprises a light configured to indicate at least one of: a status of the medical network interface, a status of the first medical device, a status of the second medical device, a status of a pairing between the first medical device and the second medical device, or a power status associated with the dongle.

In a 35th aspect, the pulse oximetry system of aspects 28-34, wherein the plurality of ports comprise first ports of a first color and second ports of a second color.

In a 36th aspect, the pulse oximetry system of aspects 28-35, wherein data received from the first ports is automatically associated with the patient identifier and wherein data received from the second ports is automatically associated with a second patient identifier of a second patient.

In a 37th aspect, the pulse oximetry system of aspects 28-36, wherein the wireless dongle comprises two pieces with a first piece that stays connected to the medical network interface, and a second piece that disconnects from the first piece.

In a 38th aspect, the pulse oximetry system of aspect 37, wherein the second piece connects in a corresponding first piece of a second dongle in the standalone medical device.

In a 39th aspect, the pulse oximetry system of aspects 28-38, wherein the processor is further programmed to: access a first identifier for pairing the third party medical device with the medical network interface; communicate the first identifier to the third party medical device; receive a communication from the third party medical device having the first identifier; and establish a communication with the third party medical device in response to a determination that the first identifier is authenticated.

In a 40th aspect, the pulse oximetry system of aspects 28-39, wherein the medical network interface comprises a front side and a back side, and wherein the front side comprises an interface port configured to receive the wireless dongle.

In a 41st aspect, the pulse oximetry system of aspect 40, wherein the wireless dongle being associated with a power cable extending between the socket housing and the medical device connector, the power cable configured to provide power supply to the wireless dongle.

In certain embodiments, the medical network interface can be implemented together with any of the features described in U.S. Provisional Application Nos. 62/463,452 and 62/463,297. For example, the medical network interface can be any of the modules or "bricks" described in U.S. Provisional Application No. 62/463,297, and may therefore be inserted into a monitoring device or any other medical device. U.S. Provisional Application No. 62/463,517 mentioned in the related applications section above is also hereby incorporated by reference in its entirety and is made a part of this specification, and any of the systems and methods described herein can be implemented together with any subset of the features described therein. For example, additional example user interfaces and systems for patient monitoring, including augmented reality monitoring, are disclosed in the U.S. Provisional Application No. 62/463,517.

Further, any subset the following features may be implemented together with the medical network interface:

The platform (for example, the medical network interface, hub 100, or the like) of the present disclosure may be highly configurable and capable of communicating with previously unknown medical systems. The connectable medical systems can be a simple dongle (for example, different from the dongle described above; see for example, in U.S. Provisional Application No. 62/463,452) with a built in processor providing specialized software processing capabilities that expand the capabilities of the platform. Alternatively, the connected medical systems can be medical devices communicating via a communication cable with the platform. The cable can include a processing board in the cable, alternatively, the processor on the medical device itself can communicate directly with the platform.

When a medical system is initially connected, for example, using a wired connection such as a cable or dongle device, an EPROM on the cable or dongle device initially describes the necessary physical communication parameters for speaking with the medical system's processor. For example, the EPROM can provide parameters including ISO/non-ISO communication requirements, baud rates, etc.

A further description of the EPROM communication parameters is described in U.S. Provisional Application Nos. 62/463,452 and 62/463,297.

Once initial communication parameters are established, the platform may begin communicating with the processor of the medical system. The medical system then describes itself and its capabilities to the platform. For example, the self-description can include the measurement channels supported by the device; the measured parameters (metrics) supported by each channel, including, but not limited to: names, relationship to metrics and coding systems defined by standards bodies, valid ranges and units of measure, body sites involved, parameter exceptions, visual presentation requirements and characteristics; alarm limits and other parameter settings; alarm, alert and other event conditions; actions that can be performed by the device (such as requests to begin performing measurements); patient demographics and externally-measured metrics needed by the device to perform its computations; manufacturer branding information; or other information as would be desired by a person of skill in the art.

The "self-describing" nature of the platform may permit a high degree of flexibility, allowing the protocol and its capabilities to evolve while maintaining compatibility across protocol and software versions. Further information regarding the self-describing protocol are provided in U.S. Provisional Application No. 62/463,452, which describes a software development kit for Masimo's Open Connect™ system.

The medical systems, once connected to the platform, can then pull from or push to the platform any information. For example, connected Medical System A can pull measured parameters from connected Medical System B. Medical System A can then use that information to generate a new measured parameter which can then be pushed to the platform for display or use by other connected medical systems.

The data obtained from the various connected medical system can be time stamped using the platform system clock. This allows various measurements to be synchronized with other measurements. Synchronization can aid with display of the data and further calculations using the data.

The platform can provide standardized graphical interfaces depending on the display characteristics of the medical systems. For example, the medical systems can self-define to a numerical readout, a graph, or other specified display options which can be self-defined. Alternatively, the attached medical device can provide image data used by the hub to provide display graphics.

XVIII. Terminology

Many other variations than those described herein will be apparent from this disclosure. For example, depending on the embodiment, certain acts, events, or functions of any of the algorithms described herein can be performed in a different sequence, can be added, merged, or left out altogether (for example, not all described acts or events are necessary for the practice of the algorithms). Moreover, in certain embodiments, acts or events can be performed concurrently, for example, through multi-threaded processing, interrupt processing, or multiple processors or processor cores or on other parallel architectures, rather than sequentially. In addition, different tasks or processes can be performed by different machines and/or computing systems that can function together.

It is to be understood that not necessarily all such advantages can be achieved in accordance with any particular embodiment of the embodiments disclosed herein. Thus, the embodiments disclosed herein can be embodied or carried out in a manner that achieves or optimizes one advantage or group of advantages as taught herein without necessarily achieving other advantages as may be taught or suggested herein.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry or digital logic circuitry configured to process computer-executable instructions. In another embodiment, a processor includes an FPGA or other programmable device that performs logic operations without processing computer-executable instructions. A processor can also be implemented as a combination of computing devices, for example, a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a device controller, or a computational engine within an appliance, to name a few.

The steps of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC.

Conditional language used herein, such as, among others, "can," "might," "may," "for example," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Disjunctive language such as the phrase "at least one of X, Y, or Z," unless specifically stated otherwise, is otherwise understood with the context as used in general to present that an item, term, etc., may be either X, Y, or Z, or any combination thereof (for example, X, Y, and/or Z). Thus, such disjunctive language is not generally intended to, and should not, imply that certain embodiments require at least one of X, at least one of Y, or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others.

Additionally, all publications, patents, and patent applications mentioned in this specification are herein incorporated by reference to the same extent as if each individual publication, patent, or patent application was specifically and individually indicated to be incorporated by reference.

What is claimed:

1. A pulse oximetry system operable to measure a blood parameter of a patient and transmit the blood parameter together with third party medical device parameters to a remote device, the system comprising:
    a patient monitor configured to measure the blood parameter of the patient by obtaining a signal from an optical sensor coupled to the patient, wherein the signal corresponds to light attenuated by body tissue of the patient;
    a wireless dongle; and
    a medical network interface, the patient monitor configured to communicate with the medical network interface which transmits the measured blood parameter and the third party medical device parameters from a third party medical device across a hospital network, the medical network interface comprising:
        a plurality of ports, at least one of which is configured to receive the wireless dongle;
        a network interface controller configured to implement a wireless communications stack;
        a memory configured to store processor-executable instructions; and
        a processor programmed to execute the instructions to:
            supply the wireless dongle with information sufficient to enable the wireless dongle to provide wireless connectivity to the third party medical device;
            wirelessly pair with the wireless dongle in response to receiving a signal from the third party medical device, which occurs in response to the wireless dongle being inserted into the third party medical device;
            subsequent to the pairing, wirelessly receive a data stream from the wireless dongle, the data stream comprising an identifier of the third party medical device and the third party medical device parameters associated with the patient;
            associate with the data stream, an identifier of the patient, an identifier of the medical network interface, and an identifier of the patient monitor to produce a modified data stream; and
            transmit the modified data stream, the measured blood parameter, and the third party medical device parameters across a hospital network to enable the modified data stream and the measured blood parameter to be accessed by a clinician.

2. The pulse oximetry system of claim 1, wherein the plurality of ports comprise two or more of the following: a Universal Serial Bus port, an Ethernet port, or a serial port with patient isolation hardware.

3. The pulse oximetry system of claim 1, wherein the processor is further programmed to receive an optical scan of a patient wristband to thereby obtain the patient identifier.

4. The pulse oximetry system of claim 1, wherein the processor is further programmed to:
    generate a permission key for pairing the third party medical device with the medical network interface;
    communicate the permission key to the third party medical device;
    receive a communication from the third party medical device having the permission key; and
    establish a communication with the third party medical device in response to a determination that the permission key is authenticated.

5. The pulse oximetry system of claim 4, wherein in response to the determination that the permission key is authenticated, the processor is further programmed to link the identifier of the patient and the identifier of the medical network interface to the identifier of the third party medical device.

6. The pulse oximetry system of claim 1, wherein the wireless dongle or the medical network interface further comprises a display configured to indicate at least one of: a status of the medical network interface, a status of a first medical device, a status of a second medical device, or a status of a pairing between the first medical device and the second medical device.

7. The pulse oximetry system of claim 1, wherein the wireless dongle or the medical network interface further comprises a light configured to indicate at least one of: a status of the medical network interface, a status of the first medical device, a status of the second medical device, a status of a pairing between the first medical device and the second medical device, or a power status associated with the dongle.

8. The pulse oximetry system of claim 1, wherein the plurality of ports comprise first ports of a first color and second ports of a second color.

9. The pulse oximetry system of claim 8, wherein data received from the first ports is automatically associated with the identifier of the patient and wherein data received from the second ports is automatically associated with a second patient identifier of a second patient.

10. The pulse oximetry system of claim 1, wherein the wireless dongle comprises two pieces with a first piece that stays connected to the medical network interface, and a second piece that disconnects from the first piece.

11. The pulse oximetry system of claim 10, wherein the second piece connects in a corresponding first piece of a second dongle in the third party medical device, the third party medical device being a standalone medical device.

12. The pulse oximetry system of claim 1, wherein the processor is further programmed to:
 access a first identifier for pairing the third party medical device with the medical network interface;
 communicate the first identifier to the third party medical device;
 receive a communication from the third party medical device having the first identifier; and
 establish a communication with the third party medical device in response to a determination that the first identifier is authenticated.

13. The pulse oximetry system of claim 1, wherein the medical network interface comprises a front side and a back side, and wherein the front side comprises an interface port configured to receive the wireless dongle.

14. The pulse oximetry system of claim 13, wherein the wireless dongle is coupleable with a power cable, the power cable configured to provide power supply to the wireless dongle.

15. A method of transmitting standalone medical device parameters to a remote device, the method comprising:
 detecting an insertion of a wireless dongle into a port of a medical network interface;
 in response to said insertion,
  supplying the wireless dongle with an identifier to enable the wireless dongle to communicate an identifier of a standalone medical device upon insertion of the wireless dongle into the standalone medical device;
 subsequent to removal of the wireless dongle from the port of the medical network interface,
  receiving, with a hardware processor, a signal from the standalone medical device to wirelessly pair the medical network interface with the dongle, the signal comprising the identifier previously supplied to the wireless dongle; and
 subsequent to the pairing,
  supplying one or both of a visual or audible indication that the pairing has been successful,
  wirelessly receiving a data stream from the standalone medical device, the data stream comprising patient data associated with a patient, and
  associating with the data stream, an identifier of the patient and an identifier of the medical network interface, to produce a modified data stream; and
 transmitting the modified data stream across a hospital network to a server so as to enable distribution of the modified data stream to a plurality of devices from the server.

16. The method of claim 15, wherein said supplying comprises actuating a light.

17. The method of claim 15, wherein said supplying comprises outputting information on a display, and wherein the information comprises the identifier of the standalone medical device.

18. The method of any of claim 15, wherein said pairing is a modified Bluetooth pairing that does not require input of a pin or other number or password in either the medical network device or the standalone medical device.

19. The method of claim 15, further comprising associating with the data stream an identifier of the standalone medical device.

20. The method of claim 15, further comprising obtaining the patient identifier from an optical scan of a wrist bracelet on the patient.

* * * * *